United States Patent
Ginsburg et al.

(10) Patent No.: US 7,037,658 B2
(45) Date of Patent: May 2, 2006

(54) METHODS AND COMPOSITIONS FOR DETECTING VARIANT ADAMTS13 GENES

(75) Inventors: David Ginsburg, Ann Arbor, MI (US); Gallia Levy, Ann Arbor, MI (US); Han-Mou Tsai, Manhasset, NY (US)

(73) Assignee: Regents of University of Michigan, Ann Arbor, MI (US)

( * ) Notice: Subject to any disclaimer, the term of this patent is extended or adjusted under 35 U.S.C. 154(b) by 527 days.

(21) Appl. No.: 10/222,334

(22) Filed: Aug. 16, 2002

(65) Prior Publication Data

US 2003/0073116 A1 Apr. 17, 2003

Related U.S. Application Data

(60) Provisional application No. 60/312,834, filed on Aug. 16, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.2; 536/23.5

(58) Field of Classification Search .............. 435/6, 435/91.2; 536/23.2, 23.5
See application file for complete search history.

(56) References Cited

OTHER PUBLICATIONS

Levy et al. Nature. Oct. 2001. 413: 488-494.*
Matsumoto et al. Blood. 2004. 103: 1305-1310.*
Kokame et al. PNAS. 2002. 99 : 11902-11907.*
Uchida et al. Blood 2004. 104: 2081-2083.*
Pimanda et al. Blood. 2004. 103: 627-629.*
Peyvandi et al (British Journal of Haematology. 2004. 127: 433-439.*

* cited by examiner

*Primary Examiner*—Carla J. Myers
(74) *Attorney, Agent, or Firm*—Medlen & Carroll, LLP

(57) ABSTRACT

The present invention relates to a disintegrin and metalloproteinase containing thrombospondin 1-like domains (ADAMTS) and in particular to a novel ADAMTS13 protease and to nucleic acids encoding ADAMTS13 proteases. The present invention encompasses both native and recombinant wild-type forms of ADAMTS13, as well as mutant and variant forms including fragments, some of which posses altered characteristics relative to the wild-type ADAMTS13. The present invention also relates to methods of using ADAMTS13, including for treatment of TTP. The present invention also relates to methods for screening for the presence of TTP. The present invention further relates to methods for developing anticoagulant drugs based upon ADAMTS13.

5 Claims, 58 Drawing Sheets

FIG. 4
A
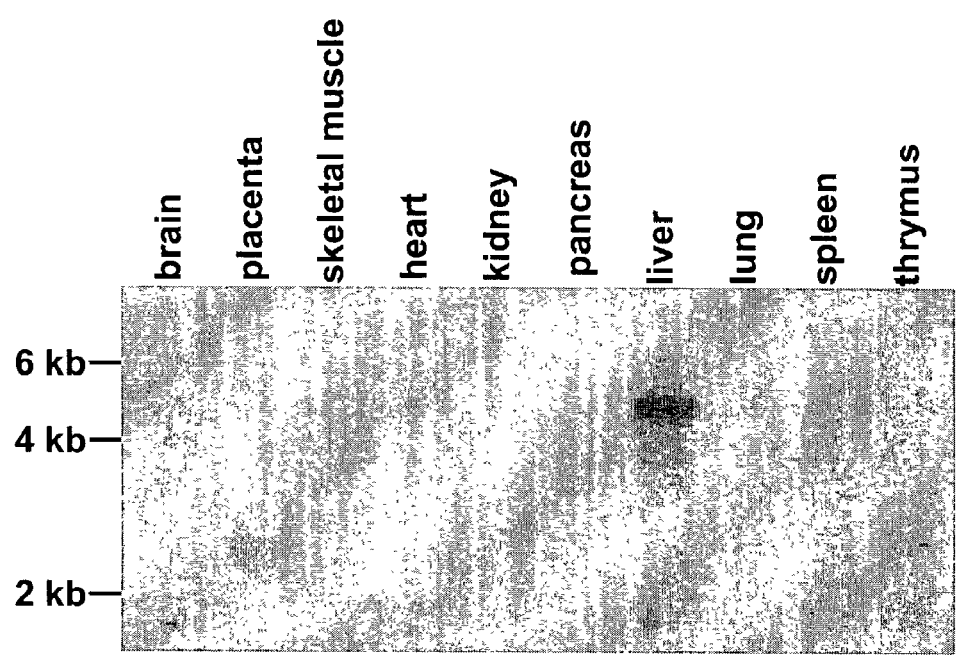
B
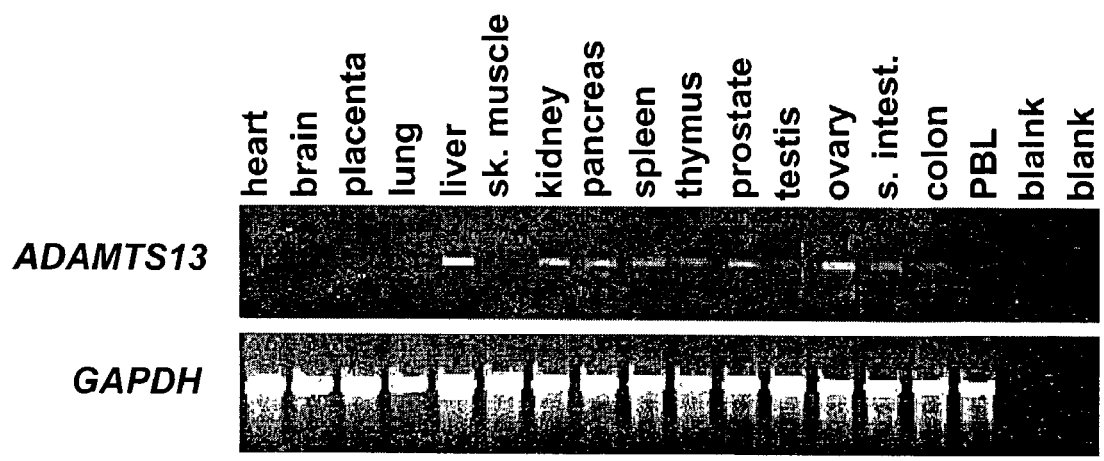

FIG. 5

Nucleotide sequence encoding a long form of an ADAMTS13

```
   1  ATTCCCAGTC ACCAAGGCCC CCTCTCACTC CGCTCCACTC CTCGGGCTGG
  51  CTCTCCTGAG GATGCACCAG CGTCACCCCY GGGCAAGATG CCCTCCCCTC
 101  TGTGTGGCCG GAATCCTTGC CTGTGGCTTT CTCCTGGGCT GCTGGGGACC
 151  CTCCCATTTC CAGCAGAGTT GTCTTCAGGC TTTGGAGCCA CAGGCCGTGT
 201  CTTCTTACTT GAGCCCTGGT GCTCCCTTAA AAGGCCGCCC TCCTTCCCCT
 251  GGCTTCCAGA GGCAGAGGCA GAGGCAGAGG CGGGCTGCAG GCGGCATCCT
 301  ACACCTGGAG CTGCTGGTGG CCGTGGGCCC CGATGTCTTC CAGGCTCACC
 351  AGGAGGACAC AGAGCGCTAT GTGCTCACCA ACCTCAACAT CGGGGCAGAA
 401  CTGCTTCGGG ACCCRTCCCT GGGGGCTCAG TTTCGGGTGC ACCTGGTGAA
 451  GATGGTCATT CTGACAGAGC CTGAGGGTGC YCCAAATATC ACAGCCAACC
 501  TCACCTCGTC CCTGCTGAGC GTCTGTGGGT GGAGCCAGAC CATCAACCCT
 551  GAGGACGACA CGGATCCTGG CCATGCTGAC CTGGTCCTCT ATATCACTAG
 601  GTTTGACCTG GAGTTGCCTG ATGGTAACCG GCAGGTGCGG GGYGTCACCC
 651  AGCTGGGCGG TGCCTGCTCC CCAACCTGGA GCTGCCTCAT TACCGAGGAC
 701  ACTGGCTTCG ACCTGGGAGT CACCATTGCC CATGAGATTG GCACAGCTT
 751  CGGCCTGGAG CACGACGGCG CGCCCGGCAG CGGCTGCGGC CCCAGCGGAC
 801  ACGTGATGGC TTCGGACGGC GCCGCGCCCC GCGCCGGCCT CGCCTGGTCC
 851  CCCTGCAGCC GCCGGCAGCT GCTGAGCCTG CTCAGCGCAG GACGGGCGCG
 901  CTGCGTGTGG GACCCGCCGC GGCCTCAACC CGGGTCCGCG GGCACCCGC
 951  CGGATGCGCA GCCTGGCCTC TACTACAGCG CCAACGAGCA GTGCCGCGTG
1001  GCCTTCGGCC CCAAGGCTGT CGCYTGCACC TTCGCCAGGG AGCACCTGGA
1051  TATGTGCCAG GCCCTCTCCT GCCACACAGA CCCGCTGGAC CAAAGCAGCT
1101  GCAGCCGCCT CCTCGTTCCT CTCCTGGATG GGACAGAATG TGGCGTGGAG
1151  AAGTGGTGCT CCAAGGGTCG CTGCCGCTCC CTGGTGGAGC TGACCCCCAT
1201  AGCAGCAGTG CATGGGCGCT GGTCTAGCTG GGGTCCCCGA AGTCCTTGCT
1251  CCCGCTCCTG CGGAGGAGGT GTGGTCACCA GGAGGCGGCA GTGCAACAAC
1301  CCCAGACCTG CCTTTGGGGG GCGTGCATGT GTTGGTGCTG ACCTCCAGGC
1351  CGAGATGTGC AACACTCAGG CCTGCGAGAA GACCCAGCTG GAGTTCATGT
1401  CGSAACAGTG CGCCAGGACC GACGGCCAGC CGCTGCGCTC CTCCCCTGGC
```

FIG. 5, cont'd

```
1451  GGCGCCTCCT TCTACCACTG GGGTGCTGCT GTACCACACA GCCAAGGGGA
1501  TGCTCTGTGC AGACACATGT GCCGGGCCAT TGGCGAGAGC TTCATCATGA
1551  AGCGTGGAGA CAGCTTCCTC GATGGGACCC GGTGTATGCC AAGTGGCCCC
1601  CGGGAGGACG GGACCCTGAG CCTGTGTGTG TCGGGCAGCT GCAGGACATT
1651  TGGCTGTGAT GGTAGGATGG ACTCCCAGCA GGTATGGGAC AGGTGCCAGG
1701  TGTGTGGTGG GGACAACAGC ACGTGCAGCC CACGGAAGGG CTCTTTCACA
1751  GCTGGCAGAG CGAGAGAATA TGTCACRTTT CTGACAGTTA CCCCCAACCT
1801  GACCAGTGTC TACATTGCCA ACCACAGGCC TCTCTTCACA CACTTGGCGG
1851  TGAGGATCGG AGGGCGCTAT GTCGTGGCTG GAAGATGAG CATCTCCCCT
1901  AACACCACCT ACSCCTCCCT CCTGGAGGAT GGTCRTGTCG AGTACAGAGT
1951  GGCCCTCACC GAGGACCGGC TGCCCCGCCT GGAGGAGATC CGCATCTGGG
2001  GACCCCTCCA GGAAGATGCT GACATCCAGG TTTACAGGCG GTATGGCGAG
2051  GAGTATGGCA ACCTCACCCG CCCAGACATC ACCTTCACCT ACTTCCAGCC
2101  TAAGCCACGG CAGGCCTGGG TGTGGGCCGC TGTGCGTGGG CCCTGCTCGg
2151  tgagctgtgg ggcagGGCTG CGCTGGGTAA ACTACAGCTG CCTGGACCAG
2201  GCCAGGAAGG AGTTGGTGGA GACTGTCCAG TGCCAAGGGA GCCAGCAGCC
2251  ACCAGYGTGG CCAGAGGCCT GCGTGCTCGA ACCCTGCCCT CCCTACTGGG
2301  CGGTGGGAGA CTTCGGCCCA TGCAGCGCCT CCTGTGGGGG YGGCCTGCGG
2351  GAGCGGCCAG TGCGCTGCGT GGAGGCCCAG GGCAGCCTCC TGAAGACATT
2401  GCCCCAGCC CGGTGCAGAG CAGGGGCCCA GCAGCCAGCT GTGGCGCTGG
2451  AAACCTGCAA CCCCCAGCCC TGCCCTGCCA GGTGGGAGGT GTCAGAGCCC
2501  AGCTCATGCA CATCAGCTGG TGGAGCAGGC CTGGCCTTGG AGAACGAGAC
2551  CTGTGTGCCA GGGGCAGATG GCCTGGAGGC TCCAGTGACT GAGGGGCCTG
2601  GCTCCGTAGA TGAGAAGCTG CCTGCCCCTG AGCCCTGTGT CGGGATGTCA
2651  TGTCCTCCAG GCTGGGGCCA TCTGGATGCC ACCTCTGCAG GGGAGAAGGC
2701  TCCCTCCCCA TGGGCAGCA TCAGGACGGG GGCTCAAGCT GCACACGTGT
2751  GGACCCCTGY GGCAGGGTCG TGCTCCGTCT CCTGCGGGCG AGGTCTGATG
2801  GAGCTGCGTT TCCTGTGCAT GGACTCTGCC CTCAGGGTGC CTGTCCAGGA
2851  AGAGCTGTGT GGCCTGGCAA GCAAGCCTGG GAGCCGGCGG GAGGTCTGCC
2901  AGGCTGTCCC GTGCCCTGCT CGGTGGCAGT ACAAGCTGGC GGCCTGCAGC
```

FIG. 5, cont'd

```
2951  GTGAGCTGTG GGAGAGGGGT YGTGCGGAGG ATCCTGTATT GTGCCCGGGC
3001  CCATGGGGAG GACGATGGTG AGGAGATCCT GTTGGACACC CAGTGCCAGG
3051  GGCTGCCTCG CCCGGAACCC CAGGAGGCCT GCAGCCTGGA GCCCTGCCCA
3101  CCTAGGTGGA AAGTCATGTC CCTTGGCCCA TGTTCGGCCA GCTGTGGCCT
3151  TGGCACTRCT AGACGCTCRG TGGCCTGTGT GCAGCTCGAC CAAGGCCAGG
3201  ACGTGGAGGT GGACGAGGCG GCCTGTGCGG CGCTGGTGCG GCCCGAGGCC
3251  AGTGTCCCCT GTCTCATTGC CGACTGCACC TACCGCTGGC ATGTTGGCAC
3301  CTGGATGGAG TGCTCTGTTT CCTGTGGGGA TGGCATCCAG CGCCGGCGTG
3351  ACACCTGCCT CGGACCCCAG GCCCAGGCGC TGTGCCAGC TGATTTCTGC
3401  CAGCACTTGC CCAAGCCGGT GACTGTGCGT GGCTGCTGGG CTGGGCCCTG
3451  TGTGGGACAG GGTACGCCCA GCCTGGTGCC CCACGAAGAA GCCGCTGCTC
3501  CAGGACGGAC CACAGCCACC CCTGCTGGTG CCTCCCTGGA GTGGTCCCAG
3551  GCCCGGGGCC TGCTCTTCTC CCCGGCTCCC CAGCCTCGGC GGCTCCTGCC
3601  CGGGCCCCAG GAAAACTCAG TGCAGTCCAG TGCCTGTGGC AGGCAGCACC
3651  TTGAGCCAAC AGGAACCATT GACATGCGAG GCCCAGGGCA GGCAGACTGT
3701  GCAGTGGCCA TTGGGCGGCC CCTCGGGGAG GTGGTGACCC TCCGCGTCCT
3751  TGAGAGTTCT CTCAACTGCA GTGCGGGGGA CATGTTGCTG CTTTGGGGCC
3801  GGCTCACCTG GAGGAAGATG TGCAGGAAGC TGTTGGACAT GACTTTCAGC
3851  TCCAAGACCA ACACGCTGGT GGTGAGGCAG CGCTGCGGGC GGCCAGGAGG
3901  TGGGGTGCTG CTGCGGTATG GGAGCCAGCT TGCTCCTGAA ACCTTCTACA
3951  GAGAATGTGA CATGCAGCTC TTTGGGCCCT GGGGTGAAAT CGTGAGCCCC
4001  TCGCTGAGTC CAGCCACGAG TAATGCAGGG GGCTGCCGGC TCTTCATTAA
4051  TGTGGCTCCG CACGCACGGA TTGCCATCCA TGCCCTGGCC ACCAACATGG
4101  GCGCTGGGAC CGAGGGAGCC AATGCCAGCT ACATCTTGAT CCGGGACACC
4151  CACAGCTTGA GGACCACAGC GTTCCATGGG CAGCAGGTGC TCTACTGGGA
4201  GTCAGAGAGC AGCCAGGCTG AGATGGAGTT CAGCGAGGGC TTCCTGAAGG
4251  CTCAGGCCAG CCTGCGGGGC CAGTACTGGA CMCTCCAATC ATGGGTACCG
4301  GAGATGCAGG ACCCTCAGTC CTGGAAGGGA AAGGAAGGAA CCTGAGGGTC
4351  ATTGAACATT TGTTCCGTGT CTGGCCAGCC CTGGAGGGTT GACCCCTGGT
4401  CTCAGTGCTT TCCAATTCGA ACTTTTTCCA ATCTTAGGTA TCTACTTTAG
```

FIG. 5, cont'd

```
4451    AGTCTTCTCC  AATGTCCAAA  AGGCTAGGGG  GTTGGAGGTG  GGGACTCTGG

4501    AAAAGCAGCC  CCCATTTCCT  CGGGTACCAA  TAAATAAAAC  ATGCAGGCTG
```

FIG. 6

Amino sequence of a long form of an ADAMTS-13

```
   1  MHQRHPRARC PPLCVAGILA CGFLLGCWGP SHFQQSCLQA LEPQAVSSYL
  51  SPGAPLKGRP PSPGFQRQRQ RQRRAAGGIL HLELLVAVGP DVFQAHQEDT
 101  ERYVLTNLNI GAELLRDPSL GAQFRVHLVK MVILTEPEGA PNITANLTSS
 151  LLSVCGWSQT INPEDDTDPG HADLVLYITR FDLELPDGNR QVRGVTQLGG
 201  ACSPTWSCLI TEDTGFDLGV TIAHEIGHSF GLEHDGAPGS GCGPSGHVMA
 251  SDGAAPRAGL AWSPCSRRQL LSLLSAGRAR CVWDPPRPQP GSAGHPPDAQ
 301  PGLYYSANEQ CRVAFGPKAV ACTFAREHLD MCQALSCHTD PLDQSSCSRL
 351  LVPLLDGTEC GVEKWCSKGR CRSLVELTPI AAVHGRWSSW GPRSPCSRSC
 401  GGGVVTRRRQ CNNPRPAFGG RACVGADLQA EMCNTQACEK TQLEFMSQQC
 451  ARTDGQPLRS SPGGASFYHW GAAVPHSQGD ALCRHMCRAI GESFIMKRGD
 501  SFLDGTRCMP SGPREDGTLS LCVSGSCRTF GCDGRMDSQQ VWDRCQVCGG
 551  DNSTCSPRKG SFTAGRAREY VTFLTVTPNL TSVYIANHRP LFTHLAVRIG
 601  GRYVVAGKMS ISPNTTYPSL LEDGRVEYRV ALTEDRLPRL EEIRIWGPLQ
 651  EDADIQVYRR YGEEYGNLTR PDITFTYFQP KPRQAWVWAA VRGPCSVSCG
 701  AGLRWVNYSC LDQARKELVE TVQCQGSQQP PAWPEACVLE PCPPYWAVGD
 751  FGPCSASCGG GLRERPVRCV EAQGSLLKTL PPARCRAGAQ QPAVALETCN
 801  PQPCPARWEV SEPSSCTSAG GAGLALENET CVPGADGLEA PVTEGPGSVD
 851  EKLPAPEPCV GMSCPPGWGH LDATSAGEKA PSPWGSIRTG AQAAHVWTPA
 901  AGSCSVSCGR GLMELRFLCM DSALRVPVQE ELCGLASKPG SRREVCQAVP
 951  CPARWQYKLA ACSVSCGRGV VRRILYCARA HGEDDGEEIL LDTQCQGLPR
1001  PEPQEACSLE PCPPRWKVMS LGPCSASCGL GTARRSVACV QLDQGQDVEV
1051  DEAACAALVR PEASVPCLIA DCTYRWHVGT WMECSVSCGD GIQRRRDTCL
1101  GPQAQAPVPA DFCQHLPKPV TVRGCWAGPC VGQGTPSLVP HEEAAAPGRT
1151  TATPAGASLE WSQARGLLFS PAPQPRRLLP GPQENSVQSS ACGRQHLEPT
1201  GTIDMRGPGQ ADCAVAIGRP LGEVVTLRVL ESSLNCSAGD MLLLWGRLTW
1251  RKMCRKLLDM TFSSKTNTLV VRQRCGRPGG GVLLRYGSQL APETFYRECD
1301  MQLFGPWGEI VSPSLSPATS NAGGCRLFIN VAPHARIAIH ALATNMGAGT
1351  EGANASYILI RDTHSLRTTA FHGQQVLYWE SESSQAEMEF SEGFLKAQAS
1401  LRGQYWTLQS WVPEMQDPQS WKGKEGT.
```

FIG. 7

Nucleotide sequence encoding a short form of an ADAMTS13

```
   1 ATTCCCAGTC ACCAAGGCCC CCTCTCACTC CGCTCCACTC CTCGGGCTGG
  51 CTCTCCTGAG GATGCACCAG CGTCACCCCY GGGCAAGATG CCCTCCCCTC
 101 TGTGTGGCCG GAATCCTTGC CTGTGGCTTT CTCCTGGGCT GCTGGGGACC
 151 CTCCCATTTC CAGCAGAGTT GTCTTCAGGC TTTGGAGCCA CAGGCCGTGT
 201 CTTCTTACTT GAGCCCTGGT GCTCCCTTAA AAGGCCGCCC TCCTTCCCCT
 251 GGCTTCCAGA GGCAGAGGCA GAGGCAGAGG CGGGCTGCAG GCGGCATCCT
 301 ACACCTGGAG CTGCTGGTGG CCGTGGGCCC CGATGTCTTC CAGGCTCACC
 351 AGGAGGACAC AGAGCGCTAT GTGCTCACCA ACCTCAACAT CGGGGCAGAA
 401 CTGCTTCGGG ACCCRTCCCT GGGGGCTCAG TTTCGGGTGC ACCTGGTGAA
 451 GATGGTCATT CTGACAGAGC CTGAGGGTGC YCCAAATATC ACAGCCAACC
 501 TCACCTCGTC CCTGCTGAGC GTCTGTGGGT GGAGCCAGAC CATCAACCCT
 551 GAGGACGACA CGGATCCTGG CCATGCTGAC CTGGTCCTCT ATATCACTAG
 601 GTTTGACCTG GAGTTGCCTG ATGGTAACCG GCAGGTGCGG GGYGTCACCC
 651 AGCTGGGCGG TGCCTGCTCC CCAACCTGGA GCTGCCTCAT TACCGAGGAC
 701 ACTGGCTTCG ACCTGGGAGT CACCATTGCC CATGAGATTG GCACAGCTT
 751 CGGCCTGGAG CACGACGGCG CGCCCGGCAG CGGCTGCGGC CCCAGCGGAC
 801 ACGTGATGGC TTCGGACGGC GCCGCGCCCC GCGCCGGCCT CGCCTGGTCC
 851 CCCTGCAGCC GCCGGCAGCT GCTGAGCCTG CTCAGCGCAG GACGGGCGCG
 901 CTGCGTGTGG GACCCGCCGC GGCCTCAACC CGGGTCCGCG GGCACCCGC
 951 CGGATGCGCA GCCTGGCCTC TACTACAGCG CCAACGAGCA GTGCCGCGTG
1001 GCCTTCGGCC CCAAGGCTGT CGCYTGCACC TTCGCCAGGG AGCACCTGGA
1051 TATGTGCCAG GCCCTCTCCT GCCACACAGA CCCGCTGGAC CAAAGCAGCT
1101 GCAGCCGCCT CCTCGTTCCT CTCCTGGATG GACAGAATG TGGCGTGGAG
1151 AAGTGGTGCT CCAAGGGTCG CTGCCGCTCC CTGGTGGAGC TGACCCCCAT
1201 AGCAGCAGTG CATGGGCGCT GGTCTAGCTG GGGTCCCCGA AGTCCTTGCT
1251 CCCGCTCCTG CGGAGGAGGT GTGGTCACCA GGAGGCGGCA GTGCAACAAC
1301 CCCAGACCTG CCTTTGGGGG GCGTGCATGT GTTGGTGCTG ACCTCCAGGC
1351 CGAGATGTGC AACACTCAGG CCTGCGAGAA GACCCAGCTG GAGTTCATGT
1401 CGSAACAGTG CGCCAGGACC GACGGCCAGC CGCTGCGCTC CTCCCCTGGC
```

FIG. 7, cont'd

```
1451    GGCGCCTCCT TCTACCACTG GGGTGCTGCT GTACCACACA GCCAAGGGGA
1501    TGCTCTGTGC AGACACATGT GCCGGGCCAT TGGCGAGAGC TTCATCATGA
1551    AGCGTGGAGA CAGCTTCCTC GATGGGACCC GGTGTATGCC AAGTGGCCCC
1601    CGGGAGGACG GGACCCTGAG CCTGTGTGTG TCGGGCAGCT GCAGGACATT
1651    TGGCTGTGAT GGTAGGATGG ACTCCCAGCA GGTATGGGAC AGGTGCCAGG
1701    TGTGTGGTGG GGACAACAGC ACGTGCAGCC CACGGAAGGG CTCTTTCACA
1751    GCTGGCAGAG CGAGAGAATA TGTCACRTTT CTGACAGTTA CCCCCAACCT
1801    GACCAGTGTC TACATTGCCA ACCACAGGCC TCTCTTCACA CACTTGGCGG
1851    TGAGGATCGG AGGGCGCTAT GTCGTGGCTG GAAGATGAG CATCTCCCCT
1901    AACACCACCT ACSCCTCCCT CCTGGAGGAT GGTCRTGTCG AGTACAGAGT
1951    GGCCCTCACC GAGGACCGGC TGCCCCGCCT GGAGGAGATC CGCATCTGGG
2001    GACCCCTCCA GGAAGATGCT GACATCCAGC TCTTTGTCTG CAGGTTTACA
2051    GGCGGTATGG CGAGGAGTAT GGCAACCTCA CCCGCCCAGA CATCACCTTC
2101    ACCTACTTCC AGCCTAAGCC ACGGCAGGCC TGGGTGTGGG CCGCTGTGCG
2151    TGGGCCCTGC TCGGGCTGCG CTGGGTAAAC TACAGCTGCC TGGACCAGGC
2201    CAGGAAGGAG TTGGTGGAGA CTGTCCAGTG CCAAGGGAGC CAGCAGCCAC
2251    CAGYGTGGCC AGAGGCCTGC GTGCTCGAAC CCTGCCCTCC CTACTGGGCG
2301    GTGGGAGACT TCGGCCCATG CAGCGCCTCC TGTGGGGGYG GCCTGCGGGA
2351    GCGGCCAGTG CGCTGCGTGG AGGCCCAGGG CAGCCTCCTG AAGACATTGC
2401    CCCCAGCCCG GTGCAGAGCA GGGGCCCAGC AGCCAGCTGT GGCGCTGGAA
2451    ACCTGCAACC CCCAGCCCTG CCCTGCCAGG TGGGAGGTGT CAGAGCCCAG
2501    CTCATGCACA TCAGCTGGTG GAGCAGGCCT GGCCTTGGAG AACGAGACCT
2551    GTGTGCCAGG GGCAGATGGC CTGGAGGCTC CAGTGACTGA GGGGCCTGGC
2601    TCCGTAGATG AGAAGCTGCC TGCCCCTGAG CCCTGTGTCG GGATGTCATG
2651    TCCTCCAGGC TGGGGCCATC TGGATGCCAC CTCTGCAGGG GAGAAGGCTC
2701    CCTCCCCATG GGGCAGCATC AGGACGGGGG CTCAAGCTGC ACACGTGTGG
2751    ACCCCTGYGG CAGGGTCGTG CTCCGTCTCC TGCGGGCGAG GTCTGATGGA
2801    GCTGCGTTTC CTGTGCATGG ACTCTGCCCT CAGGGTGCCT GTCCAGGAAG
2851    AGCTGTGTGG CCTGGCAAGC AAGCCTGGGA GCCGGCGGGA GGTCTGCCAG
2901    GCTGTCCCGT GCCCTGCTCG GTGGCAGTAC AAGCTGGCGG CCTGCAGCGT
```

FIG. 7, cont'd

```
2951  GAGCTGTGGG AGAGGGGTYG TGCGGAGGAT CCTGTATTGT GCCCGGGCCC
3001  ATGGGGAGGA CGATGGTGAG GAGATCCTGT TGGACACCCA GTGCCAGGGG
3051  CTGCCTCGCC CGGAACCCCA GGAGGCCTGC AGCCTGGAGC CCTGCCCACC
3101  TAGGTGGAAA GTCATGTCCC TTGGCCCATG TTCGGCCAGC TGTGGCCTTG
3151  GCACTRCTAG ACGCTCRGTG GCCTGTGTGC AGCTCGACCA AGGCCAGGAC
3201  GTGGAGGTGG ACGAGGCGGC CTGTGCGGCG CTGGTGCGGC CCGAGGCCAG
3251  TGTCCCCTGT CTCATTGCCG ACTGCACCTA CCGCTGGCAT GTTGGCACCT
3301  GGATGGAGTG CTCTGTTTCC TGTGGGGATG GCATCCAGCG CCGGCGTGAC
3351  ACCTGCCTCG GACCCCAGGC CCAGGCGCCT GTGCCAGCTG ATTTCTGCCA
3401  GCACTTGCCC AAGCCGGTGA CTGTGCGTGG CTGCTGGGCT GGGCCCTGTG
3451  TGGGACAGGG TACGCCCAGC CTGGTGCCCC ACGAAGAAGC CGCTGCTCCA
3501  GGACGGACCA CAGCCACCCC TGCTGGTGCC TCCCTGGAGT GGTCCCAGGC
3551  CCGGGGCCTG CTCTTCTCCC CGGCTCCCCA GCCTCGGCGG CTCCTGCCCG
3601  GGCCCCAGGA AAACTCAGTG CAGTCCAGTG CCTGTGGCAG GCAGCACCTT
3651  GAGCCAACAG GAACCATTGA CATGCGAGGC CCAGGGCAGG CAGACTGTGC
3701  AGTGGCCATT GGGCGGCCCC TCGGGGAGGT GGTGACCCTC CGCGTCCTTG
3751  AGAGTTCTCT CAACTGCAGT GCGGGGACA TGTTGCTGCT TTGGGGCCGG
3801  CTCACCTGGA GGAAGATGTG CAGGAAGCTG TTGGACATGA CTTTCAGCTC
3851  CAAGACCAAC ACGCTGGTGG TGAGGCAGCG CTGCGGGCGG CCAGGAGGTG
3901  GGGTGCTGCT GCGGTATGGG AGCCAGCTTG CTCCTGAAAC CTTCTACAGA
3951  GAATGTGACA TGCAGCTCTT TGGGCCCTGG GGTGAAATCG TGAGCCCCTC
4001  GCTGAGTCCA GCCACGAGTA ATGCAGGGGG CTGCCGGCTC TTCATTAATG
4051  TGGCTCCGCA CGCACGGATT GCCATCCATG CCCTGGCCAC CAACATGGGC
4101  GCTGGGACCG AGGGAGCCAA TGCCAGCTAC ATCTTGATCC GGGACACCCA
4151  CAGCTTGAGG ACCACAGCGT TCCATGGGCA GCAGGTGCTC TACTGGGAGT
4201  CAGAGAGCAG CCAGGCTGAG ATGGAGTTCA GCGAGGGCTT CCTGAAGGCT
4251  CAGGCCAGCC TGCGGGGCCA GTACTGGACM CTCCAATCAT GGGTACCGGA
4301  GATGCAGGAC CCTCAGTCCT GGAAGGGAAA GGAAGGAACC TGAGGGTCAT
4351  TGAACATTTG TTCCGTGTCT GGCCAGCCCT GGAGGGTTGA CCCCTGGTCT
4401  CAGTGCTTTC CAATTCGAAC TTTTTCCAAT CTTAGGTATC TACTTTAGAG
```

FIG. 7, cont'd

```
4451  TCTTCTCCAA TGTCCAAAAG GCTAGGGGGT TGGAGGTGGG GACTCTGGAA
4501  AAGCAGCCCC CATTTCCTCG GGTACCAATA AATAAAACAT GCAGGCTG
```

FIG. 8

Amino sequence of a long form of an ADAMTS-13

```
  1  MHQRHPRARC  PPLCVAGILA  CGFLLGCWGP  SHFQQSCLQA  LEPQAVSSYL
 51  SPGAPLKGRP  PSPGFQRQRQ  RQRRAAGGIL  HLELLVAVGP  DVFQAHQEDT
101  ERYVLTNLNI  GAELLRDPSL  GAQFRVHLVK  MVILTEPEGA  PNITANLTSS
151  LLSVCGWSQT  INPEDDTDPG  HADLVLYITR  FDLELPDGNR  QVRGVTQLGG
201  ACSPTWSCLI  TEDTGFDLGV  TIAHEIGHSF  GLEHDGAPGS  GCGPSGHVMA
251  SDGAAPRAGL  AWSPCSRRQL  LSLLSAGRAR  CVWDPPRPQP  GSAGHPPDAQ
301  PGLYYSANEQ  CRVAFGPKAV  ACTFAREHLD  MCQALSCHTD  PLDQSSCSRL
351  LVPLLDGTEC  GVEKWCSKGR  CRSLVELTPI  AAVHGRWSSW  GPRSPCSRSC
401  GGGVVTRRRQ  CNNPRPAFGG  RACVGADLQA  EMCNTQACEK  TQLEFMSQQC
451  ARTDGQPLRS  SPGGASFYHW  GAAVPHSQGD  ALCRHMCRAI  GESFIMKRGD
501  SFLDGTRCMP  SGPREDGTLS  LCVSGSCRTF  GCDGRMDSQQ  VWDRCQVCGG
551  DNSTCSPRKG  SFTAGRAREY  VTFLTVTPNL  TSVYIANHRP  LFTHLAVRIG
601  GRYVVAGKMS  ISPNTTYPSL  LEDGRVEYRV  ALTEDRLPRL  EEIRIWGPLQ
651  EDADIQLFVC  RFTGGMARSM  ATSPAQTSPS  PTSSLSHGRP  GCGPLCVGPA
701  RAALGKLQLP  GPGQEGVGGD  CPVPREPAAT  SVARGLRART  LPSLLGGGRL
751  RPMQRLLWGW  PAGAASALRG  GPGQPPEDIA  PSPVQSRGPA  ASCGAGNLQP
801  PALPCQVGGV  RAQLMHISWW  SRPGLGERDL  CARGRWPGGS  SD.
```

FIG. 9

CUB domain of ADAMTS13

A. Amino acid sequence

```
1192                                              CGRQHLEPT
1201  GTIDMRGPGQ ADCAVAIGRP LGEVVTLRVL ESSLNCSAGD MLLLWGRLTW
1251  RKMCRKLLDM TFSSKTNTLV VRQRCGRPGG GVLLRYGSQ              1286
```

B. Nucleotide sequence

```
35574              GGCTCCC CAGCCTCGGC GGCTCCTGCC
3601   CGGGCCCCAG GAAAACTCAG TGCAGTCCAG TGCCTGTGGC AGGCAGCACC
3651   TTGAGCCAAC AGGAACCATT GACATGCGAG GCCCAGGGCA GGCAGACTGT
3701   GCAGTGGCCA TTGGGCGGCC CCTCGGGGAG GTGGTGACCC TCCGCGTCCT
3751   TGAGAGTTCT CTCAACTGCA GTGCGGGGGA CATGTTGCTG CTTTGGGGCC
3801   GGCTCACCTG GAGGAAGATG TGCAGGAAGC TGTTGGACAT GACTTTCAGC
3851   TCCAAGAC                                                 3558
```

FIG. 10

An ADAMTS13 gene sequence, with exons and introns

```
   1   GTTTTTCTTC CGAGTGAGCG TCTTGACAGG ACCCGGCTTA GCCACGGGGC
  51   TGCTCGGGGC GCGCTTGGAG GCGGGGACCT TCGCCTTCCC CATCCTGCTG
 101   CCGTCCAGCG CCTGGGCCGG CGGCCACCCG AGACCCCGGC CTCCCCGGGC
 151   CCGGCGCCCT GGCAGCACAA GCGCCTGCCC AGGCCAGGCC GAAACACACC
 201   CACCGCAGGG ACCCCGTCCA GGAAAAGACT CCGGAAGAGA CCCCGCACGC
 251   GTTGCGCATA CCTCAGCACG CACGCTCCAG TCCCCGGAAG CGCTCGTCTC
 301   TCCACAACCG GCTGGAAACC GGATCCCTGC CTCTGGTTCC GCGCAGCCTG
 351   GGCGGTTCAC CCGCACGGGA CTTGGGCCGC CGCCTTAGCC AGCGGCATCC
 401   GGGGTCATCG ACCTCGAGTT TGACTGGGGC AAGCCGAGGA CCTCCCCAAG
 451   ATCCGGGATG GGGATGAGAG ATGCGAACGC CGGAAGGGAA CTGGGGGGCC
 501   GCTGTGTGTG TAGCACCCGG TAGGGCAGCT GAGCTGGGGG CACTGGGCGG
 551   TGGGGCTAGT GAGAGCCGGG CTAGGTCGCT CGCCTGCGTC CTGGACTCTC
 601   GAGCCTTTCC CGCCTTGGGC TGCTCCTTGC TCAGCCTCAC AGCGGCTCAT
 651   CTTCCACGTA CAGTGGGGAA ACTGAGGCCC AGGCACCGGG AGGAGTTCCT
 701   GCCAGTTCAC TCTGTAGCAG GACGAGCCGC AGACAAGAAC CCCTCAGACA
 751   CCGAATTGTA GAAGGAAAGG GCTTTATTTA GTGGGGAGCA TCGGCAGACT
 801   CACGTCTCCA AAAACCGAGC TCTCTGAGTG AGCAATTCCT GTCCCTTTTA
 851   AGCGCTTACA ACCCTAAGGG GGTCTGTGTG AGAGGGTCGT GATCGATTGA
 901   GCAAGCAGGG GGTACGTGAC TGGGGGCTGC ATGCACCGGT AATCAGAACG
 951   CAACAGAACA GGACAGGGAT TTTCACAATG CTTTTCCATA CAATGTCTGA
1001   AATCTATAGA TAACATAACC GGTTAGGTCA AGGATTGATC TTTAACCAGG
1051   CCCAGGGCGC GGCGCCGGGC TGTCTGCCTG TGGATTTTAT TTCTGCCTTT
1101   TAGTTTTTAC TTCTTTATTT GGAAGCAGAA ATTGGGCATA AGACAATATG
1151   AGGGGTGGTC TCCTCCCTTA CTTCTGCCTC CTGGGTTCAA GCGATTCTCC
1201   TGCCTCAGCC TCCTGAGTAG CTGGGATTAT AGGTGCACGC CACCACTCTC
1251   TGCCAATTTT TGTATTTTTA GTAGACCTGG GGTTTCGCCA CGTTGGCCAG
1301   GCTGTCTTGA ACTCCTGACC TCCAGTGATC CATCCGCCTC GGCCTCCCAA
1351   AGCGCTGGGA TTACAGGTGT GAGCCACCGT GCCCGGCCGG GAGTGGGTAG
1401   ATTTGATGTG CGTGTGTAAC AGGCAGAGGT TGATGGAGTA ACAGGGAAGT
```

FIG. 10, cont'd

```
1451  GAGGCTCCTA GGATTTTGGT CTGAGCAATT GGGTGTGGCC ATTTATCATC
1501  TCAATAAATG TCTGCGGGGA GCAGGGTGAA GTATGGGGGT GGAGCCATGA
1551  GCTCCTTTTC ACACTTGCTG AGTTTGAATG GGCCGTCAGT CACCAAGGAG
1601  AGACGTCTAA TCAGCAGCAG GATATAAGAT TCCTAAGCTT AGGGAAGGGT
1651  CAGTGCTGGA GATGTAATTT GGAAATCGTC AGCACATAAT TAGTGTTGAA
1701  ACATGAACCT GGGTTAGTTC ATCCAAAGAG AGAGTACCAA TATAGGGAGT
1751  GAAGGGTTAA GACCAGATAG CAGGTGCTGG GGGCTCTCCA GGGGCGAAGC
1801  AGCAGAGGAG GCTGAGGGGG AGCAGTCAGT GCAGTGGGAG GAGAAGCGGA
1851  TGTGAGTGGC ATCAGAGAAT CCAGGGGGAG AATAAACCAC ATCAGATGCT
1901  GCTGAGAGGC TGAGAAGGAC GAGGACAGAG AGATGGGAAC CAGATATGGC
1951  ACTGAGATTG TCAGCAAGTC CACCGAAAAG GGTTTTCTTT TTTTTTGTTT
2001  GTTTTGAGAC GGAGTCTTGC TCTGCTGCCC AGGCTGGAGT GCAGTGGCGT
2051  GATATCGGCT CACCACAATC TCCACCTCCC GGGTTCAAGC GATTCTCCTG
2101  CCTCAGCCTC CTGGGTAGCT GGAACTACAG GTGCACGCCA CCATGCCCAG
2151  CTAATTTTTT TTTTTTTTTT GAGACGAAGT TATGCTCTTG TCGCCCAAGC
2201  TGGAGTGCAA TGGCGCAATC TCGGCTCACC GCAACCTCCA CCTCCCGGGT
2251  TCAAGTGATT CTTCTGCCTC AGCCTCCCGA GTAGCTGGGA TTACAGGCAT
2301  GTGCCACCAC GCCCGGCTAA TTTTGTACTT TTAGTAGAGA TGGGGTTTCT
2351  CCATGTTGGC CAGGCTGGTA TGGATCTCCA GACATCAGGT GATCCTCTCG
2401  CCTCAGCCTC CCAAAGTGTT GGGATTACAG GCGTGAGCCA CCGCACCTAG
2451  CCTAATTTTT GTATTTTTGA AAAGAGACGG GGTTTCACTA TGCTGGCCAG
2501  GCTGATCTCG AACTCCTGAC CTCATGATCC GCGTGCCTCG TGATCCACCT
2551  GCCTCGGCCT CCCAAAGTGC TGGGATTAAA GGCGTGAGCC ACCACACCTG
2601  GCCCAGGTTT TCTTTTTAAA AAAGGAAAAA AACTTTGTTC CAGCAGTTTG
2651  TAAACCAGGG CAATGCAGCC TTCTGTACAA AGGTGCATTC CAGGGAACAA
2701  AGAGAACAAA GAAAGAGGTC GTCTTTTGTA GAGAACTTCC TGCCCAGGTT
2751  CCCACTTTGG TCCACTTATG CAAATGAGGA AGGCACACTT GCTTAGTTCT
2801  GATTGGTTAA TACTTGCTGA GTTCAGATTG GTCGATGCAG GTCACAGTCG
2851  ATGGGTTGAT TCTGGCGGCA TAAACAGGAA CAGATAGCTG TGAAACCATC
2901  CCAGAGTTAA GTGAGAGTGG GGCTTTCCA GGAACGCAGA ATGTGTGTGT
```

FIG. 10, cont'd

```
2951  GACCCTAGTC AGCAAATGGC TGCTAGGTCC TACTTTGAAT TTAGGCCCAG
3001  TTAGTAACTT GGGATCCATC AAGAAGGATT GGCTCTTTCA GGGTTCACAA
3051  AGTTATTGGT GACCTTTTAA AGATCAATTT CAATGGTATG TGGGAATTGA
3101  AGGCAAGGAA GTGGAGATAG CCACTGAAAA TAATGTTTCT AAGTTCTTAA
3151  AGACAGCCAG AAACAGGGCT ATGGCAGGAG ACAGTGTGG GTCAAGGGAA
3201  GGTTGTTGAT TGTAATCAAG AGACACCAGA GTGTCTGGGC TTGGTGGCTC
3251  ATGCCTGTGA TCCCAGCACT TTGGGAGGCC GAGGCAGTCA GCTCACCTGA
3301  GGTCAGGAGT TTGAGACCAG CTTGGCCAAC ATGGCGAAAC CCCACCTCTA
3351  CTAAAAATAC AAAAACTAGC CAGGCGTGAT GGCGGGTGCC TGTAATCCCA
3401  GCCACAAGGG AGGCTGAGGC AGGAGAATCA CTTGAACCTG GGTGGCGGAG
3451  GTTGCAGTGA GCCGAGATCG TGCCACTGCA CTCCAGCCTG GGTGACACAG
3501  CAAGACTCTG TCTCAAAAAA CAAACAAAAA CCAAAAGAG ACAGGAGAGT
3551  CATTCATGCT GATGGAGTGA GCCAGGTACC AGGATCTCGA TATCTAAGCA
3601  TGCCCCCTTC TCCAACAGCC TCCTTACCTT CCTGCATGAA AGCACACCCT
3651  TCCCTCCAGT CCCCCATTCC TTTATTCTGC TGTATTTTTC TCCATAACAC
3701  TTACCACCTT TGAACATACT ACATATACAA CATGTGTCTG TCTAGCAACT
3751  TTGCTGTCTG GCTCTCTTCC CTAGAATTTA AGCTGTGAGA GGCCGAGGCT
3801  GCTGTCTGCC TGGCTTGGGG CTGCTTTCCT GGTGTCTAGC ACAGAGCCTG
3851  GCCTGTTTCA GGGGCTCAGT GAAACATTTG TTGGCTGAAG GAATGAATGA
3901  ATGGCTCTAG CAGAGGGGCA GAAACTAACG ATGCAGGAGG AGAGAGCTGG
3951  GAAGGGATCC AGAGCCAGGG CCTGGCAGGA AGTGTAGGTG TGTCCTCCCT
4001  GATCGCAGAG GAGGAGAGAG GCTGCACTTT GAGGGGTGGA AAGACAAGGT
4051  GAATCCCCCT GCTGGTCATC AGCTTGTGCG GCTCTGTGGG TGTAAAAGAG
4101  TGGTTTGGAG CATGTGAAGT GAGTCTTCCA GGAGATGAAG GGGATTGCCA
4151  GGCCGTTTGT GATGATGCTG AGATCTGGTG CCGTGCAGCC TGCTTCTGCG
4201  ACTCTCCTCA TCAGGCGCAG GCACAGAGTA GGTGGAGAGT TGAGCCAGAA
4251  CCACGATGTC TTTGGCACAG CCTCTCATCT GTCAGATGGG AGCGGGGACC
4301  CCGGAGAGGG AGTCAGCCGA GGTCCTGGCA TTCCTTGTGA ACCCCCGTCT
4351  GTGGGTTTCT GGTCCAGTGT CCCTTCTCCA GATTAGATGG CTTAGGCCTC
4401  CTCTAAGGGG GTGGGCGTGC ACATCCGGAG AGCTGTCTGG TGTGCAGGAC
```

FIG. 10, cont'd

```
4451    TGGGCTGCAG GTTACCCTGA ACTGCAACCA TCTTAGAGCA AGGCCCAGCT
4501    TGCAGCAGGA GGAGCTGCAG GCCGCCCACC CTAGCCACGG CCCCTGCCCT
4551    GGCAGGAAGC TTCCAAGAGT AAACACTGCC TAATCGTCCC GCCCAGTAGT
4601    GAGCAGGCCT GTCCCATTCC ATACTGACCA GATTCCCAGT CACCAAGGCC
4651    CCCTCTCACT CCGCTCCACT CCTCGGGCTG GCTCTCCTGA GGATGCACCA
4701    GCGTCACCCC CGGGCAAGAT GCCCTCCCCT CTGTGTGGCC GGAATCCTTG
4751    CCTGTGGCTT TCTCCTGGGC TGCTGGGGAC CCTCCCATTT CCAGCAGGTG
4801    GGCTCATTTG CAGGAGCGGG GGTATTCTGG GAGCCTCTGG GTGGGGTATT
4851    CTGAGCTACC TGGGGCGAGG GGAGTGCCAA ATAGCTGACT ACATCAGCTT
4901    TGGGGTTTGC GCTGGGCAGG GGAGTCTGTA CTTGGGGCTT TGGGGGATGA
4951    AGTGTGCTCA CTGAAGAGGG AGTTGGTGTC TCAGTACGAC CTGCTCATTC
5001    GGTGAAGCTG AACAGACAGA TACTAGTTTG TCCCAAACTG TGTAGGTTGC
5051    TCTTCTCTGC CTCTCCCTTC CTCTCCCTGT CTCTGATTTC CCCCTCTCCT
5101    TCTTGGTTGG CCTCACCCAC CTCCTGCCTC CTGTCTCCCT CTTCATCCAT
5151    CTCTTTTTGT TCTTTTTTCT TTCTCTCTCT CTCTTTTTTT TTTTTTTTTT
5201    TTTTTTAAGA CATGGGGTCT TGTTATGTTG CCCCAGCTGG TCTCAAACTC
5251    CTGGACTCAA GTGATCCTCC CACCTCGGTC TCCCCAAGTG TTAGGATTAC
5301    AGGCCAGAGC CACTATGCCC GGCCCCATCC ATCTCTTTTT GTCTTGCAGA
5351    GTTGTCTTCA GGCTTTGGAG CCACAGGCCG TGTCTTCTTA CTTGAGCCCT
5401    GGTGCTCCCT TAAAAGGTAC TTGTCCTGGT GTCTTCTCTC CGGGGGGAG
5451    TTTCTCAGGA CTTTCAAGGG GTATCTCACC ACTGAGTCAG TGGTCTGGGA
5501    TTTTTGGTGG ATCTGGAAGG AGAAGGTCAG AGAAGCTGCT GTCAACCCTG
5551    TTAATTAACT CTGTTACTTC CTGCCAAGTT GATATAAGCT GGTCTGGGTG
5601    TTCCAGCCAG GCCAGGGTTC TCACCCTAGC TTCTGTTAAA TATCACAAGG
5651    GAACGGTCAC CGATTGGCTG GCCCCTCCTG CCCCATGGCC TCTGCTGAGC
5701    TGGCTGATTT TCAGGAGCTC TTGTGGTTTC TGACCGTGGA TGTAAATATT
5751    TATTCCTTCT GTGGGAAACA AGATAGGTAC TGGCTCAGGC TACCTCCTAA
5801    GGCCATGGAT TTCCTTATGA TAAAGGCCTG TCCCCATTGC CCACAGGCCC
5851    ATGTCTGTGA CCTTCTCCGG TGCGAGCCCC CTTCCCAGTA GGGCCATTGG
5901    CAACTTGACT AATGGCTGAT GGGGGCCAGA GGCAGGTGGG CTAGTGGTCA
```

FIG. 10, cont'd

```
5951    GGGGCAACAG GAGGGCAAGG CCCACTTTGT GACCTGGTTC TTTGTGGTCT
6001    AGGCCAGAGG CACACTGACC AGTGCCTGGG GCCACGCTGG GGGCTGGATG
6051    CAGCCGACGC TGTCTGGGTA TCCCATAGCC TGGGTCCTTC CAGCGCTGCC
6101    GCTCCTGAAA GGCTGGGAGA TCATTGCCCA GGGTCCCTGA CCCTCTAAGG
6151    GCTCCCTTGG GAGAGGACAG TGAGGGCTGG CCTGGGCCCC TGCTTCCCAA
6201    GAGACCACTG GCTCCACTC GTGTTCAGTT TCCTGTCGGG GTCCATGATG
6251    TTACTTGTGA AACACCTGTG CCCAGAGCAG GGTCCAGGAG GCAGGGCAGG
6301    GGCTTTCCCC TTTGGGCAGA GCCACCAGGG CAGTGGGAAT CTTGTCTTGA
6351    TGGGGTGACC CAAAGCACAC AATAGCCCAA CAGCTCCTCC TGGGCCCTGC
6401    CCTTTGCGTG CCTAGTCACT AATGGGGTCT GGCTCTTGGG GTGGGGGTGA
6451    CACGCAATGT CTTGACTTCG GAAGGCCATC CTTCCAAGAC CTGCCAGCCC
6501    CTTTCCTGTT AGCTTTCCAC TGCTTGCTCT CTAGAACCAT CGCCCTCTGC
6551    TCTCCCTCTC CCCCTCCAGG CCGCCCTCCT TCCCCTGGCT TCCAGAGGCA
6601    GAGGCAGAGG CAGAGGCGGG CTGCAGGCGG CATCCTACAC CTGGAGCTGC
6651    TGGTGGCCGT GGGCCCCGAT GTCTTCCAGG CTCACCAGGA GGACACAGAG
6701    CGCTATGTGC TCACCAACCT CAACATCGTG AGTGCCCCAC GCTGGACTGT
6751    GCAGGTCCCC ACGGCCAGGG CTGGTGACCA ATGTCTGTGG GCTGGTGTAT
6801    CTGGTAGTCT GAATACAGTG GGTTAAACTC AGGTAGAATG GCTCGGGGTT
6851    CTTCCTCTTC TCCCTCCCTC CCCTGGGTGG AGGTGGGTGA GGTCCCACAC
6901    CCTCTCTAGG CTCCATGGCA CATGCACACC CTGCAGCCTC TCACTACTCA
6951    AGTCCCTTCA CCTGGGGCCA CCCTCAAGCC TGGCCTCTTC CCCAGTATCC
7001    ATTTGACCCC CACAAAGCTC AGCTAAAGCA ACCCTGGCAA ATGGGATACG
7051    GGCTGCTCAC ACTGCCCTCT GCACCCCGAC CCTGCCCTCT CTCCATTCTC
7101    TTGTCCCCCG CTCAGAGTGG CGAGGACAGG TCACCCGTCT GAAGTCTAAA
7151    CAGAGACTGC TGGCAAAGGA GATGCCCACC TTCATTTCTT GCTAGCACCT
7201    GAATCCCTGC AGCCCCCTT CACTTGAAAG CTGGGGAAGG GCGGGCAGGG
7251    AAGCACTCCC CCACTAGCCG CCGTCTCAGA AAGACAAACA AGGCCAGGCG
7301    CGGTGGCTCA TGCCTATAAT CCCAGCACTT TGGGAGGCCA AGGCGGGTGG
7351    ATCACCCGAA GTCAGGAGTT CAAGACCAGC CTGGCCAACA TGGTGAAACC
7401    CCGTAGCTAC TAAAAATACA AAACTTAGCT GGGCATGGTG GCAGGCGCCT
```

FIG. 10, cont'd

```
7451  GTAATCTGAG AGGAGCCTGC GATCTGAGAG GAGCAGCGTT TGACCGGAAT
7501  ATCCGACTCG TGACCATCTG TGTGCTCTCA TCCCCTTGCT TTGGAGTTTG
7551  TTTTCCTTGC GTTAGTTGGC CTTCCTGAGC CATGAGCTGA GGAGCAACAG
7601  AGGCACGGCT GACTGTGCAG CACATTTTAG GAGCCCCCCG CCCCGCCCGG
7651  TTCCCACACA TGCTGGTGGA GTAGCCTCTC CAGCTCTTCA CACTCCGGGG
7701  GCCCCTGGGA GTCAGCAGCT GCCTGGGGCT GGCAATGCCC ACCCGACGGG
7751  TTACCTCTCT CATCTGCCCT TGCACAGGGG GCAGAACTGC TTCGGGACCC
7801  GTCCCTGGGG GCTCAGTTTC GGGTGCACCT GGTGAAGATG GTCATTCTGA
7851  CAGAGCCTGA GGTAGGCATG GAGCTGGAAC TCAGCACACC ATACAGAGCG
7901  GGAAGCCCAA GTCATCGCAT CTCCATCCTC TTTAACCTCT TGTCCCGGAT
7951  GCCCCAAGCA GCATGGATCA CAGAATGCAT TCAGCCAGAC AGACCAGCTG
8001  CCCTCCCAGC TCTACCCAGC ACTCAGCACA GGCTGCCTGA CTACTTCTCT
8051  GAGCCTCAGT TGTCTCATCC CTAACACGGG CTAGTCATAG GGTTGTTAGG
8101  AGGACTAACT GGGAAACAAA CCGACCGCAG TCAGCACCGT GCCTGGTTGG
8151  GGTGTCCTAA ATGCAGGCTT TGCTGTGGGT CCGCAGGGTG CCCCAAATAT
8201  CACAGCCAAC CTCACCTCGT CCCTGCTGAG CGTCTGTGGG TGGAGCCAGA
8251  CCATCAACCC TGAGGACGAC ACGGATCCTG GCCATGCTGA CCTGGTCCTC
8301  TATATCACTA GGTAGCCGAG CTTTCTGATG GGTGCTGGCC AGCCAGCCTG
8351  GGAAGGCTGC TCCCTCAGCC TCCTGCCCTC TGCAAAGGTG ACCCCAGGGC
8401  AGGCACGTGC CTTGGCACCA CCCAAGTGAC TGTTTTCTCT CACCGAGGTT
8451  TGACCTGGAG TTGCCTGATG GTAACCGGCA GGTGCGGGGC GTCACCCAGC
8501  TGGGCGGTGC CTGCTCCCCA ACCTGGAGCT GCCTCATTAC CGAGGACACT
8551  GGCTTCGACC TGGGAGTCAC CATTGCCCAT GAGATTGGGC ACAGGTATGT
8601  AGCCCCACCA GCTGTCCCCA GGATCTGGCA AGGAGCTGAC CTGGGTACCC
8651  AGGGTGGAGG TGGTCTTAGC AAGCAGTGGG TCCTTGTAGA GTTTCTCCAG
8701  AGGAGCCTGT ACCCCTCACC CCGACAGACT CAGGTGTGAG GACAGGGGAA
8751  CCTGATACTG TTTGATTAAA AGAACTTTTT TTCCAAAAGA CGAGCAAGAC
8801  ACCTTTAGCA GGTAGAAAAT AACTTCTGTA GAAAATTCAG GTAAAGAAAG
8851  AGCAGGCTGT AAAAATTATC TCAAATCCCA CCATTTAGAG ATAATGTCTC
8901  TTCACATTTT GTATTTAATT TCAGTCTTTT CTTTACATAC ACACACATAT
```

FIG. 10, cont'd

```
 8951   TTCTTATTTG CAAAATTGGG ATTTAGTTTG GATCCCTGAA AAAAAGGAAA
 9001   ATTGTGATTA TGCTGTGCAT TGCTTTGTTA CCTGCTATTT CTTTTTCTTT
 9051   TCTTTTCTTT TTTTTTTTTG AGATGAAGTT TCGCTCTTGT TGCCCAGGCT
 9101   GGAGGGCAAT GACGTGATCT CAGCTCATTG CAACCTCCAC CTCCTGGGTG
 9151   CAAGTGATTC TCCCACCTCA GCCTCCCAAG TAGCTGGGAT TACAGGCATG
 9201   TGCCACCACG CCCAGCTAAT TTTGTATTTT TAGTAGAGAC AGGGTTTCTC
 9251   CATGTTGGTC AGGCTGGTCT CGAACTCCCA ACCTCAGGTG ATCCACCTGC
 9301   CTCGGTCTCC CACAGTGCTG GGATTACAGG CGTGAGCCAC TGCATCCAGC
 9351   CTTTCTTTTT TCTTCCTAGG GTAAGTGCAG GATTTACCTG TTCTTTATGT
 9401   AATAATATAT CCCAAACATT ATCCCAGGTA TCTTAGAGGT GTGCACCGTA
 9451   ATTTATTTAA TCAGTCCCCT CTTCTTGGAT GTCTAGGTTG TCTGAACACG
 9501   TCTTCCTGTT GTGAATGTTA TGCATTCTTG TGGGCAAACC TTCACTCTTA
 9551   CCTATAACCA TTTACCTAGA GTGATGGGTT TCTTTTCATT TCTTTAGTTT
 9601   TTTAAGTATG AAAATAATAC CCAATTGTTG TAAAAATTCA AACAGTGCAG
 9651   AGATTTCTAA AGTAAAAAGT GAATTTCCAC ATTCCTTGCC CACCAACCCC
 9701   CACCCGACCC CTTTCAACCC CTCTGAGCCT GGGAGGGTTG AGGCAGGGTT
 9751   CCTGGGTGTG GGACAAGGCA GGGCTCCTTC TCCCTCAGAG GGAGCATAGT
 9801   TCCCTTCTGC TCCTGTGATG CAGAAGACGT GAGCCCCCAA ACTGGGGCTT
 9851   AGCCTGGGAG GGTTCTTGGC TTCACCGAGG AAAGAATTCA AGAGGGAGCA
 9901   GGTGGTGTTA GACAGCAACT TGATTGATG TGGCAGTGGG CAGAGTGTAC
 9951   AGCCCTGTGA CTGTATACAG CACAGCATAG CCCCTTTTGA AGCCAGGCTA
10001   CCCCATAGAC ACTGTGCCCA AAAGAGCAGC TCAAAGGCAG GGCTGCAGTC
10051   CTAGTTAATA CCCACTTCTA ATTATATGCA AATTAAGGGG CCAGATTATG
10101   CAGAAATTTC TAGAAAAAGG GCAGTAACTT CTAGGTTTTC GTCATGGAAA
10151   AGGGGCAGTA ACTTCTGGGT TTTGCCATGG CAATGGCAAA CTGGTATGGC
10201   ACACTGGTGG GCGTGTCTTA TGGAAAGGGG CTTCCCACCC CTCCCTGTTT
10251   TAGCTAGTCC TCTGGTCCAG TGTCCAAGCG GGGCCTCCAG AGTGGAGTCC
10301   ACCTCCTACC TCACCGGTGC CTGGCCTCTC CCACCCCATT AGGAGTCCTC
10351   CATCAGTTCC GCTTTGGGTA AAGCAAGCTC TGTTGTGACA GTTTGGAAAC
10401   GGTTCACCTT CCTGGCCTAG GAATGCAAAC AATGGCCAAG GGCAAGCACG
```

FIG. 10, cont'd

```
10451  TTTTAACTGA ACTTTAAAAT CGTGCTTTCC TCACAGTAGG TGAATTTCAC
10501  GCTCAACACA TCCATGTAAA CAGTCCCCAG AGCAGCCCTT CAAGGCCCCG
10551  GCCAGTCCCC ACCTCCCCAC AGACTCCTAA CACCATGATT TAATGTGGCT
10601  TGCACATTTT TAAAGGCTTT TGATATTTAT TAGCAAAAGA TGCGAGAGCC
10651  ACCCTGCTGG GCTAGCGCTC CCTTCTGGGG GAAACTGAGG CAGGGCGCAC
10701  GCGACCCTCT CCACTGCGCC CAGTTAGCAG ATGGCGGCGT CAGGGGTCGA
10751  CCCGGGTCGG AAAACTCGCT GGCGCTGCGG CACTAGGGCG CCGGGCCGCT
10801  GACTCGCCGA CCCCCGTCCC GCCCCCACCC CCGCCCCGC  CCCTGCCGGC
10851  CGCCTTAGCG CAACTCCCCG CCCCCCGACC AGCTTCGGCC TGGAGCACGA
10901  CGGCGCGCCC GGCAGCGGCT GCGGCCCCAG CGGACACGTG ATGGCTTCGG
10951  ACGGCGCCGC GCCCCGCGCC GGCCTCGCCT GGTCCCCCTG CAGCCGCCGG
11001  CAGCTGCTGA GCCTGCTCAG GTAGCGGCCG CCCCGTGGGA GGGGCGCGCG
11051  AGCCTCCAGC CAGCCCGCTG GGCCGCCAGC GCCACCTCTC TCTACGTCCG
11101  TCCCCACTCC GCATTCAGCC CTCCTTCCTG TCCCACCCCT CCGTCCAACC
11151  CACCCCTCCG TCCAACCCCG CGCCCACCGC TCCGTCCGTG GAGGGGCGGG
11201  CGCGCGAGCC TCCAGCCAGC CCGCTGGGCC GCCCGCGCCA CCCCTCCCTA
11251  CGTCCGTCCC CACCTCTCCC TACGTCCGTC CCCACTCCGC ATTCAGCCCT
11301  CCTTCCTGTC CTACCTCTCC ATCCTGACCC ACTCCTCCGT CCAACCCCGC
11351  GCCCACAGCT CCGTCCCATC CCGCTGCGCC CACTCCTGCG CCCACCCCTC
11401  CGTCCCAACC CCTGCACCCA CCCCCCCGTC CCACCCACCT GCCCCACCCC
11451  CTGCACCTCC CCCCGTGCTG TCCCACTCTG CGGCCACCCT TCTGTCCAAC
11501  CCCTGCGCCC ACCGCTCCGT TCCACCCCCT CCCTGCGCCC ACCCCTGCGT
11551  CCTCCCTCGC CCCCTTGCGC CCACACTTTC GTTCCAGCCA ATCTGGGCAC
11601  GCACCCCTCC GTCCATCCCC ATCCCGCCCC TTGACTCCAC ATACACTCCC
11651  TGGTTCTCTC CCACTTGCCT ACACCCACCC CTGCATCCTA CCCTCCTCCA
11701  TCCACCCCTC CATCTCAGCC CCCTGCACCC ACCCCGTTCC TGGGCCCACC
11751  CTGTTCCTGC ACCCACCCCC TCACTTCACC CCCTTACCCT TCGTCTGCCT
11801  CCACCCGCCC CTACCCCTCC GTCCACTCTC CACGCTCCAT CAGTCCCACA
11851  CCCCTATCTC CCCCACCCGC GTACATGTAT CCCTGCGTCC CCTTCCCGCC
11901  GACCGCACCG CTCCCGGGCC TAACCTGCAT CTGCTCCATC CCACTCAGAC
```

FIG. 10, cont'd

```
11951   CCGTCCCTCC GTCGCCGCTC CCTCTGCTGG CCACCCACCT CTGCGCCGGC
12001   AGGAGCCTTA GTCTTGGTCC CAGCCAAGAG CCGGCTCCTG GTGGGGGGCG
12051   CGGGCCGAGA ACTCCTGTTC CCACTCACAA AAGGCCACGC TTCCAAACGC
12101   TTCCATCCTC GTGCCCACTC CTCCGTCCCG CCTCCTCCCG GTGTACACCC
12151   CGGGACTGAG CCGGGCCTGA GCCGGGCCTT GTCGCAGCGC AGGACGGGCG
12201   CGCTGCGTGT GGGACCCGCC GCGGCCTCAA CCCGGGTCCG CGGGGCACCC
12251   GCCGGATGCG CAGCCTGGCC TCTACTACAG CGCCAACGAG CAGTGCCGCG
12301   TGGCCTTCGG CCCCAAGGCT GTCGCCTGCA CCTTCGCCAG GGAGCACCTG
12351   GTGAGTCTGC CGGCGGTGGC CTGGGATTGG CTGTGAGGTC CCTCCGCATC
12401   ACCCAGCTCA CGTCCCCCAA AACGTGCATG GTGAGAACCT GCTGGGTGCC
12451   GTGCTAGGCT GAGGTACTAA GCCAGGGCGG CTTAGTTTAA TGCTGTCTGT
12501   GCCCTCTAGA AATTATTTAA AATGTTGAA  CAAAAGCTCC AACATTTTG
12551   TTTGACTGGG CCCCACAAAT TATGTAGCTA GTCCTGGGAG GGCCCCTGTG
12601   CCCAAGGACT CCTGGCTGAG TGAGGACACC AATCTTAAAC AGTTACCAAG
12651   GACTTCCCCA TCTATTGTGG CTGGAGTCAG ACTGGAGGGC TTCCTGGAGG
12701   AAGTGGCCTC TAAACTGAAC CCACAGCAGA AGTGGGGCTG GTAGGGGGAG
12751   GGGAGATGAA GGAGAGCAGG CACCCCAAAA GACAGACTTC CTCGCAGGAT
12801   TGCATAGGAC ATTCATGGGC TCCAGGCACT TTTGCCTTGA TGGGCCCCTT
12851   CCTCCACAAA AAAATTGAGA ATTATGTTTT AATATTCTTA TACAATGTAT
12901   AAAGTTTTAT GTGTTACTAT AAATACAAGT CTTTTTTTTT CCTTTTTTTT
12951   TTTTTTTTTG AGACAGAGTC TCCCTCTCTG CTCACTGCAG GCTCCGCCTG
13001   CCAGATTCAC ACCATTCTCC TGCCTCAGCC TCCCGAGTAG CTGGGACTAC
13051   AGGCGCCCGC CACCACGCCT GGCTAATTTT TTGTATTTTT AGTAGAGACG
13101   GGGTTTCACT GTGTTAGCCA GGATGGTCTC GATCTCCTGA CCTCGTGATC
13151   CGCCCGCCCT GGCCTCACAA AGTGCTGGGA TTACAGGCAT GAGCCACAGC
13201   GCCCCGCCAA GTCTTTTTTT TTAAATTATT TTGAGACAGG GCCTCGTTCT
13251   GTTGCCCAGG GTGGAGTGCA GTAGCACAAT CATAGCTCAC TGTTGCCTCA
13301   ACTTCTTGGG CACAAACGAT CCTCCCACCT CGGCCTTGGA GTAGCTGGGA
13351   CTACAGGCAC ATGCCACAAT GCCCAGCTAA TTTTTAAATT TTTTGTAGAG
13401   ATGGGGTCTC CCTTTGTTAC CCAGGCTTGT CTAGGACTCC TGGCTTCAAG
```

FIG. 10, cont'd

```
13451   CCATCCTCCC ACCTCGGCGT CCCAAAGCAC TGGGATTACA GACATGAGCC
13501   ACCACCCACG CCTGATCAGC AAATCTATTA ATATTATATA TTACAACATT
13551   AATTTTGACC TGGAAGTTCA TTTTTTCATT TTTTTTTTTT TTTTGAGACA
13601   GAGTCTCACT CTGTCACCCA GGCTGGAGTG CAGTGGCACA GTCTTGGCTT
13651   ACTGCAACCT CCGCCTCCCA GGTTCAAGTG ATTCCCGGGC CTACGCCTCC
13701   CGAGTAGCTG GGACTACAGG CATGTGCCAC CATGCCCAGC TAAGTTTTGT
13751   ATTTTTTAGT AGAGACAGGG TTTCATCATG TTGGCCGGGC TGGTCTCGAA
13801   TTCTGACCTC AGGTGATCCG CCCGCCTTGG CCTCCCAAAG TGCTGGGATT
13851   ACAGGATAAG CCACCACACC CAGCCTAGTT CATTTTTTTC TTCTGATTTT
13901   ATTTTATTTA TTTATTTATT TTGAGACGGA GTCTCGCTCT GTCACCCAGG
13951   CTGGAATGCA GTGGCTCAAT CTTGGCTCAC TGCAAGCTCT GCCTTCAGGG
14001   TTCAAGCCAT TCTCCTGCAT CAGCCTCCCG AATAGCTGGG ACTACAGGTG
14051   CCTGCCACCA CACCCGGCTA ATTTTTTGTA TTTTTAGTAG AGATGGGGTT
14101   TCACTGTGTT AGCCAGGATG GTCTCGCTCT CCTGACCTCA TGATTTGCCC
14151   GCCTCGGCCT TCCAAATTGC TGGGATTACA GGCGTGAGCC ACAGTGCCCG
14201   GCCTTTTTCC TTCTGATTTT AAAAGAAATT AGGCCAGGTG TGGCTGCACG
14251   CCTGTAATCC CAGCACTTTG GGAAGCCAAG GCAGGCGGAT CACCTGAGGT
14301   CGGGAGTTTG AGACCAGCCT GACCAACATG GAGAAATGCC ATCTGTGCTA
14351   AAAATACAAA AAATTAGCCG GGCGTGGTGG CGCATGCCTG TAATCCCAGC
14401   TACTCGGAAG GCTGAGGTAG GAGAATTGCT TGAACCCAGG AGGCAGAGGT
14451   TGAGGTGAGC CAAGATCGCG CCATTGCCCT CCAGCCTGGG CAACAAGAGC
14501   GAAACTGTCT CAAAAAAAAA CAAGAAAGAA AAAGAAATTA AAACATTTGC
14551   CTCTTGAGCT TCAAGTCAGT GACAAGTTAA GAAGGAAAAA AAGAAAAAAG
14601   ACACAAAAAA CACATTTCCA TGGGCCCCCA AAAGTGTGAC AGGACCTGGT
14651   CATGGTCCCG GTTCCCCATC GATGGGTCAG TCATGCCTTG TCCTCTGAGG
14701   GCACCAGTGC CCACGGTGCA GAGTGTTGGC TGTGTCAGTG TGTCCTGCAG
14751   TCTGGGAGGG ACAGTTAAGG TTGGACACTG GCCTGGAAGG CCCTGGTGGC
14801   CCCTGAGCTC GCCACCCACC TGTCCACCCT CCTAGGATAT GTGCCAGGCC
14851   CTCTCCTGCC ACACAGACCC GCTGGACCAA AGCAGCTGCA GCCGCCTCCT
14901   CGTTCCTCTC CTGGATGGGA CAGAATGTGG CGTGGAGAAG GTCAGAGCCA
```

FIG. 10, cont'd

```
14951   AGAGTGAATG AGTGGGCTCC TGTGAGCACG TGCACGTGGG TGCCTCCAGC
15001   CAGGCCGCCC TATTCCTAGG TCAGGAGGCA GGACCAGTAT GGGGCAGAGA
15051   GTCTTGGAGT TGGCCTTGGG GACTGTCCTT TGGGTTGGTG GTCTGACCTC
15101   TTTCCTTTAG CATTTGCTCC CATGCAGAAT GGGAATGTGG GCTGCCTGTT
15151   GTATGGGGGG TGCCCATGGG TGTGGGGTTC CTTTGGGTGG GGTCCCTGTG
15201   TGAAGGTCCT TGTGGATATG GGGTGTCTCG GGGGGATCCC TGTGTAAGGG
15251   GTCCCTGTGA GTGTAGAGTC CCTGTGGGTG GGGTCCTTAT GTGTGTGTTG
15301   GAGGATCCCT GTGTGTTGAG GGGTCCCTGG GGGGTTCTGT GTGTATGTTG
15351   GGGGGTCTCT GGGTGTTGGA GGATCCCTGT GGGTCTGGGG GATCCATGTG
15401   GCTGGGGTAC CTGTGTGTTG GGGGGTCTCT GTGTGTGTTG GAGATCCCTG
15451   TGTGTTGGGG GATCCCTATG GGTGAGTTCC TTGTGTGTGT TTGGGGGTCG
15501   CTGTGGGTGG GGTCCCTGTG TGTGTTGGGG ATCCCTGAGG ATGTTGGGGG
15551   ACTCTCTGTG TGTGTTGGGA GTCCTGTGGT GGGGTCACTG TGGGATGGGA
15601   GATGAAGCCA TCCTTGCCTT GCAGTGGTGC TCCAAGGGTC GCTGCCGCTC
15651   CCTGGTGGAG CTGACCCCCA TAGCAGCAGT GCATGGGCGC TGGTCTAGCT
15701   GGGGTCCCCG AAGTCCTTGC TCCCGCTCCT GCGGAGGAGG TGTGGTCACC
15751   AGGAGGCGGC AGTGCAACAA CCCCAGGTAC CGCAGGGAGG GTGCTTTTCT
15801   GTCAGGGAGT GTGGCCATAC CATAGTCCCT AGTTGAAGGC AGTGGTCACC
15851   CTGCTGTCTC ACCCTCCTGT CTGCTGGGCA TTTTCAGACC TGCCTTTGGG
15901   GGGCGTGCAT GTGTTGGTGC TGACCTCCAG GCCGAGATGT GCAACACTCA
15951   GGTAGGCCTG CTTCCTGGGG TAGGAGGGGG CAGCTGGTGG CACCGGGCCC
16001   TGGGGAGCC  AAAGTGACCA TCTGTGGTTC ACACCAGGAC ACATTTGAGA
16051   AGGACATTGG GGCCAGGTGA GGTGGCTTAT GCCTGTAATC CCAGCACTTT
16101   GGGAGGCCAA GGCAGGTGGA TCACCTGAGG TCAGGGGTTC AAGACCAGCC
16151   TGGCCAACAT GGTGAAATCT CGTCTCTACA GAAAATACAA AAATTAGCCG
16201   GGCGTGGTGG TGGGCGCCTG TAGTCCCAGC TACTCGGGAA GCTGAGGCAG
16251   GAGAATCACT TGAACCCAGG AGGTAGAGCT TGCAGTGAGC CGAGATTGGG
16301   CCATTGCACT CCAGCCTGGG CGACAGAGTG AGACTCTGTC TCAAAAAAAA
16351   AATAAAAATT AAAAAAGAGA GAGAAGGACA TTGGGACCCC AGTTCATAAA
16401   CCAGGCCAGT CCTGCTGATG CCCACAGAGC CCCTGAAGCG TCCCGCCTCC
```

FIG. 10, cont'd

```
16451   CTCCCTGAGT GCCACTTTGC CCTCCAGAGC GCATCTCTGC AGGGAGAACC
16501   TCCCCACTAG GAATACAGTG YGCTGCTGCA TGCCTGCAAA GGAATTTTTT
16551   AAATATTATT TTTATTTTTT TAGACAGAGT CTCTCCCTGT CACCCAGACT
16601   GGAGTGCAGT GGTGCTATCT CAGCTCACTG CAACCTCTGC CTCCCAGGTT
16651   CAAGCGATTC TCCTGCCTCA GTCTCCTGAG TAGgCTGGGA CTACAGGTGC
16701   CCGCCACCAC GCCCGGCTAA TTTTTTGTAT TTTTAGTAGA GGAGGGGTTT
16751   gCACCGTGTT AGCCAGGATG GCCTTGATCT CCTGACCTCG TGATCCGCCT
16801   GCCTCGGCCT CCCAAAGTGC TGGGATTACA GGTGTCACTG CGCCTGGCCG
16851   AAGGAGTCTT TTATTTATAA ATTGAGGTGA CATTCATGTA GCATGAAATC
16901   AAGCATTTTA AAGTGGCAAC TCAGTGGCCT TTAGTACACT CACAAGGTTG
16951   GGCAAGTACT GCCTCTGTCT AGTTTCAGAA CGTTTCCAGT ACTCTGGAGT
17001   ACTCTGGAGT GAACCCCATA TGGTAGGCTG TCACTCCCCA TTTCTCCTCC
17051   GCCACTCAGC GGCCATTGGT TTCCCTTCTG TCTCTGTGGA TTGACCTGTT
17101   CTAGACATGC CACGTACCTG AGGCCAGACA ACAGGTGTGC TTCCTGCCTG
17151   CCTTCCTCCC CCAGCGGCAC GTCCCCAAGG CTCACCTGTG TTGTAGCCTG
17201   TGTCAGCGCC TCATTCCTCT TTCTGGCTGA ATCATATTCC ACTGCAGGGA
17251   TAGACCACAT TTTCATCCAG TCGTCTGCTG ATGGACATCT GAGGTGTTTT
17301   CACCTTTTGG CTCCTGTGAA CAGAGCCGCT GCCAATGTGC TTGTACATGT
17351   TTGAATCCCT GTTTTCAATT CTTTTGGCAG TATGCTGAAG AGCGGAGTTA
17401   CTGGATCGTA TGGGAATTGT ATGTTTGACT TTTTTTTTTC TTTTTTTTTT
17451   TTTTGAGACA GAGTCTTGCT CTGTCGCCAG GCTGGAGTGC AGTGGTGCAA
17501   TCTCAGCTCC CTGCAACCTT CGCCTCCTGG GTTCAAGCGA TTCCCCTGCC
17551   TCACCTTCCG GAGTAGCTGG GATTACAGGC ACGCGCCACC ATGCCTGGCT
17601   AATTTTTTGT ATTTTTAGTA GAGATGGAGT TTCCACCACG TCAGCCAGGA
17651   TGGTCTGGAT CTCCTGACCT CAGGTGATCT GCCCGCCTTG GCCTCCCAAA
17701   CTGTTGGGAT TACAGGCATG AGCCACCGCT CCCGGCCTAT GTTTGACTTT
17751   TTTTTTTCT TATTTTTTC TTTCTTTCTT TATTTTTTTT TTTTTAGAGA
17801   TGGAGTCTCG CTCTGTCGCC CAAGCTGGAG TGCGGTGGCG CGATCTCGGC
17851   TCACTCTAAG CTCCGCCTCC CAGGTTCACC CCATTCTCCT GCCTCAGCTT
17901   CCCGAATAGC TGGGACTACA GACGCCCGCC ACCACGCCCG GCTAATTTTT
```

FIG. 10, cont'd

```
17951   TTTTGTATTT TTAGTAGAGG CGGGGTTTCA CCATGTTAGC CGGGATGGTC
18001   TTGATCTCCT GACCTCGTGA TCTGCCTGCC TCGGCCTCCC AAAGGGCTGA
18051   GATCACAGGC GTGAGCCACC GCGCCCAGCA TGTTTGGCTT TTAAAGAAAC
18101   TGCCAAACCG TTTTCCACAG TGCCTGAACT GTTTCACATT CCCACCAGCA
18151   TTGCGCCAGG GTTCCAGTTT CCCCACATCC GCTGCAGCAC TTGCTGTTTT
18201   CTGTTGTTGT TTTTCTTTT CTCTTCTTTT TTTTTTTTT TTTTTTAATA
18251   GAGATGGGGT TTTGTCATGT TGGCCAGGCT GGTCTTGAAC TCCGACCCCA
18301   GGTGATCCGC CCACCTTAGC CTCCCAAAGT GCTGGGATTA CACGYGTGAG
18351   CCATGGCGCC CGGCCTGTTT TCTGTTTTTT GATTTTGGCC ATCTCGGTGG
18401   TATGAAATGG TAGAAAGATT CTTTTTACAT TGAGTTAAAT TCTATCTCCT
18451   GCTTCGATGG CCCTGGGTGT GGGTTTGTCC CTGGCTGTAT TACAGTTCTG
18501   CATGTGGTGA GACCCTCCCT TTCCTCCTTC TCCAAATGGA CCACCAAGAC
18551   CTCCCCAGAC CGTGAGGGGA GGGTCTTTGG CTGGAGCACA GGGTGGTGGG
18601   ATTTCGTGGA GGCAGTGTGG TCAGTGTGGC TGTCCAGGGA GTCAACTCCG
18651   GTTATCTTCT GTCAGCCCAT AAAAGTCCAA GACGCCTGCC TGAGTGCAGA
18701   GGCTTCGGTG GTGAGGTCTT TGCTCCATGC TTTGGTTACC TGCCTCTAGG
18751   TGCACTACCT AAAGAATACA CATCCCCGTC CTGTTTTAT TGAGTTCAGG
18801   CCTTGGAAGC AGAGGCTCTG AGCGTAATGC TCTTTCCTGG CTTTCTTCTT
18851   CGTTGCTGCC CTGTGTTCTT TACGGATTCC CCGGGGTTTT CCCATCAATA
18901   GAGAGAGGCA GGCACTTTTG TCACCCCAGT TTACAGAGCA GGGAACCGAG
18951   GCACGGCCTG GAGCTGAGGC CACACCCACA TCTTGATCCT GTACTGTAGG
19001   GTGCCATGTA GTCTCCCAGT GACAACACCC GCCCCCGCC CCACCGCCAT
19051   CCCCCTCCTC TGCCTCCTCC TGGCCAGGCC TGCGAGAAGA CCCAGCTGGA
19101   GTTCATGTCG CAACAGTGCG CCAGGACCGA CGGCCAGCCG CTGCGCTCCT
19151   CCCCTGGCGG CGCCTCCTTC TACCACTGGG GTGCTGCTGT ACCACACAGC
19201   CAAGGTGGGG CCTGCGGAGT GTGGGGTTGG GGGAGGAGCC AGCCCTGGAG
19251   ACCCTCGGAC AGGGCAGAGT CATAGGGGGG TTGGCCTACT ATCCCTCCAG
19301   CACTGGGCAA AGTGGTTCAG GCTCTGGCAT CCCACAGACC ATGGATGACA
19351   TAGTGGCCAG GCCTCGCTGG TAGATCAGGC ACTGACATCC CATCTCTGAG
19401   TCTCAATTTC CCATCTGTGA AATGGAGATA ATAGCAGTAG GTCCCTCCCT
```

FIG. 10, cont'd

```
19451  GGGCGCTACA AGGATTCAGG GAGATAATCG GAAAATGCCA AGTGTGTTCC
19501  TTGGTTCATG ATACTTTTTT TGTGAGACAG AGTCTTGCTC TGTCGCCCAG
19551  GCTGGAGTGC AGGGGCGTAA TCTCAGCTYA CTGTAACCTC CGCCTCTGGG
19601  ATTCAAGGGA TTCTTGCCCC TCAGCCTCTC GAATAGCTGG GACTACAGGC
19651  TTGCACTACC ATGCCGGCTA ATTTTTTTGT ATTTTTAGTA GAGATGGGGT
19701  TTCGCCATGT TGGCTAGGCT GGTTTCAAAC TCCTGACGTC AGGTGATCCG
19751  CCTGCCTCGG CTTCCCAAAG TTCTGGGATT ACAGGCATGA ACCATTGCGC
19801  CCAGCCTTGG TTCCTAATTC AATACCATTA ATTATTAGAT TAGATTAGGA
19851  TCGTGATTAG GATTATTGCC TTAGGAGGTG GGATGTGGGG AAGATAGAAA
19901  CCCTTGCCCC AGATGCAAAG GATGAAGCTG GTGGGGGCT GGGGGACTTG
19951  CCCCTCCTGC TCGGTTCAGG ACACCCTTTT TCACTCTGCC CTCCCAGGGG
20001  ATGCTCTGTG CAGACACATG TGCCGGGCCA TTGGCGAGAG CTTCATCATG
20051  AAGCGTGGAG ACAGCTTCCT CGATGGGACC CGGTGTATGC CAAGTGGCCC
20101  CCGGGAGGAC GGGACCCTGA GCCTGTGTGT GTCGGGCAGC TGCAGGGTAG
20151  GCGTGTGTGG ACATTGGCGA TGGCCCTGGG GCCTACCTGT CCTATCGGAA
20201  GGCTCCTGGG GGCAGGTTGG TGGGTGCTGG CCCTGATGGA GCTGCAGTGC
20251  CCTCTGCAGG GGAGTGGTGC TGGGGAAAAG GATCTGGACT TGGAGTCAGC
20301  CTGGGTTAAG GGCTGCAGTG TGACCTTGGG CAAGTCACTG AGCCCTCTAA
20351  GCTTGCTTCC TGTGTAGATG GTGGGGTGCT ATAGAAGTGT TGCTGGTTTT
20401  GTGGATCCCA GAATCTCAGA GCTGGCAGGG CTGCAGAGTC ATTGAGGCCA
20451  GCACCCTCCA GTGACACGGG CCCTCTGTCC TTCCCTTTGC ATAGACATTT
20501  GGCTGTGATG GTAGGATGGA CTCCCAGCAG GTATGGGACA GGTGCCAGGT
20551  GTGTGGTGGG GACAACAGCA CGTGCAGCCC ACGGAAGGGC TCTTTCACAG
20601  CTGGCAGAGC GAGAGGTAGG CGGCCTCCCT CGGGGCAGAG GCTGGGCTTC
20651  CCCCAGCCTC CAAGATGGCC ACAGCCCAGA GCGTTGGTGC AGGGGCTGCT
20701  CAGGTCACAG GGCCTGCACA CTCACTCAGC CCTGGATGCC TCCTGTGGTG
20751  TCAGCGTCTC CCTCTTCCAC TTCGCCACCC TTCTGTGGCA GGCTCAGGTT
20801  TTGGCCTTGA TGCTGCTGGG ACTGTGGTGC CTCAGTAATG GTCACTCACT
20851  GTAGCCGTGC TGCAAAAAAA ACACAGACAT TGGCCGGGCG CTGTGCTCAC
20901  GCCTGTACTC CCRGCACTTT GGGAGGCTGA GGCGGGTGGA TCACCTGTAG
```

FIG. 10, cont'd

```
20951  TCGGGAGATC ACCTACAGCC TGGCCAGTAT GGTGAAACCC CATCTCTACT
21001  AAAAATACAA AAATTAGCTG GGCATGATGG CGGGCGCCTG TAGTCCTAGC
21051  TACTCAGGAG GCTGAGGCAG GAGAATTGCT TGAACCCAGG AGGCAGAGGT
21101  TGCAGTGAGC CGAGATCCCT CTGCACTCCA GCCCGGGCAA CAGAGTGAGA
21151  CACTGTCTCA AAAAAAAAA AAAAAAAGT ATGGACGTTG TGCATTCTGT
21201  GGCAGCTACC CTCTTCTCTC CTGCTCAAGA AATCCCACTG AGAGGGACAC
21251  AAGTGAATGA GAGGGATGGT AGTTACATTT GGAAAATCTT TGACTTTGGT
21301  GTATATATGA GGTCAAAAAC CATTTGCAAA TGCCAGTGCT TCTATGGAGA
21351  GCAGAGACTT SAGCCCTGCC TCCCTCTGGC TTGCCCCACT GTGCTGGAGA
21401  ACCTTGGACC CGGTCCCTTC TCCCAGCCAG GGCAGAGCCT TGGCAGGTGG
21451  TCCTCCAGCC TGCTTTTAAT TGCCCCCATG ACAGGGACT CACTGCTGCT
21501  GGAGCCAGCC CCATGGCATT GTTCAATTTT TCCCGACCAG CTAAGATCAG
21551  CTCCCTTTGT CTGTGGTGTG GTGGCTGTGA GGTCCACGCA TCTCTCCTTC
21601  TTTTCTTCTT TCTAGAATAT GTCACATTTC TGACAGTTAC CCCCAACCTG
21651  ACCAGTGTCT ACATTGCCAA CCACAGGCCT CTCTTCACAC ACTTGGGTGA
21701  GTTGACTGGA GGACTCCCAC CCAGTTAGCT AGACTGCAAA GGTGCAGAGC
21751  ACTGTTGCCA AGATGCCCTC ACTTCTGACA TCACCCGCAA GTTCAGGGGG
21801  TTCCCCAAAC CACCCTCAGG CTTGATAGTT GACTAGGAAG ACTCCCAGAG
21851  CTCACTGAGA GCTGTGGCAC ATGGCTGCGG CTCCTTCCAG AAGAACACAG
21901  GTTAGAATTG TCCAAGGGAA GAGATGTAGG CAGAGTCTGG GAGGGTCCAA
21951  CCAGGAGGCC TGATGTCTCA GGGATGTGAC ACCCTTCTAG CATTGGAGCG
22001  TGGCCATACG CATGGAGTAT TGCCCACACA GAAAGCCCAC TGAGTGGGAG
22051  TTGAGAGTTT TTCCTGGGGT TTGAGTGCAA AGACATGATT GACTAATTGG
22101  CCAGGTGGAT ACTCTCAGTC TCTTGGTGAC CCAGCCCCTA YCCTAAATCA
22151  CATAGTTGGT CTTTCTGGTA CAGCCAGCCC CTGCCCTAAA GGAGGACACT
22201  TCTGCCTGGT GTGACCCGTG TTTCCTCTTG GAAGCCAACA GCAAAAGCTG
22251  GACTTCTCTT TGGGCAAGGC CCGCTTCTTT GCTATTGAGG GCCACAGTGG
22301  GTCTTTCTGG AGTGTGTCTG CACCTAACCT TTGAAGCCTT GGTTGCCGGC
22351  ACTTGCCATG GGGTCCCTGA GCCCTGAGCC TGTTGAGTTC TGTGCGTGAG
22401  TGCACTTGGT CATAGCACTC ACCAGGTTGT GGAAAGAGGC CTAGAGCCTC
```

FIG. 10, cont'd

```
22451  CGCTGTGGGG AAGCCTCTAG CTCAGATGCC TGTGGCTCCT TAGAGGAGGG
22501  CTGGGGACCC CGGGAAGGAG AGTCACTGAC ATGTGCCTGT GAGGAGGATG
22551  GGTGCTCAGC TCCACACGGC TAACAGGGCT GGTTCCCCGA CAGCGGTGAG
22601  GATCGGAGGG CGCTATGTCG TGGCTGGGAA GATGAGCATC TCCCCTAACA
22651  CCACCTACCC CTCCCTCCTG GAGGATGGTC GTGTCGAGTA CAGAGTGGCC
22701  CTCACCGAGG ACCGGCTGCC CCGCCTGGAG GAGATCCGCA TCTGGGGACC
22751  CCTCCAGGAA GATGCTGACA TCCAGGTCAG CAGGAGAGCC TGGGGGAGGC
22801  CAGTGGGGGC TTCTTCTTGG GGGCTATGGC TGCTTGCTCG TTTGTCTATC
22851  CATCCATTCC CTGATTCGTT CATTTATTCA TTCAGCGGTC ACTTACAGGG
22901  GACCCACTAT GTGTTGGGCC CTGTGCTAGG CAAAATGTAG CTAGCTCCTC
22951  CAGGGCTTA GGGTCCCACA AATATCCAAA TGTGYCTGTG CCCAGAGCCC
23001  GTGGGAGAAG GCCCTGCAGT TCTGGGATCA GGTAAGGTTG GAGGGCCCAA
23051  TGCAGGGGTC CAGGGCTCCC TGGGAAAGAG TGATGGAGCT GAGGTGTCAG
23101  ATGAGCAGAT GTTGCTGGGC CAAGCAGGGA AGGAAGCGTA TGGCTGAGGG
23151  AACAGTGTCA GTGTGGGAGG GATGAAGGAA GGTCCTACTG TGTGGGTTTG
23201  TGGGAGATG AAGGCATGGA CGCAGGTGCA GTGGCATCTG GGGAGTAGGC
23251  CTTGGTGCTG AGGAAGCTGA GAACAGATGC TGGCTCTCAC TGCTTCTTTG
23301  GTGCAGTGTG TGTGGGAACC GGAAGGCCTT GTTCAGGCGT GTCCTCAGTG
23351  ACGTGTGCTC GCCCATGTAT GTCCCCATTG GTGCTTCGCT GAGGAAGGCA
23401  CGTGGAGGGT GGAGAGACAT AAGCGCAGGC TGAAACAGAC CTGAGAACCT
23451  TGGGAGAGGG GCCCAGTCTC AGCGGCCGGA GCAGCGTCCT CTGCCCCTAC
23501  AGCAGCCAGA GACAGGAGGG CCTCCCACAG ATCAGGCCAG GCCGGGCCAA
23551  AGCAAGCCCC TGTGAGCGGC TTATCCCTTC TCTTCCCCTG ATATGGTTCC
23601  CTTCCTCCCC TCCCCTTGCC TGGGACATTG TATCCAGATG CTAGCTGCCG
23651  AGTGGCTCTC CCATCATCCT CTGCAGTGTG TAAAAAGCA GATTCCCGGG
23701  TCCTCTGCAT ATTCCCTGAA TCAGGACTTC CCTGTGTTGG GCCTGAGAAA
23751  CCGCACCGTA ACCAACACAG GCTTGCGGCA CTGGCCAGAT GTGGGCATCG
23801  AGGGGGCAGG TGCGGAATGT CACCTCGCCC TGGGCTCTGG CCTYCAGGCT
23851  GGCCTCTTTC TTGGGCTGGT CTTGGGCACA GGACCCAGTT ACCCTCCTGA
23901  AGAGCCTTAG GCCCAGGAAC CTGCTGAAGT TCTTCCTAGT GCTCTCCGGG
```

FIG. 10, cont'd

```
23951    CCAGTCCCAA GCCAGTAGCT GGCCACAGGT CCCCAGGGAT CCAGTTTCTT
24001    CCTGCCGACC CTACCACAGG TCCCCAGGGA TCCAGTTTCT TCCTGCCGAC
24051    CCTACGGGCC TCAGCTCTGG CTCCAGAAGC ACTTTCTGTG CTGGCCCTGC
24101    CCTAGCCCTT CTTGGGCTCC TTAGCCCAGC CTAAGGTGGG CCTGCCTCCT
24151    CCACTGCACT TTATCCTCTA CCCAGCCAGC TTAGGGAACC TTCTCTGTGC
24201    TGCCCAAATA CCCTATCRTG TAACCCACCA ATGACTTGGT AATTACCTCC
24251    CCGAGCCCTC TATCCCAACC CACTGAGAGC TCCTTGCAGC TCAGCCAGTG
24301    TCCTGTGCAC TGTGCTATCC CCAGAGCCTG GTACAGGTCA GTGTTGGTGA
24351    TTGCTTCCCG TTATTTTTGT CTTTGTTGTT TTTTAGAGA GGGTCTCACT
24401    GTTGGCCAGG CTGGAGTGCT ATGTTGCCCA GGCTGCTCTG AAACTCCTGG
24451    GCTCAAGTGA TCTGCCTGCC TCAGGCTCCC AAAGTTTTGG GTTTACAGGC
24501    ATGAGCTACC GTGCCTGGCC AGTGATTGCT TGCTGARCGA AAGATTATAG
24551    GGATGCAAGA AGAAGTTGGA AGGCTTCCCA GGGGAGGTGG CCATGACAGT
24601    GACCCTCAGG GAACCCACTG GACAAGGCCT GAAGCTCTTT GTCTGCAGGT
24651    TTACAGGCGG TATGGCGAGG AGTATGGCAA CCTCACCCGC CCAGACATCA
24701    CCTTCACCTA CTTCCAGCCT AAGCCACGGC AGGCCTGGGT GTGGGCCGCT
24751    GTGCGTGGGC CCTGCTCGGT GAGCTGTGGG GCAGGTGAGA CCTGGGGAAG
24801    GCTCATCCAC AGCACGGCTT GCCCCTGCAG GGAGGCGGCC TAGCCCTCCC
24851    TCTTCCCTCC CAGGGCTGCG CTGGGTAAAC TACAGCTGCC TGGACCAGGC
24901    CAGGAAGGAG TTGGTGGAGA CTGTCCAGTG CCAAGGGAGC CAGCAGCCAC
24951    CAGCGTGGCC AGAGGCCTGC GTGCTCGAAC CCTGCCCTCC CTAGTGAGTG
25001    TGGTGCTGTC TGCGCAGCTC AAGGGGGAG AGAGGGTTCC GCTGGGGCTG
25051    CTGGGCTCTG TCCCTGGCCT ATGGGGCCCA TGTGGCAGGG CCGGGCTGAG
25101    CTGCTCCTGT GCAGGCTCTC ATTACCCCTG CCCACAGCCC TGCAAGGGGG
25151    GCTCTGTGAG TGCCCCATT CTGCAGGTGA GGACACTGAG GCTTGGGGCA
25201    GACATGGTGA CAATGTCAGC CCAGTGGGAC CCACACCTGC TGCCACCTTG
25251    TCTGGGCCAC CGAGGCCTCT CTTGAGCTCA GGTACTCATG GTGAGATGGA
25301    GGTGATTGCC TACCTGGAGG GTTGTAGGGA GACTTGCGGA GCTCCTGGTG
25351    CAAAGCCCCT GGCTGTCACC ACACCTGACG GGGCACACTG TTAGGGACGA
25401    GGCCATTCCT GCTGGGTGCA GGACAGGGCA GCTGCTCACC AGCCTGTGAT
```

FIG. 10, cont'd

```
25451   TCGGTTGTCC TCAGGCTCAG CCGTCTGGCA GCCTGGGAAC ACCTGGAGAG
25501   GCTAGGCTGG CCGTAGTGCC CATTGCTTGT CCCAGACCGG GGGAGTACAT
25551   CAGCACCTGC CACCCCATCA CCCCAGGCCA GCCTGGGACC TGGCCAGGGT
25601   CCCGACGCTC TGTCTCCTTC CTCAGCTGGG CGGTGGGAGA CTTCGGCCCA
25651   TGCAGCGCCT CCTGTGGGGG CGGCCTGCGG GAGCGGCCAG TGCGCTGCGT
25701   GGAGGCCCAG GGCAGCCTCC TGAAGACATT GCCCCAGCC  CGGTGCAGAG
25751   CAGGGGCCCA GCAGCCAGCT GTGGCGCTGG AAACCTGCAA CCCCCAGCCC
25801   TGCCCTGCCA GGTGAGCCCA GGGCTAGGTG GGGCTGGGAG AGGGCCTTCC
25851   TGGCAGAGCT CGTCCCTGCG CTGAGCCCCC ATCCTTCTGA GAATCCCCTC
25901   CTCCTGAGGC CTCCGGCGGG GCCTCACCAT CCAGGGTGAT GGGCAGTGTC
25951   ACCTGGCGGT TGTAAGTGCT GCTGTCAGAG TTCCTACTA  CCCAGGAGAG
26001   CCTGGGCCCA TTGTTTCCCT CTCTGAGCTT CCGAGCCCCT GCTCTGAAAT
26051   GGGGATGCCG ACCTGCCTGG GGAGGGGGG  CTTCGAGGAT GAGGTCAAAC
26101   TGAACGGAGT GGGAGATGTC ACTTTCTCAT CACCACCATC TCCCCCGTGC
26151   CCACGTGGCT GCATCTCATC CCCTCAGTGT CCAAGTTGAC AGTGGCTTAT
26201   CATCCTGCCC TGCCACTAAC GAGCTGAGTG ACAGGGCAAG TCCCCTCCTC
26251   TGTGGGCTTC AGTTTTGCGA CCTGTCCGGT GGGAGGGGAT TGGTCTGGAT
26301   TGTTGGTGGC CCACTCATAG CTCTGGACTC CTTTCCCCGC CTCGTCATCC
26351   GTGGCAGACA AAACAGTCAC CACTCTTCCC CGCTGAGGCC AGATAGGGCC
26401   TCAGAATCCT TCTCACACAG CTCTCCAGGC AGCCACTTTA GCGCAGGGCT
26451   GACTCACAGC TGAAACCCAT TGGCCACCCT TGAACCTGGT GATCCAATTC
26501   CATGTGGCAC CTGTTTCTCT GCACCTGCTA TGGTGCATGG AGTCAGTGAT
26551   TACCTGGCTG GAGGTCGGCC TCTGCCTCTG GAGAGTAGGA GGGATGGGTT
26601   CTCTTTTTTT TTTTTATTAA AGACAGAGT  CTTGTTCTCT CACCCAGGCT
26651   GGTATGCAGT GGCATGATCT TGGCTCACTG CAACCTCCTG CCTCAGCAAG
26701   TGTGCGCCAC CAAGCCCAAC TAATTTTTGT ATTTTTTGTA GAAACAGGGT
26751   TTTGCCATGT TGCCCAGGCT GGTCTCCAAC TCCCGGGCTC AAGCAGTCTG
26801   CTCACCTCAG CCTCCTAAAG TGCTGAGCTA CCGTGCCTGG CCAGGGATAG
26851   GTTCTGTCTC TGCACCCTGG GTGCAGGTGG GGTGCCTGAC TGTTGAGCAG
26901   CGAGTGCTTG TTGAATGGGA ACCTGCTGGC TGATGAATGG GGAACCCGGT
```

FIG. 10, cont'd

```
26951  GCTTCAGGGA GAGACCCTGW GCTTCACTTC TCTGTGGGGC TCCTCTTTGG
27001  GCTCCTGGAT GTTGGGGAGC AGGTCCCCTT CCTCCCTGCC CCTAGCAGCT
27051  GGGCTATACC TTCCCCTGGG TGGCAGAGGC AGGGCCTGAT GACTGTCTCA
27101  TGCCATCCTC AGGTGGGAGG TGTCAGAGCC CAGCTCATGC ACATCAGCTG
27151  GTGGAGCAGG CCTGGCCTTG GAGAACGAGA CCTGTGTGCC AGGGGCAGAT
27201  GGCCTGGAGG CTCCAGTGAC TGAGGGGCCT GGCTCCGTAG ATGAGAAGCT
27251  GCCTGCCCCT GAGCCCTGTG TCGGGATGTC ATGTCCTCCA GGCTGGGGCC
27301  ATGTGAGTGC CCTGGGCATG AGGGTGGCTG GGCTGTTGA GTCCTTTACC
27351  TGGCTGGGAG AACGAGGAGC ACCCATTGCC ACCGTCCTCC AGGCCAGAGC
27401  AAGAACACCA TCCTTCTGTG GAATGCTGT CTGAGGGCCA CCCCTGCTCA
27451  GAAAAGAAGC TTAGAAAGAG GGCTCAGGGC CCCTGGGAAG GCTCCCATTC
27501  CCCTTGCAAG CCGGGCTGAG GGAAGCATCT GAGGAGAGTG TAATGCAGCT
27551  GCTGTGCAGA GAAATGCTGC CAGGCTCCCG CCTGGCGTCC AGGGGCTGGA
27601  GGCTGACTGG CCTTGCTCTC TGGCCTGGGT GCTGGCAACC CTCGCCCCTC
27651  ATGGCTGGGG GGATTGCAGG GCCAGGCATG CTCCCATGTC CCACTCTTGG
27701  TCCCCAGCTC TCGGCCAGGC CCACAGTGAG CACTCATGCT GCTGAGGAGC
27751  CTGCAAAGGT GGGGTGTGCA GCAAGGATAC CCGCTGCGAG ACCGGGGAGC
27801  CGATCTCGCC AAGGGAGGAG GGGAGGGAGC CCCTGGTGCA CACACGCCAC
27851  TTCCTGGTCT CTCTGCTGCT GCCTGAGAAG ATCGAGACGG GGATCGCTGG
27901  GTCCTCAGAG GAGGCCCAGA CCCACCAGCT TGTTGCTATT CCCCACAGCT
27951  GGATGCCACC TCTGCAGGGG AGAAGGCTCC CTCCCCATGG GGCAGCATCA
28001  GGACGGGGGC TCAAGCTGCA CACGTGTGGA CCCCTGYGGC AGGGTCGTGC
28051  TCCGTCTCCT GCGGGCGAGG TGAGGGCCCC CGGGATGCTC CTGGGGACCA
28101  GCACTCATGG TAACTCTCCT GTCCACTTGC ATCTTGCCTC GTTCTRAAAA
28151  GCATTTGAGG TGGATTGCAG AAAATCCAGA CTATATGGGA ACACGTGGTA
28201  ATACACAAGG AGACTAAGCA TAGTAGCTGA CAGCCACTTC AAATGTGGGT
28251  GTTGATTGGC TGAAAGGTAG GAAAAGACAA TAACGCCCGG CAGTGTGGCA
28301  CGAGAGCCAT TCCTTATGGT CCTAGCAGAG CGGCCGGGGG GTCCCCAATT
28351  GATGACCCGA GCAGAGAAAC CTTAGCTTTA AGATACACAG CGTTCTTCTA
28401  TTTTCCCAAT CTTGTTTTAT TGCAGTATAA CACAGATATT ATAAAATTTA
```

FIG. 10, cont'd

```
28451   CCATCCAAAC TGTTTCTCCC TGTGCAGGTC AGTGGCATAA AAGCACAGTC
28501   ACATTGTTGT GCGGCCATCA CCACCAACCT CTCCAGAACT TTTCCAGTTT
28551   CGCAAACTGG AGCTCTGTCC CTGTGAAACA CGAACTCCCA TTTCCCCCTC
28601   CGCAGCCCCT GGCAACCTCC ATTCTCCTTT CTGTCTCCAG ATTCCACAAT
28651   TCTAGGGACC TTGTAGAAGT GGAATCATAT AGCATTTGCC TTTTGTTAC
28701   TAGTTTTCAC TCAGCATGAT GTCCTCACAG TTCATCCATG TTGTAGCATG
28751   TGTGAGTGTT TCCTTCTTAA GGCTGAAAAA GATTCCATTG TGAGTGTATC
28801   CTTTACAKGT TTATCCATTT ATTCATCAGT GGACACTTGG CTTCCTTCCA
28851   CACTTTGGCT ATTGTGAATA ATGCTTCTGT GAACATGGGT GTGCAAATAT
28901   CTGTTTGAGT TCCTGCTTTC AGTTCTTTTG GGTGTATATC TAGAAGTGTG
28951   GTAGCTGGGT AAGATGAGAA TTCTATGTTT AATTTTTGTG GAACTGCTGG
29001   ACTGTTTTCC CCAGTGGCTG CACCATTTTA CATTTCCACT AATGGTGCAT
29051   AAGAGTTCCA ATGTCCTCCC ATCCTTGCCA ACACTTTTTA TTTCTATGGT
29101   TTTTTTTGTT TTTGTTTTTG TTTTTGAGAC AGAGTCTCAT TCTGTTGCCG
29151   AGGCTGGAGT GCAGTGGCAT GATCTTGGCT CATTGTAACC TTCGCCTCCG
29201   GGGCTCAAGT GATTCTCGTG CTTCAGCCTC CCGAGTAGCT AGGACTACAG
29251   GCGTCTGCCA CCATGCCTGG CTAATTTTTT GTTTAGTAGA GATGGGGTTT
29301   CACCATGTTG GCCAGGCTGG TCCCAAACTC TTGACCTCAG GTGATCTGCC
29351   TGCCTTGGCC TCCCAACGTG CTGGGATTAC AGGCGTGAGC CCCCACACCT
29401   GGCCTATTTC TGTGTTTTTT TTATAATGGC CATCCTAATG GGCTTGAGAA
29451   GACACACCAT GTTCTTAAAC GAAAACCCTG ACCACTTGCT CAGTAAAATG
29501   TCAGCCTGTT TAAAACCGAG ACCAAAAAGA GATTTCTTTT TCTCTCTTTT
29551   CTTTTctttt TTGAGACAAA AAAGAAAACC TCTGTCACCA GGTTGGAGTG
29601   TAGTGGCACA ATCTTAGCTC ACTACAACCT CCACCACCTG GGCTGAAGCC
29651   ATCCTCCCCC CTCAGCCTCC TGAATAGCTA CTATACCCTG CTAATTTTTG
29701   TAGTTTTGGC AGAGATGGGA TCTCCCTATG TTGCCCAGCC TGATCTCCTG
29751   AGCTCAAGCG ATCCTTCTGC CTCGGCCTCT CAAAGTGCTG GGATTATAGG
29801   CATGAGCCAC TGTGCCCAAC CAAGAGATTT TTTTTCTTTT TCTTTTTTTT
29851   CTTTTTTTTG AGACTAAGAG TTTTCCTCTG TCGCCCAGGC TGAAGTGCAG
29901   TGGTGTGATC TTGGCTCACT GCAACCTCCG CCTCCCATGT TCAAACGATT
```

FIG. 10, cont'd

```
29951   CTCATGCCTC AGCCTCCTGA GCAGCTGGGA CTCCAGCTAT GTGCCACCAC
30001   ACCTGGCTAA TTTTTTGTAT TTTATTTTAT YAGAGAGGGG GTTTCGCCAT
30051   GATGGCCACG CTGGTCTCAA ACTCCTGACC TCAGGTGATC CACCCGCCTT
30101   GGCCTCCCAA AGTGCTGGGA TTACAGGCAT GAGCCACTGA GCCTATTTCT
30151   TTTGAGGATA TTCCTAAAAG AGAGACTTGA GAAAACTGGC CCTAATAACA
30201   TCTTTATGAT AGACACAATC AGAGATTTTC ATATTGTGAT TTTTTTTTCT
30251   TTTTTYTTTT TTTGAGATGG AGTCTCGCTC TGTCACCCAG GCTGGAGTCC
30301   AGTGGCGCAG TCTTGGCTCA CTGCAACCTC TGCCTCCTGG GTTCAAGTGA
30351   TTCTCCGTCT CAGCCTCCTG AGTAGCTGGG ATTACAGGTG CGCACCACCA
30401   CGCTCAGCTA ATTTTTGTAT TTTTAGTAGA GACGGGGTTT CACCATGTTG
30451   GTCAGGCTCG TCTCGAACTC CTGACCTTGT GATCCGCCGC CCAAAGTGCT
30501   GTGATTACAG GCGTGAGCCA CTGTGCCTGG CCCATATTGC AATTCTTATA
30551   ATGCCTCTCG GTCAACAATA ACAGCTACCA TTTGTCAAGT GTCTACTGTG
30601   TGCCAGGCAC TTGTTATCTT CCCTTTTAAA AATCTTTATA AATGATTCTG
30651   CAAGGTAGAT GCCATTATCT TTTTTTCTAA ATCTAAGATT CAGAGGGTTA
30701   AGTCAGTTGT CTGAGGTCAC ACAGCTGGTA AGTGGCAGAG CCGGGATTGA
30751   AACCCATGCG GGCCTTATGT GCTAGAGGTG TCCAGTGAGC CTGGGCTGCA
30801   GTCCTTGCTG AGCCTGTCCC TTGGGGCTCT GGGTCTCTGC TTTGTCCACG
30851   CAGGTCTGAT GGAGCTGCGT TTCCTGTGCA TGGACTCTGC CCTCAGGGTG
30901   CCTGTCCAGG AAGAGCTGTG TGGCCTGGCA AGCAAGCCTG GGAGCCGGCG
30951   GGAGGTCTGC CAGGCTGTCC CGTGCCCTGC TCGGTGAGTG AGGGGAGCAA
31001   GACTGTGTGC TGGCCTTCTC CCTGTAAGTG GGAGACCYGA GCCTTGGCTC
31051   CATGCCCGGT GACCTGCGGA GGGGGGCAGG TGCTGCTGGC TGTGCACTGT
31101   GTGAGGCTGG ACCATGGCCG CCCCATCCCC CTGCCTCACT CCAAGTGCAG
31151   GCCAGAGCCC CGGCCCAGCC CCTTTGAGGA CTGCAACCCA GAGCCCTGCC
31201   CTGCCAGGTG GGCCCCTTCC CAAGGAGACA GGGGGTGCTA GGTCTGCATC
31251   CTGGCTCTTT CCTCACCTCC AAGCCAGACC TTTTGACCCT CAGTGTCCTC
31301   ACCAGTGGGA GCAGGTCATT TTGTGCCCCC AGAAGACTGG GGGAGTTTAA
31351   TGAAAGGATT AGATGCATGT AAAGTACATG CTAAATGCAA TGAGTGTAAA
31401   ATGCATGCTC GATGCAACGC GTGTAAAGTA CATTGCACAG GATCTGGGAT
```

FIG. 10, cont'd

```
31451   GCTGTGGGTG  CACATGGTTG  CTGGTGCGTT  TCTTCATCGC  CTGCTCTTTA
31501   TGGAGCACCT  AGGCCCCGGG  GCCGTCCTGG  AGCTAGGGGA  CACAGCAGAG
31551   AACAAGGCAG  ACAAATGTCC  CTGACCTCCT  GGAGCAAATG  CAGGGGGAAA
31601   GGGGGACAGA  TAATAATAGG  ACAGGYGGGG  AATGCAGTTT  GATGGATGGT
31651   GTTCAGTGCG  ATGCAGCCAA  ACACAGCGGG  AGGGGAGGAG  GGGAGGGCTG
31701   GCGGGGTGGG  CTCCAGGGCG  GTGGTGCTGG  GATCACTGTT  GAAGACAGAC
31751   ATGCAGGGCC  CTTGGGTGCC  CGGACCCCTG  CCCCACTGT   CTCTGGATA
31801   CGACATCTGT  CGTTTGCCCT  CACCTTTCTC  TTCTGTAAAA  TGGGTTTGTC
31851   CAAATGTTCT  GTCCACTCTG  CCAAGCCTCT  TGGTGAGGAC  ACAAGGGGGC
31901   CTCCAGAAAG  AGAACCTCTC  CGGGCCCTTC  CCAGCTTCCT  GTCTCTTCCT
31951   AGTCTGGGGA  AATGAAGGGG  AGACCTGGCT  CCCCTGGGTT  CCCAGGCCCT
32001   GGGGCTGTTT  GGGGTCCCTG  ACTCCAGTTT  GCTCCAGGTG  GCAGTACAAG
32051   CTGGCGGCCT  GCAGCGTGAG  CTGTGGGAGA  GGGGTCGTGC  GGAGGATCCT
32101   GTATTGTGCC  CGGGCCCATG  GGGAGGACGA  TGGTGAGGAG  ATCCTGTTGG
32151   ACACCCAGTG  CCAGGGGCTG  CCTCGCCCGG  AACCCCAGGA  GGCCTGCAGC
32201   CTGGAGCCCT  GCCCACCTAG  GTGAGTCAGC  CGGTGATGGG  AGGGGCAGCT
32251   CCTGGTGTGT  GCAGATGCCA  GGCCAGGCGC  TGTGGTGTGT  GCCTGTAATC
32301   GCAGCTACTT  GGAAAGCTGA  ATCAGGAGAA  CCACTTGAGT  CCAGGAGTGC
32351   AAGTCCAACC  TGGCAACAC   AGTGAGACCT  CATCTCTAAA  AAAAAAACAA
32401   GACGGGGCCA  GGTGTGGTGG  CTCACGCCTG  TAATCCCAGC  GCTATGGAAG
32451   GCTGAAGCGG  GTGGATTACC  TGAGGTCAGG  AGCTTGAGAC  CAGCCTGGCC
32501   AACATGGTGA  AACCCCATCT  TTACTAAAAA  TACAACAATT  AGGCTGGGCG
32551   CGGTGGCTCA  CTCCTGTAAT  CCCAGCACTT  TGGGAGGCTG  AGGCGGGCAG
32601   ATCACCTGAG  GTTGGGAGTT  CGAGACCAGC  CTGTCCAACA  TACAGAAACC
32651   CTGTCTCTAC  TAAAAATACA  AAATTAGCCG  GGTGTGGTGG  TACATGCCTG
32701   TAATCCCAGT  TACTTGGGAG  GCTGAGGCAG  AATCGCTTGA  ACCGGGGAGG
32751   CCAAGGTTGT  GGTGAGCCAA  GATTACGCCA  CTGGACTCCA  GCCTGGCTAA
32801   CAGCAGCAAA  ACTCCATCTC  AAAAAAAAAA  AAAAAAAAAG  AAAACCCACA
32851   AAAATTAGCC  TGGCGTGGTG  GTGTGCACCT  GTCATCCCAG  CTACTTCAGA
32901   GGCGGAGGCA  GGAGAATCGC  TTGAACCCGG  GAGGCGGAGG  TTGCAGTGAG
```

FIG. 10, cont'd

```
32951   CCGAGATGGC GCCGCTGGCA CTCCAGCCTG GGCTACAGAG CGAGACTCCG
33001   TCTCAAAAAC AAAACAACAA AACAAAACAA GACGGGGTGG GGGGCTCAGT
33051   GGCCCAAGAG CCAGTCTGTA AGGAATAGGG CTACCTGGCA GGCTGTGCTA
33101   GTTGTGGGAG GTGAAGTTTA AGCACCATGC AGGCAGGGTG CAGTGTGGGG
33151   AGGCCTGGGG GACAGAGGAG GCAGCATTTG AGCAGAACCT AAAGCTGTGA
33201   GCACCAGCAT TCTGATGTGG AAGACGGGAG GGATGGAGGT CTCCACAGGG
33251   ACACACACAG CCACACTAGG ACACGGGACA GAATCATGTT CAAGTCCGTG
33301   GGGTCCGGAG CCCAGTGGTA AAGGCGAAC ATTTGCCTAC CTCATTTACA
33351   ATTCTTTAAT GGTTTCTTTT TGTAGGTTTG CATTTTTAGT AAAGAAATAC
33401   TTTTCTATAT CATACAGAAA CGTCCAGAAA AGAATGTAAC AGACATGTAT
33451   GTTCCAGCAC TCCAGTTTAA TAGATAGCAT CCTACTGCCA TGTTTCCTTC
33501   CTGTCCACTT ACTTTTATTT ATTTAATTTA TTTATTTTGA GACGGAGTCT
33551   CGCTTTGTTG CCCAGGCAGT GATGCAATCT TGGCTCACTG CAACCTCCGC
33601   CTCCCGGGTT CAAGCCATTC TCCTGTCTCA GCCTCCCAAG TAGCTGGGAA
33651   TACAGGCACC CACAACCACA CCCAGCTAAC TTTTGTATTT TTAGTAGAGA
33701   CAGGGTTTCA CCATATTGGT CAGGCCGATC TTGAACTCCT GACCTCAGGA
33751   GATCTGCCTA CCTCAGCATT CCAAAGTGCT GGGATTACAG ATGTGAGCCA
33801   TCACACCTGG CCAGCCTCCT TAGTTTTAAA TAAATCCAGT TACAGATAAG
33851   ATTTCACTTA AATTTAGGCT GGTCATGGCT CACGCCTGTA ATCTCAGCAC
33901   TTCAGGAGGC TGAGATGGGT GGATCATTTG AGCCCAGGAG TTTGAGACcA
33951   GCCTGGACAA CATGCCAAAA CCTTGTCTCT ACTATAAATA CAAAAATTAG
34001   CCGGGCATGG TGGTGCATGC CAGTATCCCC AGCTACTCGG GAGGCTGAGG
34051   CAGGAGAATC ACCTGAACCT TGGGAGGTCA AGGCTGCAGT GAGCAGAGAT
34101   CAMACCACCA CTGCATGCCA GCCTGGGCAA CAGCATGAGA CCCTGTCTCa
34151   AAAAAAAAAA AAAAAAAAA AAAGATTTTA CTTAAATTTA AACCCTGTAC
34201   TAATCTGTGA TTTATTTGGA GTATGTTGCA AGTAGGGAC CAAAGGATTT
34251   TTTTTTTTTT CTAAATTGTT AACTAGCATC TGTTGGACAA GCCCTGATGC
34301   CTCCAGGTGG CTCCTTGGTG GTATTGGTGT GTGTTAGAAT CTATGTCTGG
34351   GCTTTCTACT GGGTTTTTTT CTTCTCCTTT TTTTTTTTTG AGACAGTTTT
34401   TCTCTGTCAC CCAGGGTGGG GTGCAGTGGC GCGATCTCAG CTCACTGCAA
```

FIG. 10, cont'd

```
34451   CCTCCGCCTC CYGGGTTCAA GTGATTTTCA TGCCTCAGCT TCCCGAGTAG
34501   CTGGGATTAC AGGTGCCCGC CACCACCCCC AACTGATTTT GTGTTTTTAA
34551   TAGAGACAGG GTTTCACTAT GTTGGCCAGG CTGGTCTTGA ACTCCTGACC
34601   TCAAGTGATC TGCCAGGTTC TGTTTTTTGT GCTTTTTTTT TCTAGCTATT
34651   CTCTTGCCCA TACAAAATTG TTTTAAATGT TGTAGCTTTA TAACCATTTA
34701   ACATCTGTGT CACTAGTGTG TCCTGATTTC TTTGCCTATG CTAAAGTCCC
34751   TTGGCTGTGT GTCCCATTTA TTTTTCCACA TCACATTTAG AGATGATCTG
34801   GGATTTTATG GGAATTGCAG GGTTTTTCAC ACTGCACGCT GCCTGCATGG
34851   TGCTTAAACT TCACCTCCCA CACCTAGCAC AGCCTACCAG GTAGCCCTGT
34901   TCTCTACAGA CCACCTCTTG GGCCACTGAG CCTCCCCTCA CTTTTTTTTA
34951   GAGATGGGGT CTCACTATGT TGCCCAGTCT GGACTTGAAT TCCTGGGCTC
35001   AAGTGATCCT CCTGCTTCAG CCTCCCGAGT AGCTGGGATG CAGGCACACA
35051   CTACATGAGC TCTGGCCATC CCTCTGACGT TGCTGTAGCC ACGCTGGCCT
35101   CATTGTCCTG GAACATTCCA GGGATACTCC CCTGACTTAG GGCTTCTGTG
35151   CTAGCTCTCG CTGCCTGATG TCTTCTGTGG ATATCCTCGA GGCCCTGGAT
35201   ATCCCTCCCC CAGGCTCGGC TCAGACACCA CAACTCCAAA GTGGCCCAGT
35251   GCCCTCCCTG AGCGTCGGTC CAGAACGGCA CTCTCGTCCC TCCTGTGACG
35301   CTCTGCTTGG CACTTTGGGA GGCTGAGGCG GGAGGATTGC TTGAGCCCAG
35351   GAGTTCTAGA CCAGCCTGGG CAACATAGTG AGACCCCGTC TCTACAAAAA
35401   ATACAAAAAT TGGCTGTGCG CGGTGGCTTA TGCCTGTAAT CCCAGCACTT
35451   TGGGAGGCGA AGGCAGGCAG ATCACGAGGT CAGGAGATCG AGACCATCCT
35501   GGCTAACACG GTGAAACCCT GTCTCTACTA AAAATACAAA AAATTAGCTG
35551   GGTGTAGTGG TGGGTGCCTG TAGTCCCAGC TACTTGGGAG GCTGAGGCAG
35601   GAGAATGACG TGAACCCAGG AGGCGGAGCT TGCAGTGAGC TGAGATTGTG
35651   CTACTGCACT CCAGCCTGGG TGGTTGCAGT GAGCTGAGAT TGTGCCACTG
35701   CACTCCAGCC TGGGCGATGA GTGAGACTCC ATCTCAAAAA CAAAAACAAA
35751   CAAACAAAAA TTACAAAAAT TAGCCAGGCA TGATGGCACA TGCCTGTAGT
35801   CTCAGCTACT TGGGAGGCTG AGGTGAGAGG ATGGCTTGAA CCCTGGAGGT
35851   TGAGGCTGCA GTGAGCCGTG ATCACACCAC TGCCCTCCAG CCTGGGTGAC
35901   AGGGCGAGAC CGTGTCTCAA AGAAAACCAT TAAAATAAAA TAAAAAATAA
```

FIG. 10, cont'd

```
35951  AATTTCTGCG ATGCACACGA CAGCCTCCAC AGCAAATCAG CATCCAGTTG
36001  CTCATGCCAG TGATGCCCCA ATGGAGAACA ATCCACGCTC TGAGAGGAGG
36051  TGGGGTCTGG TTTGGTTCAC TGCCACCTCC CAGTGTCATG TAGAACAGTG
36101  CCAAGCCGCG GAAGGCACGG GTCCAAGAGG CAGCGCTGCA GGGTCATGGG
36151  GGAGCACAGT ATTGCGATGA AGATCCCAGC TCCCTTGCAG GCTGCCTGGG
36201  TTCGTGTCTG GGCTCTGAAG AATGCGGGCC ATAATTAGTT ATTGATTGAT
36251  TACAGATCAA CATGGGCAGC CTTCCCTTGC CCAAGGGAAG GGAACTCGGC
36301  CTTCCCTTGC AGAACGTGGG GTGTTGAGAT CTGTCTCCTG TTACCCAGGG
36351  GCTCGCTTCC TGTTGCTGTT ACTTGGGTCC ATAGGCAACC CCTGGGGTGC
36401  TGACAGGTGT TCTGTGATAA AGGCGACTAG AGGGGGATGT GCAATTAGGG
36451  AAACAGGGGC CTCTTCCCCC TAGGGCCTTT TGGTAGCTCT CCTGTGGCCG
36501  TGAGCCCTGG CCCCAGACAG GAGGGCTCA GTGGCTGCAC TTTCCATCTT
36551  GCCTGGCCAC GGAAGCTGTC TAGGCAACTG TCCGAGTACA CGTGGGTGGA
36601  GAGGGGCCTG CGTGGGGCAG TACTGTCTCT GGGGAGACCT AGCCTCTCTC
36651  TGGGGTCTTC TCTTCCTGCA GGTGGAAAGT CATGTCCCTT GGCCCATGTT
36701  CGGCCAGCTG TGGCCTTGGC ACTGCTAGAC GCTCGGTGGC CTGTGTGCAG
36751  CTCGACCAAG GCCAGGACGT GGAGGTGGAC GAGGCGGCCT GTGCGGCGCT
36801  GGTGCGGCCC GAGGCCAGTG TCCCCTGTCT CATTGCCGAC TGCACCTACC
36851  GCTGGCATGT TGGCACCTGG ATGGAGGTGA GCACAGCGGG CACTCGGAAT
36901  CCCTATGGGG CTGGGGTGGG CATCAGCTGT GGCTCCTCAT GTGTGAGGGA
36951  GTCTAGGAGG CATTGGCTCA TCGTGTCCCC TGAAAGGAAG GAGAGAGCTG
37001  CGCCCGTTGG TGAGGGGCA CCTAGAGGCA GAGAGACAGA GGGCCTAGAG
37051  ACCTGCGGGC AGCTAGGACT TAAGAGGCCC TTAGGTTTGG GGACGCTGGA
37101  AGATGAATGG CAGGCCACTC AGCTCTACAC AGATGAGGGA ATGCCAGCTG
37151  TGCCACGCAC CTGGCAAGGC AGGACAGACA AGGGTAAATG GGGTTCAGGC
37201  TGCCCCCTGG AGGGGCTCGC TCATGGTGTG GAGGGGGCAT AGGGGCACAG
37251  CAGACAGAGA TGAGCCGCAG CCCCGCAGAC CTGCTTGCTC TAAGGCTTGG
37301  AGGGACAGAG AGGCCGTGAG GGTGACAGGG ACCCAGACTT GAATTATGGC
37351  TCCTCCCACC TATATGACCC ATGCAAGGTG CCCTCTCTGA GCCTCAGTTT
37401  TCTCATCTGT GGAATGGAGA CACTTAACTG CCTCCCAGCT TGTACAAGGA
```

FIG. 10, cont'd

```
37451  TTATATTGGA TCACTCCTGG CCTGTGGTTA CCACTGTCCT TGTCACCTTC
37501  TGGCAGGGTC AGCTGTGACT CCTCCTCCCC TCTCTTGGCA GTGCTCTGTT
37551  TCCTGTGGGG ATGGCATCCA GCGCCGGCGT GACACCTGCC TCGGACCCCA
37601  GGCCCAGGCG CCTGTGCCAG CTGATTTCTG CCAGCACTTG CCCAAGCCGG
37651  TGACTGTGCG TGGCTGCTGG GCTGGGCCCT GTGTGGGACA GGGTACGCCC
37701  AGCCTGGTGC CCCACGAAGA AGCCGCTGCT CCAGGACGGA CCACAGCCAC
37751  CCCTGCTGGT GCCTCCCTGG AGTGGTCCCA GGCCCGGGGC CTGCTCTTCT
37801  CCCCGGCTCC CCAGCCTCGG CGGCTCCTGC CCGGGCCCCA GGAAAACTCA
37851  GTGCAGTCCA GTTATGTCCT GTCCTCCTTC CTGTCAGGCA GCTGCTGCAG
37901  GAGGGGTGGG CAAAGGCATC TTCCTCTGGG AAGGACTGGC ACAAGCACTT
37951  GGTCCCTGGG TTGTGTGCCT GGGAGGCCGG GATCAGGGCT GGCCCTCTTT
38001  CTCCCTGGCA AAGCAAAACC TCCCTTTTAC TACTATCAAG GGGAAGTAAC
38051  TTGAAGGTAG GAACCCAGCT TGTGAGCCCC CTAGCCTCTG GGCTGCTCTG
38101  CATGTGCCCC CTCTTGCTGG ATCATCTGGT AGCAGCCCTG TGCCCTGAGG
38151  GTGATGCTCT GACCTATGCA GCCCCCCTCC CTGTCCTGAG AAGGCTTCCA
38201  GCTGGGCCTT GGAGGACAGG GTCCACCCCT ACCTCCTGGT CTCCTTCCTC
38251  AGCTTGGAAG CCCCGGAGCC TGCCCTGCTG GGAATCGGGG AAGCACTGCT
38301  TACCTGTCTC CTGCTCCCTT TTCAGGTGCC TGTGGCAGGC AGCACCTTGA
38351  GCCAACAGGA ACCATTGACA TGCGAGGCCC AGGGCAGGCA GACTGTGCAG
38401  TGGCCATTGG GCGGCCCCTC GGGGAGGTGG TGACCCTCCG CGTCCTTGAG
38451  AGTTCTCTCA ACTGCAGTGC GGGTATGTCT AGGGCCATGC AAGCGATGCT
38501  GCCAGTTATG GGCCCTGCCA GGAGCCAGCA CGACGCTGCA TGCCCCATTC
38551  CTGGCAGGAG CCCATGTGCA TTCCCACCTG TAGTTTGCAT CCCATCTCAT
38601  GACTGGGGAG TGATGATCTG CATTTTACAG ATGAGGAAAC TGAGGCTAGG
38651  AGAGATTAAG TGATGTGCCC AGTTACTTAG AGTCACATAG CCAGCAGTGG
38701  GAGAGGTGGG ACTTGAACTC GGCTCAGTCT ACCCTGGAGC CACTCCTCTG
38751  CTGACCAGGC GTGGGAGTGC TGGACCCTCA CTGCCCTGCC GCTTCCTAGG
38801  GGACATGTTG CTGCTTTGGG GCCGGCTCAC CTGGAGGAAG ATGTGCAGGA
38851  AGCTGTTGGA CATGACTTTC AGCTCCAAGA CCAACACGCT GGTGGTGAGG
38901  CAGCGCTGCG GCGGCCAGG AGGTGGGGTG CTGCTGCGGT ATGGGAGCCA
```

FIG. 10, cont'd

```
38951  GCTTGCTCCT GAAACCTTCT ACAGAGGTAT GGCCAGGCCT TCTCCACCTC
39001  CCTTGGGTGC TCCAGTCCTG GCAGGGAGGC TGGGTGGGTG CTGCTGGGGA
39051  TGGGGCCAGT CCCAGTGGGG CAGTGGGAAG ATACGGAGGG AACTGACTGA
39101  GATGGAAGGA ACTGGGGTTG GCCAGTGTCA GTCTGCACGT GCCAGGGAGG
39151  GGTCACAGGA TGAATGCTAT ATCCCTCCTT TTTGGGACCG TGCAGCAAGA
39201  TGGACGGATG TGGGACATGG TCCACATCCT CAGTCAGTCC CTCAGGCCTC
39251  TGCCCCACAC CCACCTGCCC CGCCCCACC CCTCCAGCCT TTCAAGGGCT
39301  TTTAGGGTTT TGTGGAAGCC ACTGTCCCTC AGCCCTGTTT CAGTGCACTG
39351  GTGTAAGCAG ACATGCTTGT ACATGCATGT GCACCACAA GCACACCTCA
39401  GGCAGAGGAT GCCACCTCAG GGACTCCAGC CTTGCCCGTG GCCCCCTCGA
39451  TATCCTCTGA TAGCCCTCTC GGTTGTCCTG GGGGGCTTGC CCTCTCCCAA
39501  CAGCCCGAGC TGGCCGAAGT TGGCTTCCCT AGCTGGTTCC AGAGGTTCCT
39551  CGGCTCCCCC AGGTGTCTGG GGCTTAGTGG CAACAGGGGC TTAGCCTCTG
39601  CAGAGACCTA GTGCGCCGCC TCCTTGCCCC AGACCTGCCC GGGCAGAGAG
39651  CCGTGTATGT GTCTCAGTGC ACAGGCGCTG CTGGGCCCTG CCAAAAGGCC
39701  ACAAGCCCAC TGTCACCGTT CACATTGCTT CTCGCTTCCC GGCCCAGCCC
39751  CGCCCACACA GGCATCTGCC TTGAAAGAGG TGCAGGAGGT ACAGGCAGGT
39801  GGGGGCTCCA GTGAGCTCTG AGGAACAGCA GTGGCCGCCA TGGGTGGAGC
39851  CTATCTTTGT TGCCAGTTTC AGTGTTAAAC ACTCTTGCAC GTGTGACATC
39901  ATTGAGTCCT AAAGACCACT CTGCTCAGTG CATGCCATTG TTTCCTTCAG
39951  TTACAGAGGA GGGAACCAGA GCCCAGAACA TTTAGCCTTT GCCTAAAGTC
40001  ACTGGGCCAG GAAGTGGTAG AGGTGGGGTT CAGCAGGATT TGCCTGGGAA
40051  CCCCAATATT GACCACAGTG CCATGCTGCC CTGCACGGCT CCCTGGCTGT
40101  GAGTTGTCCT GGCCTCTGGC ACCACCGGTC TGTCTGGGTT CCTATGTCCC
40151  TATGTCCCAC CTGCAGAATG TGACATGCAG CTCTTTGGGC CCTGGGGTGA
40201  AATCGTGAGC CCCTCGCTGA GTCCAGCCAC GAGTAATGCA GGGGGCTGCC
40251  GGCTCTTCAT TAATGTGGCT CCGCACGCAC GGATTGCCAT CCATGCCCTG
40301  GCCACCAACA TGGGCGCTGG GACCGAGGGA GCCAATGCCA GCTACATCTT
40351  GGTGAGGCCC AGCATGGGGA CTTGTGCTGT GACTCTGGAC AGCTTTCCCT
40401  AGGGCGTGCA GGGCTAGGGG ACCCCCTTCA GTTTATTTCA GACTAAAACC
```

FIG. 10, cont'd

```
40451   CTCAAAATCA TTAGTGAAAG AATGGGAGAA GATAGCTTCC TCCACATATT
40501   CACCAAGAAA TGTTTTTTGA GCTACCTACA AGAGTGAAAT AGTGGCTCAC
40551   AACTGTAATC CCAGCACTTT GGGAGGCCCA GGAGGGCAGA TCACTCAAGG
40601   TCAGGAGTTC GAGACCAGCC TGGCCAACAT GATGAAACCT TGTCTCTACT
40651   AAAAATAGAA AAAGTAGCCA GGCATGGTGG CGTGTGCCTG TAATCCCAGC
40701   TACTTGGGAG GCTGAGGCAC AAGAATCACT TGAACCCGGG AGGTGGAGGT
40751   TGCACTAAGC CCAGATCGCA CCACTGCACT CCAGCCTGGG CAACAGAGTG
40801   AGACTCTGTC TCAAAAAAAA AAAAAAAAAA AAGCGAAATG GTAAAGAATG
40851   GTAAAGACCT TTCTGATGTA GACTGACAGC TAACCCAGGA CTGAAGCATA
40901   ATTTTACAGT CTGATATAAC TTGGACAGAA TAGCACCCTG CACCCTCCCC
40951   GAGGTTTCAT GTGTCCTGGG AGAACTGTGT TCTGCAGGGT ATCAGCTTCC
41001   CCAGAGGAGG CAGCCTGGCC CCGCTCTGGC ACCCTGACTG TGTGTCCTTG
41051   GGGAAGTGAT GTAACGTCCC TGGACCTCGG TTTTCTGGGT AGAGTAATGG
41101   CGTATTCCTA GTAGGGCTTT GTAAGCATTA AATGTGATCC GGAATCTGTG
41151   AGCCCTTGCA CACGAAGGCT TCCGTGAGTG CTAATTATTA CTTGTGGCCG
41201   GTCCTTCTGG GCTGCCCCTT TTCTCTCAGA TCCGGGACAC CCACAGCTTG
41251   AGGACCACAG CGTTCCATGG GCAGCAGGTG CTCTACTGGG AGTCAGAGAG
41301   CAGCCAGGCT GAGATGGAGT TCAGCGAGGG CTTCCTGAAG GCTCAGGCCA
41351   GCCTGCGGGG CCAGTACTGG ACCCTCCAAT CATGGGTACC GGAGATGCAG
41401   GACCCTCAGT CCTGGAAGGG AAAGGAAGGA ACCTGAGGGT CATTGAACAT
41451   TTGTTCCGTG TCTGGCCAGC CCTGGAGGGT TGACCCCTGG TCTCAGTGCT
41501   TTCCAATTCG AACTTTTTCC AATCTTAGGT ATCTACTTTA GAGTCTTCTC
41551   CAATGTCCAA AAGGCTAGGG GGTTGGAGGT GGGGACTCTG GAAAAGCAGC
41601   CCCCATTTCC TCGGGTACCA ATAAATAAAA CATGCAGGCT GACCGGCGTT
41651   TTTTTCTTAT AAGCTGTCCA GACCTGGCTT GAAAACCCAT CCCATGGCAA
41701   GGCAGGGATT CGCTGGCCGC GGTTGGCTCT ATCTTGATCT GAGCAAGCCG
41751   CTGGACGTCC CTAGTTATCT TCTTCCTATC CAGGAAGAAA ATCCAATCAG
41801   GATTCCACTC CGAGGATGGC GCATTAGCCA GCTCCCTGCG AAGCCCCACC
41851   CGTGTGTCCT GGTGTGAGGC TCTGACCGCT AAGGTGTCTG CGCGCCTCCA
41901   GGCCCCGCCC CCTATGCTAA TAAGCGCCCG CCTCCTTTGG GAGCAAGTCG
```

FIG. 10, cont'd

```
41951  CCGCAAACTG CGAGCCCCCG CCCCCTACGC TAATGACGCC CGCCCCCCTC
42001  GGGCACACCT CTCCGATGCC TGCGAGCCCC GCCCCGTATG CTAACGAGCT
42051  CCCCACCCCC AGCTCCTCGC CGCAGCCTGC GGGTCCCGCC CCCTACAATA
42101  ATGAGCACCT ACCTCCCCTC AAACGCCCCT AGTCGCGGCA TGAGGGTCCC
42151  GCTCACTATG TTAATGAGCA CCCGCCTCCC TTCGGGCGCG CCTCGCCGCA
42201  GCCTGAAAGC CCCGCCCCCT ATGCTAATAT GCTCCCTCTC CCACAAGGCA
42251  GCGCGCCGGC TCGGACGCGG CCGGCTACCG AGCCCTTTGT GAGGGCTGTG
42301  AGCTGCGCCT GACGGTGGCA CCATGAGCAG CTCAGGTGGG GCGCCCGGGG
42351  CGTCCGCCAG CTCTGCGCCG CCCGCGCAGG AAGAGGGCAT GACGTGGTGG
42401  TACCGCTGGC TGTGTCGCCT GTCTGGGGTG CTGGGGGCAG TCTGTGAGTA
42451  TCCAGTCGGG GAGAGGGGCC GGCCCCGCCG CGCATGCGCT CCTCGCCCTG
42501  CCCTGCCCCG CCCCGCCCCG GCGGCCCCAG GGGAAAGGAC CCGCTGGGGG
42551  TCGGGGGTCT GCCGGGCGCC TCCCGGGGCG GAGGAATGGC GGGGCCGCCG
42601  GGAGCCGGCG TCCTGGGGTT GCCATGGTTA CCCGCTCGGG CCTGGGCGCC
42651  TTGGTACCCC GGGCTGGGCT GGGCTGGCGC TTCTGGGAAC ATTCCCGGAG
42701  GGACCAGAAA CCCCAGGGCG GGGGGCGGC GGGGGCGGGG GGGCGGCGGG
42751  GGCGGGGGGG CGGCGGGGGC GGGGGCGGGG GTGGGGCACC GGCCTGGGGC
42801  ACGTGACTGA GCCCTCCCCC CGCTCCCCAG GGGCTTTTGT GAGACTTTCT
42851  CGGTGATGCT CACGGGCGC ATGCCCACCT GGCCCGTACT AAAGCGTCAA
42901  CTGTTGACTT GGGCGTAGGT GACGGCAGCC ACATTGCTAA CCTTTGGGCA
42951  AGGATTGTTT GTAAGGGAGG CGGGTGCACG GCTGGCTAGA TTTCTGGCAG
43001  GAAGCCACTG GCGGAAGTT TGCTGAGGGT CAGGTGGTGT CAGGGCACAG
43051  GTGGCCCCTG GGGCCGCGGG GCAGTGAGCT GAGGGCCCGG CCTCTCCCTG
43101  GGTCCTCTGT CCGCTCTCAT ATCTCCCCCG TTGCTGCTGC CTTAGCCGCC
43151  TGTCACCGGC CTTCCTCCCC TTCTCCGCAC GCATCCCAGT CACAGACCCT
43201  GACCTTAGGC TGCCAGGGAA GCTAGGCTCT TAAGCACAGC CAGAAAAGGA
43251  CAAAGAGGGA GGCAGGTCAG CTCCAGGAGT GAATGGAAGC CGTACAGCTG
43301  GCCTTCCAGG GAAAGACAAG TCTGTCTGAG TGATACCCTT TCCTTTCCTG
43351  TCTGCCCTCA ATCTTGTGGA TTACTGGAGT GGGCAAGGTC TTAGAGAATG
43401  TCTGTCGAGG ATGTCTGCAG GGTTTAAACA GTGCCTGCCT GGCAGAGAGG
```

FIG. 10, cont'd

```
43451  GCTAGCTCTG GGCCTGGGCA GGGCAGGCCC CATCAGCAAT CCTGCCAGAA
43501  GGACCACCTT TTCAGGGTCA CCTTGGGTTC CACAGCCTTT CCAGGTGGGT
43551  AGAGGGTGGA GGGAGGTTGA GGCAGGAGGG TGCTGGGCTA GGAGTGTGCT
43601  GCCCTCGCTA GGCATGCCCT TATCCAGAGG CAACGGATAC GGTAGGGCAG
43651  GCCCTACCCC CAAATCACAA AAAGGCCCCG AGTTTGTGTC ACTGCTCTTC
43701  AGGGCAAGTA CGCTTTTGAC TTTGTAGTAG AGACTGGTGG GTTTGAAGTT
43751  AGGCATTGGA TCCAGTCCTG TCATGTCTGG TTAGCTGTTT TCCCTGCAGA
43801  TTAGGGTGGG CAGTGCAGTG GGGTGACATG GTCAGTGGTG AGAAAGGAAA
43851  GGTCCTGACT ATGGCCTGTA GGCCACACCT CCTTCCTTCT TGGTCAGTGG
43901  CCCTGCCGAC TCCCAGATTT GCTGTGGAGT CTTACTCAGT TCTGTGCCTC
43951  TCAAAGTGAG GTACCTCTGC CTTTCCTGGG AGTTCCTGGG GCTCTGTTGG
44001  GTCTACAGAT GAAGCTTCAG GAGAAACTTG CGGCATTGCC CTGAGTTGTC
44051  AGTTGCATCT GCAGATTTTT GGGGGCATGG TTATGTGAAC ATCAAAATGC
44101  TGTATTACAG GGTAGAATGC AAAAATGCAG GGTGTTTTAG AGATGCGGCA
44151  GGAGTTCAGA CAAGGGTTGT GTGCCGGGCT GGTCCTTGGG TAAGGTTTTC
44201  CTCCTCCAGG GTGAGGGGAT CAGAGAGAGT ACCTGGAGAG GGTCTACCCT
44251  GGGTCCTAAG AGCATCTGGA GGTGATACCT TGGGAGGGGA CAGGATTGCA
44301  TGGTGACAGC CCCCTCACGT GGAAGATATC AGCATTGAGG CCCCCAAGTG
44351  GACATCCTCC AGCCCTTTAT TGCTAAAGGA TTCCTGGCTG GAGCCTGCTG
44401  GTCTGGCTTG ACACCTGGTC CTCCCCCAAG GCTGGCTGTG GGTTGGACAG
44451  CTGGGGTAGG GTTGGAGCTG GAGGCAAAT GCTGACTGCA GCAGGAAGCA
44501  CAGCCGAGCT GTCAGGTGAG GCCAGGCACA GCAGAGAGGC AGGGAGCCGT
44551  GTCACCCTTT GGGCACTCTG CTAGGACAGG CAGGCCCCTG TGTACCTGTG
44601  GTTCTGGAAC ACCTTGCTGT CTGAAGGCAG ATGTCTAAGG CTGTGCTGAG
44651  GAGCAGTGCA ACGCTTGAGT CCTTTGTTTT AGAAGGAGAC CCTGGGGGCC
44701  CATGAAGCAG TCCCATTGCA GTTCGGCTCA CTTTATCTGG CTTCTTTGCC
44751  TGCTGTCTGC ATAAGGTTAC CTGGGAAAAT GGAAAACAGC AGAATTCCAG
44801  ACCCAGGTGG AGGGATCAGG TGCAGAGGAG CTGCTGCAAG TTTAATGAGC
44851  TGGGTGCTAA TTGCTGCCTC CAAGGCCCCC CTCAGTGATG GCCTGGGCTT
44901  GCTCCCTGCC CAGCAGCCAC CTCCTTGGAC CTGCCTTGAA GGCTCCTGGA
```

FIG. 10, cont'd

```
44951   GTTCCTGGTG AAGCCAGGCT GCAGGCTGTG GGTGGAGGAG GGAGTTGGGT
45001   GCAAGAGACC CTGCTGGTGA GGTGCAGCTG GGAGGCGGGG CGTCAAGGCT
45051   GCACATCTGA GCATCAGAGA AGCCACGTTC TGGGGTGGAA AACGATGCCC
45101   CCTCCCCTTC CTGGCCTTAT GGCATTTCAG CGGTGGGTGG CTGGGCTGTG
45151   GGACTTGCTC ATGTGCAAGA GGAGAAACGG GTCTAGGAAG ATGAAGATAG
45201   CGTGCCAGTG GCACAGGGCT GGTGAGGAAG TTAGAGCTGG AACTGCTGCT
45251   CAGTCTTACC TGGTTCCCAT CTCTGTTCTG AGAGAGGCAC CCCTTGTCCC
45301   AACCAAAATC CAAGCCACAT TTTCTGAGTC AGAGGACTTC TTGTGTGGCC
45351   GGCCCTGTGA ATGGTGGCAA GTGACCCTTA CCGAAGGCTG AGTCTTGGGG
45401   GAGCACTGGC CTGAATCCTT GAGGGACATT CACTCTTTAA TCCTTCTTTA
45451   ATCCTAACCT CCCTTTGAGG TGGATATTGA TGTAGCTGGG GTCAGAGGGC
45501   CAGCTCCTCT GAGCCCTGAA ACGGGGAGAG GATGCTGTGA GATCCACCTG
45551   CCACCTTGCT GCCACCTTGC TGTGGGGCCT GGGGCAAGCA AGGCACTGCA
45601   CCTCTCTGCG TCTCCTCACC TGTCTCAGAC GATAGAGGGC AGGCTTCTGG
45651   GTGCTGTGAG AACTGTGTGC TGAGCATCCG CAGAGACTCT CGTCCTTTCC
45701   AGTCATCTCC CAAGGCCGCC TTCCCAGCGG GCTCCGCCTG CCTCCCTGCT
45751   GACTCCTGCC CGTGTCTCTT GTTTCAAGCT TGCGCGATCT CTGGCCTCTT
45801   CAACTGCATC ACCATCCACC CTCTGAACAT CGCGGCCGGC GTGTGGATGA
45851   TGTGAGTAAT GCATGGCCGT CCCACCCCGG GGGTCTTGCT GGTCGGGAAT
45901   CTGCTGGGCA CCTCCCGGGA CAGAGGAGTG GCAGGGGCCG TGGGAGTGGG
45951   CATCCTTGTG GTTGCCATGG CTACTGGCTC CAGCCTGGGT GCCTCGGGCA
46001   TGTGAGTTTC TGGCCACAGC ATGCGGCTTC TTCCCCTTCA TACCCCCACC
46051   ATGTTTAGTT TCCTAATGAG AGGTCAAGGC CCAGGGAATG CCCACCCCGG
46101   CCTTCATCCG GTGCAGGGGC AAGGCCATCA GTGCTCCAGA CATTTCTGGA
46151   GCATCCACTG AGACTGCAGA TGCCAAGTCC ACTATACTGG GGCCCTCGCC
46201   CTCTGGGAGC TCCCAGGACT GGGGTGGGGA AGGCTGTTCA TTGGGGCTGG
46251   CTGAGGACTG GGTTGAATGG TCTGCTGGGA GAGGGCACTC GAGCTCGGAG
46301   CTGTGCCAAA GATAGATGGG AGAGGCGGGT CGGAGTTGTC ACGGGAACCC
46351   GTGGTCAGAA CACCCTCATG TGCGTTCCAT GCCCACCTCC TGCCAGGGTT
46401   TCGCCATCCC ATCGGAAGGG AAGGCGGGGT GAGGGCAGGC CCGTGTGGCT
```

FIG. 10, cont'd

```
46451   TGGGGCACGT GAGAAGTGGC GGTGCACCAG GAATTGATGA GTGTCCTCAT
46501   GGGGCTTGGT GCCTTGAGGG GTACAGAGCT AGACGAGATT CAGGTCCCGT
46551   CCCCAGTGAC CTATGGCCAG TGGAGAGCCT CGGGGGCCTG CTGTGGTGGG
46601   GTCCTCAGTG CTTGTGCTGG CCAGTGGTGG ATAGGGAAGG GGGATGGACA
46651   GAGAGGCGCC CAGCCCAGCT TCAGGGGGTG GAGTCGGAGC CTGGCCGAGT
46701   TTGAAGTGGA AGGGCTGGCC CAGCACAGAG TGAGCCCGTG CTTGGAGGCC
46751   TGGTGTGTGG GAGGCTCGGG GCGGGTGCAG TGGTTAAGAG TTGTGAAGAG
46801   AGTGCCTGCC CCGGGCTTGG GGTGGCTCTT AGGTGTCCTG AGCCTGCATT
46851   TCTGTTACAC AGGCATAATG ATGGCACTTT TCTCCCAGGC CTGGGGACAG
46901   AAGGGCCTGG CTCAGTGTCT GCTAACTGAT TGTTATCCAT GCATAGAGAA
46951   TACCAAGACC ACAGCAGACA CCTTCCGTCA CCAGTGGCTT AGCTGTTCCC
47001   ACCCCAAACA TAGGGCTGGA TGCAAGGACT TGCTAAAGTT CTTCCTCCCC
47051   AGCGTGGGCT TCCCCTGGGT GTCCCCGGGC CTGGGGCCGG TGGCATCAGG
47101   TGTGTGGGCA GCTCTCCGTG ACTGTTTCGG GACTGCGTGG CTCCAGCTCT
47151   CTGCCTCCCT GGTGGGGCAG CCTTCCTGGT GCTGGTGCCA CTGACGGCTT
47201   TTGGTGGCCA TGGCGATAAT ACTAACAGCA GACAGAGGAC ACAGCTGCCA
47251   GTGCTCCATC TGTGGATGAA CCTGCCGCAG CGTTGTAGCA GTGCCATGAT
47301   GTGGGGTCCC CTTTCCTCCA TGTCACACAG GAGGAGGATA AAGGGAAGCA
47351   GAAGCCCAGG GGCTTCCCTC TAGGAGTGTT CAGTTCAGCT GGGGAGATGG
47401   GTGTGCAGGA GCAGCTGGGG AGTGCTGGAG TCTTCAGCAG AGGCTCTCCG
47451   AGGGGTACGA GCAGGTGCCC TGGAGCAGCC GGGCGGCTTC CCAGAGGAGG
47501   AGGGATGAGG GCAGGAGGGT GAGGGAGGTG GCATTCCTTA TGGCACTGGC
47551   ACTGGGGGCC GCCCTCATCC TCCTGGGATT GTCAGTCGCT GCTCTTCTCC
47601   TGCCCTGGTC CCTGCAGCAT GAATGCCTTC ATCTTGTTGC TGTGTGAGGC
47651   GCCCTTCTGC TGCCAGTTCA TCGAGTTTGC AAACACAGTG GCGGAGAAGG
47701   TGGACCGGCT GCGCTCCTGG CAGAAGGCTG TCTTCTACTG CGGGTGAGGG
47751   GTTGCTGGGC AGGGTCCCGT GACACAGTTC CCCAAAACCC CACTGACAAA
47801   ATAGGACCCA AAAGTCAGGT GAGGGTGGGC AGTGTATTCA GTTCCTCTCT
47851   GTGGAAGTGT AAACTGGGAT TGCCTTTGTG CACAGTGATT TGCTCATAGC
47901   TGCCAAAACG TGCCCCAGTG GTTCTGCGCC CAGGAACTCA GCTGTCGCTG
```

FIG. 10, cont'd

```
47951   TGCCGTAGTC ACTGGAAGGT TCAGAGGTAT ATGAGCATGT GTGGCAGCAT
48001   CCGTGCAGTG GAGAGAAAGT GGGAAGCGTC TGGAATTTTG GTCCGTCCAC
48051   TGGGAGTTGT TAACCAGATG ATAGTAGGTC TGTAGGACAT GTTTCTCTGC
48101   AGCCTTTCCG AAGAGTGGGT TCATCTAGAT GTCCTGACGT GAAGGGGGAG
48151   AAGCAGGTTG CAGAGCAGAA AATGTGGTTG CCCTCTAAAT ACACTTGTTA
48201   AAAATTTTCC CATTTCTAAC AATGAAATCA ATATGTAATA CTTCTCCTCT
48251   CAGTCATAAG AAGGAACTAA TTTCAGGATA AGCTTAATAC ACGGAAACTC
48301   CTAGAATAAT GCCTCTAGTG CATAGGAGGC TGGTGGCAGC TGTATTCATT
48351   ATTGTCTAGG TTATCTTTAG AAAGAAGTCT AGATGCAAGC TTGCTTCCCC
48401   TTCAGAGAGG CCCGGTAGTT TTGATGGTAA GAGCACAAGC CACATGCTTA
48451   GTTCTGGAGC CATCTTGTGC CATATCTAAA TCACGAAGAA CACAGGATCA
48501   CAAAGCTCTT ATCTACACGC AGTGTCATGT CCTTAGGGGT TCAAAAAACT
48551   GTATTTTAAA AATGCTAGAC ATCATAGAAA TTCATTCACA ATAATTTGGA
48601   ATATAGAACA ATGTTACTCG AAGCCCGCTG CCTGCTAATC TTCTGATGTG
48651   TGTGCTTCCT GTCTGCAGGC ATTTTTTAAA AGCCTGCTTT TAACACAGTT
48701   ATAACCATTA TGAATAAGTT TGTATCCTGC CTTTTTTCAC TTAGAGTAAT
48751   GATATAAGCA TTTGAACATC ACCACAGACT TTATAACATT CTTTCAATAC
48801   AGGAATATTC ATTCAGCTGG ATGTATCATG CTGTTCTTAA TTTCTTAACT
48851   GGTGTAAATC GAGGTGTGAT AAACATGTGT CTGCTAAAAC TTTTTCTGTG
48901   TTTATGATGA TTTCCTTAAT ATCTATTTTC AGGTGTGGAA TTACTGGGTC
48951   AAAGATTCTG ATCATTAAAA ATATTTTAAG ATGCGTGGCT ACGTTGCTTT
49001   CCAAAGAGGT CCCTTGAGTC TCTCCCCCGC CCCCACCCCA GCCCAGGGCT
49051   GCACACCACT TCACATTCGC ATTTATCTAT TTGTTATCTA AGAGGGAAAA
49101   ATATTTTCCC ACGTGTTTCC ATTGCATTTT CTGATATGAA AATTTTCGAG
49151   TTTACTTTTT AACCTGTGGG AACCTCAGTG TTCTGCTTAG CAAGTTCAGT
49201   GTGTTTTCTG TATTAAAGAT TTCATGATCC TTGGTTGTAT TTCCTGCAAC
49251   TATTTTTCCA GGCTCTTGTT TGCCTTTAAT TTTGTTTTTG TCAGAAGGTT
49301   CCCCGCCGTG GTCTTTTTCT TTGTAATTTC TATTATTATT TTATCATTTT
49351   GAAATTTTTT AACGACAGAA AAATCTCACA ACCACATGTC TACAAGAATG
49401   GAAACTGAGG TAGAATGCAA TTGGCCACGA GTCTTGTCCT CCTGCACAGG
```

FIG. 10, cont'd

```
49451  CAGCCTCCTC TAGGGAGGCG ACAGGACAGA GCGCTGGCCT CCAGGCTGCA
49501  GGTATCCTCC TGGCCCAGTT AGCCCAGGAA TTGCTGCTGG CCTGGAAATT
49551  CCAGCCAGGA TGGAGAATCA GCCCCGGGGA CGCTTAAGCC CCAGTGGACC
49601  CTGCCACCAG GTGACGCCAA ACTGCAGCAA GGTCTGGGCC GACCCCGCAG
49651  ACCCCGCAGC CTGCAGCCCT CCCATGATGA GACCCTGTGT TCCATGTGGT
49701  TGAATTCCAG GGACCTTACT TGTGGCGATG TGGCTGGTGT TACTCTATAA
49751  CTCAGAGCAT TTATTTAGTG CCTGTGGTGG TCAGCATTGT GTAGGTAACA
49801  TGACTGACCT CGGACAAGCT TTGATCCCCT CTCCGCGGTG GAGATTCCGA
49851  GTAACTTGCC CGCGAAGCTA GTAGGTCCTG GATGGGAAGC AGATTCTCT
49901  GTCACAGGCA CTTTCTGGCC AGTTTTTCTC ACAGTGAGGG CACTGGACCA
49951  TCTCGTTACT GTTTAGCTCT TTTTGGGATC ACAGACCCCT TCAAAAATCT
50001  GATGAAAGCT TTGGATCCTA TTCCCAGAAT GGAACAGTTT TACAGACAAG
50051  TTCAGGGCTG ATGAAGGACT TTCTGAAGCT GTGTCTCAGT TGATTTTTGG
50101  GGATCCTTCC TGTGCCCTGG GTGTCTAGGA AGGATGCTGG GCCGAGTCTG
50151  GGAAGCGGGG AAGGATGTGG TGGCTGTGGG GCCGGAGTGC CCCCTTGACC
50201  TCTGCTTTCC CCCCAGGATG GCGGTCGTTC CCATCGTCAT CAGCCTGACC
50251  CTGACCACGC TGCTGGGCAA CGCCATCGCC TTTGCTACGG GGGTGCTGTA
50301  CGGACTCTCT GCTCTGGGCA AAAAGTGCGT CTGCCAGGCC CAGCCCCTGG
50351  GCAGGGCCTT CCTCCCTCCG CCCCCCGAAG TCCTTCAGTG AGGAGGATCT
50401  GAGAGTGGCC CCTTTTAGCT AGTGGAGACC GAGGCAGAGG TCCCAGTAAC
50451  TCATTGGTGC CTCCAGGGCT CAGCTCGAGT GGGTGAAGAC AGAGGACTTA
50501  CAACACTTCT GCGTGGCCCA GTCTTGCCCC GTCACGGCCT GCAGCAAGGA
50551  TAGCAAAAAC ATGGCTGGTG GGAGCCCCTT CCCCTCCCAG GTCTGCACCG
50601  GGCATTGTAC TCAGTTGCCA CCCTCTCTCC TGCAGAGCCC AGACTGAGGC
50651  TGGTTCCTTC ACAGCCCAGC ATCCCAGGGA GCCTGGGCCA TTCTCAGAGG
50701  GGACAAGACA GGCCTTTGCC ACCCCAGCAG TTGTCTCTGG GGAAATCAGA
50751  ATGCCTGCAG GTCACACCTG GGTCACAGGG CAGGAACCGG GCAGTGGTCA
50801  GGAGGGCTGT GGGCATGGGG CTGGTGCTCC ACGTGACGCT GCCTCTCTCT
50851  CTCCCCAGGG GCGATGCGAT CTCCTATGCC AGGATCCAGC AGCAGAGGCA
50901  GCAGGCGGAT GAGGAGAAGC TCGCGGAGAC CCTGGAGGGG GAGCTGTGAA
```

FIG. 10, cont'd

```
50951  GGGCTGGGCG CCCCTCCCTC CCTGTCCCCT CTTCTGGCTC TGTGTGGGTC
51001  CAAGTGAGGC CTGGACTGTC CACGCTGAGG CACAGCCTGG AGAGGGGCCT
51051  TTGCACGTGT CCCTACACCT GGAGTCCTCT GCTCCTTTCT CCAGACTGGC
51101  TTAAGCCAGG AGCCACTGGC TGCTGGTGTG AGGGTCTGGG CTGCTGGACT
51151  TGAGGCAGAG CCTGCAGCAG CTGTGTGGAC ACTACCCAGC CCTACTCCTC
51201  TGCTGGGTGG GTCTGCAGAT CTCACACCAC AGACAGGGCT GCCTGTGACC
51251  TGCTGTGACC TGGGAGCAGC TTCCCCTGGA GATGCTGGTC CTGGCTTGAG
51301  GGGAGGGGCA AGTGGGACCC TGCCACCTGG GCACTGAGCA GAGGGACCTC
51351  CCCCAGCTCT CTTAGCAGGT GGAGCCCCAG GGCCTGGGAC AGCCTGCCGC
51401  TGCCAGCAAC CTCCCACTGC TGCCTAGGGT GCAGCGCCCA CTGTCACCCT
51451  GCCTTCTGAA GAAGCCCACA GGGCTCCTAA GGTGCACCCC GGTACCTGGA
51501  ACTGCAGCCT TGGCAGTGAC TGGACAGCTG GGTGGGGGAT GCTCCCTGCT
51551  GGCCCTGGGA ACCTTGGACA GGCCACCTCA AGGCCCCTCG GCTGCCCCTC
51601  CTCCCTGGGC CTGCTGGGGC CCCTAGGTTC TGCCCATCAC CCCCCGCCCC
51651  TGCTGGCCTT GGTGCTAAGG AAGTGGGGAG AGCAGGCTCT CCCTGGCACC
51701  GAGGGTGCCC ACCCTCTCCC TGGTGTGGCC CCGTCAACAT CAGCCACAGC
51751  CCAGCCCCAT TAGTGGGTTA GCGGGTCTGA CCTCAGCCCC ACTCAGGTGC
51801  TCCTGCTGGC CTGCCCAAGC CCTGCCCTCA GGGAGCTTCT GCCTTTTAAG
51851  AACTGGGCAG AGGCCACAGT CACCTCCCCA CACAGAGCTG TCCCCACTGC
51901  CCTGGGTGCC AGGCTGTCCG GAGCCAGGCC TACCCAGGGA GGATGCAGAG
51951  AGCTGGTGCC CAGGATGTGC ACCCCCATAT TCCCTCTGCC CTGTGGCCTC
52001  AGCCCGCTGG CCTCTCTGAC CGTGAGGCTG GCTCTCAGCC ATCGGGCAGG
52051  TGCCTGGTCG GCCTGGCTT AGCCCAGGTG GGGCTTGGCA GAAGCGGGCG
52101  GGTGTGGAAG ATATTCCATC TGGGGCCAAC CCCAGGCTGG GCCTGCGCTG
52151  AGCTTCTGGA GCGCAGGTAC TGGGTCTTGC TAAGTGAACT GTTTCCCAGG
52201  AACACCTCTC GGGCCCATCT GCGTCTGAGG CTGGGAGTGG CATCTGAGGC
52251  CGGGAGTGGC ATCTGAGGCC AGGAGTGGCA GGCTGGTGGG CTGGGCGTGG
52301  GGTTTTCTGG GCCCTGCCCA GTACTGCCCT GGGGACTTGG TGGGCTCCTG
52351  GGTCAGCAGC ATCCCACCCC TGGGAGTCTG GCCAGCTGAG CCCCAGGGTG
52401  GCAGGGGCAT TATAGCCTGG TGGACATGTG CCTTCAGGGT TCCTCCGGGG
```

FIG. 10, cont'd

```
52451   CCACCTTCCT  CAGGCCAGTG  CTGGGTTCAA  AGGGCTGTGT  GTGTGTGTGT
52501   GTGTGTGTGT  GTATGTATAT  GTGTGTGGGT  GCACACATCT  GTCCCATGTA
52551   TGCAGTGAGA  CCTGTCTACC  TCCCACAAGG  AGCAAGGGCT  CTGCCCGCCC
52601   TCTGCTCATT  CCTACCCAGG  TAGTGGGACC  CCGGGCCCCC  TTCTGCCTGG
52651   CTTGCCTGCT  TCTGCCCTTT  CCAGAGGGGT  CTCACTGACA  GCCAGAGACA
52701   GCAGGAGAAG  GGTTGGCTGT  GGATCAAGGA  AGGCTGCCCC  TGTACCCTGT
52751   GGGGAAATGG  TGGGTGCATG  GCTGGATGCA  GAGGTGGAAG  GCCCTGGGCC
52801   ACAGGCGAGA  GTGGGCGTGT  CACCTGTCCC  AGGTTCCCAG  CAAGTCTGCA
52851   GCTGTGCAGT  CCTGGGGTCC  CTGACCCTGT  CGCCCAGGGG  GCGTGCTGTC
52901   CAGCAGGGGC  CCTGCCTTGC  AAGGAACGTC  TCTTCCGGCG  GCTGGGCCGC
52951   TCCTGCCTGG  TCTGGGCTGT  GTGTGGCGCC  CTTTCCTTCT  TGTTTGTTCC
53001   TCTGTGTTCT  GTGTGCGTCT  TAAGCAATAA  AGCGTGGCCG  TGGCTCGCGT
53051   GCCTGCCCTC  TGCTCCCTTC  TGCCTTGGTG  CCTGTGTGTG  AGTGTGGAAG
53101   CCAGGCAGGA  GCCGCTGGCC  CAGGAAATAA  CTACAGGTCC  TGTCCCGAGG
53151   CTGCCCCCAG  CATCCCAGAC  AAGGAAAGTG  ACCTGCCCAA  GGTCACACAG
53201   CTAGAAAGAG  CCTGTTAAGG  GTGGGCCTCG  CAGTGGGCTT  CCCCTCACTG
53251   CAGCCTTTTC  CCTGCCCTGC  TTTTGCTATG  GATCAGCAGT  CAGTGGCCCT
53301   GGCAACCTTG  GCTGGTTCGG  GTCTAGCCTG  GCTGCTGTGG  GGGCTCCTGG
53351   AGTAGACCCC  ACTCTTTTCC  TCGCTAGGAC  TACGGGTCCA  GTTCCTTTAT
53401   TTTTACAAAA  GGGTGAACAC  AGTTTGCAGA  TAGGAGCTGC  CTGTTCCCAG
53451   AGGTTGGGCT  GGGGCAGGAG  GAAGTGGCCA  CGCCAGGTCC  TTTGCCCTGG
53501   CTTTTTTTTT  TTTTTTTTTG  GCAGGGGGTG  GGGACGGAGT  TTCACTCTCG
53551   TTGCCCAGGC  TGGAGTGCAA  TGGCATGATC  TCAGCTCATT  GCAGCCTCCA
53601   CCTCCCGGGT  TCAAGCAATG  CTGCCTCAGC  CTCCCAAGTA  GCTGGAACTA
53651   CGGGTGTGTG  CCACCACACC  CAGCTTTTTT  GTATTTTTA   GTAGAGACGG
53701   GGTTTCACCA  TGTTGGCCAG  GCTGGTCTTG  AACTCCTGGC  CTTGGGTAAT
53751   CCACCTGCTT  TGGCCTCCCA  AAGTGCTGGG  ATTACAGGCG  TGAGCCACTG
53801   TGCCCGGCCT  GCCCTGGCTT  TTTAAGTCCA  GGATGTTCCC  TGTGGTGCCC
53851   ATAAGACTTG  TGAGGGCAAA  GCCGGGTCTT  CCTTGCACAG  CCAGATGCCA
53901   CCAGATCAGA  GCGCGATGAT  ATGACTACGT  TACTTGGCTG  CCTCCAGCCC
```

FIG. 10, cont'd

```
53951   TGTCCTCTCA GTCCTCCCCG TAGCCTTCTG TGGGGCGTGT CCTTCACGCA
54001   AGGGAAAGGG ACTAGGCCTG AGGTCACCCA GCAGGGCCGT GTCCCTGGAT
54051   GCAGGGTTGT ATGCACTCCT GCGGCCCATG GCTACGTGCA GCACTGTGGG
54101   CTGCCTGGGC TGGGGCTGTG GCTGGACAGC AGTGCTACCT GTCCCGAGCC
54151   AGGGGCACCC GCTGCTGAGG CCCCATCACA CTGCTCTTCC TGTGCTCTGG
54201   CTGGTGGCAG GGATGACTGC TGCCTCTTGG TCCCAGGGTG CAGGTTTGTA
54251   GCCAACACAG AGGCCCAGCC ACTGGGGGTT TGGCCCCCTC CAGGCGGGGA
54301   CCTTGACCTA GCGCAAGAAG GACCTTCTCC CCATGCGGAA GAAGGACTCG
54351   ATCTGCTCCA GGGACCGTCC CTTGGTCTCG GCACACAGC AGCCTGTGAA
54401   CACCAGGCTC ACCAAGCAGA TGGCCGCGAA GAAGAAGAAA GGCACCTGGA
54451   GGCCGAAGGT GCTCTGCGGG TGAAGAGCGG GGCCGGGTCA CAGGGAGAAG
54501   CTCCAGGGTC CTCCTGCCCC AGAGGAGCTC GTGGGCGCTG CTGGTAGTGA
54551   CCAGCCCTGT GGGGCCTTCA TCTGGTCCTT CCTGTGTTCA GAGACCGCCC
54601   CCCCACACCA GGGCTCCCCC ACTGTCCCCA GGACAAATCC GAAGTAGCCC
54651   TTGAAGTCTG CATCCCGTCT GCCCCTCGGC CTTCCTCAGG GGCTGGGCCC
54701   TCTGGCGTCA GCTCAGGTAC CCCCTCCACA CCCCCTACCC AGCGCTGGCA
54751   TCCCAGCTGT TCCATGCCGC GGCCTGCAGG AGGCCCGCCC TGCAGCCTGG
54801   TGGGCACGCA GGTTCTTCTT GGACCCTCTA GGCTGATGGA CTCACTCTGG
54851   GTTGCCTGCC CTCCCCCAAC CCCCCTGCCC TGACCACTGC AGGGACAGCT
54901   TAGGCGCTGG CCTAGGCTGC CCTAGCCAGC TTCTCCCTCA TGGGAACTTA
54951   CTCTGGGCCT CACAGATTCT GGCTGGTCAC AGGGCCCGTA GTTTTGAACC
55001   AGGAGGCAGG GGGAGTGGGT GGGGTTGAGG GGGGAGTGTG GCTGCTGCTG
55051   AGACCCAGCG CCCAGGAGGA CGGGAGATGA GGCACGGTGG GGAGGTGGCT
55101   TCCGGGGCCC CTGGCAGGGT CCTGGGCCAT GTCCTGCCCT GGCCCAGGAG
55151   GTAACCTGAC TTCCCAGAAC AGTTGCCTAC GCCCGTTCCT GTTTCTTATA
55201   ATGAAGAGCG TTTGCTAGGC TATCACGTGA CCACTCTGGG GTCTCTGAGT
55251   TCAGGGGGTG TGTGCTCATC TCCTAGGGTC ACTGAGAGTT AGGGTCCTGA
55301   CAGCAGGCCT TGGCACAGCC CCTGGCACTG AGAAGGGTCC TGGCCAGTCA
55351   GCGAGGGCCT AGGGGCCTGG GGCCTGGGGC TGAACACTCA CCACCACTGG
55401   CAGGAAGGAC TTGGTGAGGA CGAAGGCGGT GAGCCAGCTG GCCAGCACGC
```

FIG. 10, cont'd

```
55451  AGAGCCCTGA GGCCACGCCA CGGGCACGCA GGGGCAGGAC CTCAGACATG
55501  AGCAGCCAGG TGATGGGACC CCAGCCCACG GCGTAGCCTG CTCGGAGGAG
55551  GAGGCAGGTT CAGGCCCTGT GGGGTGACTG GAGGCGGCTG TGTCTGTCTC
55601  CGCTGAGCTG CTGGAGACCC CCCTCTCCAG CCACCCCAGA CACATCACCC
55651  ATCCCTTAAC ACCCAAGACA GCCTGCCCCT CTGAGCCACC ACCACACCTA
55701  CCCATGATGA AGAGCATGGT GGCCAGCAGG GGCACCAGGG TGAGGTAGCC
55751  AGCGGGTGCT GCCAGGGGCT GCGCCAAGTC CCCCAGGAC TCGCTTTCCA
55801  GGCCCGCAGT GCTGTTGGGG CTCAGAGGCC TGGGGCCAAA GTGGATGTAC
55851  AGCCCCAGAG TCAGGTTGGC AGCAAACATG ATGGCCGCTG TGGACAGACA
55901  GGTGGCCTCG TGGGCCAGG ACCCTCTGAG CCAGCTGTTT CTCTCAGAGC
55951  TCCTTCTGCA GAGCCCCTTG ATACTTGCGT GGTCCAGCTC GTGTCTGGGA
56001  CTAGAGACCC CCAGCAGGGC AGCAAGCTCT GTCTCCAGCC GCGTGTTAGG
56051  CTCCCACCGT GGAGTGTCAC AGCCAGTGTG TCCACTCGGA GCCCCAGCGG
56101  ACCTTTCTGG ACCACTGGCC TGGGCCAGGG CCCTGCCGAT GCTAGGGAGG
56151  CAGGTGCTCT GCAGTTCCCA GCCACACAGC CCCACCCCGA GGCAGGCCTG
56201  CACACCCAGC CCAGCCCTGA CCCATGCGGA GGAGTGGGGC AGGAGGGCTG
56251  CCTGCAGGGT GCTTACCTGA GACGAAGAGC AGCACCTTGC GGCCTGCGAG
56301  GTCCATGGTG AGGGCGGCGA TCAGCACGGA CAGGAGCCGC ACGGCCCCAA
56351  CGATGGCTGC GTCGTCCTTG GGGGCTATC GGGGGGAGAC CACCAGGGCT
56401  GAGGGACCTG CCTGCTGTTC CCATCCCCCT CCAGGACCCA GCTTGTCCCG
56451  GCAGGCATTG CAGGGGCTCA GGCCAGCAGC TCAGTGCAGT ACTGAGTGGC
56501  CTGGCACCTG CAGCGTGCTG GGCATCTATA CTGTCCGAGC CTATGGGGCT
56551  CCTGGGCAGG GACACATCTG CTCTGCCCAC CACTATGCCC AGCTGGCACA
56601  GAATCCAGGC GTGATGATGA CTTGCTGAAC CGTGCTGTTA CTAATCTTCA
56651  AATCTCATCT CACTTTGAGC CTTGGGGCAG GCTGATGGAG ATGTGCTGCT
56701  ATCTTCATCT TGCAGAGGAG GAAGTTGAGG TTCAGAGGGG AAAGTGACTT
56751  CCCTCATTAA GTGGCAGATG CCACAGGGCT CTGAACCTGG GGTCTGTGGC
56801  CTCAAGGGGT CCACGTTTCT ATAAAGCTGG TTTCCTTTGT AATCCCATGT
56851  ATTTTATTTA ATTTTTAAAA TTTCTATATG TTTTTAGAGA CAGGGTCCTG
56901  CTCTGTCACC AGGATGGAGC GCAGTGGTGA GATCGTGGCC ACTGCAGTCT
```

FIG. 10, cont'd

```
56951   CACACTCCTG GGCTTAAGTG ATCCTCCCGC CTTGGCCTCG TGTTGGGATT
57001   TTGCCAGTAT TTTATTTTAA AACACTTAAG CTTATCTTAA AAACATTCTG
57051   AGAACAGGTG AAGGCACTGG AACTGTCTCC ACAAGGCCCA GATCTCAGAT
57101   CTTGCTGTGG CATCCCTGAC ACCCGGCACA GAGCAGGTGT GGGTAAGACC
57151   AGGGGTTGGG TAAGTGCAGG AGCAGGCCCT GCCTCCCCTG CCCTGCCAGC
57201   CTCCAGGGGA CCCCGTGGGT GGGCGCCGGC CGGGGCTGGG CTCTCACCAG
57251   CAGGACAGCG GTGCTGTCGA AGATGGACTG CAGGTAGACC AGGATGGGCG
57301   TGATGCCCGT CAGCTGCTGC AGGAGGCGCA TCAGCAAGGC CACGGTGATG
57351   GGCCGGCACA CGTGTGGGGC CCGTGCCTCA GCCCACGATA CTCGGCTGCT
57401   CTGAAACACA AGGCCGCCGC TGAGGGCGTT GGGCCAGCCT CTCCAGCAGG
57451   CGCCATCCTG CCCTGGACCG CCAGGGGTTG TGTGGGAGAC CTCCTTTTTC
57501   CCTCCTCCAG GAAAGAACCA GCTTACCAGG CCACCCAGGC TCTGGGAACA
57551   GCCCCCCACC CCAACCCAGG CACTTGGATT AGTGGGAACT ACTGTGGTCC
57601   TGTCTTCCAG GAAAAGCCTC CACGGCCACA CACAGCTGAA GTGCTGGAGG
57651   TGGGCCTGCC CGGTTCGGGC GCACACCCTC CTGCACCTGT CTCCGGACGT
57701   TGTCCTGGAT CTGCTCGAAC TCCCAGTGGA CATCGACGTC CGTCCCACGC
57751   AGCCAGGCCA GCGCCCGCAG GGCCTCTTCG TCCCTGCCCC GAGAGAGCAG
57801   GAAGCGCGGC GAGTTGGGCA TGAAGCTGAG CAGCAGGATC ATGATGAGCA
57851   CAGGCGCCTC CCCGGCCACA GCCAGCCAGC GCCACGGCAG CAGGAGGCCT
57901   GGGGGCGAGG GGTGGGTGAG GGGCCAGGTC CAGGCCTGGT ACAGCCCCTT
57951   CCCTCTGGAG CCTCTGAATA ACCTCATCTG CCCTTCAAGG TCTAGTCCAA
58001   GGGCCATCTC CTACAGGAAG CCTACCCTGA TTGCCCCAGG CAGGGTGGGG
58051   CTGCAGGGAT TGCTCAGCCC CTGGCACATA GTGGGAAGTC CTTGGAAAGT
58101   CTTAGGGCCA GGGCAGGATG AGGAAGGGGT AGGTTGGGCA GGCAAGGCCC
58151   TAGGCCTCCA CCCAAGACCT CCACGCCCCC TCAACTGAGC AGCTGCACGC
58201   ACTGTGATTT CTTTTCTATC TGGACTTCCC ATCTGAGATG GCATTTGATG
58251   GAAGCTTTCT GCCGTTAAAA GATAGTCTGG CGACTGTGGG TCCAGGAGAA
58301   GCCCTGGCTG CCCCAGCTAG AGACTGGGCC TGTGGCTAGA GGGGCAGGCC
58351   CTGCCTGGAG GTGCCCAGCA AGGTGCTGAC TGAGTGGGGC CGGGATGCCA
58401   GATCTCTTGC CTCTCAGCCC AGGATCTGTT CTGGGACAAA TCATTCCCTT
```

FIG. 10, cont'd

```
58451   TCCACCCACG TCTACCTTGG CGGCACCCAC CCCTCCCACC AGCCTGCACA
58501   CAGGAGTGCG GGGCCATACT TGCCAAGGGC GTAGAGGGAC AGGGATCCGA
58551   ACACTGCCAT GAGCTGGGGT GTGGCCCCCA GAGCCCCACG AACGCCTGGG
58601   GGAGCAATCT CAGACACGTA CACCTGCAAG ACACAGCCGC CGCACCAGGT
58651   TTTGCTGAAA ATACTGGTTC CTAGGCCCGG CCGAGATGGG AGAGTCAGCC
58701   CCTGTGAACC CCGGAAAGTG GGAAGTGGAG GCTTTCTGGT GGGGCTGAGT
58751   CCTGGTCATG ACTCACTGCA AGACCTTGGG CGGCCTGCCT GATCTCTCTC
58801   TGTCCTCAGT TTCCCTAACT GTGACGTGGG TGGAAGTACG CAGCTCGGAA
58851   ATGGGCAGCA TGACGCTGGG AAGGAGGCCC GAGGGCTCCC AGGCTTCAGG
58901   GCTGAGCAGG TGAGTCCATG CCTCCCAGTG AGTTTTGTCT CCTCTGCTGG
58951   GCTCACCACC AGGCCCCGTG TGGAGTACCA CATAAGATAA GAAGGTCCCG
59001   GGGAGGGTGT AGGGCAGGGA CTTCCCTCTC CTACCCATTG CTCAATGCGG
59051   ATTTTCTCCA ATTGAGTAAT ACATCTGACC GGTCAAGAAA CGGGGTAGAA
59101   GGCTTGGAAA GTCCAGAGTG GGGGCAGCTG GGGACCTGGA GACAATTTCC
59151   CCCAAATTAG CTGCCCTGCT GGGGGTGAGC TGAGGCGCCC TGGGCATCCG
59201   CAGGGAAGGC AAACAATTCT CATTGCCCAG AAGGCATGGA GGCTGGGAGG
59251   CCTTAGTCAG ATGGAGGCTC AGCACCAATA CAGACGCATT GGGGCGCCTG
59301   GGTGGGAAGG CCTGGCCTTA CCGGGATGCA GGCAGCTGTG AGCCCCCCGG
59351   CGAAGCCCGT CAGCGTCCTT CCGAGCAGCA GCATCCAGAG GCCGTGCGCA
59401   CCCGCCATGA GCGCATAGCC GGCCGCCGAC GGCACAGCTG AGAACATGAT
59451   GCTCAGCTTC CGGCCCAGGA GGTCGTTGAG GATCATGGCA CTCAGGCCTC
59501   CGGCCGCTGC TCCCAGGGTG AACACGGACT GCAGGGGAAG GGGGTGCAGG
59551   GCAGATATGT CTGGGCACTT GGCACCCCAG TCTCATCAGA GTCCAGGGAC
59601   AGCTTCTTCC CTAGGCCGAC CCCAGGAGCT GGTCAAGCAC TTGGCCAAGT
59651   CAAGCACTTG AAACAGGGAG CCTCCTGTCT TCAAGGAACA GCCATTTGTT
59701   AGGGATGCCC AAACGGGGAA TTCTGCTCTA AGGAAGAGGT GCTGCGCCAC
59751   ATATCCACAG TGGTTCTGTC CAGCCTGATG TTTAAATGTC TAATATTTTA
59801   ATACAGGAGA ATTCTGTGAC TTGAAGGTAC TGGGCTTTAA GATTTGGAGG
59851   TTCTTAAGTT CCCTGTACAG CAGCAACTGG GACCCCTCT  GGACTCTGCT
59901   AACTGGTAGT GGGACCTGGG CACATTGCCC AGCCTGTCTG CACCTCAGTT
```

FIG. 10, cont'd

```
59951   TCTTCAGCTG TCTTATGGGG AGAGCGCAAG TTCTACCTCG TGGCGTTGGC

60001   CCTGAGAATC AATGAACGTT CAGTGCCCAA CACATGCCTG GCACATAGGA

60051   AGTGCTCAGT AAACCTTGGG AATTTTTATC TTAACTACTA TGTTAACAAC

60101   TCTACATATG AGGCTATTAA GATTATAATT TTAGACTCTG GGACTCTGGG

60151   ATC
```

METHODS AND COMPOSITIONS FOR DETECTING VARIANT ADAMTS13 GENES

The present application claims priority from provisional application Ser. No. 60/312,834, filed Aug. 16, 2001.

The present application was funded in part with government support under grant number RO1 HL39693 and RO1 HL62131 from the National Institutes of Health (NIH). The government may have certain rights in this invention.

FIELD OF THE INVENTION

The present invention relates to a disintegrin and metalloproteinase containing thrombospondin 1-like domains (ADAMTS), and in particular to a novel ADAMTS13 protease and to nucleic acids encoding ADAMTS13 proteases, and to methods of using the same.

BACKGROUND OF THE INVENTION

Thrombotic Thrombocytopenic Purpura (TTP) is a disorder of the blood characterized by low platelets, low red blood cell count (caused by premature breakdown of the cells), and neurological abnormalities. The sharp drop in the number of red blood cells and platelets in the blood is associated with severe problems affecting the kidneys and brain, along with fever and bleeding. Purpura refers to the characteristic bleeding that occurs beneath the skin, or in mucus membranes, which produces bruises, or a red rash-like appearance; the bleeding can be catastrophic. The neurological symptoms associated with this disease include headaches, confusion, speech changes, and alterations in consciousness, which vary from lethargy to coma; other symptoms include development of kidney abnormalities. These symptoms can be very severe, and fatal.

Although TTP-like disorders have been associated with various medications, bone marrow transplantation, pregnancy, HIV infection, and autoimmune disease, most cases appear sporadically, without an obvious precipitating factor. This disease is seen most commonly in adults from 20 to 50 years old, with women affected slightly more often than men. In most TTP patients, the onset of the disease occurs in otherwise healthy individuals, and there is no history of a similar condition in other family members. However, in a smaller set of individuals, there is evidence suggesting that the condition may be inherited. This evidence is rare reported cases of familial TTP, where the disease begins early in life or sometime shortly after birth, with multiple recurrences and thus a chronic relapsing course; other family members may also be affected. The disease strikes about 4 out of every 100,000 people.

Current treatment consists of infusion of fresh frozen plasma with or without plasma exchange or plasmapheresis. In plasmapheresis, blood is withdrawn from the patient as for a blood donation. Then the plasma portion of the blood is removed by passing the blood through a cell separator. The cells are saved, reconstituted with a plasma substitute, and returned to the patient as a blood transfusion. In TTP, this treatment is repeated daily until blood tests show improvement. People who do not respond to this treatment, or who have frequent recurrences, may require removal of the spleen.

Prior to the development of modern treatment protocols, fatality during an acute episode of TTP was greater than 90% (Rock et al. [1991] N. Engl. J. Med. 325, 393–397; George [2000] Blood 96, 1223–1229). Plasmapheresis has improved the outcome of this disease so that now 80 to 90% of patients recover completely; however, fatalities still occur. Although most incidents of the disease are acute, when relapses occur, the disease can become chronic. Despite marked improvement in treatment outcome, the molecular pathogenesis of TTP is still unknown and the specific plasma factor(s) responsible for the acute onset of this disease, or recovery following treatment, remains to be identified. Because the cause is unknown, there is no way to prevent the disease.

Thus, what is needed are improved methods to treat the disease, to decrease fatality and to decrease the appearance and/or severity of the consequent debilitating symptoms associated with the disease. What is also needed is a method to determine the susceptibility of individuals to the disease, in efforts to prevent the appearance and/or severity of symptoms. What is also needed is a method to identify those individuals for whom the disease appears to be genetic.

SUMMARY OF THE INVENTION

Thus, it is an object of the present invention to provide methods to determine the susceptibility of individuals to TPP, and to identify those individuals for whom the disease appears to be genetic. It is a further object of the present invention to provide improved methods to treat TPP.

These objectives and others are met by the present invention, which in some embodiments provides a method of identifying subjects at risk of developing TTP disease comprising: providing nucleic acid from a subject, wherein the nucleic acid comprises a ADAMTS13 gene; and detecting the presence or absence of one or more variations in the ADAMTS13 gene. In other embodiments, the method further comprises the step of determining if the subject is at risk of developing TTP disease based on the presence or absence of the one or more variations. In yet other embodiments, in the method of the present invention the variation is a single nucleotide polymorphism, or the variation causes a frame-shift mutation in ADAMTS13, or the variation causes a splice mutation in ADAMTS13, or the variation causes a nonconservative amino acid substitution ADAMTS13; preferably, the variation is selected from the group consisting of the mutations shown in Table 1. In some embodiments, in the method of the present invention, the detecting step is accomplished by hybridization analysis. In further embodiments, the detecting step comprises comparing the sequence of the nucleic acid to the sequence of a wild-type ADAMTS13 nucleic acid.

The present invention also provides a method of identifying subjects at risk of developing TTP disease comprising: providing a blood sample from a subject, wherein the blood sample comprises an ADAMTS13 protease; and detecting the presence or absence of one or more variants of the ADAMTS13 protease. In some embodiments, the detecting step is accomplished by an antibody assay.

The present invention also provides a kit for determining if a subject is at risk of developing TTP disease comprising a detection assay, wherein the detection assay is capable of specifically detecting a variant ADAMTS13 allele. In some embodiments, the detection assay comprises a nucleic acid probe that hybridizes under stringent conditions to a nucleic acid sequence comprising at least one mutation selected from the group consisting of the mutations shown in Table 1.

The invention further provides a kit for determining if a subject is at risk of developing TTP disease comprising a detection assay, wherein the detection assay is capable of specifically detecting a variant ADAMTS13 protease. In some embodiments, the detection assay comprises an antibody capable of binding to an ADAMTS13 protease selected from the group consisting of wild-type proteases and proteases comprising at least one amino acid mutation shown in Table 1.

The invention also provides an isolated nucleic acid comprising a sequence encoding a polypeptide selected from the group consisting of SEQ ID NOs: 2 and 4 and variants of SEQ ID NO:2 as shown in Tables 1 and 2. In some embodiments, the sequence is operably linked to a heterologous promoter. In further embodiments, the invention provides a vector comprising the isolated sequence. In yet further embodiments, the invention provides a host cell comprising the vector. In some embodiments, the host cell is selected from the group consisting of animal and plant cells; in other embodiments, the host cell is located in an organism.

The invention also provides an isolated nucleic acid sequence comprising a sequence selected from the group consisting of SEQ ID NOs: 1 and 3 and variants of SEQ ID NO:1 as shown in Tables 1 and 2. In some embodiments, the invention provides a computer readable medium encoding a representation of the nucleic acid sequence of claim 22.

The invention also provides an isolated polypeptide comprising an amino acid sequence selected from the group consisting of SEQ ID NOs: 2 and 4 and variants of SEQ ID NO:2 as shown in Tables 1 and 2. In some embodiments, the invention provides a computer readable medium encoding a representation of the polypeptide of claim 24.

The invention also provides a method of identifying subjects at risk of carrying an allele for TTP disease comprising: providing nucleic acid from a subject, wherein the nucleic acid comprises a ADAMTS13 gene; and detecting the presence or absence of one or more variations in the ADAMTS13 gene. In other embodiments, the method of the present invention further comprises a step of determining if the subject is at risk of carrying TTP disease based on the presence or absence of the one or more variations.

The present invention also provides an isolated nucleic acid comprising a sequence encoding a polypeptide CUB domain of ADAMTS13; preferably, the nucleic acid comprises SEQ ID NO: 5. The present invention also provides an isolated polypeptide comprising a CUB domain of ADAMTS13; preferably, the polypeptide comprises SEQ ID NO: 6.

The present invention also provides a method of treating a patient with TTP disease, comprising administering a therapeutically effective amount of ADAMTS13 protease such that the symptoms of the disease are alleviated, wherein the ADAMTS13 protease is selected from the group consisting: recombinant ADAMTS13; synthetic ADAMTS13; mutants, variants, fragments, and fusions of recombinant ADAMTS13; and mutants, variants, fragments, and fusions of synthetic ADAMTS13.

DESCRIPTION OF THE FIGURES

FIG. 4 shows the results of Northern and RT-PCR analysis of ADAMTS13. Panel a shows a human Northern blot hybridized with a probe spanning exons 11–13 and part of exon 14. An ~4.7 kb message can be seen specifically in the liver and a truncated, ~2.3 kb message is faintly visible in placenta. Panel b shows a panel of cDNAs derived from human tissues screened by PCR for the presence of exons 11–14. Strong signals were seen in the liver and ovary, with weak expression also evident in kidney pancreas, spleen, thymus prostate, testis, intestine and peripheral blood leukocytes. No expression was detected in heart, brain, placenta, lung or muscle.

FIG. 5 shows the nucleotide sequence of an ADAMTS13 cDNA which encodes a long form of ADAMTS13 (SEQ ID NO: 1). This sequence includes ambiguity codes for all single nucleotide polymorphisms. The IUPAC ambiguity codes are as follows:

M=A or C
R=A or G
W=A or T
S=C or G
Y=C or T
K=G or T

FIG. 6 shows the amino acid sequence of a long form of an ADAMTS13 (SEQ ID NO:2) encoded by the nucleotide sequence of FIG. 5. This sequence contains one of the two possible amino acids for regions where Single Nucleotide Polymorphisms (SNPs) change an amino acid; the SNPs and encoded amino acids are shown in Table 2.

FIG. 7 shows the nucleotide sequence of an ADAMTS13 cDNA which encodes a short form of an ADAMTS13 (SEQ ID NO:3). This sequence includes ambiguity codes for all Single Nucleotide Polymorphisms (SNPs). The IUPAC ambiguity codes are as indicated for FIG. 5.

FIG. 8 shows the amino acid sequence of a short form of ADAMTS13 (SEQ ID NO:4). This sequence contains one of the two possible amino acids for regions where Single Nucleotide Polymorphisms (SNPs) change an amino acid; the SNPs and encoded amino acids are shown in Table 2.

FIG. 9 shows the amino acid sequence (panel a, SEQ ID NO:5) and the nucleotide sequence (panel b, SEQ ID NO:6) of an ADAMTS13 CUB domain.

FIG. 10 shows the nucleotide sequence of an ADAMTS13 gene which encodes a wild-type ADAMTS13 (SEQ ID NO:7). This sequence includes ambiguity codes for some Single Nucleotide Polymorphisms (SNPs). The IUPAC ambiguity codes are as indicated for FIG. 5.

Figure 11:
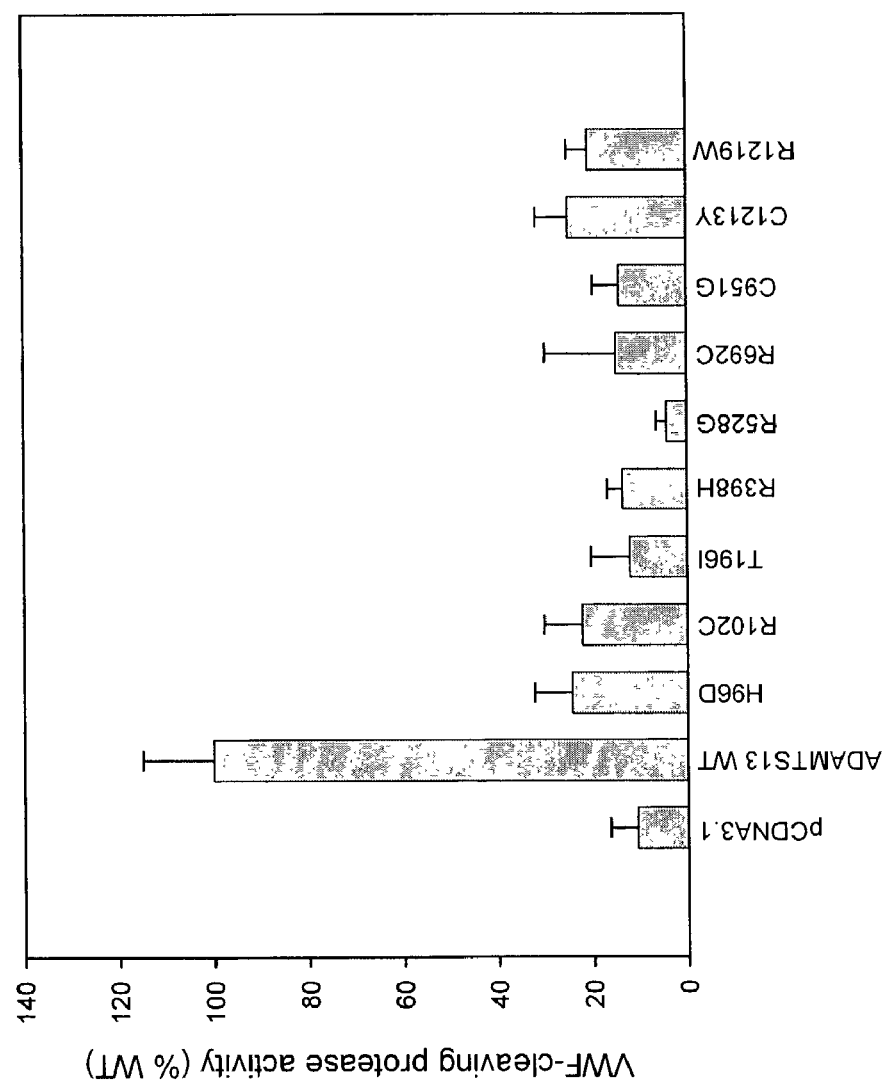

FIG. 11 shows the VWF-cleaving protease activity of ADAMTS13 mutants. VWF-cleaving protease activity was measure in conditioned media of CHO-Tag cells transfected with wild-type (WT) and mutant ADAMTS13 constructs. Activities are represented as the percentage of the activity of wild-type recombinant ADAMTS13.

DEFINITIONS

To facilitate an understanding of the present invention, a number of terms and phrases as used herein are defined below:

The term "thrombotic thrombocytopenic purpura" or "TTP" refers to a disease characterized by intravascular destruction of erythrocytes and consumption of blood platelets resulting in anemia and thrombocytopenia. Diffuse platelet rich microthrombi are observed in multiple organs, with the major extravascular manifestations including fever, and variable degrees of neurologic and renal dysfunction. Purpura refers to the characteristic bleeding that occurs beneath the skin, or in mucus membranes, which produces bruises, or a red rash-like appearance.

The term "ADAMTS13" refers to a protein encoded by ADAMTS13, a gene responsible for familial TTP. ADAMTS13 has been identified as a unique member of the metalloproteinase gene family, ADAM (a disintegrin and metalloproteinase), whose members are membrane-anchored proteases with diverse functions. ADAMTS family members are distinguished from ADAMs by the presence of one or more thrombospondin 1-like (TSP1) domain(s) at the C-terminus and the absence of the EGF repeat, transmembrane domain and cytoplasmic tail typically observed in ADAM metalloproteinases. It is contemplated that ADAMTS13 possesses VWF (von Wildebrandt factor) cleaving protease activity.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. An example of a protein domain is the CUB domain in ADAMTS13, which has been identified in a number of developmentally regulated proteins.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

In particular, the term "ADAMTS13 gene" refers to a full-length ADAMTS13 nucleotide sequence (e.g., as shown in SEQ ID NO:5). However, it is also intended that the term encompass fragments of the ADAMTS13 sequence, as well as other domains with the full-length ADAMTS13 nucleotide sequence. Furthermore, the terms "ADAMTS13 nucleotide sequence" or "ADAMTS13 polynucleotide sequence" encompasses DNA, cDNA, and RNA (e.g., mRNA) sequences.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith & Waterman [1981] *Adv. Appl. Math.*, 2:482) by the homology alignment algorithm of Needleman and Wunsch (Needleman & Wunsch [1970] *J. Mol. Biol.*, 48:443), by the search for similarity method of Pearson and Lipman (Pearson & Lipman [1988] *Proc. Natl. Acad. Sci. U.S.A.*, 85:2444), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a sequence or a variant nucleic acid sequence (e.g., mutation or polymorphism in a given allele of a particular gene, as e.g., ADAMTS13 gene), or for detecting the presence or absence of a particular protein (e.g., ADAMTS13) or the structure or activity or effect of a particular protein (e.g., VWF-cleaving protease activity) or for detecting the presence or absence of a variant of a particular protein.

The term "hybridization analysis" refers to detection of variant nucleotide sequences in a hybridization assay. In a hybridization assay, the presence of absence of a given single nucleotide polymorphism (SNP) or mutation is determined based on the ability of a nucleotide sequence from the sample to hybridize to a complementary nucleotide molecule (e.g., a oligonucleotide probe). A variety of hybridization assays using a variety of technologies for hybridization and detection are available. A description of a selection of exemplary assays is provided later in the specification, and includes direct detection of hybridization, detection of hybridization using "DNA chip" assays, enzymatic detection of hybridization, and mass spectroscopic assays of hybridization.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q_replicase, MDV-1 RNA is the specific template for the replicase (Kacian et al. [1972] Proc. Natl. Acad. Sci. USA, 69:3038). Other nucleic acid will not be replicated by this amplification enzyme. Similarly, in the case of T7 RNA polymerase, this amplification enzyme has a stringent specificity for its own promoters (Chamberlain et al. [1970] Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu & Wallace [1989] Genomics 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process.

"Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al. [1987] Science 236:1237). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119–127 [1994]) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham & van der Eb [1973] Virol., 52:456), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding," "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a host cell or an organism refers to a host cell or an organism that contains at least one heterologous or foreign gene in the host cell or in one or more cells of the organism.

The term "host cell" refers to any cell capable of replicating and/or transcribing and/or translating a heterologous gene. Thus, a "host cell" refers to any eukaryotic or prokaryotic cell (e.g., bacterial cells such as $E.$ $coli$, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative."Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos. 6,074, 859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, $\beta$-galactosidase, alkaline phosphatase, and horse radish peroxidase.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31–9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39–7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding ADAMTS13 (e.g., SEQ ID NO:2) or fragments thereof may be employed as hybridization probes. In this case, the ADAMTS13 encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

GENERAL DESCRIPTION OF THE INVENTION

Although the cause of TTP is unknown, some evidence suggested that the treatment resulted from removal of a toxic factor from the blood, while other evidence suggested that it replaced a missing factor. Recent evidence suggested that the missing factor could be a type of protein called a protease, and in particular a protease which degrades another blood clotting factor called von Willebrand factor (VWF). In 1982, Moake et al (Moake et al. [1982] N. Engl. J. Med. 307, 1432–1435) observed unusually large multimeric forms of von Willebrand factor (VWF) in the plasma of TTP patients and postulated that these patients may lack an activity that is responsible for decreasing the size of VWF secreted from endothelial cells. In 1996, two groups independently isolated a protease from plasma that appears to be responsible for the physiologic cleavage of VWF at the Tyr842-Met843 peptide bond, producing the characteristic 176 kd and 140 kd proteolytic fragments observed in normal plasma (Tsai, H. M. [1996] Blood 87, 4235–4244; Furlan et al. [1996] Blood 87, 4223–4234). Increased susceptibility to this proteolytic cleavage appears to be responsible for the loss of large VWF multimers central to the pathophysiology of a different disease, type 2A von Willebrand disease (VWD) (Tsai et al. [1997] Blood 89, 1954–1962). The same protease activity was subsequently shown to be deficient in the plasma of TTP patients (Tsai and Lian [1998] N. Engl. J. Med. 339, 1585–1594; Furlan et al. [1998] N. Engl. J. Med. 339, 1578–1584). The hypothesis that the disease results from the presence of a toxic factor in the blood is supported by reports of circulating autoantibodies detected in most adults with disease (Tsai and Lian [1998] N. Engl. J. Med. 339, 1585–1594; Furlan et al. [1998] N. Engl. J. Med. 339, 1578–1584), as well as recent reports of antibodies against this protease which been identified in a form of TTP associated with the antiplatelet drug ticlopidine (Tsai et al. [2000] Ann. Intern. Med. 132, 794–799).

Despite the strong association of low VWF-cleaving protease activity with TTP, a direct causative link has not yet been established. Other studies have implicated platelet aggregating proteins or endothelial injury as the underlying mechanism (Mitra et al. [1997] Blood 89, 1224–1234); Dang et al. [1999] Blood 93, 1264–1270; Cines et al. [2000] Thromb. Haemost. 84, 528–535) and enhanced rather than decreased VWF proteolysis has been observed in some patients (Mannucci et al. [1989] Blood 74, 978–983]. Though the protease responsible for VWF cleavage has been partially purified and characterized (Tsai et al. [1997] Blood 89, 1954–1962; Furlan et al. [1996] Blood 87, 4223–4234), it appears to be present at relatively low levels in plasma and its identification at the sequence level has remained elusive.

The present invention provides identification and characterization of the gene responsible for familial TTP. This was accomplished by studying a series of families in which TTP appears to be inherited and then using a positional cloning approach to map a gene responsible for reduced VWF-cleaving protease activity to a locus on 9q34. The gene was identified as ADAMTS13 which encodes ADAMTS13, a unique member of the metalloproteinase gene family. Expression of ADAMTS13 from cloned full-length cDNA confirmed its VWF-cleaving protease activity. At least two different forms of ADAMTS13 have been identified, which vary in length. Moreover, mutations in this gene were discovered in individuals affected with TTP. All but 3 of 13 ADAMTS13 mutations identified were missense mutations. Moreover, the two frameshift and one splice mutations identified were present in trans with a missense mutation on the other allele, which suggests that complete deficiency of ADAMTS13 may be lethal. Nine TTP-related ADAMTS13 missense mutations severely impair VWF-cleaving protease activity, accounting for the loss of activity observed in the corresponding patient plasmas.

Thus, the present invention provides nucleotide sequences encoding wild-type, mutants, variants, and fragments of ADAMTS13, as well as the encoded proteins. The present invention further provides methods of using the ADAMTS13 gene and protein, which include but are not limited to precise and rapid diagnosis of this condition in other individuals with inherited TTP, such as with nucleic acid probes or with antibodies, treatment of patients with TTP with a recombinant ADAMTS13, and treatment of patients at risk of or suffering from heart attack or stroke with this protease or other drugs developed from this protease which act as anticoagulants.

In the following description of the discovery and characterization of the ADAMTS13 gene, mutants, and variants, hypotheses may be advanced to explain certain results, or to correlate results with previous observations. It is not necessary to understand the mechanism underlying the invention, nor is it intended that the invention be limited to any particular mechanism.

A. Discovery of the ADAMTS13 Gene

1. Analysis of Plasma Level of VWF-Cleaving Protease.

Figure 1:
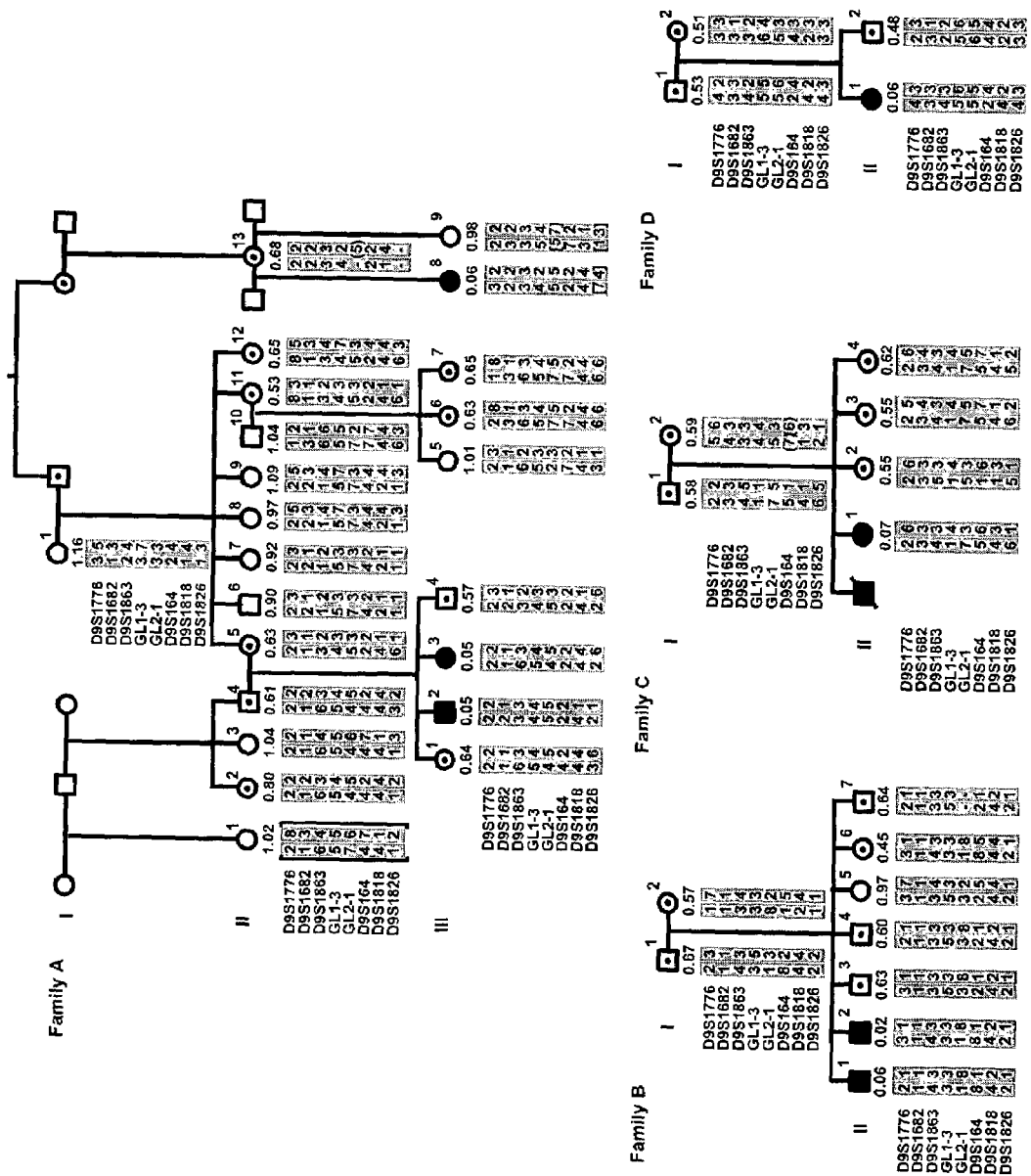
FIG. 1 shows the pedigrees used for linkage analysis. VWF-cleaving protease levels (in U/ml) are indicated beneath the symbol for each individual. Affected individuals are indicated by solid symbols and carriers by dotted symbols. A total of 17 markers as described in Example 1 were used for haplotype analysis. Only select markers are shown. Chromosomes carrying affected alleles are framed, whereas normal chromosomes are not marked. Areas where recombination cannot be definitively assigned are indicated by shading. Only recombination events between affected and unaffected chromosomes are shown. Inferred genotypes are indicated in parentheses. Genotypes of unknown phase are indicated by square brackets. Recombination events in individuals AIII3 and BII6 place the responsible gene below marker GL2-1 and a recombination event in individual AIII2 places the gene above marker D9S1818.

Four pedigrees of families in which TTP appears to be inherited were available for analysis, and are shown in FIG. 1. The levels of plasma VWF-cleaving protease were analyzed as described in Example 1B; the results indicated that the plasma level of VWF-cleaving protease segregated as a semidominant autosomal trait.

Figure 2:
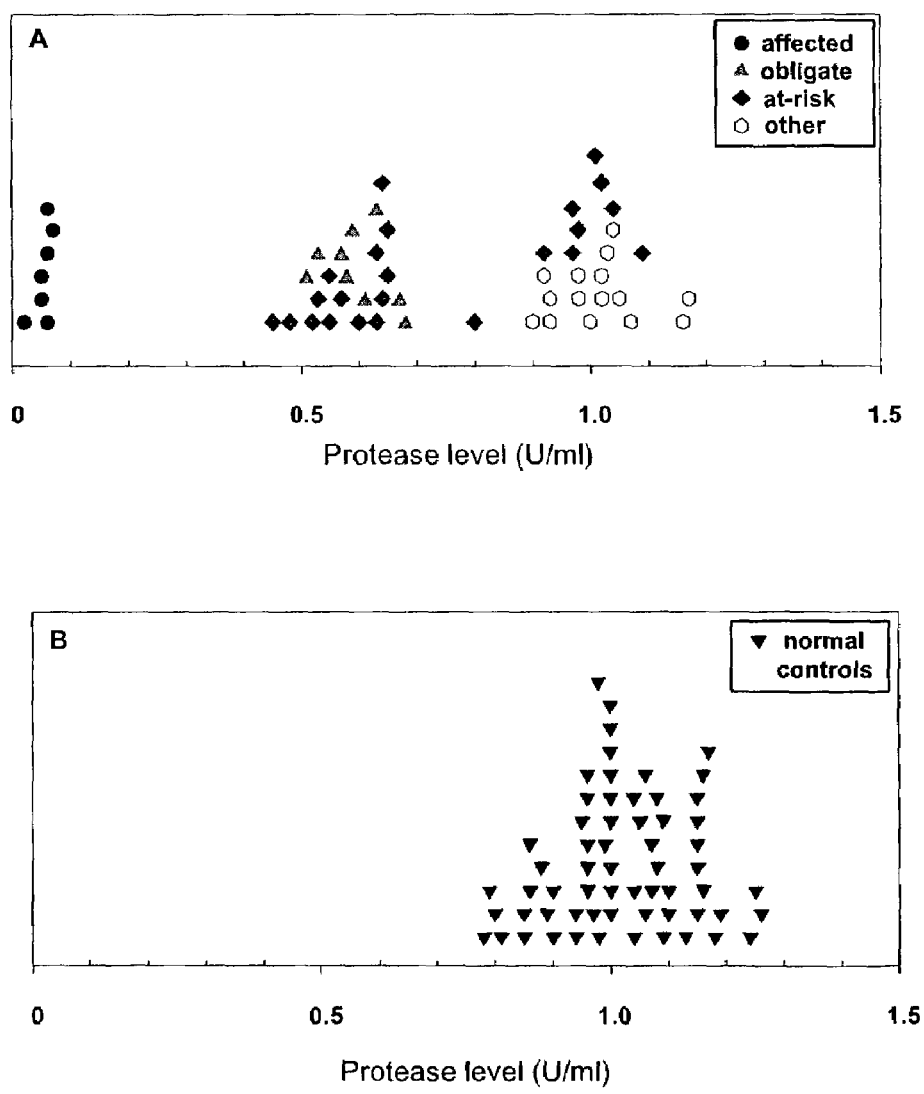
FIG. 2 shows blood plasma VWF-cleaving protease levels. Panel a shows levels for all individuals shown in FIG. 1, as well as additional members of family A. Panel b shows levels for 61 normal control individuals. Affected individuals are indicated by circles, obligate carriers (parents of affected individuals) by triangles, other individuals at-risk for inheriting an affected allele by diamonds, and additional not at-risk members of family A by hexagons. Normal controls are shown as triangles. Levels for at-risk individuals (diamonds in panel a fall into a bimodal distribution, with one peak ranging from 0.45–0.68 U/ml, consistent with carriers and the other from 0.90–1.17 U/ml, indistinguishable from the normal distribution shown in panel b.

VWF-cleaving protease activity measured in the plasma of the 7 affected individuals ranged from 2–7% of normal (0.02–0.07 U/ml) and none of the patients tested positive for inhibitors of the protease. Plasma protease levels in the parents of the affected individuals ranged from 0.51–0.68 U/ml, consistent with a heterozygous carrier state. Similarly, levels for at-risk siblings of the patients and parents fell into a bimodal distribution, with one peak consistent with carriers and the other indistinguishable from the normal distribution (FIG. 2). These results demonstrate that the protease activity assay used here reliably distinguishes between normal and carrier individuals in these families. This observation suggested that the plasma level of VWF-cleaving protease could be used as a phenotypic trait for linkage analysis to map the corresponding locus, providing considerably greater genetic power than would be available from analysis of the clinical phenotype alone.

2. Mapping the Gene for Familial TTP to Chromosome 9q34.

A genome wide linkage scan was thus performed on the four pedigrees shown in FIG. 1 using 382 polymorphic microsatellite markers to analyze DNA from affected individuals and other informative family members, as described in Example 1. Two-point linkage analysis using a recessive model gave a maximum LOD score of 2.36 at θ=0.0 for marker D9S164 on chromosome 9q34, with a LOD score of 3.83 at θ=0.01 for a codominant model. Multipoint analysis for D9S164 and 4 flanking markers (cen-D9S1682-D9S290-D9S164-D9S1826-D9S158-tel) yielded a maximum LOD score of 4.77 at a location 2.4 cM telomeric to marker D9S164. Genotypes for 7 other markers in this region (Dib, C. et al. [1996] Nature 380, 152–154; Broman, K. W. et al. [1998] Am. J. Hum. Genet. 63, 861 -869) allowed the gene to be placed in the ~7 cM interval between markers D9S1863 and D9S1818 (FIGS. 1 and 3A). Analysis of additional polymorphic markers (see Table 3 in Example 1) designed from simple sequence repeat data available from the Human Genome Working Draft narrowed the candidate interval to an ~2.3 Mb genomic segment between markers GL2-1 and D9S1818. In all but one case, carrier status as determined by haplotype analysis was consistent with the phenotypic designation according to plasma protease level. The exception, individual II2 in pedigree A, shares the affected haplotype of her brother (II4), but has a protease level of 0.8 U/ml, which is borderline between the normal and carrier ranges.

3. Identification of a Candidate Gene for Familial TTP.

Analysis of the candidate interval using public genome database resources identified ~20 known or predicted genes (FIG. 3A). Initial attention focused on genes likely to encode a protease or protease cofactor. FCN2 (ficolin 2) mapped to distal chromosome 9 but could not be identified in available BAC sequence from the candidate interval. However, in light of previous reports suggesting a protease associated function for some ficolin family members (Matsushita, M. & Fujita, T. Ficolins [2001] Immunol. Rev. 180, 78–85) and the possibility that FCN2 might lie in one of the three large genomic sequence gaps shown in FIG. 3A, the coding exons and intron/exon boundaries of this gene were amplified by PCR from patient DNA and subjected to sequence analysis. No candidate mutations were identified. Two putative genes in the candidate interval, KIAA0605, an uncharacterized EST from a brain cDNA library (Nagase, T. et al. [1998] DNA Res. 5, 31–39), and the predicted open reading frame C9ORF8, exhibited homology to the ADAMTS family of metalloproteinases, but appeared to lack the conserved protease catalytic domain. Partial DNA sequence analysis of exons and flanking intron sequences failed to identify any mutations in KIAA0605. However, the identification of several candidate missense mutations in the predicted exons of C9ORF8 led to further, more detailed analysis of this candidate gene.

Exon 1 of C9ORF8 overlapped with a cluster of EST sequences (Unigene cluster Hs.149184), predicting a large 5' untranslated region. A segment of putative C9ORF8 coding sequence was used to probe a human fetal cDNA library identifying several partial cDNA clones, which were extended in both the 5' and 3' direction by RT-PCR and RACE. The assembled cDNA sequence corrected an error in the predicted boundaries of C9ORF8 exon 2, resulting in a continuous open reading frame including two exons upstream of the 5' EST cluster, 3 new exons within the predicted intron 10 of C9ORF8 and 6 additional downstream exons overlapping a second hypothetical gene in this region, DKFZp434C2322 (Unigene cluster Hs.131433). Thus, through a combination of cDNA cloning, RACE, and genomic sequence analysis, the full length cDNA sequence (FIG. 5) and corresponding genomic structure were deduced, as depicted in FIG. 3B, and found to encode a complete, potentially catalytically active ADAMTS protease (FIG. 6). This gene was discovered to be a novel member of the ADAMTS family of metalloproteases, and was therefore designated ADAMTS13.

B. Characterization of ADAMTS13 Gene and ADAMTS13 Protein

ADAM (a disintegrin and metalloproteinase) family members are membrane-anchored proteases with diverse functions. Known members include fertilins α and β, implicated in sperm-egg fusion, and the "sheddases" such as TACE (TNFα convertase), which mediate the shedding of cell surface proteins (Blobel, C. P. [1997] Cell 90, 589–592).

ADAMTS family members are distinguished from ADAMs by the presence of one or more thrombospondin 1-like (TSP1) domain(s) at the C-terminus and by the absence of the EGF repeat, transmembrane domain and cytoplasmic tail typically observed in ADAM metalloproteinases. The TSP1 motifs are thought to mediate interactions with components of the extracellular matrix (Kaushal, G. P. & Shah, S. V. [2000] J. Clin. Invest 105,1335–1337; Hurskainen, T. L. et al. [1999] J. Biol. Chem. 274, 25555–25563; and Tang, B. L. [2001] Int. J. Biochem. Cell Biol. 33, 33–44). ADAMTS4 and 5/11 (aggrecanases) cleave the proteoglycan core of articular cartilage and may play a role in inflammatory joint disease (Tortorella, M. D. et al [1999] Science 284, 1664–1666). and mutations in ADAMTS2 (procollagen N-proteinase) result in the connective tissue disorder Ehlers-Danlos Syndrome, Type V (Colige, A. et al. [1999] Am. J. Hum. Genet. 65, 308–317). Though ADAMTS1 mutations have not been identified in humans, genetically deficient mice exhibit growth retardation, adipose tissue abnormalities, and fibrotic changes throughout the genitourinary system, suggesting a critical role for ADAMTS1 in organogenesis and tissue remodeling (Shindo, T. et al. [2000] J. Clin. Invest. 105, 1345–1352). The function and protein substrates for the remaining ADAMTS family members are unknown.

1. ADAMTS13 Coding Sequence.

The full-length ADAMTS13 mRNA is 4,550 nucleotides in length, encoding a 1,427 amino acid open reading frame that begins with the first ATG, leaving short 5' and 3' untranslated regions of 61 bp and 208 bp, respectively. The ADAMTS13 gene spans 29 exons encompassing approximately 37 kb in the human genome and encoding a 1,427 amino acid protein (FIG. 3B). Analysis of RT-PCR and cloned cDNA sequences provided evidence for alternative splicing of exon 17, resulting in a frameshift that predicts a truncated 842 amino acid form of the protein lacking the 6 C-terminal TSP1 repeats (as shown in FIGS. 7 and 8). Comparative analysis with draft mouse genomic sequences demonstrates a high degree of conservation throughout the coding exons and identifies an additional potential exon located between the current exons 22 and 23, which may indicate another splice isoform. These findings suggest the potential for differentially regulated alternative isoforms of ADAMTS13 with diverse biologic functions in addition to the proteolytic processing of VWF. Alternative splicing has also been observed in other ADAMTS proteins, including ADAMTS9, resulting in a similar variation in the number of C-terminal TSP1 repeats (Tang, B. L. [2001] Int. J. Biochem. Cell Biol. 33, 33–44).

2. ADAMTS13 Protein

The domain structure of ADAMTS13 is depicted at the bottom of FIG. 3B. A predicted signal peptide is followed by a short propeptide domain ending in a potential propeptide convertase cleavage site at amino acids 71–74 (RQRR), suggesting that proteolytic processing, either in the trans Golgi or at the cell surface, is required for activation. The protease domain that follows contains a perfect match for the HEXGHXXGXXHD extended catalytic site consensus sequence shared between snake venom metalloproteinases, and ADAM family members (Kaushal, G. P. & Shah, S. V. [2000] J. Clin. Invest 105: 1335–1337; Blobel, C. P. [1997] Cell 90, 589–592; and Kuno, K. et al. [1997]. J. Biol. Chem. 272, 556–562). The catalytic domain is followed by the disintegrin, thrombospondin type 1 (TSP1), and spacer domains characteristic of the ADAMTS family. An RGDS sequence not present in other ADAMTSs is located immediately C-terminal to the first TSP1 domain, suggesting a possible novel integrin interaction. The C-terminus contains an additional 6 TSP1 repeats, followed by a segment with homology to a CUB domain. CUB domains have been identified in a number of developmentally regulated proteins (Bork, P. & Beckmann, G. [1993] J. Mol. Biol. 231, 539–545); however, this domain has not been reported for an ADAMTS protein, and appears to be novel to ADAMTS13. The previously reported inhibitor profile and metal cation dependence of the VWF-cleaving protease (Tsai, H. M. [1996] Blood 87, 4235–4244; Furlan, et al. [1996] Blood 87, 4223–4234; Tsai, et al. [1997] Blood 89, 1954–1962) are consistent with its identity as an ADAMTS. The predicted, nonglycosylated molecular mass of ADAMTS13 is 154 kd, consistent with a previously estimated mass of 200 kd for partially purified VWF-cleaving protease (Tsai, H. M. [1996] Blood 87, 4235–4244), though considerably smaller than the 300 kd mass reported by other (Furlan et al. [1996] Blood 87, 4223–4234).

3. ADAMTS13 Expression and Activity

The full-length ADAMTS13 cDNA was assembled and cloned into a mammalian expression vector and transfected into CHO-Tag cells (as described in the Examples). Conditioned medium from transfected cells was tested for VWF-cleaving protease activity by a previously-described assay (Tsai et al. [2001] Clin. Lab 47, 387–392) and was found to exhibit a VWF-cleaving protease activity of 0.47 U (+/−0.07), as compared to a value of 0.06 (+/−0.03) in conditioned media from mock-transfected cells (p<0.01). These data directly demonstrate the VWF-cleaving protease activity of recombinant ADAMTS13.

These results demonstrate the feasibility of producing recombinant ADAMTS13 and confirm that the latter possesses VWF-cleaving protease activity. The VWF-cleaving protease assay used here (Tsai et al. [2001] Clin. Lab 47, 387–392) relies on the detection of the 176 kD dimer formed by VWF cleavage at the peptide bond between Tyr842 and Met843 (Dent et al. [1990] Proc. Natl. Acad. Sci. U.S.A. 87, 6306–6310), further indicating that cleavage of VWF by recombinant ADAMTS13 occurs at or near this bond. These results support the use of providing an active form ADAMTS13 for the treatment of TTP; moreover, it is contemplated that the production of recombinant protein will facilitate the development of improved diagnostic reagents for both familial and acquired forms of TTP.

C. Mutants and Variants of ADAMTS13

1. Mutants of ADAMTS13 Cause Familial TTP.

DNA sequence analysis identified mutations within the ADAMTS13 gene in all 4 of the pedigrees depicted in FIG. 1, as well as in 3 additional TTP patients not included in the original genome scan (families E–G, Table 1). These mutations are shown in Table 1.

Table 1:

ADAMTS13 Mutations in Thrombotic Thrombocytopenic Purpura (TTP).

Genomic DNA from patients was used to amplify exons and intron/exon boundaries of ADAMTS13. For mutations in families A to D, candidate mutations were confirmed in both parents. Analysis of the potential splice mutation in family G with a splice site prediction tool suggests that it should abolish splicing from this donor site. Consistent with this prediction, sequence analysis of PCR amplified mRNA from patient lymphoblasts identified a major product of wild-type sequence derived only from the normal allele. A second, slightly larger product not seen in control samples was derived only from the mutant allele, utilizing a cryptic donor splice site at +69, resulting in a 23 amino acid insertion. Approximately 180 normal control chromosomes were screened by allele-specific oligonucleotide hybridization, restriction digest or PCR for the following mutations, with no mutant alleles identified: H96D, R102C, R398H, R528G, R692C, C1213Y, 2374–2399del, and 1584+5G>A.

| exon | family | nucleotide | amino acid |
|---|---|---|---|
| 3 | B | 286C > G | H96D |
| 3 | E | 304C > T | R102C |
| 6 | E | 587C > T | T196I |
| 10 | D | 1193G > A | R398H |
| 13 | C | 1582A > G | R528G |
| 13 | G | 1584 + 5G > A | splice |
| 17 | A | 2074C > T | R692C |
| 19 | F | 2374–2399del | frameshift |
| 22 | B | 2851T > G | C951G |
| 24 | D | 3070T > G | C1024G |
| 26 | F | 3638G > A | C1213Y |
| 26* | 8* | 3655C > T* | R1219W* |
| 27 | C | 3769–3770insA | frameshift |

Figure 3:
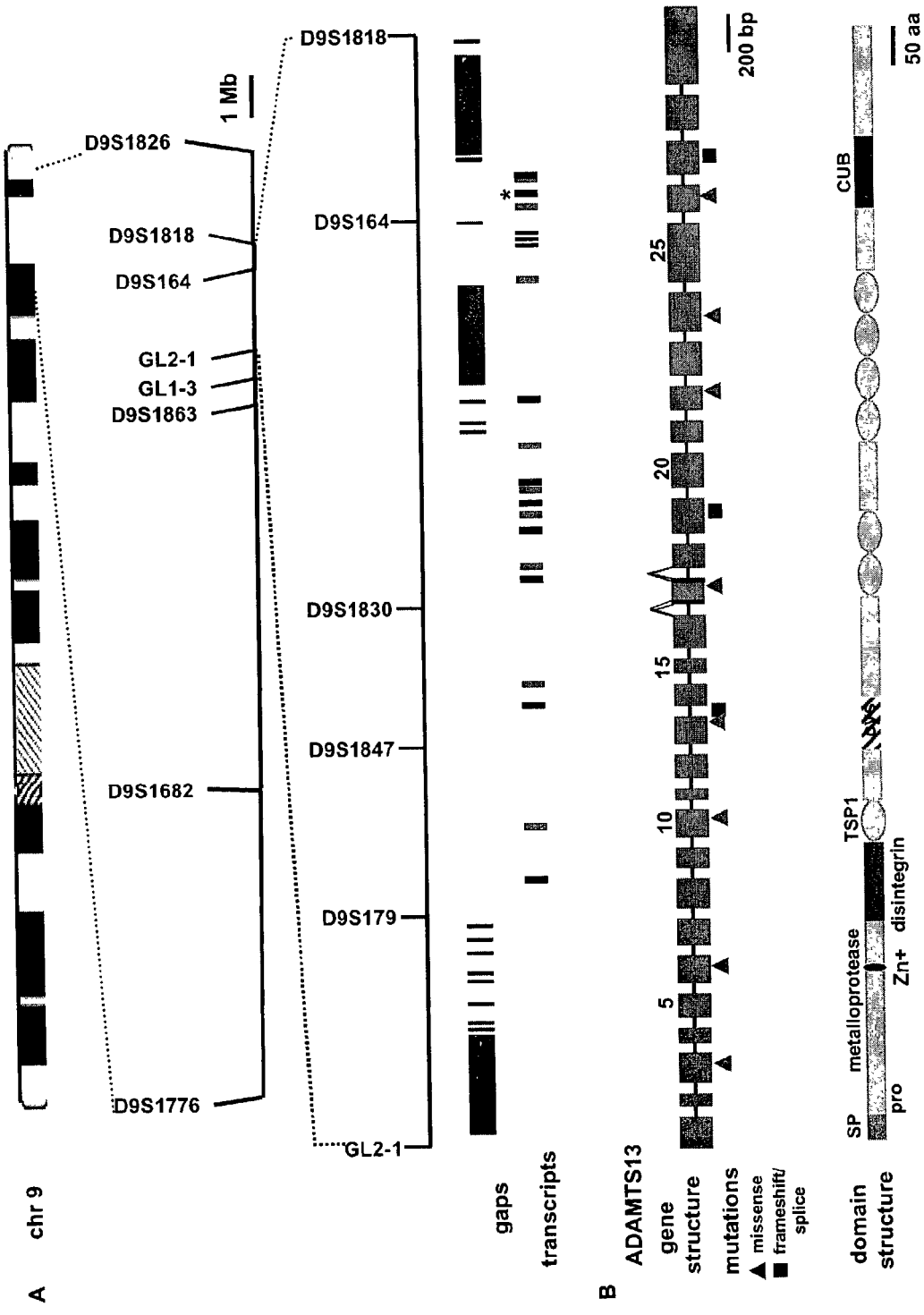
FIG. 3 shows the identification of the ADAMTS13 gene. Panel a shows a physical map of chromosome 9 in the interval surrounding marker D9S164. The 2.3 Mb nonrecombinant interval identified in FIG. 1 is located between the markers that designate this interval, which are shown in larger and bold type. Sequence gaps in public genomic draft assembly are denoted by black bars. Transcripts localized to this interval are depicted by black and hatched bars; the different patterns are used solely to make it easier to see the individual transcripts in areas where they are spaced closely together. The predicted gene C9ORF8 is indicated with an asterisk. The reference bar represents 1 Mb. Panel b shows the intron-exon of an ADAMTS13 gene and the domain structure of the encoded ADAMTS13 protein. The coding regions are indicated by gray bars and the 5' and 3' untranslated regions are indicated by patterned bars. Intron sizes are not drawn to scale. Exon 1 of C9ORF8 overlaps with a cluster of EST sequences (Unigene cluster Hs.149184), initially interpreted as predicting a large 5' untranslated region. A segment of putative C9ORF8 coding sequence was used to identify 2 partial human fetal liver cDNA clones, which were extended in both the 5' and 3' direction by RT-PCR and RACE. The assembled cDNA sequence corrected an error in the predicted boundaries of C9ORF8 exon 2, resulting in a continuous open reading frame including two exons upstream of the 5' EST cluster, 3 new exons within the predicted intron 10 of C9ORF8 and 6 additional downstream exons encompassing a second hypothetical gene in this region, DKFZp434C2322 (Unigene cluster Hs. 131433). Analysis of RT-PCR and cDNA sequences identified an alternatively spliced variant of exon 17 using both alternate donor and acceptor splice sites; the alternatively spliced exon pieces are indicated by black bars. Mutations are depicted underneath the corresponding exons, with triangles representing missense mutations and squares representing frameshift and splice mutations. The reference bars represents 200 nucleotides. The predicted domain structure of ADAMTS13 is shown at the bottom of panel b. The predicted signal peptide is indicated as "SP," the short propeptide is indicated as "pro," the metalloproteinase domain is indicated by "metalloprotease," the disintegrin domain is indicated by "disintegrin," and TSP1 domains are indicated as ovals. The locations of the zinc-binding catalytic consensus sequence within the metalloproteinase domain and the cysteine rich region within the spacer domain are also indicated. The CUB domain (indicated as "CUB") has not been identified in other ADAMTS family members. The reference bar represents 50 amino acids. Panel c shows the domain structure of ADAMTS13, with the locations of mutations indicated. Missense mutations identified in TPP patients are indicated by arrows. The asterisk indicates an additional mutant identified in a TPP family.
Figure 3:
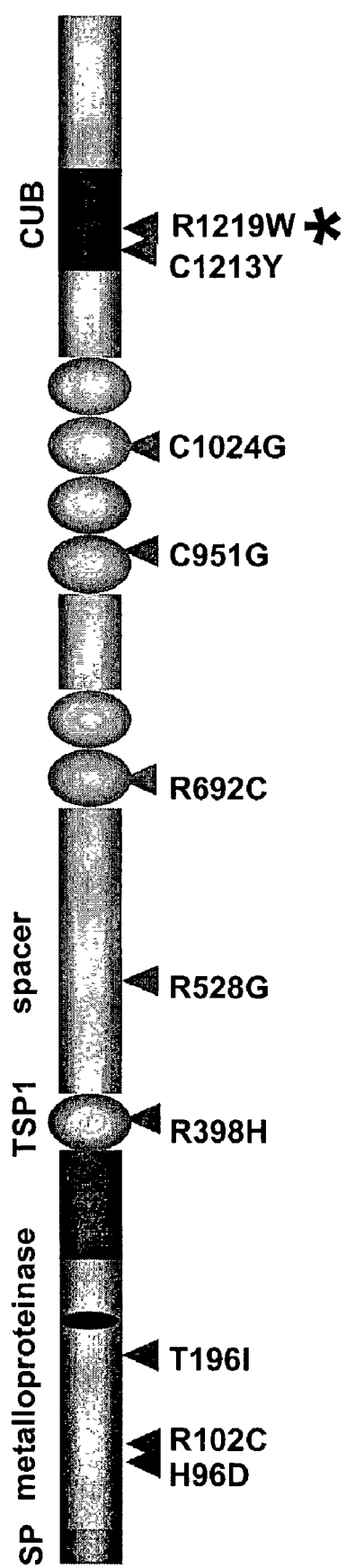

An additional mutation accounting for 1 of 2 disease alleles in an 8th familial pedigree was also identified (indicated in Table 1 above by an asterisk (*)). Sequence analysis of exons and exon-intron junctions of ADAMTS13 was performed on genomic DNA obtained from the proband of an additional familial TTP pedigree. The patient was found to be heterozygous for a 3655C>T substitution in exon 26. The substitution was also present in the heterozygous state in the affected brother and obligate carrier father, but absent in the mother and 6 unaffected siblings. In addition, the T allele was confirmed to be absent from 180 control chromosomes by allele-specific oligonucleotide hybridization. The resulting amino acid change, R1219W, occurs within the CUB domain at the C-terminus of ADAMTS13 (FIG. 3, panel C). No mutation was identified for the other allele in this family.

The 12 mutations initially identified accounted for all but one of the 15 disease alleles initially expected in this set of patients (Table 1). With the additional mutation (which accounts for 1 of 2 disease alleles in the 8th family pedigree), these analyses resulted in the identification of 15 of the 17 disease alleles in the families studied. The two unidentified mutations may lie within exon 7, or within noncoding regions not covered by the sequence analysis. The presence of at least one mutation in all hereditary TTP families identified thus far indicates that most if not all cases of this disease are due to mutations in ADAMTS13. Moreover, successful identification of 15 of 17 disease alleles suggests that the majority of ADAMTS13 mutations in hereditary TTP are likely to lie within the coding sequence and exert effects on either protein stability or function.

No recurrent mutation was observed, except in family A, where all 3 affected individuals are homozygous for the same mutation carried on the same extended haplotype, suggesting a founder mutation within the South American population of origin for this family. Two mutations result in frameshifts (a 26 bp deletion in exon 19 and single A insertion in exon 27) and a single splice mutation leads to an in frame 23 amino acid insertion. The remaining observed mutations all result in nonconservative amino acid substitutions (Table 1 and following paragraph), and all occur at positions that are perfectly conserved between the human and murine genes; these mutations are also located throughout the length of the protein, with no apparent clustering in any specific domain or region of the molecule.

However, several of these mutations occur at highly conserved positions that could disrupt proper folding or may affect substrate binding. The R398H mutation within the first TSP1 motif occurs at a residue that is perfectly conserved among all 18 ADAMTS family members identified to date. This mutation occurs within a conserved motif of the TSP1 domains shown to be modified by an unusual O-linked disaccharide Glc-Fuc-O-Ser/Thr in platelet TSP1 (Hofsteenge et al. [2001] J. Biol. Chem. 276, 6485–6498) and thought to be important for ligand binding (Adams & Tucker [2000] Dev. Dyn. 218, 280–299). H96D in the metalloprotease domain occurs at a residue that is also conserved in all ADAMTS family members identified to date, with the exception of ADAMTS5/11 and ADAMTS8. The R102C mutation introduces a cysteine residue which may disrupt a disulfide bond between C 155 and C208, predicted based on a comparison with a molecular model of adamalysin II (Zheng et al. [2001] J. Biol. Chem. 276, 41059–41063). The C951G mutation (as well as the C1024G mutation) also affect conserved cysteine residues (Adams & Tucker [2000] Dev. Dyn. 218, 280–299; Zheng et al. [2001] J. Biol. Chem. 276, 41059–41063) in the fourth and sixth TSP1 motifs of ADAMTS13, respectively. The C1213Y and R1219W mutations occur within the CUB domain located at the C-terminus of ADAMTS13. The C1213Y mutation affects one of several highly conserved cysteine residues within CUB domains that have been proposed to form disulfide bonds (Sieron et al. [2000] Biochemistry 39, 3231–3239). CUB domains have been described in a number of developmentally regulated proteins, including several zinc metalloproteases (Bork & Beckmann [1993] J. Mol. Biol. 231, 539–545); the CUB domain of BMP-1, or procollagen-C-proteinase, has been implicated in substrate binding (Sieron et al. [2000] Biochemistry 39, 3231–3239).

The spectrum of ADAMTS13 mutations observed here is notable for the relative paucity of obvious null alleles. In addition, both frameshift mutations are located toward the C-terminus, potentially giving rise to truncated forms of the protease that retain an intact catalytic domain. These data suggest that complete deficiency of ADAMTS13 may be lethal. This hypothesis is supported by the observed trend toward trace activity above background seen in the majority of the mutants tested, and by the low levels of residual VWF-cleaving protease activity observed in all 10 deficient patients described here (0.02 to 0.07 U/ml).

Northern blot analysis detected an ~4.7 kb ADAMTS13 mRNA specifically in the liver, with a truncated, ~2.3 kb, mRNA faintly visible in placenta (FIG. 4A). These data suggest that plasma VWF-cleaving protease may be derived primarily from ADAMTS13 expression in the liver. The strong RT-PCR signal seen in the ovary, and variable expression in other tissues (FIG. 4B), suggest other potential functions for this protein. The absence of detectable transcripts in other highly vascular tissues such as the lung, kidney and heart may indicate that the vascular endothelium is not a primary site of ADAMTS13 expression.

The findings reported here provide the first direct proof of an etiologic role for a VWF-cleaving protease in the pathogenesis of TTP and identify the enzyme associated with this activity as the novel metalloproteinase ADAMTS13. These data are consistent with the hypothesis that accumulation of hyperactive large VWF multimers in the absence of normal proteolytic processing triggers pathologic platelet aggregation and is the direct mechanism responsible for TTP. Alternatively, decreased VWF proteolysis may be a marker for the loss of ADAMTS13 activity. ADAMTS13 may also have important biologic functions elsewhere in the coagulation system or in the blood vessel wall, with loss of one or more of these activities providing the direct link to the pathogenesis of TTP.

2. ADAMTS13 Mutations in TTP Patients Result in Loss of VWF-Cleaving Protease Activity.

The functional significance of the ADAMTS13 mutations identified here was evaluated by analysis of the VWF-cleaving protease activity of recombinant mutant ADAMTS13. Each of the missense mutations was engineered into the wild-type ADAMTS13 construct and transfected into CHO-Tag cells. Analysis of VWF-cleaving protease activity in conditioned media revealed that all 9 mutations examined resulted in markedly decreased activity, which is not statistically distinguishable from that present in conditioned media from mock-transfected cells (FIG. 11).

Conditioned media from CHO-Tag cells transfected with the wild-type and the missense mutant constructs were subjected to Western blot analysis with 4 different anti-peptide antibodies raised against ADAMTS13 peptides. Although one of these antibodies (antibody 4, see Materials and Methods in the Examples) has been successfully used to detect appropriate segments of bacterially-expressed ADAMTS13, no specific fragments corresponding to the expected size of ADAMTS13 were detectable in conditioned media from cells transfected with either the wild-type or mutant constructs. In addition, epitope (FLAG)-tagged recombinant ADAMTS13 was also undetectable by Western blot analysis using a commercially-available anti-FLAG antibody.

Though all 9 mutations described above exhibit marked loss of VWF-cleaving protease activity, the loss of activity may be due to change in protein function, synthesis, secretion, or stability. The plasma concentration of ADAMTS13 has been estimated at ~1 mg/ml (Gerritsen et al. [2001] Blood 98, 1654–1661). Therefore, based on the VWF-cleaving protease activity of wild-type recombinant ADAMTS13, mutant ADAMTS13 is present at roughly half this concentration in the recombinant mutant ADAMTS13 samples. Although initial attempts to determine whether mutant proteins are secreted from the cell at levels similar to wild-type recombinant ADAMTS13 by Western blot analysis were unsuccessful, as described above, it is contemplated that generation of more sensitive antibody reagents or of epitope-tagged mutant constructs will result in such determination.

3. Variants of ADAMTS13.

A large number of SNPs were also identified, though only 7/25 result in amino acid substitutions (see Table 2). These SNPs all constitute naturally occurring wild-type ADAMTS13 alleles; any particular allele may comprise from one to more than one SNP, and different combinations of SNPs may occur together.

TABLE 2

| Single nucleotide polymorphisms | | |
| --- | --- | --- |
| exon/intron | nucleotide | amino acid |
| ex1 | 19C > T | R7W |
| ex4 | 354G > A | silent |
| ex5 | 420T > C | silent |
| ex6 | 582C > T | silent |
| int6 | 686 + 4T > G | N/A |
| int8 | 987 + 11C > T | N/A |
| int8 | 987 + 69C > T | N/A |

TABLE 2-continued

Single nucleotide polymorphisms

| exon/intron | nucleotide | amino acid |
|---|---|---|
| int9 | 1092 + 67G > A | N/A |
| int10 | 1245 − 32C > G | N/A |
| ex12 | 1342C > G | Q448E |
| int13 | 1584 + 106C > G | N/A |
| int13 | 1584 + 236T > C | N/A |
| ex15 | 1716G > A | silent |
| int15 | 1787 − 26G > A | N/A |
| ex16 | 1852C > G | P618A |
| ex16 | 1874G > A | R625H |
| ex18 | 2195C > T | A732V |
| ex19 | 2280T > C | silent |
| ex21 | 2699C > T | A900V |
| int22 | 2861 + 55C > T | N/A |
| ex23 | 2910C > T | silent |
| ex24 | 3097G > A | A1033T |
| ex24 | 3108G > A | silent |
| int28 | 4077 + 32T > C | N/A |
| ex29 | 4221C > A | silent |

Of the 25 single nucleotide polymorphisms (SNPS) identified in ADAMTS13 genomic sequences, 15 polymorphisms occurred within coding sequence, and 7 cause amino acid substitutions. This surprising degree of polymorphism in the ADAMTS13 gene raises the possibility that one or more of the putative disease mutation identified in the initial panel of patients, though absent from 180 control chromosomes, might represent a rare "private" polymorphism within the corresponding family. However, the functional data shown in FIG. 11 demonstrate that all 9 mutations described above represent authentic disease mutations resulting in partial or complete loss of ADAMTS13 function.

D. Utility of ADAMTS13 Genes and Proteins

The present invention also provides several methods of use of wild-type and mutants, variants and fragments of ADAMTS13 and the encoded proteins, as well as of antibodies to wild-type and mutants, variants, and fragments of ADAMTS13. In some embodiments, methods are provided for precise and rapid diagnosis of TTP in individuals with inherited TTP. Such diagnosis is effected by any number of detection assays based upon nucleotide sequences, as described in more detail below, in which the types of alleles present in an individual are identified. In other embodiments, rapid diagnosis of TTP both in the inherited and in the more common acquired form of TTP is based upon the use of antibodies to detect the presence or levels of ADAMTS13 and variants and mutants, as for example in blood or plasma samples obtained from in individual.

The identification of ADAMTS13 deficiency as the cause of TTP also has major implications for the treatment of this important human disease. In these embodiments, the present invention provides methods of treating patients with TTP. In some embodiments, a patient is administered a therapeutically effective amount of a recombinant protein. This treatment is likely to be much more effective, as well as much safer, than the plasma replacement therapy that is currently the only alternative. In yet other embodiments, a patient is treated with a therapeutically effective amount of genetic material comprising an ADAMTS13 gene or mutant or variant thereof that results in production of an ADAMTS13 protease in the patient.

In addition, ADAMTS13 or variants or other drugs based upon this protease can also be used in several different ways. In some embodiments, ADAMTS13 or drugs developed from it can be used in normal individuals as a novel approach to effect anticoagulation (preventing abnormal blood clots). Since blood clots are the basis of many important human diseases including heart attack and stroke, ADAMTS13 is used itself or as a suitable platform for the development of new pharmaceuticals to treat these common human diseases, where the pharmaceuticals are anticoagulants. In other embodiments, ADAMTS13 or variants are used to deliver other therapeutic proteins specifically to the microvasculature. These embodiments are based upon the observation that ADAMTS13 uses VWF in a specific conformation to cleave the Met842-Tyr843 bond. This conformation is reproduced in vitro by slightly "denaturing" VWF in urea or guanidine. It is believed that such "denaturation" is achieved in vivo by shear stress in the microvasculature. Therefore, it is contemplated that therapeutic proteins are administered in an inactive form that can be activated by cleavage of a peptide bond specifically by ADAMTS13 or variants under conditions of high shear stress in vivo.

DETAILED DESCRIPTION OF THE INVENTION

The present invention relates to a disintegrin and metalloproteinase containing thrombospondin 1-like domains (ADAMTS) and in particular to a novel ADAMTS13 protease and to nucleic acids encoding ADAMTS13 proteases. The present invention encompasses both native and recombinant wild-type forms of ADAMTS13, as well as mutant and variant forms including fragments, some of which posses altered characteristics relative to the wild-type ADAMTS13. The present invention also relates to methods of using ADAMTS13, including for treatment of TTP. The present invention also relates to methods for screening for the presence of TTP. The present invention further relates to methods for developing anticoagulant drugs based upon ADAMTS13.

1. ADAMTS13 Polynucleotides

As described above, a novel member of the family of disintegrin and metalloproteinases containing thrombospondin 1-like domains, ADAMTS13, has been discovered. This was accomplished by studying a series of families in which TTP appears to be inherited and then using a positional cloning approach to map a gene responsible for reduced VWF-cleaving protease activity to a locus on 9q34. Accordingly, the present invention provides nucleic acids encoding ADAMTS13 genes, homologs, variants (e.g., polymorphisms and mutants), and fragments, including but not limited to, those described in SEQ ID NOs: 1, 3, 5 and 7. In some embodiments, the present invention provide polynucleotide sequences that are capable of hybridizing to SEQ ID NOs: 1, 3, 5, and 7 under conditions of low to high stringency as long as the polynucleotide sequence capable of hybridizing encodes a protein that retains at least one or a portion of at least one biological activity of a naturally occurring ADAMTS13. In some embodiments, the protein that retains at least one or a portion of at least one biological activity of naturally occurring ADAMTS13 is 70% homologous to wild-type ADAMTS13, preferably 80% homologous to wild-type ADAMTS13, more preferably 90% homologous to wild-type ADAMTS13, and most preferably 95% homologous to wild-type ADAMTS13. In preferred embodiments, hybridization conditions are based on the melting temperature ($T_m$) of the nucleic acid binding complex and confer a defined "stringency" as explained above (See e.g., Wahl, et al., [1987] Meth. Enzymol., 152:399–407, incorporated herein by reference).

In other embodiments of the present invention, additional alleles of ADAMTS13 are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Non-limiting examples of the alleles of the present invention include those encoded by SEQ ID NOs: 1, 3, 5, and 7 (wild type), as well as those described in Tables 1 and 2.

In some embodiments of the present invention, the nucleotide sequences encode a CUB domain (e.g., nucleic acid sequences encoding the polypeptide fragment from amino acid 1192 to amino acid 1286 as shown in FIG. 6).

In still other embodiments of the present invention, the nucleotide sequences of the present invention may be engineered in order to alter an ADAMTS13 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of ADAMTS13 may be extended utilizing the nucleotide sequences (e.g., SEQ ID NOs: 1, 3 and 7) in various methods known in the art to detect upstream sequences such as promoters and regulatory elements. For example, it is contemplated that restriction-site polymerase chain reaction (PCR) will find use in the present invention. This is a direct method which uses universal primers to retrieve unknown sequence adjacent to a known locus (Gobinda et al. [1993] PCR Methods Applic., 2:318–22). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al. [1988] Nucleic Acids Res., 16:8186). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., [1991] Nucleic Acids Res., 19:3055–3060). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed ADAMTS13 sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Non-limiting examples of variants are shown in Table 2 Common mutational changes that give rise to variants are generally ascribed to deletions, additions or substitutions of nucleic acids; non-limiting examples are shown in Table 1. Each of these types of changes may occur alone, or in combination with the others, and at the rate of one or more times in a given sequence.

It is contemplated that it is possible to modify the structure of a peptide having a function (e.g., ADAMTS13 protease function) for such purposes as altering (e.g., increasing or decreasing) the substrate specificity or selectivity affinity of the ADAMTS13 for VWF or another substrate. Such modified peptides are considered functional equivalents of peptides having an activity of ADAMTS13 as defined herein. A modified peptide can be produced in which the nucleotide sequence encoding the polypeptide has been altered, such as by substitution, deletion, or addition. In particularly preferred embodiments, these modifications do not significantly reduce the protease activity of the modified ADAMTS13. In other words, construct "X" can be evaluated in order to determine whether it is a member of the genus of modified or variant ADAMTS13's of the present invention as defined functionally, rather than structurally. In preferred embodiments, the activity of variant ADAMTS13 polypeptides is evaluated by the methods described in Example 1B. Accordingly, in some embodiments, the present invention provides nucleic acids encoding a ADAMTS13 that cleaves VWF. In preferred embodiments, the activity of a ADAMTS13 variant is evaluated by utilizing guanidine hydrochloride-treated VWF.

Moreover, as described above, variant forms of ADAMTS13 and nucleotides encoding the same are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ADAMTS13 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17–21, 2nd ed, W H Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a ADAMTS13 coding sequence including, but not limited to, alterations that modify the cloning, processing, localization, secretion, and/or expression of the gene product. Such mutations may be introduced using techniques that are well known in the art (e.g., site-directed mutagenesis to insert new restriction sites, alter glycosylation patterns, or change codon preference, etc.).

II. ADAMTS13 Polypeptides

In other embodiments, the present invention provides ADAMTS13 polypeptides and fragments. Non-limiting examples of ADAMTS13 polypeptides (e.g., SEQ ID NOs: 2, 4 and 6) are described in FIGS. 3, 6, and 7. Other embodiments of the present invention provide fusion proteins or functional equivalents of these ADAMTS13 proteins. In still other embodiments, the present invention provides ADAMTS13 polypeptide variants, homologs, and mutants. In some embodiments of the present invention, the polypeptide is a naturally purified product, in other embodiments it is a product of chemical synthetic procedures, and in still other embodiments it is produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or it may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO: 1 and 3 which encode substantially the same or a functionally equivalent amino acid sequences, may be used to clone and express ADAMTS13. In general, such polynucleotide sequences hybridize to SEQ ID NO:1 under conditions of high to medium stringency as described above. As will be understood by those of skill in the art, it may be advantageous to produce ADAMTS13-encoding nucleotide sequences possessing non-naturally occurring codons. Therefore, in some preferred embodiments, codons preferred by a particular prokaryotic or eukaryotic host (Murray et al. [1989] Nucl. Acids Res. 17) are selected, for example, to increase the rate of ADAMTS13 expression or to produce recombinant RNA transcripts having desirable properties, such as a longer half-life, than transcripts produced from naturally occurring sequence.

A. Vectors for Production of ADAMTS13

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOS: 1, 3, and 5). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO: 1) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. Coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of ADAMTS13

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines, T-1 (tobacco cell culture line), root cell and cultured roots in rhizosecretion (Gleba et al., [1999] Proc Natl Acad Sci USA 96:5973–5977).

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al. [1986] Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

C. Purification of ADAMTS13

The present invention also provides methods for recovering and purifying ADAMTS13 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOs: 1, 3, and 5) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al. [1984] Cell, 37:767).

D. Fragments and Domains of ADAMTS13

In addition, the present invention provides fragments of ADAMTS13 (i.e., truncation mutants, e.g., SEQ ID NO:4). In other embodiments, the present invention provides domains of ADAMTS13 (e.g., the CUB domain, SEQ ID NO:6) In some embodiments of the present invention, when expression of a portion of the ADAMTS13 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. [1987] J. Bacteriol., 169:751) and *Salmonella typhimurium* and its in vitro activity has been demonstrated on recombinant proteins (Miller et al. [1990] Proc. Natl. Acad. Sci. USA, 84:2718). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP.

E. Fusion Proteins Containing ADAMTS13

The present invention also provides fusion proteins incorporating all or part of ADAMTS13. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a ADAMTS13 protein. In some embodiments of the present invention, the VP6 capsid protein of rotavirus is used as an immunologic carrier protein for portions of the ADAMTS13 polypeptide, either in the monomeric form or in the form of a viral particle. In other embodiments of the present invention, the nucleic acid sequences corresponding to the portion of ADAMTS13 against which antibodies are to be raised can be incorporated into a fusion gene construct which includes coding sequences for a late vaccinia virus structural protein to produce a set of recombinant viruses expressing fusion proteins comprising a portion of ADAMTS13 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of ADAMTS13 and the poliovirus capsid protein are created to enhance immunogenicity of the set of polypeptide antigens (See e.g., EP Publication No. 025949; and Evans et al. (1989) Nature 339:385; Huang et al. (1988) J. Virol., 62:3855; and Schlienger et al. (1992) J. Virol., 66:2).

In still other embodiments of the present invention, the multiple antigen peptide system for peptide-based immunization can be utilized. In this system, a desired portion of ADAMTS13 is obtained directly from organo-chemical synthesis of the peptide onto an oligomeric branching lysine core (see e.g., Posnett et al. (1988) J. Biol. Chem., 263:1719; and Nardelli et al. (1992) J. Immunol., 148:914). In other embodiments of the present invention, antigenic determinants of the ADAMTS13 proteins can also be expressed and presented by bacterial cells.

In addition to utilizing fusion proteins to enhance immunogenicity, it is widely appreciated that fusion proteins can also facilitate the expression of proteins, such as the ADAMTS13 protein of the present invention. Accordingly, in some embodiments of the present invention, ADAMTS13 can be generated as a glutathione-S-transferase (i.e., GST fusion protein). It is contemplated that such GST fusion proteins will enable easy purification of ADAMTS13, such as by the use of glutathione-derivatized matrices (See e.g., Ausabel et al. (1992) (eds.), Current Protocols in Molecular Biology, John Wiley & Sons, NY). In another embodiment of the present invention, a fusion gene coding for a purification leader sequence, such as a poly-(His)/enterokinase cleavage site sequence at the N-terminus of the desired portion of ADAMTS13, can allow purification of the expressed ADAMTS13 fusion protein by affinity chromatography using a $Ni^{2+}$ metal resin. In still another embodiment of the present invention, the purification leader sequence can then be subsequently removed by treatment with enterokinase (See e.g., Hochuli et al. (1987) J. Chromatogr., 411:177; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

F. Variants of ADAMTS13

Still other embodiments of the present invention provide mutant or variant forms of ADMTS13 (i.e., muteins; see for example Table 1). It is possible to modify the structure of a peptide having an activity of ADAMTS13 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject ADAMTS13 proteins as defined herein. A modified peptide can be produced in which the amino acid sequence has been altered, such as by amino acid substitution, deletion, or addition.

Moreover, as described above, variant forms (e.g., mutants or polymorphic sequences) of the subject ADAMTS13 proteins and the nucleotides encoding them are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present ADAMTS13 proteins, as well as truncation mutants, and is especially useful for identifying potential variant sequences (i.e., mutants or polymorphic sequences) that are functional in cleaving VWF proteins or other protein substrates. The purpose of screening such combinatorial libraries is to generate, for example, novel ADAMTS13 variants that can act as anticoagulants.

Therefore, in some embodiments of the present invention, ADAMTS13 variants are engineered by the present method to provide altered substrate specificity or selectivity. In other embodiments of the present invention, combinatorially-derived variants are generated which have a selective potency relative to a naturally occurring ADAMTS13. Such proteins, when expressed from recombinant DNA constructs, can be used in gene therapy protocols.

Still other embodiments of the present invention provide ADAMTS13 variants that have intracellular half-lives dramatically different than the corresponding wild-type protein. For example, the altered protein can be rendered either more stable or less stable to proteolytic degradation or other cellular process that result in destruction of, or otherwise inactivate ADAMTS13. Such variants, and the genes which encode them, can be utilized to alter the location of ADAMTS13 expression by modulating the half-life of the protein. For instance, a short half-life can give rise to more transient ADAMTS13 biological effects and, when part of an inducible expression system, can allow tighter control of ADAMTS13 levels within the cell. As above, such proteins, and particularly their recombinant nucleic acid constructs, can be used in gene therapy protocols.

In some embodiments of the combinatorial mutagenesis approach of the present invention, the amino acid sequences for a population of ADAMTS13 homologs, variants or other related proteins are aligned, preferably to promote the highest homology possible. Such a population of variants can include, for example, ADAMTS13 homologs from one or more species, or ADAMTS13 variants from the same species but which differ due to mutation or polymorphisms. Amino acids that appear at each position of the aligned sequences are selected to create a degenerate set of combinatorial sequences.

In a preferred embodiment of the present invention, the combinatorial ADAMTS13 library is produced by way of a degenerate library of genes encoding a library of polypeptides which each include at least a portion of potential ADAMTS13 protein sequences. For example, a mixture of synthetic oligonucleotides can be enzymatically ligated into gene sequences such that the degenerate set of potential ADAMTS13 sequences are expressible as individual polypeptides, or alternatively, as a set of larger fusion proteins (e.g., for phage display) containing the set of ADAMTS13 sequences therein.

There are many ways by which the library of potential ADAMTS13 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ADAMTS13 sequences. The synthesis of degenerate oligonucleotides is well known in the art (See e.g., Narang (1983) Tetrahedron Lett., 39:39; Itakura et al. (1981) Recombinant DNA, in Walton (ed.), *Proceedings of the 3rd Cleveland Symposium on Macromolecules*, Elsevier, Amsterdam, pp 273–289; Itakura et al. (1984) Annu. Rev. Biochem., 53:323; Itakura et al. (1984) Science 198:1056; Ike et al. (1983) Nucl. Acid Res., 11:477). Such techniques have been employed in the directed evolution of other proteins (See e.g., Scott et al. (1980) Science 249:386; Roberts et al. (1992) Proc. Natl. Acad. Sci. USA 89:2429; Devlin et al. (1990) Science 249: 404; Cwirla et al. (1990) Proc. Natl. Acad. Sci. USA 87: 6378; as well as U.S. Pat. Nos. 5,223,409, 5,198,346, and 5,096,815; each of which is incorporated herein by reference).

It is contemplated that the ADAMTS13 encoding nucleic acids (e.g., SEQ ID NO:1 and 3, and fragments and variants thereof can be utilized as starting nucleic acids for directed evolution. These techniques can be utilized to develop ADAMTS13 variants having desirable properties such as increased or decreased specificity for VWF or other protein substrates.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458; Leung et al. (1989) Technique, 1:11; Eckert and Kunkel (1991) PCR Methods Appl., 1: 17–24; Caldwell and Joyce (1992) PCR Methods Appl., 2:28; and Zhao and Arnold (1997) Nuc. Acids. Res., 25:1307). After mutagenesis, the resulting clones are selected for desirable activity (e.g., screened for ADAMTS13 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370:324; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer [1994] Nature, 370:398; Stemmer [1994] Proc. Natl. Acad. Sci. USA, 91:10747; Crameri et al. [1996] Nat. Biotech., 14:315; Zhang et al. [1997] Proc. Natl. Acad. Sci. USA, 94:4504; and Crameri et al. [1997] Nat. Biotech., 15:436). Variants produced by directed evolution can be screened for ADAMTS13 activity by the methods described in Example 1B.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of ADAMTS13 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

G. Chemical Synthesis of ADAMTS13

In an alternate embodiment of the invention, the coding sequence of ADAMTS13 is synthesized, whole or in part, using chemical methods well known in the art (See e.g., Caruthers et al. (1980) Nucl. Acids Res. Symp. Ser., 7:215; Crea and Horn (1980) Nucl. Acids Res., 9:2331; Matteucci and Caruthers (1980) Tetrahedron Lett., 21:719; and Chow and Kempe (1981) Nucl. Acids Res., 9:2807). In other embodiments of the present invention, the protein itself is produced using chemical methods to synthesize either an entire ADAMTS13 amino acid sequence or a portion thereof. For example, peptides can be synthesized by solid phase techniques, cleaved from the resin, and purified by preparative high performance liquid chromatography (See e.g., Creighton (1983) *Proteins Structures And Molecular Principles*, W H Freeman and Co, New York N.Y.). In other embodiments of the present invention, the composition of the synthetic peptides is confirmed by amino acid analysis or sequencing (See e.g., Creighton, supra).

Direct peptide synthesis can be performed using various solid-phase techniques (Roberge et al. [1995] Science 269: 202) and automated synthesis may be achieved, for example, using ABI 431A Peptide Synthesizer (Perkin Elmer) in accordance with the instructions provided by the manufacturer. Additionally, the amino acid sequence of ADAMTS13, or any part thereof, may be altered during direct synthesis and/or combined using chemical methods with other sequences to produce a variant polypeptide.

III. Detection of ADAMTS13 Alleles

A. ADAMTS13 Alleles

In some embodiments, the present invention includes alleles of ADAMTS13 that increase a patient's susceptibility to TTP disease (e.g., including, but not limited to, the mutations shown in Table 1). Analysis of naturally occurring human ADAMTS13 alleles revealed that patients with increased susceptibility to TTP disease have a mutant ADAMTS13 allele that, for example, result in a frameshift (a 26 bp deletion in exon 19, 2374–2399del, and a single A insertion in exon 27, 3769–3770insA), an in frame 23 amino acid insertion as result of a single splice mutation (1584+5>A), or a non-conservative amino acid substitution (286G>G, H96D; 304 C>T, R102C; 587C>T, T196I; 1193G>A, R398H; 1582A>G, R528G; 2074C>T; R692C; 2851T>G, C951G; 3070T>G, C1024G; 3638G>A, C1213Y). These patients all have greatly decreased levels of VWF-cleaving protease levels (see FIG. 1).

The present invention is not limited to a particular mechanism of action. Indeed, an understanding of the mechanism of action is not necessary to practice the present invention. Nevertheless, it is contemplated that ADAMTS13 is involved in normal proteolytic processing of VWF. It is contemplated that in TTP the accumulation of hyperactive large VWF multimers in the absence of normal proteolytic processing triggers pathologic platelet aggregation and is the direct mechanism responsible for TTP.

However, the present invention is not limited to the mutations described in Table 1. Any mutation that results in the undesired phenotype (e.g., a low level of VWF cleaving protease activity, or the presence of or susceptibility to TTP) is within the scope of the present invention. Assays for determining if a given polypeptide has a decreased level of VWF cleaving protease activity are provided in Example 1C.

For example, in some embodiments, the present invention provides alleles containing one or more single-nucleotide changes of ADAMTS13 (e.g., mutants or polymorphic sequences) (e.g., including but not limited to the mutations shown in Table 1, and the polymorphisms shown in Table 2).

B. Detection of Variant Alleles

Accordingly, the present invention provides methods for determining whether a patient has an increased susceptibility to TTP disease by determining whether the individual has a variant ADAMTS13 allele. In other embodiments, the present invention provides methods for providing a prognosis of increased risk for TTP disease to an individual based on the presence or absence of one or more variant alleles of ADAMTS13. In preferred embodiments, the variation is a mutation resulting in decreased levels of VWF cleaving protease activity. In more preferred embodiments, the variation is a mutation described in Table 1.

A number of methods are available for analysis of variant (e.g., mutant or polymorphic) nucleic acid sequences. Assays for detections polymorphisms or mutations fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assays

In some embodiments of the present invention, variant sequences are detected using a PCR-based assay. In some embodiments, the PCR assay comprises the use of oligonucleotide primers that hybridize only to the variant or wild type allele of ADAMTS13 (e.g., to the region of polymorphism or mutation). Both sets of primers are used to amplify a sample of DNA. If only the mutant primers result in a PCR product, then the patient has the mutant ADAMTS13 allele. If only the wild-type primers result in a PCR product, then the patient has the wild type allele of ADAMTS13.

3. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assays

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assays

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

4. Hybridization Assays

In preferred embodiments of the present invention, variant sequences are detected by hybridization analysis in a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.) (1991) Current Protocols in Molecular Biology, John Wiley & Sons, NY). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the amidite A is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717; 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

5. Mass Spectroscopy Assays

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged, when an electrical field pulse is subsequently applied to the tube the diagnostic product is launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3–5 second including repetitive data collection. The SpectroTYPER software then calculates, records, compares and reports the genotypes at the rate of three seconds per sample.

6. Variant Analysis by Differential Antibody Binding

In other embodiments of the present invention, antibodies (See below for antibody production) are used to determine if an individual contains an allele encoding an ADAMTS13 gene containing a mutation. In preferred embodiments, antibodies are utilized that discriminate between mutant (i.e., truncated proteins); and wild-type proteins (SEQ ID NO:2).

7. Kits for Analyzing Risk of TTP Disease

The present invention also provides kits for determining whether an individual contains a wild-type or variant (e.g., mutant or polymorphic) allele of ADAMTS13. In some embodiments, the kits are useful determining whether the subject is at risk of developing TTP disease. The diagnostic kits are produced in a variety of ways. In some embodiments, the kits contain at least one reagent for specifically detecting a mutant ADAMTS13 allele or protein. In some preferred embodiments, the kits contain reagents for detecting a SNP caused by a single nucleotide substitution of the wild-type gene. In these preferred embodiments, the reagent is a nucleic acid that hybridizes to nucleic acids containing the SNP and that does not bind to nucleic acids that do not contain the SNP. In other preferred embodiments, the reagents are primers for amplifying the region of DNA containing the SNP. In still other embodiments, the reagents are antibodies that preferentially bind either the wild-type or mutant ADAMTS13 proteins. In some embodiments, the kit contains instructions for determining whether the subject is at risk for developing TTP disease. In preferred embodiments, the instructions specify that risk for developing TTP disease is determined by detecting the presence or absence of a mutant ADAMTS13 allele in the subject, wherein subjects having an allele containing a single nucleotide substitution mutation have an increased risk of developing TTP disease. In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test. In some embodiments, the kits also preferably include a positive control sample.

8. Bioinformatics

In some embodiments, the present invention provides methods of determining an individual's risk of developing TTP disease based on the presence of one or more variant alleles of ADAMTS13. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting TTP disease associated with a given polymorphism, as well as the sequences). Results are then delivered to the user (e.g., via one of the computers or via the internet).

IV. Generation of ADAMTS13 Antibodies

Antibodies can be generated to allow for the detection of ADAMTS13 protein. The antibodies may be prepared using various immunogens. In one embodiment, the immunogen is an ADAMTS13 peptide to generate antibodies that recognize human ADAMTS13. Such antibodies include, but are not limited to polyclonal, monoclonal, chimeric, single chain, Fab fragments, and Fab expression libraries.

Various procedures known in the art may be used for the production of polyclonal antibodies directed against ADAMTS13. For the production of antibody, various host animals can be immunized by injection with the peptide corresponding to the ADAMTS13 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward ADAMTS13, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler & Milstein [1975] Nature 256:495–497), as well as the trioma technique, the human B-cell hybridoma technique (See e.g., Kozbor et al. (1983) Immunol. Tod., 4:72), and the EBV-hybridoma technique to produce human monoclonal antibodies (Cole et al. [1985] in *Monoclonal Antibodies and Cancer Therapy*, Alan R. Liss, Inc., pp. 77–6).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al. [1983] Proc. Natl. Acad. Sci. USA 80:2026-2030) or by transforming human B cells with EBV virus in vitro (Cole et al. [1985] in *Monoclonal Antibodies and Cancer Therapy*, Alan R. Liss, pp. 77–96).

In addition, it is contemplated that techniques described for the production of single chain antibodies (U.S. Pat. No. 4,946,778; herein incorporated by reference) will find use in producing ADAMTS13 specific single chain antibodies. An additional embodiment of the invention utilizes the techniques described for the construction of Fab expression libraries (Huse et al. [1989] Science 246:1275–1281) to allow rapid and easy identification of monoclonal Fab fragments with the desired specificity for ADAMTS13.

It is contemplated that any technique suitable for producing antibody fragments will find use in generating antibody fragments that contain the idiotype (antigen binding region) of the antibody molecule. For example, such fragments include but are not limited to: $F(ab')_2$ fragment that can be produced by pepsin digestion of the antibody molecule; Fab' fragments that can be generated by reducing the disulfide bridges of the $F(ab')_2$ fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of ADAMTS13 (e.g., for Western blotting), measuring levels thereof in appropriate biological samples, etc. The antibodies can be used to detect ADAMTS13 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of ADAMTS13 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of ADAMTS13 detected by immunoblotting (Western blotting). Immunoblotting techniques are generally more effective with antibodies generated against a peptide corresponding to an epitope of a protein, and hence, are particularly suited to the present invention.

In other embodiments, the antigen is a peptide fragment of ADAMTS13; preferably, the fragment is of high antigenicity. In yet other embodiment, the immunogen is a variant or mutant of ADAMTS13 peptide to generate antibodies that recognize the variant or mutant ADAMTS13. Such antibodies include, but are not limited to polyclonal, monoclonal, chimeric, single chain, Fab fragments, and Fab expression libraries, and are prepared and used as described above. These antibodies can then be used to detect the presence of a fragment or variant or mutant ADAMTS13 in a biological sample from an individual, as described above, and thus to predict the susceptibility of the individual to TTP.

For example, peptide antibodies have been synthesized against one peptide in exon 5 and one peptide in exon 13. These peptide fragments were selected on the basis of determinations by computer algorithms and other methods as having high "antigenicity" (likely to elicit an immune response); the selected peptides were then synthesized. The peptide fragments were injected into rabbits, and the rabbits periodically bled and boosted with the peptide antigen between bleeds. This serum was used as the source of the antibodies, while the serum before peptide injection was used as a negative control. The antibodies are affinity purified by passing the serum over a column composed of the peptide to purify only antibodies that bind the peptide. At least one of these antibodies in the unpurified state detects a protein of approximately the right size that is present in normal plasma but not patient plasma. Antibodies are also prepared against other peptide fragments.

V. Methods of Treatment of TTP

A. Gene Therapy Using ADAMTS13 Coding Sequences

The present invention also provides methods and compositions suitable for gene therapy to alter ADAMTS13 expression, production, or function. As described above, the present invention provides ADAMTS13 genes and provides methods of obtaining ADAMTS13 genes from different species. Thus, the methods described below are generally applicable across many species. In some embodiments, it is contemplated that the gene therapy is performed by providing a subject with a wild-type allele of ADAMTS13 (i.e., an allele that does not contain a mutation which results in a decrease of VWF-cleaving protease activity; examples of such mutations are shown in Table 2). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g. (1992) Miller and Rosman, BioTech., 7:980–990). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. [1991] Mol. Cell. Neurosci., 2:320–330), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626–630 [1992]; See also, La Salle et al. [1993] Science 259:988–990); and a defective adeno-associated virus vector (Samulski et al. [1987] J. Virol., 61:3096–3101; Samulski et al. [1989] J. Virol., 63:3822–3828; and Lebkowski et al. [1988] Mol. Cell. Biol., 8:3988–3996).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. The present invention contemplates adenoviruses of both human and animal origin. (See e.g., WO94/26914). Various serotypes of adenovirus exist. Those adenoviruses of animal origin that can be used within the scope of the present invention include adenoviruses of canine, bovine, murine (e.g., Mav1, Beard et al. (1990) Virol., 75–81), ovine, porcine, avian, and simian (e.g., SAV) origin. Preferably, the adenovirus of animal origin is a canine adenoviris, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BgII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al. (1991) Gene 101:195; EP 185 573; and Graham (1984) EMBO J., 3:2917). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al. [1977] J. Gen. Virol., 36:59), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al. (1983) Cell 33:153; Markowitz et al. (1988) J. Virol., 62:1120; PCT/ US95/14575; EP 453242; EP178220; Bernstein et al. (1985) Genet. Eng., 7:235; McCormick, (1985) BioTechnol., 3:689; WO 95/07358; and Kuo et al., (1993) :845). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al. [1987] Virol., 61:1639). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. [1987] Proc. Natl. Acad. Sci. USA 84:7413–7417; See also, Mackey, et al. (1988) Proc. Natl. Acad. Sci. USA 85:8027–8031; Ulmer et al. (1993) Science 259:1745–1748). The use of cationic lipids may promote encapsulation of negatively charged nucleic acids, and also promote fusion with negatively charged cell membranes (Felgner and Ringold [1989] Science 337:387–388). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267:963; Wu and Wu (1988) J. Biol. Chem., 263:14621; and Williams et al. (1991) Proc. Natl. Acad. Sci. USA 88:2726). Receptor-mediated DNA delivery approaches can also be used (Curiel et al. [1992] Hum. Gene Ther., 3:147; and Wu & Wu [1987] J. Biol. Chem., 262:4429).

B. Administration of ADAMTS13 Polypeptides

The present invention also provides methods and compositions suitable for administering ADAMTS13 to a patient suffering from TTP. As described above, the present invention provides nucleotides encoding ADAMTS13 and fragments, mutants, variants, and fusions thereof, and methods of producing the encoded polypeptides. The methods described below are generally applicable across many species.

In some embodiments, the invention provides a composition comprising purified ADAMTS13 peptides; in other embodiments, the invention provides a composition comprising purified ADAMTS13 polypeptide fragments, mutants, variants, or fusions, all of which possess the biological activity of ADAMTS13. Fragments, mutants, variants, or fusions may be used as necessary to alter characteristics of ADAMTS13 to improve its performance as a therapeutic treatment of TTP. Such characteristics include stability during storage and administration, circulating half-life, levels of activity, substrate specificity, localization to a particular tissue, and interaction with other molecules, such as receptors or enzymatic complexes. For example, the protein is preferably engineered to have a very long circulating half life. Such characteristics can be introduced as described above. The polypeptides can be produced as described above. The compositions are formulated as described.

In other embodiments, the invention provides a method of treating a patient with TTP disease, which comprises administering a therapeutically effective amount of ADAMTS13 such that symptoms of the disease are alleviated. As is well known in the medical arts, dosages for any one patient depends upon many factors, including the patient's size, body surface area, age, the particular compound to be administered, sex, time and route of administration, general health, and interaction with other drugs being concurrently administered. Although any method of administration is anticipated, as described further below, preferably the polypeptide is administered intravenously.

VI. Drug Screening Using ADAMTS13

The present invention provides methods and compositions for using ADAMTS13 as a target for screening drugs that can alter, for example, VWF-cleaving protease activity and associated symptoms (e.g., TTP disease). For example, drugs that induce or inhibit VWF-cleaving protease activity can be identified by screening for compounds that target ADAMTS13 or regulate ADAMTS13 gene expression.

The present invention is not limited to a particular mechanism of action. Indeed, an understanding of the mechanism of action is not necessary to practice the present invention. Nevertheless, it is contemplated that a decrease of VWF-cleaving protease activity leads to an accumulation of hyperactive large VWF multimers which triggers pathologic platelet aggregation and is the direct mechanism responsible for TTP. Thus, it is contemplated that drugs which induce VWF-cleaving protease activity can be used to prevent symptoms of TTP.

Alternatively, it is also contemplated that increased VWF-cleaving protease activity could also be used in normal individuals as a novel approach to anticoagulation (preventing abnormal blood clots). Since blood clots are at the basis of many important human diseases including heart attack and stroke, this new insight could be critical to the development of new pharmaceuticals to treat these very common human diseases as well as the rare disorder TTP. Such increased VWF-cleaving activity could be achieved by inducing the enzyme activity as described above. Other embodiments contemplate drugs based upon variants of the ADAMTS13 protease itself. Such proteases would, for example, be effective at reducing clots, be easily administered, and have a life span of sufficient duration as to treat the disease, but not to cause subsequent harm.

In one screening method, candidate compounds are evaluated for their ability to alter VWF-cleaving protease activity by adding the compound in the presence of an ADAMTS13 protease to an assay for the VWF-cleaving protease activity, for example as is described in Example 1B, and determining the effects of the compound on the level of protease activity.

In another screening method, variants of ADAMTS13 are evaluated for their ability to cleave VWF by adding the variants to an assay for the VWF-cleaving protease activity, for example as is described in Example 1B, and determining the level of protease activity of the variant.

Another technique uses ADAMTS13 antibodies, generated as discussed above. Such antibodies capable of specifically binding to ADAMTS13 peptides can be used to detect the presence of any peptide that shares one or more antigenic determinants of the ADAMTS13 peptide. Such peptides can then be evaluated for protease activity as described above.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with ADAMTS13 and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in reporter gene assays that monitor cellular responses at the transcription/translation level. In still further embodiments, the cells can be used in cell proliferation assays to monitor the overall growth/no growth response of cells to external stimuli.

The cells are useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminescent products of specific substrates (e.g., X-gal and luciferin). Comparisons between compounds of known and unknown activities may be conducted as described above.

VII. Pharmaceutical Compositions Containing ADAMTS13 Nucleotides, Peptides, and Antibodies, and Analogs The present invention further provides pharmaceutical compositions which may comprise all or portions of ADAMTS13 encoding polynucleotide sequences, ADAMTS13 polypeptides, inhibitors or antagonists of ADAMTS13 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by decreased VWF-cleaving protease activity, and/or pathologic platelet aggregation. The invention provides methods for increasing VWF-cleaving protease activity and/or decreasing pathologic platelet aggregation by administering peptides or peptide fragments or variants of ADAMTS13. Alternatively, drugs which act to increase VWF-cleaving protease activity and/or decreasing pathologic platelet aggregation, as discovered through screening methods described above, are administered.

Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, ADAMTS13 nucleotides and ADAMTS13 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, ADAMTS13 encoding polynucleotide sequences or ADAMTS13 amino acid sequences may be administered alone to individuals subject to or suffering from a disease, such as TTP or stroke.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of ADAMTS13 may be that amount that results in VWF-cleaving protease activity, or decreased levels of platelet aggregation, comparable to normal individuals who are not suffering from TTP or stroke. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of ADAMTS13, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0. 1%–2% sucrose, 2%-% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts ADAMTS13 levels.

A therapeutically effective dose refers to that amount of ADAMTS13 or variant or drug that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for ADAMTS than for the inducers or enhancers of ADAMTS13. Administration to the bone marrow may necessitate delivery in a manner different from intravenous injections.

VIII. Transgenic Animals Expressing Exogenous ADAMTS13 Genes and Homologs, Mutants, and Variants Thereof The present invention contemplates the generation of transgenic animals comprising an exogenous ADAMTS13 gene or homologs, mutants, or variants thereof. In preferred embodiments, the transgenic animal displays an altered phenotype as compared to wild-type animals. In some embodiments, the altered phenotype is the overexpression of mRNA for an ADAMTS13 gene as compared to wild-type levels of ADAMTS13 expression. In other embodiments, the altered phenotype is the decreased expression of mRNA for an endogenous ADAMTS13 gene as compared to wild-type levels of endogenous ADAMTS13 expression. In other embodiments, the transgenic mice have a knock out mutation of the ADAMTS13 gene. In still further embodiments, the altered phenotype is expression of an ADAMTS13 mutant gene; non-limiting examples of such mutants are shown in Table 1. In preferred embodiments, the transgenic animals display a TTP disease phenotype. Methods for analyzing the presence or absence of such altered phenotypes include Northern blotting, mRNA protection assays, RT-PCR, detection of protein expression with antibodies, and detection of protein activity with VWF-cleaving protease activity, such as is described in Example 1B.

The transgenic animals of the present invention find use in drug and treatment regime screens. In some embodiments, test compounds (e.g., a drug that is suspected of being useful to treat TTP disease) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonic cells at various developmental stages are used to introduce transgenes for the production of transgenic animals. Different methods are used depending on the stage of development of the embryonic cell. The zygote is the best target for microinjection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al. [1985] Proc. Natl. Acad. Sci. USA, 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich [1976] Proc. Natl. Acad. Sci. USA, 73:1260). Efficient infection of the blastomeres is obtained by enzymatic treatment to remove the zona pellucida (Hogan et al. [1986] in *Manipulating the Mouse Embryo*, Cold Spring Harbor Laboratory Press, Cold Spring Harbor, N.Y.). The viral vector system used to introduce the transgene is typically a replication-defective retrovirus carrying the transgene (Jahner et al. [1985] Proc. Natl. Acad. Sci. USA 82:6927). Transfection is easily and efficiently obtained by culturing the blastomeres on a monolayer of virus-producing cells (Van der Putten, supra; Stewart, et al. [1987] EMBO J., 6:383). Alternatively, infection can be performed at a later stage. Virus or virus-producing cells can be injected into the blastocoele (Jahner et al. [1982] Nature 298:623). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al. [1982] supra). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen (1995) Mol. Reprod. Dev., 40:386).

In other embodiments, the transgene is introduced into embryonic stem cells and the transfected stem cells are utilized to form an embryo. ES cells are obtained by culturing pre-implantation embryos in vitro under appropriate conditions (Evans et al. [1981] Nature 292:154; Bradley et al. [1984] Nature 309:255; Gossler et al [1986] Proc. Acad. Sci. USA 83:9065; and Robertson et al. [1986] Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoele of a blastocyst-stage embryo and contribute to the germ line of the resulting chimeric animal (for review, See, Jaenisch (1988) Science 240:1468). Prior to the introduction of transfected ES cells into the blastocoele, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoele.

In still other embodiments, homologous recombination is utilized knock-out gene function or create deletion mutants. Methods for homologous recombination are described in U.S. Pat. No. 5,614,396, incorporated herein by reference.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml or mL (milliliters); μl or μL (microliters); cm (centimeters); mm (millimeters); μm (micrometers); nm (nanometers); DS (dextran sulfate); ° C. (degrees Centigrade); U (units); ADAM (a disintegrin and metalloproteinase); TPP (thrombotic thrombocytopenic purpura); TSP (thrombospondin); von Wildebrandt factor (VWF) and Sigma (Sigma Chemical Co., St. Louis, Mo.).

EXAMPLE 1

Methods

This example describes the methods used to identify and characterize the gene ADAMTS13.

A. Subjects. Patients included in this study were referred for evaluation of thrombocytopenia, hemolytic anemia, and schistocytes on blood smear. Probands for the 4 families (A–D) used in the linkage analysis all had a chronic relapsing course, responded to plasma infusion, and had the disorder as neonates or had a family member with such a disorder as a neonate. The additional probands studied from families E–G exhibited some or all of these features. Plasma samples were obtained from sodium citrate anticoagulated blood by centrifugation and saved at −70° C. as previously described (Tsai, H. M. & Lian, E. C. Y [1998] N. Engl. J. Med. 339, 1585–1594). Mononuclear cells were obtained from heparin anticoagulated blood by centrifugation on Ficoll-Hypaque, washed and transformed with Epstein-Barr virus. Informed consent was obtained from all individuals prior to sample collection following an Institutional Review Board approved study protocol.

B. VWF-cleaving protease activity of patient sera. For the measurement of VWF-cleaving protease activity, guanidine hydrochloride-treated VWF was used as the substrate. Protease activity was represented by the optical density of the dimer of the 176kd fragment generated from the VWF substrate (Tsai, H. M. & Lian, E. C. Y. [1998] N. Engl. J.

Med. 339, 1585–1594) and was expressed in U/mL, with the activity measured in pooled normal control plasma defined as 1 U/mL. Each sample was measured on at least three occasions and the mean of the results is presented. Assays for inhibitors of VWF-cleaving protease were performed as described (Tsai et al. [2001] Clin. Lab. 47, 387–392).

C. Haplotype analysis. A total of 17 markers were used for haplotype analysis. 13 of these markers were obtained from the comprehensive genetics maps of Genethon (Dib, C. et al. [1996] Nature 380, 152–154) and Marshfield (Broman, K. W. et al. [1998] Am. J. Hum. Genet. 63, 861–869), and 4 of these markers were designed from sequence repeat information available at http://genome.ucsc.edu (see Table 3).

TABLE 3

New STS markers.

| Marker | Accession # | BAC | 5' primer | 3' primer |
|---|---|---|---|---|
| GL1-3 | pending | AL157938 | 5'-gctttgctctcctgagcttc-3' (SEQ ID NO: 8) | 5'-gtggtgcagttcactgtcgt-3' (SEQ ID NO: 9) |
| GL2-1 | pending | AL160271 | 5'-gttgcagtgagctgagatcg-3' (SEQ ID NO: 10) | 5'-tgcaggggtttttatctccta-3' (SEQ ID NO: 11) |
| GL3-2 | pending | AL160165 | 5'-tgggtgacagagcaagactg-3' (SEQ ID NO: 12) | 5'-cttgtatccacgcacagagg-3' (SEQ ID NO: 13) |
| GL4-1 | pending | AC002104 | 5'-agcctgggtgacagagtgag-3' (SEQ ID NO: 14) | 5'-tacaccaattccccaggtgt-3' (SEQ ID NO: 15) |

D. Linkage analysis. A genome-wide linkage screen was performed using 382 polymorphic microsatellite markers spaced an average of 10 cM (panels 1–27 of the ABI Prism Linkage Mapping Set-MD10 (Applied Biosystems)). 20 ng of genomic DNA was amplified using AmpliTaq Gold DNA polymerase (Applied Biosystems). PCR products were run on an ABI Prism 3700 DNA Analyzer and analyzed using Genescan v3.5NT and Genotyper v3.6NT. Inspection of the pedigrees indicated an autosomal recessive mode of inheritance for TTP in this set of families. The frequency of the disease gene was assumed to be one per ten thousand chromosomes in the population. Population frequencies of the marker alleles were estimated from the genotyped individuals. Two-point LOD scores were calculated using the program MLINK as implemented in the FASTLINK package, version 3.0 (Schaffer, A. A. et al. [1994] Hum. Hered. 44, 225–237) using an autosomal recessive model. A second series of analyses was performed using a codominant model to reflect the lowered enzyme levels of individuals who were assumed to be carriers of the disease gene. For the latter analysis, individuals were classified as affected (those with clinical diagnoses), carriers (those with protease levels in the range of 0.45–0.68 U/mL) and unaffected (those with protease levels in the range of 0.8–1.17 U/mL). Penetrance was set at 100% for both models. Multipoint analyses were performed with the program VITESSE (O'Connell, J. R. & Weeks, D. E. [1995] Nat. Genet. 11, 402–408), using the same two disease models and the 5 markers at or flanking the maximum two-point LOD score. Order and distances between markers were determined using the ABI Prism Linkage Mapping Set-MD10 map information.

E. Sequence analysis. All exons and intron/exon boundaries of the predicted ADAMTS13 gene were amplified from patient genomic DNA with the exception of exon 7, which could not be amplified with multiple primer sets. Intron primers were selected using the Primer3 software package to allow for analysis of exon sequence as well as flanking donor and acceptor splice sites. (See Table 4 for primer sequences). 100 ng of genomic DNA was used in a PCR reaction using either Platinum Taq DNA polymerase (Invitrogen), the Expand Long-Template DNA polymerase mix (Roche) or the Advantage 2 DNA polymerase mix (Clontech). PCR products were either purified directly from the PCR reaction using the Qiaquick PCR purification kit (Qiagen) or gel-purified from low-melting agarose (Invitrogen) using the Wizard PCR preps purification kit (Promega). Total cellular RNA from lymphoblast cell lines was prepared using Trizol (Invitrogen) and RT-PCR performed using the One-Step RT-PCR kit (Invitrogen), according to the manufacturer's instructions. Sequencing reactions were performed by the University of Michigan DNA Sequencing Core. Selected PCR products were subcloned into a pCR-TOPO plasmid (Invitrogen) for further sequence analysis.

TABLE 4

Primers used for the amplification of ADAMTS13 exons and intron/exon boundaries

| Exon | Forward Primer Sequence | Reverse Primer Sequence | Annealing Temp. |
|---|---|---|---|
| 1 | 5'-CCC TGA ACT GCA ACC ATC TT-3' (SEQ ID NO: 16) | 5'-CAA ACC CCA AAG CTG ATG TA-3' (SEQ ID NO: 17) | 56[1] |
| 2 | 5'-TCG GTC TCC CCA AGT GTT AG-3' (SEQ ID NO: 18) | 5'-AAC AGG GTT GAC AGC AGC TT-3' (SEQ ID NO: 19) | 56[1] |
| 3 | 5'-TCT AGA ACC ATC GCC CTC TG-3' (SEQ ID NO: 20) | 5'-CCG AGC CAT TCT ACC TGA GT-3' (SEQ ID NO: 21) | 56[1] |
| 4 | 5'-GCC TCT CCA GCT CTT CAC AC-3' (SEQ ID NO: 22) | 5'-GCA TTC TGT GAT CCA TGC TG-3' (SEQ ID NO: 23) | 56[1] |
| 5–6 | 5'-ACG GGC TAG TCA TAG GGT TG-3' (SEQ ID NO: 24) | 5'-TAC AAG GAC CCA CTG CTT GC-3' (SEQ ID NO: 25) | 56[1] |
| 7 | Not yet available | Not yet available | |

TABLE 4-continued

Primers used for the amplification of ADAMTS13 exons and intron/exon boundaries

| Exon | Forward Primer Sequence | Reverse Primer Sequence | Annealing Temp. |
|---|---|---|---|
| 8 | 5'-CTT CCA AAC GCT TCC ATC CT-3' (SEQ ID NO: 26) | 5'-CCC TCC CAG GAC TAG CTA CA-3' (SEQ ID NO: 27) | 56[2] |
| 9 | 5'-TCT GGG AGG GAC AGT TAA GG-3' (SEQ ID NO: 28) | 5'-TAC TGG TCC TGC CTC CTG AC-3' (SEQ ID NO: 29) | 56[1] |
| 10–11 | 5'-GGG ATC CCT ATG GGT GAG TT-3' (SEQ ID NO: 30) | 5'-CCT GGT GTG AAC CAC AGA TG-3' (SEQ ID NO: 31) | 56[1] |
| 12 | 5'-GCA CTT TTG TCA CCC CAG TT-3' (SEQ ID NO: 32) | 5'-CCA GAG CCT GAA CCA CTT TG-3' (SEQ ID NO: 33) | 56[2] |
| 13–14 | 5'-CCC AGA TGC AAA GGA TGA AG-3' (SEQ ID NO: 34) | 5'-ATC CAG GGC TGA GTG AGT GT-3' (SEQ ID NO: 35) | 56[1] |
| 15 | 5'-TTT TTC CCG ACC AGC TAA GA-3' (SEQ ID NO: 36) | 5'-TCA GAA GTG AGG GCA TCT TG-3' (SEQ ID NO: 37) | 56[1] |
| 16 | 5'-CCG GGA AGG AGA GTC ACT G-3' (SEQ ID NO: 38) | 5'-CCC TGT AAG TGA CCG CTG A-3' (SEQ ID NO: 39) | 60[1] |
| 17–18 | 5'-GTG ATT GCT TGC TGA ACG AA-3' (SEQ ID NO: 40) | 5'-CAG TGT CCT CAC CTG CAG AA-3' (SEQ ID NO: 41) | 56[1] |
| 19 | 5'-GAA CAC CTG GAG AGG CTA GG-3' (SEQ ID NO: 42) | 5'-ACT TAC AAC CGC CAG GTG AC-3' (SEQ ID NO: 43) | 58[3] |
| 20 | 5'-GAA CCT GCT GGC TGA TGA AT-3' (SEQ ID NO: 44) | 5'-GGA TGG TGT TCT TGC TCT GG-3' (SEQ ID NO: 45) | 56[1] |
| 21 | 5'-CAC ACA CGC CAC TTC CTG-3' (SEQ ID NO: 46) | 5'-CCA CGT GTT CCC ATA TAG TCT G-3' (SEQ ID NO: 47) | 56[1] |
| 22 | 5'-CAC AGC TGG TAA GTG GCA GA-3' (SEQ ID NO: 48) | 5'-CAC AGC TGG TAA GTG GCA GA-3' (SEQ ID NO: 49) | 60[1] |
| 23 | 5'-TCC CAG CTT CCT GTC TCT TC-3' (SEQ ID NO: 50) | 5'-TCT CCT GAT TCA GCT TTC CAA-3' (SEQ ID NO: 51) | 60[1] |
| 24 | 5'-AGT ACA CGT GGG TGG AGA GG-3' (SEQ ID NO: 52) | 5'-CTT TCA GGG GAC ACG ATG AG-3' (SEQ ID NO: 53) | 56[1] |
| 25 | 5'-TTA ACT GCC TCC CAG CTT GT-3' (SEQ ID NO: 54) | 5'-CTT TGC CAG GGA GAA AGA GG-3' (SEQ ID NO: 55) | 56[3] |
| 26–27 | 5'-ACA GGG TCC ACC CCT ACC T-3' (SEQ ID NO: 56) | 5'-CCC AGT TCC TTC CAT CTC AG-3' (SEQ ID NO: 57) | 56[1] |
| 28 | 5'-TAT TGA CCA CAG TGC CAT GC-3' (SEQ ID NO: 58) | 5'-TGG TGA ATA TGT GGA GGA AGG-3' (SEQ ID NO: 59) | 56[1] |
| 29 | 5'-CCT CGG TTT TCT GGG TAG AG-3' (SEQ ID NO: 60) | 5'-CCA TCC TCG GAG TGG AAT C-3' (SEQ ID NO: 61) | 56[1] |

[1]PCRs done with Platinum Taq DNA polymerase (Invitrogen)
[2]PCRs done with Expand Long Template DNA polymerase mix (Roche)
[3]PCRs done with Advantage 2 DNA polymerase mix (Clontech)

Genomic DNA was obtained from an additional family. Samples from 2 affected individuals as well as from the parents and 6 unaffected siblings were available for analysis. Amplification and sequence analysis of exons 1–6 and 8–29 and the corresponding exon/intron junctions of the ADAMTS13 gene were performed on genomic DNA from one of the probands as described above. As described above, amplification of exon 7 could not be achieved despite the use of additional primer pairs designed from updated draft genomic sequence. Amplification and sequence analysis of exon 26, in which a C>T substitution was identified, was performed on genomic DNA from all other members of this family. Allele-specific oligonucleotide hybridization was performed as described above.

F. Allele-specific oligonucleotide hybridization and restriction digestion. Individual exons were amplified from 92 unrelated control individuals. For allele-specific oligonucleotide hybridization, PCR products were spotted onto nitrocellulose membranes using a dot-blot apparatus (Invitrogen). 15-mer oligonucleotides corresponding to wild-type or mutant alleles were end-labeled with γ-32P-ATP using T4 polynucleotide kinase (New England Biolabs). Hybridization was performed in ExpressHyb solution (Clontech) at 37° C. Blots were washed in 5×SSPE, 0.1% SDS at a temperature determined empirically for each oligonucleotide. For restriction digests, 10 μl of PCR product were digested with enzyme (New England Biolabs), according to the manufacturer's instructions and products analyzed on a 3% NuSieve GTG agarose (BioWhittaker Molecular Applications), 1% agarose (Invitrogen) gel.

G. RT-PCR and Northern blot analysis. RT-PCR analysis was performed on cDNA obtained from a Multiple Tissue cDNA panel (Clontech) using primers 5'-CAGTGCAA-CAACCCCAGAC-3' (SEQ ID NO: 62) and 5'-GGCACCT-GTCCCATACCTG-3' (SEQ ID NO: 63), which amplify cDNA nucleotides 1265–1636. A First-Choice Human Northern Blot (Ambion) was screened with a probe generated by random priming using the Rediprime II kit (Amersham) of a PCR product amplified from a human MOLT4 T cell cDNA library (generated as previously described (Ginsburg, D. et al. [1985] Science 228, 1401–1406) using the above primers. Hybridization was performed in ExpressHyb solution (Clontech) according to manufacturer's specifications. The final wash step was performed in 0.1×SSC, 0.1% SDS at 50° C.

H. Isolation of cDNA. A human fetal liver cDNA library in 1gt10 (Clontech) was screened with the Northern probe described above. Two overlapping cDNA clones were obtained, spanning exons 5–14 and 8–20 of the predicted ADAMTS13 cDNA sequence, respectively. Phage DNA was purified using a Nucleobond lambda midi kit (Clontech), digested with EcoRI (New England Biolabs) and subcloned into pBSII–SK+(Stratagene). 5' RACE was performed on RLM-RACE-ready human liver cDNA (Ambion) using the following primers: 5'-GTGTCGTCCTCAGGGT-TGAT-3' (SEQ ID NO: 64) (outer) and 5'-GGCTCTGTCA-GAATGACCATC-3' (SEQ ID NO: 65) (inner). Marathon RACE-ready human liver cDNA (Clontech) was used for 3' RACE using primers 5'-TGCCAGGTGGGAGGTGTCA-GAG-3' (SEQ ID NO: 66) (outer) and 5'-GCCTGGC-CTTTGAGAACGAGAC-3' (SEQ ID NO: 67) (inner) and for nested RT-PCR using primers 5'-CATTGGC-GAGAGCTTCATC-3' (SEQ ID NO: 68) and 5'-ATGGG-GAGGGAGCCTTCT-3' (SEQ ID NO: 69) (outer) and 5'-ACCCTGAGCCTGTGTGTGTC-3' (SEQ ID NO: 70) and 5'-GCAGAGGTGGCATCCAGA-3' (SEQ ID NO: 71) (inner) to amplify a product spanning cDNA nucleotides 1552–2625. RACE and RT-PCR products were cloned into a pCR-TOPO vector (Invitrogen) and individual clones were subjected to sequence analysis. Sequence bridging that obtained by 5' RACE and that of the overlapping cDNA clones (cDNA nucleotides 389–534) was obtained from the C9ORF8 EST cluster (Unigene cluster Hs.149184). Exon-intron boundaries and sequence accuracy were verified against available draft human sequence at http://www.ncbi.nlm.nih.gov/.

I. Generation of ADAMTS13 Mammalian Expression Construct and Mutants. An ADAMTS13 cDNA encompassing exons 1–29 was assembled and cloned into the EcoRI and EcoRV sites of pcDNA3.1 (Invitrogen). The cloned fragment corresponds to nucleotides 62–4390 in the ADAMTS13 cDNA (GenBank accession number AF414401), encompassing the entire ADAMTS13 coding sequence. The following sequence was inserted into the EcoRI site of the vector in order to include an optimized Kozak consensus sequence (Kozak [1991] J. Biol. Chem. 266, 19867–19870) (uppercase) 5'-tcgatcctcgagtctagaGC-CGCCACCATG-3' (SEQ ID NO: 72), with the underlined ATG serving as the start codon. Nucleotides 1–707 (with the A of the ATG designated +1) were derived from IMAGE EST clone 1874472 (GenBank accession number A1281246); nucleotides 708–896, and 897–1748 were derived from two previously described cDNA clones isolated from a human fetal liver cDNA library (Clontech), nucleotides 1749–2918 and 2919–4329 were derived from previously described RT-PCR and 3' RACE products. An error in the 3' RACE clone (insertion of a G at position 3631 of AF414401) was corrected by site-directed mutagenesis using the GeneEditor mutagenesis system (Promega).

Nine ADAMTS13 missense mutations shown in Table 1 were engineered into the full-length construct by site-directed mutagenesis using the GeneEditor mutagenesis system (Promega).

A construct encoding a C-terminal epitope tagged version of the ADAMTS13 cDNA was engineered by PCR through the replacement of the sequence spanning the ADAMTS13 termination codon to the Not I site of pcDNA3.1 in the construct above (encoding exons 1–29) with the following sequence encoding a FLAG epitope (DYKDDDDK) (SEQ ID NO: 73) 5'-gactacaaggacgacgacgacaagtaggcggccgc-3' (SEQ ID NO: 74).

DNA for transfection was prepared using the PerfectPrep plasmid XL (Eppendorf) or Maxi (Qiagen) kits.

J. Transfections. Polyoma T-antigen expressing CHO cells (CHO-Tag) (Smith & Lowe [1994] J. Biol. Chem. 269, 15162–15171) were cultured in alpha-MEM (supplemented with deoxyribonucleotides and ribonucleotides), containing 10% heat-inactivated fetal bovine serum, 0.4 mg/ml G418, penicillin and streptomycin (Life Technologies). Cells were split into 6-well culture dishes (Costar, 3516) at 6×105 cells/well 48 hours before transfection. Transfections were performed in triplicate for each construct. Four mg of each DNA (pcDNA3.1, pcDNA3.1-ADAMTS13 and pcDNA3.1-ADAMTS13 mutants 1–9) were introduced into the cells using Lipofectamine 2000 (Invitrogen) according to manufacturer's optimized conditions for CHO-K1 cells. As a transfection control, 25 ng of pSEAP2-Control vector (BD Biosciences), encoding secreted alkaline phosphatase, was co-transfected with each DNA. Cells were washed three times with D-PBS (Life Technologies) and serum-free α-MEM was added 18 hours following transfection. Conditioned media were collected 48 hours following transfection. One milliliter of conditioned media was concentrated approximately 20-fold using Ultrapure-30 columns (Amicon). Secreted alkaline phosphatase activity in 1 ml of concentrated conditioned media was measured using the Great EscAPe SEAP detection kit (BD Biosciences) and read in a TD-20 luminometer (Turner Designs). Volumes of conditioned media were normalized to the sample with the lowest transfection efficiency and equal volumes (10 ml) were used for the measurement of VWF-cleaving protease activity. Secreted alkaline phosphatase activity in conditioned media from cells transfected with pcDNA3.1 alone was 1.9–43 fold higher than in media from cells transfected with the various constructs. The latter controls were thus not normalized for transfection efficiency (samples were used undiluted) in order to obtain the most conservative estimate of background VWF-cleaving protease activity present in conditioned media. When taking into account the concentration factor for each of the wild-type samples (8.5–10.2 fold), and the VWF-cleaving protease activity in conditioned media of cells transfected with wild-type, the ADAMTS13 construct ranged from 4.2–4.7 U/ml, with 1 U/ml representing the VWF-cleaving protease activity present in pooled normal plasma.

K. VWF-cleaving protease assay of transfected cells. VWF-cleaving protease assays were performed as previously described (Tsai et al. [2001] Clin. Lab 47, 387–392). Assays were performed blindly and in triplicate for each transfection. The activity in 1 ml of pooled normal human plasma was designated as 1 U. The lack of activity in serum-free and serum-replete media was verified. Results shown in FIG. 11 represent the means of three transfections for each mutant, with error bars representing standard deviations. Statistical significance was determined using ANOVA.

L. Generation of anti-peptide antibodies. Anti-peptide antibodies against ADAMTS13 were generated and affinity purified by a commercial supplier (Research Genetics). Antibodies were raised in rabbits against the following peptides: 1) SQTINPEDDTDPGHAD (SEQ ID NO: 75) (metalloprotease domain), 2) ESFIMKRGDSFLDGTR (SEQ ID NO: 76) (cysteine-rich domain), 3) GRLTWRK-MCRKLLD (SEQ ID NO: 77) (CUB domain), and 4) CPEMQDPQSWKGKEGT (SEQ ID NO: 78) (C-terminus). The cysteine at the N-terminus of the last peptide was artificially added for conjugation purposes.

M. Western blot analysis. Conditioned media from CHO-Tag cells transfected with wild-type and mutant ADAMTS13 constructs, or mock-transfected with empty pcDNA3.1 vector, were subjected to SDS-PAGE and transferred to nitrocellulose membranes. Membranes were blocked in 5% powdered milk in PBS and incubated with anti-peptide antibodies (1:500) or anti-FLAG M2 monoclonal antibody (Sigma, 1:500). Membranes were then washed in TBS-Tween and incubated with either HRP-conjugated goat anti-rabbit (Sigma, 1:5000) or HRP conjugated goat anti-mouse (Sigma, 1:10,000). Chemiluminescent detection was performed using ECL reagent (Amersham).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

What is claimed is:

1. A method of identifying subjects at risk of developing TTP disease comprising:
   a) providing nucleic acid from a subject, wherein the nucleic acid comprises a ADAMTS13 gene;
   b) detecting the presence or absence of one or more variations in the ADAMTS13 gene, wherein said variation is selected from the group consisting of the mutations shown in Table 1; and
   c) determining if the subject is at risk of developing TTP disease based on the presence or absence of the one or more variations.

2. The method of claim 1, wherein the detecting in step b) is accomplished by hybridization analysis.

3. The method of claim 1, wherein the detecting in step b) comprises comparing the sequence of the nucleic acid to the sequence of a wild-type ADAMTS13 nucleic acid.

4. A method of identifying a variant ADAMTS13 gene, comprising:
 a) providing nucleic acid from a subject, wherein the nucleic acid comprises a ADAMTS 13 gene; and
 b) detecting the presence or absence of one or more variations in the ADAMTS13 gene, wherein said variation is selected from the group consisting of the mutations shown in Table 1.

5. The method of claim 4, further comprising step c) determining if the subject is at risk of carrying a TTP disease allele based on the presence or absence of the one or more variations.

* * * * *

SEQUENCE LISTING

<160> NUMBER OF SEQ ID NOS: 78

<210> SEQ ID NO 1
<211> LENGTH: 4550
<212> TYPE: DNA
<213> ORGANISM: Homo sapiens

<400> SEQUENCE: 1

```
attcccagtc accaaggccc cctctcactc cgctccactc ctcgggctgg ctctcctgag      60
gatgcaccag cgtcaccccy gggcaagatg ccctcccctc tgtgtggccg gaatccttgc     120
ctgtggcttt ctcctgggct gctggggacc ctcccatttc cagcagagtt gtcttcaggc     180
tttggagcca caggccgtgt cttcttactt gagccctggt gctcccttaa aaggccgccc     240
tccttcccct ggcttccaga ggcagaggca gaggcagagg cgggctgcag gcggcatcct     300
acacctggag ctgctggtgg ccgtgggccc cgatgtcttc caggctcacc aggaggacac     360
agagcgctat gtgctcacca acctcaacat cggggcagaa ctgcttcggg acccrtccct     420
gggggctcag tttcgggtgc acctggtgaa gatggtcatt ctgacagagc ctgagggtgc     480
yccaaatatc acagccaacc tcacctcgtc cctgctgagc gtctgtgggt ggagccagac     540
catcaaccct gaggacgaca cggatcctgg ccatgctgac ctggtcctct atatcactag     600
gtttgacctg gagttgcctg atggtaaccg gcaggtgcgg ggygtcaccc agctgggcgg     660
tgcctgctcc ccaacctgga gctgcctcat taccgaggac actggcttcg acctgggagt     720
caccattgcc catgagattg ggcacagctt cggcctggag cacgacggcg cgcccggcag     780
cggctgcggc cccagcggac acgtgatggc ttcggacggc gccgcgcccc gcgccggcct     840
cgcctggtcc ccctgcagcc gccggcagct gctgagcctg ctcagcgcag gacgggcgcg     900
ctgcgtgtgg gacccgccgc ggcctcaacc cgggtccgcg gggcacccgc cggatgcgca     960
gcctggcctc tactacagcg ccaacgagca gtgccgcgtg gccttcggcc caaggctgt    1020 cgcytgcacc ttcgccaggg agcacctgga tatgtgccag gccctctcct gccacacaga    1080
cccgctggac caaagcagct gcagccgcct cctcgttcct ctcctggatg ggacagaatg    1140
tggcgtggag aagtggtgct ccaagggtcg ctgccgctcc ctggtggagc tgaccccat    1200 agcagcagtg catgggcgct ggtctagctg gggtccccga agtccttgct cccgctcctg    1260
cggaggaggt gtggtcacca ggaggcggca gtgcaacaac cccagacctg cctttgggg    1320 gcgtgcatgt gttggtgctg acctccaggc cgagatgtgc aacactcagg cctgcgagaa    1380
gacccagctg gagttcatgt cgsaacagtg cgccaggacc gacggccagc cgctgcgctc    1440
ctcccctggc ggcgcctcct tctaccactg gggtgctgct gtaccacaca gccaagggga    1500
tgctctgtgc agacacatgt gccgggccat tggcgagagc ttcatcatga agcgtggaga    1560
cagcttcctc gatgggaccc ggtgtatgcc aagtggcccc cggaggacg ggaccctgag    1620
```

```
cctgtgtgtg tcgggcagct gcaggacatt tggctgtgat ggtaggatgg actcccagca    1680
ggtatgggac aggtgccagg tgtgtggtgg ggacaacagc acgtgcagcc cacggaaggg    1740
ctctttcaca gctggcagag cgagagaata tgtcacrttt ctgacagtta cccccaacct    1800
gaccagtgtc tacattgcca accacaggcc tctcttcaca cacttggcgg tgaggatcgg    1860
agggcgctat gtcgtggctg gaagatgag catctcccct aacaccacct acscctccct    1920
cctggaggat ggtcrtgtcg agtacagagt ggccctcacc gaggaccggc tgccccgcct    1980
ggaggagatc cgcatctggg gacccctcca ggaagatgct gacatccagg tttacaggcg    2040
gtatggcgag gagtatggca acctcacccg cccagacatc accttcacct acttccagcc    2100
taagccacgg caggcctggg tgtgggccgc tgtgcgtggg ccctgctcgg tgagctgtgg    2160
ggcagggctg cgctgggtaa actacagctg cctggaccag gccaggaagg agttggtgga    2220
gactgtccag tgccaaggga gccagcagcc accagygtgg ccagaggcct gcgtgctcga    2280
accctgccct ccctactggg cggtgggaga cttcggccca tgcagcgcct cctgtggggg    2340
yggcctgcgg gagcggccag tgcgctgcgt ggaggcccag ggcagcctcc tgaagacatt    2400
gcccccagcc cggtgcagag caggggccca gcagccagct gtggcgctgg aaacctgcaa    2460
cccccagccc tgccctgcca ggtgggaggt gtcagagccc agctcatgca catcagctgg    2520
tggagcaggc ctggccttgg agaacgagac ctgtgtgcca ggggcagatg gcctggaggc    2580
tccagtgact gaggggcctg gctccgtaga tgagaagctg cctgcccctg agccctgtgt    2640
cgggatgtca tgtcctccag gctggggcca tctggatgcc acctctgcag gggagaaggc    2700
tccctcccca tggggcagca tcaggacggg ggctcaagct gcacacgtgt ggacccctgy    2760
ggcagggtcg tgctccgtct cctgcgggcg aggtctgatg gagctgcgtt tcctgtgcat    2820
ggactctgcc ctcagggtgc ctgtccagga agagctgtgt ggcctggcaa gcaagcctgg    2880
gagccggcgg gaggtctgcc aggctgtccc gtgccctgct cggtggcagt acaagctggc    2940
ggcctgcagc gtgagctgtg ggagagggt ygtgcggagg atcctgtatt gtgcccgggc    3000
ccatggggag gacgatggtg aggagatcct gttggacacc cagtgccagg ggctgcctcg    3060
cccggaaccc caggaggcct gcagcctgga gccctgccca cctaggtgga aagtcatgtc    3120
ccttggccca tgttcggcca gctgtggcct tggcactrct agacgctcrg tggcctgtgt    3180
gcagctcgac caaggccagg acgtggaggt ggacgaggcg gcctgtgcgg cgctggtgcg    3240
gcccgaggcc agtgtcccct gtctcattgc cgactgcacc taccgctggc atgttggcac    3300
ctggatggag tgctctgttt cctgtgggga tggcatccag cgccggcgtg acacctgcct    3360
cggaccccag gccaggcgc ctgtgccagc tgatttctgc cagcacttgc ccaagccggt    3420
gactgtgcgt ggctgctggg ctgggccctg tgtgggacag ggtacgccca gcctggtgcc    3480
ccacgaagaa gccgctgctc caggacggac cacagccacc cctgctggtg cctccctgga    3540
gtggtcccag gcccggggcc tgctcttctc cccggctccc cagcctcggc ggctcctgcc    3600
cgggccccag gaaaactcag tgcagtccag tgcctgtggc aggcagcacc ttgagccaac    3660
aggaaccatt gacatgcgag gcccagggca ggcagactgt gcagtggcca ttgggcggcc    3720
cctcggggag gtggtgaccc tccgcgtcct tgagagttct ctcaactgca gtgcggggga    3780
catgttgctg cttgggggcc ggctcacctg gagaagatg tgcaggaagc tgttggacat    3840
gactttcagc tccaagacca acacgctggt ggtgaggcag cgctgcgggc ggccaggagg    3900
tggggtgctg ctgcggtatg ggagccagct tgctcctgaa accttctaca gagaatgtga    3960
```

-continued

```
catgcagctc tttgggccct ggggtgaaat cgtgagcccc tcgctgagtc cagccacgag    4020
taatgcaggg ggctgccggc tcttcattaa tgtggctccg cacgcacgga ttgccatcca    4080
tgccctggcc accaacatgg gcgctgggac cgagggagcc aatgccagct acatcttgat    4140
ccgggacacc cacagcttga ggaccacagc gttccatggg cagcaggtgc tctactggga    4200
gtcagagagc agccaggctg agatggagtt cagcgagggc ttcctgaagg ctcaggccag    4260 cctgcgggc cagtactgga cmctccaatc atgggtaccg gagatgcagg accctcagtc    4320
ctggaaggga aaggaaggaa cctgagggtc attgaacatt tgttccgtgt ctggccagcc    4380
ctggagggtt gaccccctggt ctcagtgctt tccaattcga acttttttcca atcttaggta    4440 tctactttag agtcttctcc aatgtccaaa aggctagggg gttggaggtg gggactctgg    4500
aaaagcagcc cccatttcct cgggtaccaa taaataaaac atgcaggctg              4550
```

<210> SEQ ID NO 2
<211> LENGTH: 1427
<212> TYPE: PRT
<213> ORGANISM: Homo sapiens

<400> SEQUENCE: 2

```
Met His Gln Arg His Pro Arg Ala Arg Cys Pro Pro Leu Cys Val Ala
1               5                   10                  15

Gly Ile Leu Ala Cys Gly Phe Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270
```

```
Leu Leu Ser Ala Gly Arg Ala Arg Cys Val Trp Asp Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
        355                 360                 365

Gly Arg Cys Arg Ser Leu Val Glu Leu Thr Pro Ile Ala Ala Val His
370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Gln Cys Asn Asn Pro Arg Pro
                405                 410                 415

Ala Phe Gly Gly Arg Ala Cys Val Gly Ala Asp Leu Gln Ala Glu Met
        420                 425                 430

Cys Asn Thr Gln Ala Cys Glu Lys Thr Gln Leu Glu Phe Met Ser Gln
            435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Asp Ala Asp Ile Gln
                645                 650                 655

Val Tyr Arg Arg Tyr Gly Glu Tyr Gly Asn Leu Thr Arg Pro Asp
            660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
```

-continued

```
                690                 695                 700
Trp Val Asn Tyr Ser Cys Leu Asp Gln Ala Arg Lys Glu Leu Val Glu
705                 710                 715                 720

Thr Val Gln Cys Gln Gly Ser Gln Gln Pro Ala Trp Pro Glu Ala
                725                 730                 735

Cys Val Leu Glu Pro Cys Pro Tyr Trp Ala Val Gly Asp Phe Gly
                740                 745                 750

Pro Cys Ser Ala Ser Cys Gly Gly Leu Arg Glu Arg Pro Val Arg
                755                 760                 765

Cys Val Glu Ala Gln Gly Ser Leu Leu Lys Thr Leu Pro Pro Ala Arg
770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
                820                 825                 830

Pro Gly Ala Asp Gly Leu Glu Ala Pro Val Thr Glu Gly Pro Gly Ser
                835                 840                 845

Val Asp Glu Lys Leu Pro Ala Pro Glu Pro Cys Val Gly Met Ser Cys
850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
                900                 905                 910

Met Glu Leu Arg Phe Leu Cys Met Asp Ser Ala Leu Arg Val Pro Val
                915                 920                 925

Gln Glu Glu Leu Cys Gly Leu Ala Ser Lys Pro Gly Ser Arg Arg Glu
                930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Asp Gly Glu Glu Ile Leu Leu Asp
                980                 985                 990

Thr Gln Cys Gln Gly Leu Pro Arg Pro Glu Pro Gln Glu Ala Cys Ser
                995                 1000                1005

Leu Glu Pro Cys Pro Pro Arg Trp Lys Val Met Ser Leu Gly Pro
1010                1015                1020

Cys Ser Ala Ser Cys Gly Leu Gly Thr Ala Arg Arg Ser Val Ala
1025                1030                1035

Cys Val Gln Leu Asp Gln Gly Gln Asp Val Glu Val Asp Glu Ala
                1040                1045                1050

Ala Cys Ala Ala Leu Val Arg Pro Glu Ala Ser Val Pro Cys Leu
1055                1060                1065

Ile Ala Asp Cys Thr Tyr Arg Trp His Val Gly Thr Trp Met Glu
1070                1075                1080

Cys Ser Val Ser Cys Gly Asp Gly Ile Gln Arg Arg Arg Asp Thr
1085                1090                1095

Cys Leu Gly Pro Gln Ala Gln Ala Pro Val Pro Ala Asp Phe Cys
1100                1105                1110
```

| | | | | | | | | | | |
|---|---|---|---|---|---|---|---|---|---|---|
|Gln|His|Leu|Pro|Lys|Pro|Val|Thr|Val|Arg|Gly|Cys|Trp|Ala|Gly|
| |1115| | | |1120| | | |1125| |

Gln His Leu Pro Lys Pro Val Thr Val Arg Gly Cys Trp Ala Gly
    1115                1120                1125

Pro Cys Val Gly Gln Gly Thr Pro Ser Leu Val Pro His Glu Glu
    1130                1135                1140

Ala Ala Ala Pro Gly Arg Thr Thr Ala Thr Pro Ala Gly Ala Ser
    1145                1150                1155

Leu Glu Trp Ser Gln Ala Arg Gly Leu Leu Phe Ser Pro Ala Pro
    1160                1165                1170

Gln Pro Arg Arg Leu Leu Pro Gly Pro Gln Glu Asn Ser Val Gln
    1175                1180                1185

Ser Ser Ala Cys Gly Arg Gln His Leu Glu Pro Thr Gly Thr Ile
    1190                1195                1200

Asp Met Arg Gly Pro Gly Gln Ala Asp Cys Ala Val Ala Ile Gly
    1205                1210                1215

Arg Pro Leu Gly Glu Val Val Thr Leu Arg Val Leu Glu Ser Ser
    1220                1225                1230

Leu Asn Cys Ser Ala Gly Asp Met Leu Leu Leu Trp Gly Arg Leu
    1235                1240                1245

Thr Trp Arg Lys Met Cys Arg Lys Leu Leu Asp Met Thr Phe Ser
    1250                1255                1260

Ser Lys Thr Asn Thr Leu Val Val Arg Gln Arg Cys Gly Arg Pro
    1265                1270                1275

Gly Gly Gly Val Leu Leu Arg Tyr Gly Ser Gln Leu Ala Pro Glu
    1280                1285                1290

Thr Phe Tyr Arg Glu Cys Asp Met Gln Leu Phe Gly Pro Trp Gly
    1295                1300                1305

Glu Ile Val Ser Pro Ser Leu Ser Pro Ala Thr Ser Asn Ala Gly
    1310                1315                1320

Gly Cys Arg Leu Phe Ile Asn Val Ala Pro His Ala Arg Ile Ala
    1325                1330                1335

Ile His Ala Leu Ala Thr Asn Met Gly Ala Gly Thr Glu Gly Ala
    1340                1345                1350

Asn Ala Ser Tyr Ile Leu Ile Arg Asp Thr His Ser Leu Arg Thr
    1355                1360                1365

Thr Ala Phe His Gly Gln Gln Val Leu Tyr Trp Glu Ser Glu Ser
    1370                1375                1380

Ser Gln Ala Glu Met Glu Phe Ser Glu Gly Phe Leu Lys Ala Gln
    1385                1390                1395

Ala Ser Leu Arg Gly Gln Tyr Trp Thr Leu Gln Ser Trp Val Pro
    1400                1405                1410

Glu Met Gln Asp Pro Gln Ser Trp Lys Gly Lys Glu Gly Thr
    1415                1420                1425

<210> SEQ ID NO 3
<211> LENGTH: 4548
<212> TYPE: DNA
<213> ORGANISM: Homo sapiens

<400> SEQUENCE: 3
attcccagtc accaaggccc cctctcactc cgctccactc ctcgggctgg ctctcctgag     60
gatgcaccag cgtcaccccy gggcaagatg ccctcccctc tgtgtggccg gaatccttgc    120
ctgtggcttt tcctgggct gctggggacc ctcccatttc agcagagtt gtcttcaggc    180 tttggagcca caggccgtgt cttcttactt gagccctggt gctcccttaa aaggccgccc    240

-continued

```
tccttcccct ggcttccaga ggcagaggca gaggcagagg cgggctgcag gcggcatcct    300
acacctggag ctgctggtgg ccgtgggccc cgatgtcttc caggctcacc aggaggacac    360
agagcgctat gtgctcacca acctcaacat cggggcagaa ctgcttcggg acccrtccct    420
gggggctcag tttcgggtgc acctggtgaa gatggtcatt ctgacagagc ctgagggtgc    480
yccaaatatc acagccaacc tcacctcgtc cctgctgagc gtctgtgggt ggagccagac    540
catcaaccct gaggacgaca cggatcctgg ccatgctgac ctggtcctct atatcactag    600
gtttgacctg gagttgcctg atggtaaccg gcaggtgcgg ggygtcaccc agctgggcgg    660
tgcctgctcc ccaacctgga gctgcctcat taccgaggac actggcttcg acctgggagt    720
caccattgcc catgagattg ggcacagctt cggcctggag cacgacggcg cgcccggcag    780
cggctgcggc cccagcggac acgtgatggc ttcggacggc gccgcgcccc gcgccggcct    840
cgcctggtcc cctgcagcc gccggcagct gctgagcctg ctcagcgcag acgggcgcg    900 ctgcgtgtgg gacccgccgc ggcctcaacc cgggtccgcg gggcacccgc cggatgcgca    960
gcctggcctc tactacagcg ccaacgagca gtgccgcgtg gccttcggcc ccaaggctgt   1020 cgcyctgcacc ttcgccaggg agcacctgga tatgtgccag gccctctcct gccacacaga   1080
cccgctggac caaagcagct gcagccgcct cctcgttcct ctcctggatg ggacagaatg   1140
tggcgtggag aagtggtgct ccaagggtcg ctgccgctcc ctggtggagc tgaccccat    1200 agcagcagtg catgggcgct ggtctagctg gggtccccga agtccttgct cccgctcctg   1260
cggaggaggt gtggtcacca ggaggcggca gtgcaacaac cccagacctg cctttggggg   1320
gcgtgcatgt gttggtgctg acctccaggc cgagatgtgc aacactcagg cctgcgagaa   1380
gacccagctg gagttcatgt cgsaacagtg cgccaggacc gacggccagc cgctgcgctc   1440
ctcccctggc ggcgcctcct tctaccactg gggtgctgct gtaccacaca gccaagggga   1500
tgctctgtgc agacacatgt gccgggccat tggcagagc ttcatcatga agcgtggaga    1560
cagcttcctc gatgggaccc ggtgtatgcc aagtggcccc cgggaggacg ggaccctgag   1620
cctgtgtgtg tcgggcagct gcaggacatt tggctgtgat ggtaggatgg actcccagca   1680
ggtatgggac aggtgccagg tgtgtggtgg ggacaacagc acgtgcagcc cacggaaggg   1740
ctctttcaca gctggcagag cgagagaata tgtcacrttt ctgacagtta cccccaacct   1800
gaccagtgtc tacattgcca accacaggcc tctcttcaca cacttggcgg tgaggatcgg   1860
agggcgctat gtcgtggctg ggaagatgag catctcccct aacaccacct acscctcct    1920 cctggaggat ggtcrtgtcg agtacagagt ggccctcacc gaggaccggc tgccccgcct   1980
ggaggagatc cgcatctggg gacccctcca ggaagatgct gacatccagc tctttgtctg   2040
caggtttaca ggcggtatgg cgaggagtat ggcaacctca cccgcccaga catcaccttc   2100
acctacttcc agcctaagcc acggcaggcc tgggtgtggg ccgctgtgcg tgggccctgc   2160
tcgggctgcg ctgggtaaac tacagctgcc tggaccaggc caggaaggag ttggtggaga   2220
ctgtccagtg ccaagggagc cagcagccac cagygtggcc agaggcctgc gtgctcgaac   2280
cctgccctcc ctactgggcg gtgggagact tcggcccatg cagcgcctcc tgtggggyg    2340 gcctgcggga cggccagtg cgctgcgtgg aggcccaggg cagcctcctg aagacattgc    2400
ccccagcccg gtgcagagca ggggcccagc agccagctgt ggcgctggaa acctgcaacc   2460
cccagccctg ccctgccagg tgggaggtgt cagagcccag ctcatgcaca tcagctggtg   2520
gagcaggcct ggccttggag aacgagacct gtgtgccagg ggcagatggc ctggaggctc   2580
```

```
cagtgactga gggcctggc tccgtagatg agaagctgcc tgcccctgag ccctgtgtcg    2640
ggatgtcatg tcctccaggc tggggccatc tggatgccac ctctgcaggg gagaaggctc    2700 cctcccatg gggcagcatc aggacggggg ctcaagctgc acacgtgtgg accccctgygg   2760 cagggtcgtg ctccgtctcc tgcgggcgag gtctgatgga gctgcgtttc ctgtgcatgg    2820
actctgccct caggggtgcct gtccaggaag agctgtgtgg cctggcaagc aagcctggga   2880
gccggcggga ggtctgccag gctgtcccgt gccctgctcg gtggcagtac aagctggcgg    2940
cctgcagcgt gagctgtggg agaggggtyg tgcggaggat cctgtattgt gcccgggccc    3000
atggggagga cgatggtgag gagatcctgt tggacaccca gtgccagggg ctgcctcgcc    3060 cggaaccca ggaggcctgc agcctggagc cctgcccacc taggtggaaa gtcatgtccc     3120
ttggcccatg ttcggccagc tgtggccttg cactrctag acgctcrgtg gcctgtgtgc     3180
agctcgacca aggccaggac gtggaggtgg acgaggcggc ctgtgcggcg ctggtgcggc    3240
ccgaggccag tgtcccctgt ctcattgccg actgcaccta ccgctggcat gttggcacct    3300
ggatggagtg ctctgtttcc tgtggggatg gcatccagcg ccggcgtgac acctgcctcg    3360
gaccccaggc ccaggcgcct gtgccagctg atttctgcca gcacttgccc aagccggtga    3420
ctgtgcgtgg ctgctgggct gggccctgtg tgggacaggg tacgcccagc ctggtgcccc    3480
acgaagaagc cgctgctcca ggacggacca cagccacccc tgctggtgcc tcctggagt     3540 ggtcccaggc ccggggcctg ctcttctccc cggctcccca gcctcggcgg ctcctgcccg    3600 ggcccccagga aaactcagtg cagtccagtg cctgtggcag gcagcacctt gagccaacag    3660
gaaccattga catgcgaggc ccagggcagg cagactgtgc agtggccatt gggcggcccc     3720
tcggggaggt ggtgaccctc cgcgtccttg agagttctct caactgcagt gcggggggaca    3780 tgttgctgct ttggggccgg ctcacctgga ggaagatgtg caggaagctg ttggacatga     3840
ctttcagctc caagaccaac acgctggtgg tgaggcagcg ctgcgggcgg ccaggaggtg     3900
gggtgctgct gcggtatggg agccagcttg ctcctgaaac cttctacaga gaatgtgaca     3960
tgcagctctt tgggcctgg ggtgaaatcg tgagcccctc gctgagtcca gccacgagta     4020
atgcaggggg ctgccggctc ttcattaatg tggctccgca cgcacggatt gccatccatg     4080
ccctggccac caacatgggc gctgggaccg agggagccaa tgccagctac atcttgatcc     4140 gggacacca cagcttgagg accacagcgt tccatgggca gcaggtgctc tactgggagt      4200
cagagagcag ccaggctgag atggagttca gcgagggctt cctgaaggct caggccagcc    4260 tgcgggcca gtactggacm ctccaatcat gggtaccgga gatgcaggac cctcagtcct     4320
ggaagggaaa ggaaggaacc tgagggtcat tgaacatttg ttccgtgtct ggccagccct    4380 ggaggttga ccctggtct cagtgctttc caattcgaac tttttccaat cttaggtatc       4440
tactttagag tcttctccaa tgtccaaaag gctaggggt tggaggtggg gactctggaa     4500
aagcagcccc catttcctcg ggtaccaata aataaacat gcaggctg                  4548
```

<210> SEQ ID NO 4
<211> LENGTH: 842
<212> TYPE: PRT
<213> ORGANISM: Homo sapiens

<400> SEQUENCE: 4

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

```
Phe Gln Gln Ser Cys Leu Gln Ala Leu Glu Pro Gln Ala Val Ser Ser
         35                  40                  45
Tyr Leu Ser Pro Gly Ala Pro Leu Lys Gly Arg Pro Pro Ser Pro Gly
 50                  55                  60
Phe Gln Arg Gln Arg Gln Arg Arg Ala Ala Gly Gly Ile Leu
 65              70                  75                  80
His Leu Glu Leu Leu Val Ala Val Gly Pro Asp Val Phe Gln Ala His
                 85                  90                  95
Gln Glu Asp Thr Glu Arg Tyr Val Leu Thr Asn Leu Asn Ile Gly Ala
            100                 105                 110
Glu Leu Leu Arg Asp Pro Ser Leu Gly Ala Gln Phe Arg Val His Leu
            115                 120                 125
Val Lys Met Val Ile Leu Thr Glu Pro Glu Gly Ala Pro Asn Ile Thr
        130                 135                 140
Ala Asn Leu Thr Ser Ser Leu Leu Ser Val Cys Gly Trp Ser Gln Thr
145                 150                 155                 160
Ile Asn Pro Glu Asp Asp Thr Asp Pro Gly His Ala Asp Leu Val Leu
                165                 170                 175
Tyr Ile Thr Arg Phe Asp Leu Glu Leu Pro Asp Gly Asn Arg Gln Val
                180                 185                 190
Arg Gly Val Thr Gln Leu Gly Gly Ala Cys Ser Pro Thr Trp Ser Cys
            195                 200                 205
Leu Ile Thr Glu Asp Thr Gly Phe Asp Leu Gly Val Thr Ile Ala His
        210                 215                 220
Glu Ile Gly His Ser Phe Gly Leu Glu His Asp Gly Ala Pro Gly Ser
225                 230                 235                 240
Gly Cys Gly Pro Ser Gly His Val Met Ala Ser Asp Gly Ala Ala Pro
                245                 250                 255
Arg Ala Gly Leu Ala Trp Ser Pro Cys Ser Arg Arg Gln Leu Leu Ser
            260                 265                 270
Leu Leu Ser Ala Gly Arg Ala Arg Cys Val Trp Asp Pro Pro Arg Pro
        275                 280                 285
Gln Pro Gly Ser Ala Gly His Pro Pro Asp Ala Gln Pro Gly Leu Tyr
    290                 295                 300
Tyr Ser Ala Asn Glu Gln Cys Arg Val Ala Phe Gly Pro Lys Ala Val
305                 310                 315                 320
Ala Cys Thr Phe Ala Arg Glu His Leu Asp Met Cys Gln Ala Leu Ser
                325                 330                 335
Cys His Thr Asp Pro Leu Asp Gln Ser Ser Cys Ser Arg Leu Leu Val
                340                 345                 350
Pro Leu Leu Asp Gly Thr Glu Cys Gly Val Glu Lys Trp Cys Ser Lys
            355                 360                 365
Gly Arg Cys Arg Ser Leu Val Glu Leu Thr Pro Ile Ala Ala Val His
        370                 375                 380
Gly Arg Trp Ser Ser Trp Gly Pro Arg Ser Pro Cys Ser Arg Ser Cys
385                 390                 395                 400
Gly Gly Gly Val Val Thr Arg Arg Gln Cys Asn Asn Pro Arg Pro
                405                 410                 415
Ala Phe Gly Gly Arg Ala Cys Val Gly Ala Asp Leu Gln Ala Glu Met
            420                 425                 430
Cys Asn Thr Gln Ala Cys Glu Lys Thr Gln Leu Glu Phe Met Ser Gln
        435                 440                 445
```

```
Gln Cys Ala Arg Thr Asp Gly Gln Pro Leu Arg Ser Ser Pro Gly Gly
    450                 455                 460
Ala Ser Phe Tyr His Trp Gly Ala Ala Val Pro His Ser Gln Gly Asp
465                 470                 475                 480
Ala Leu Cys Arg His Met Cys Arg Ala Ile Gly Glu Ser Phe Ile Met
                485                 490                 495
Lys Arg Gly Asp Ser Phe Leu Asp Gly Thr Arg Cys Met Pro Ser Gly
            500                 505                 510
Pro Arg Glu Asp Gly Thr Leu Ser Leu Cys Val Ser Gly Ser Cys Arg
        515                 520                 525
Thr Phe Gly Cys Asp Gly Arg Met Asp Ser Gln Gln Val Trp Asp Arg
    530                 535                 540
Cys Gln Val Cys Gly Gly Asp Asn Ser Thr Cys Ser Pro Arg Lys Gly
545                 550                 555                 560
Ser Phe Thr Ala Gly Arg Ala Arg Glu Tyr Val Thr Phe Leu Thr Val
                565                 570                 575
Thr Pro Asn Leu Thr Ser Val Tyr Ile Ala Asn His Arg Pro Leu Phe
            580                 585                 590
Thr His Leu Ala Val Arg Ile Gly Gly Arg Tyr Val Val Ala Gly Lys
        595                 600                 605
Met Ser Ile Ser Pro Asn Thr Thr Tyr Pro Ser Leu Leu Glu Asp Gly
    610                 615                 620
Arg Val Glu Tyr Arg Val Ala Leu Thr Glu Asp Arg Leu Pro Arg Leu
625                 630                 635                 640
Glu Glu Ile Arg Ile Trp Gly Pro Leu Gln Glu Asp Ala Asp Ile Gln
                645                 650                 655
Leu Phe Val Cys Arg Phe Thr Gly Gly Met Ala Arg Ser Met Ala Thr
            660                 665                 670
Ser Pro Ala Gln Thr Ser Pro Ser Pro Thr Ser Ser Leu Ser His Gly
        675                 680                 685
Arg Pro Gly Cys Gly Pro Leu Cys Val Gly Pro Ala Arg Ala Ala Leu
    690                 695                 700
Gly Lys Leu Gln Leu Pro Gly Pro Gln Glu Gly Val Gly Gly Asp
705                 710                 715                 720
Cys Pro Val Pro Arg Glu Pro Ala Ala Thr Ser Val Ala Arg Gly Leu
                725                 730                 735
Arg Ala Arg Thr Leu Pro Ser Leu Leu Gly Gly Arg Leu Arg Pro
            740                 745                 750
Met Gln Arg Leu Leu Trp Gly Trp Pro Ala Gly Ala Ala Ser Ala Leu
        755                 760                 765
Arg Gly Gly Pro Gly Gln Pro Pro Glu Asp Ile Ala Pro Ser Pro Val
    770                 775                 780
Gln Ser Arg Gly Pro Ala Ala Ser Cys Gly Ala Gly Asn Leu Gln Pro
785                 790                 795                 800
Pro Ala Leu Pro Cys Gln Val Gly Gly Val Arg Ala Gln Leu Met His
                805                 810                 815
Ile Ser Trp Trp Ser Arg Pro Gly Leu Gly Glu Arg Asp Leu Cys Ala
            820                 825                 830
Arg Gly Arg Trp Pro Gly Gly Ser Ser Asp
        835                 840

<210> SEQ ID NO 5
<211> LENGTH: 98
<212> TYPE: PRT
```

<213> ORGANISM: Homo sapiens

<400> SEQUENCE: 5

```
Cys Gly Arg Gln His Leu Glu Pro Thr Gly Thr Ile Asp Met Arg Gly
1               5                   10                  15
Pro Gly Gln Ala Asp Cys Ala Val Ala Ile Gly Arg Pro Leu Gly Glu
                20                  25                  30
Val Val Thr Leu Arg Val Leu Glu Ser Ser Leu Asn Cys Ser Ala Gly
            35                  40                  45
Asp Met Leu Leu Leu Trp Gly Arg Leu Thr Trp Arg Lys Met Cys Arg
        50                  55                  60
Lys Leu Leu Asp Met Thr Phe Ser Ser Lys Thr Asn Thr Leu Val Val
65                  70                  75                  80
Arg Gln Arg Cys Gly Arg Pro Gly Gly Val Leu Leu Arg Tyr Gly
                85                  90                  95
Ser Gln
```

<210> SEQ ID NO 6
<211> LENGTH: 285
<212> TYPE: DNA
<213> ORGANISM: Homo sapiens

<400> SEQUENCE: 6

```
ggctccccag cctcggcggc tcctgcccgg gccccaggaa aactcagtgc agtccagtgc      60
ctgtggcagg cagcaccttg agccaacagg aaccattgac atgcgaggcc cagggcaggc     120
agactgtgca gtggccattg gcggcccct cggggaggtg gtgaccctcc gcgtccttga     180
gagttctctc aactgcagtg cgggggacat gttgctgctt tggggccggc tcacctggag     240
gaagatgtgc aggaagctgt tggacatgac tttcagctcc aagac                    285
```

<210> SEQ ID NO 7
<211> LENGTH: 60153
<212> TYPE: DNA
<213> ORGANISM: Homo sapiens

<400> SEQUENCE: 7

```
gtttttcttc cgagtgagcg tcttgacagg acccggctta gccacggggc tgctcggggc      60
gcgcttggag gcggggacct tcgccttccc catcctgctg ccgtccagcg cctgggccgg     120
cggccaccg agaccccggc ctccccgggc ccggcgccct gcagcacaa gcgcctgccc     180
aggccaggcc gaaacacacc caccgcaggg accccgtcca ggaaaagact ccggaagaga     240
ccccgcacgc gttgcgcata cctcagcacg cacgctccag tccccggaag cgctcgtctc     300
tccacaaccg gctggaaacc ggatccctgc ctctggttcc cgcagcctg gcggttcac     360
ccgcacggga cttgggccgc cgccttagcc agcggcatcc gggtcatcg acctcgagtt     420
tgactggggc aagccgagga cctccccaag atccgggatg gggatgagag atgcgaacgc     480
cggaagggaa ctgggggggcc gctgtgtgtg tagcacccgg tagggcagct gagctggggg     540
cactgggcgt tggggctagt gagagccggg ctaggtcgct cgcctgcgtc ctggactctc     600
gagcctttcc cgccttgggc tgctccttgc tcagcctcac agcggctcat cttccacgta     660
cagtggggaa actgaggccc aggcaccggg aggagttcct gccagttcac tctgtagcag     720
gacgagccgc agacaagaac ccctcagaca ccgaattgta gaaggaaagg gctttatta     780
gtggggagca tcggcagact cacgtctcca aaaaccgagc tctctgagtg agcaattcct     840
gtccctttta agggcttaca accctaaggg ggtctgtgtg agagggtcgt gatcgattga     900
```

```
gcaagcaggg ggtacgtgac tgggggctgc atgcaccggt aatcagaacg caacagaaca    960
ggacagggat tttcacaatg cttttccata caatgtctga aatctataga taacataacc   1020
ggttaggtca aggattgatc tttaaccagg cccagggcgc ggcgccgggc tgtctgcctg   1080
tggattttat ttctgccttt tagttttttac ttctttatttt ggaagcagaa attgggcata  1140
agacaatatg aggggtggtc tcctcccttta cttctgcctc ctgggttcaa gcgattctcc   1200
tgcctcagcc tcctgagtag ctgggattat aggtgcacgc caccactctc tgccaatttt   1260
tgtatttttta gtagacctgg ggtttcgcca cgttggccag gctgtcttga actcctgacc   1320
tccagtgatc catccgcctc ggcctcccaa agcgctggga ttacaggtgt gagccaccgt   1380
gcccggccgg gagtgggtag atttgatgtg cgtgtgtaac aggcagaggt tgatggagta   1440
acagggaagt gaggctccta ggattttggt ctgagcaatt gggtgtggcc atttatcatc   1500
tcaataaatg tctgcgggga gcagggtgaa gtatgggggt ggagccatga gctccttttc   1560
acacttgctg agtttgaatg ggccgtcagt caccaaggag agacgtctaa tcagcagcag   1620
gatataagat tcctaagctt agggaagggt cagtgctgga gatgtaattt ggaaatcgtc   1680
agcacataat tagtgttgaa acatgaacct gggttagttc atccaaagag agagtaccaa   1740
tatagggagt gaagggttaa gaccagatag caggtgctgg gggctctcca ggggcgaagc   1800
agcagaggag gctgagggggg agcagtcagt gcagtgggag gagaagcgga tgtgagtggc   1860
atcagagaat ccaggggggag aataaaccac atcagatgct gctgagaggc tgagaaggac   1920
gaggacagag agatgggaac cagatatggc actgagattg tcagcaagtc caccgaaaag   1980
ggttttcttt tttttttgttt gttttgagac ggagtcttgc tctgctgccc aggctggagt   2040
gcagtggcgt gatatcggct caccacaatc tccacctccc gggttcaagc gattctcctg   2100
cctcagcctc ctgggtagct ggaactacag gtgcacgcca ccatgcccag ctaattttt    2160
tttttttttt gagacgaagt tatgctcttg tcgcccaagc tggagtgcaa tggcgcaatc   2220
tcggctcacc gcaacctcca cctcccgggt tcaagtgatt cttctgcctc agcctcccga   2280
gtagctggga ttacaggcat gtgccaccac gcccggctaa ttttgtactt ttagtagaga   2340
tggggtttct ccatgttggc caggctggta tggatctcca gacatcaggt gatcctctcg   2400
cctcagcctc ccaaagtgtt gggattacag gcgtgagcca ccgcacctag cctaattttt   2460
gtatttttga aaagagacgg ggtttcacta tgctggccag gctgatctcg aactcctgac   2520
ctcatgatcc gcgtgcctcg tgatccacct gcctcggcct cccaaagtgc tgggattaaa   2580
ggcgtgagcc accacacctg gcccaggttt ctttttaaa aaggaaaaa aactttgttc   2640
cagcagtttg taaaccaggg caatgcagcc ttctgtacaa aggtgcattc cagggaacaa   2700
agagaacaaa gaaagaggtc gtcttttgta gagaacttcc tgcccaggtt cccactttgg   2760
tccactttatg caaatgagga aggcacactt gcttagttct gattggttaa tacttgctga   2820
gttcagattg gtcgatgcag gtcacagtcg atgggttgat tctggcggca taaacaggaa   2880
cagatagctg tgaaaccatc ccagagttaa gtgagagtgg gggctttcca ggaacgcaga   2940
atgtgtgtgt gaccctagtc agcaaatggc tgctaggtcc tactttgaat ttaggcccag   3000
ttagtaactt gggatccatc aagaaggatt ggctctttca gggttcacaa agttattggt   3060
gaccttttaa agatcaattt caatggtatg tgggaattga aggcaaggaa gtggagatag   3120
ccactgaaaa taatgtttct aagttcttaa agacagccag aaacagggct atggcaggag   3180
gacagtgtgg gtcaagggaa ggttgttgat tgtaatcaag agacaccaga gtgtctgggc   3240
```

```
ttggtggctc atgcctgtga tcccagcact ttgggaggcc gaggcagtca gctcacctga    3300
ggtcaggagt ttgagaccag cttggccaac atggcgaaac cccacctcta ctaaaaatac    3360
aaaaactagc caggcgtgat ggcgggtgcc tgtaatccca gccacaaggg aggctgaggc    3420
aggagaatca cttgaacctg ggtggcggag gttgcagtga gccgagatcg tgccactgca    3480
ctccagcctg ggtgacacag caagactctg tctcaaaaaa caaacaaaaa ccaaaaagag    3540
acaggagagt cattcatgct gatggagtga gccaggtacc aggatctcga tatctaagca    3600
tgcccccttc tccaacagcc tccttacctt cctgcatgaa agcacaccct tccctccagt    3660
cccccattcc tttattctgc tgtattttc tccataacac ttaccacctt tgaacatact     3720
acatatacaa catgtgtctg tctagcaact ttgctgtctg gctctcttcc ctagaattta    3780
agctgtgaga ggccgaggct gctgtctgcc tggcttgggg ctgctttcct ggtgtctagc    3840
acagagcctg gcctgtttca ggggctcagt gaaacatttg ttggctgaag gaatgaatga    3900
atggctctag cagaggggca gaaactaacg atgcaggagg agagctggg aagggatcc     3960 agagccaggg cctggcagga agtgtaggtg tgtcctccct gatcgcagag gaggagagag    4020
gctgcacttt gaggggtgga aagacaaggt gaatcccct gctggtcatc agcttgtgcg     4080
gctctgtggg tgtaaaagag tggtttggag catgtgaagt gagtcttcca ggagatgaag    4140
gggattgcca ggccgtttgt gatgatgctg agatctggtg ccgtgcagcc tgcttctgcg    4200
actctcctca tcaggcgcag gcacagagta ggtggagagt tgagccagaa ccacgatgtc    4260
tttggcacag cctctcatct gtcagatggg agcggggacc ccggagaggg agtcagccga    4320
ggtcctggca ttccttgtga acccccgtct gtgggtttct ggtccagtgt cccttctcca    4380
gattagatgg cttaggcctc ctctaagggg gtgggcgtgc acatccggag agctgtctgg    4440
tgtgcaggac tgggctgcag gttaccctga actgcaacca tcttagagca aggcccagct    4500
tgcagcagga ggagctgcag gccgcccacc ctagccacgg cccctgccct ggcaggaagc    4560
ttccaagagt aaacactgcc taatcgtccc gcccagtagt gagcaggcct gtcccattcc    4620
atactgacca gattcccagt caccaaggcc ccctctcact ccgctccact cctcgggctg    4680
gctctcctga ggatgcacca gcgtcacccc cgggcaagat gccctcccct ctgtgtggcc    4740
ggaatccttg cctgtggctt tctcctgggc tgctggggac cctcccattt ccagcaggtg    4800
ggctcatttg caggagcggg ggtattctgg gagcctctgg gtggggtatt ctgagctacc    4860
tggggcgagg ggagtgccaa atagctgact acatcagctt tggggtttgc gctgggcagg    4920
ggagtctgta cttgggcttt tgggggatga agtgtgctca ctgaagaggg agttggtgtc    4980
tcagtacgac ctgctcattc ggtgaagctg aacagacaga tactagtttg tcccaaactg    5040
tgtaggttgc tcttctctgc ctctcccttc ctctccctgt tctgatttc ccctctcct     5100 tcttggttgg cctcacccac ctcctgcctc ctgtctccct cttcatccat ctctttttgt    5160 tctttttct ttctctctct ctcttttttt ttttttttt tttttaaga catgggtct       5220 tgttatgttg ccccagctgg tctcaaactc ctggactcaa gtgatcctcc cacctcggtc    5280
tccccaagtg ttaggattac aggccagagc cactatgccc ggcccatcc atctcttttt     5340 gtcttgcaga gttgtcttca ggctttggag ccacaggccg tgtcttctta cttgagccct    5400
ggtgctccct taaaggtac ttgtcctggt gtcttctctc ccggggggag tttctcagga     5460
cttcaagggg gtatctcacc actgagtcag tggtctggga ttttggtgg atctggaagg     5520 agaaggtcag agaagctgct gtcaaccctg ttaattaact ctgttacttc ctgccaagtt    5580
gatataagct ggtctggtg ttccagccag gccagggttc tcaccctagc ttctgttaaa     5640
```

```
tatcacaagg gaacggtcac cgattggctg gcccctcctg ccccatggcc tctgctgagc   5700
tggctgattt tcaggagctc ttgtggtttc tgaccgtgga tgtaaatatt tattccttct   5760
gtgggaaaca agataggtac tggctcaggc tacctcctaa ggccatggat ttccttatga   5820
taaaggcctg tccccattgc ccacaggccc atgtctgtga ccttctccgg tgcgagcccc   5880
cttcccagta gggccattgg caacttgact aatggctgat gggggccaga ggcaggtggg   5940
ctagtggtca ggggcaacag gagggcaagg cccactttgt gacctggttc tttgtggtct   6000
aggccagagg cacactgacc agtgcctggg gccacgctgg gggctggatg cagccgacgc   6060
tgtctgggta tcccatagcc tgggtccttc cagcgctgcc gctcctgaaa ggctgggaga   6120
tcattgccca gggtccctga ccctctaagg ctcccttgg gagaggacag tgagggctgg   6180
cctgggcccc tgcttcccaa gagaccactg gctccactc gtgttcagtt tcctgtcggg   6240
gtccatgatg ttacttgtga acacctgtg cccagagcag gtccaggag gcagggcagg   6300 ggctttcccc tttgggcaga gccaccaggg cagtgggaat cttgtcttga tggggtgacc   6360
caaagcacac aatagcccaa cagctcctcc tgggccctgc cctttgcgtg cctagtcact   6420 aatgggtct ggctcttggg gtggggtga cacgcaatgt cttgacttcg gaaggccatc   6480
cttccaagac ctgccagccc ctttcctgtt agctttccac tgcttgctct ctagaaccat   6540
cgccctctgc tctccctctc ccctccagg ccgcccctcct tccctggct tccagaggca   6600 gaggcagagg cagaggcggg ctgcaggcgg catcctacac ctggagctgc tggtggccgt   6660
gggccccgat gtcttccagg ctcaccagga ggacacagag cgctatgtgc tcaccaacct   6720
caacatcgtg agtgccccac gctggactgt gcaggtcccc acggccaggg ctggtgacca   6780
atgtctgtgg gctggtgtat ctggtagtct gaatacagtg ggtaaactc aggtagaatg   6840 gctcggggtt cttcctcttc tccctccctc cctgggtgg aggtgggtga gtcccacac   6900 cctctctagg ctccatggca catgcacacc ctgcagcctc tcactactca agtcccttca   6960
cctggggcca ccctcaagcc tggcctcttc cccagtatcc atttgacccc cacaaagctc   7020
agctaaagca accctggcaa atgggatacg ggctgctcac actgccctct gcaccccgac   7080
cctgccctct ctccattctc ttgtcccccg ctcagagtgg cgaggacagg tcacccgtct   7140
gaagtctaaa cagagactgc tggcaaagga gatgccacc ttcatttctt gctagcacct   7200
gaatccctgc agcccccctt cacttgaaag ctggggaagg gcgggcaggg aagcactccc   7260
ccactagccg ccgtctcaga aagacaaaca aggccaggcg cggtggctca tgcctataat   7320
cccagcactt tgggaggcca aggcgggtgg atcacccgaa gtcaggagtt caagaccagc   7380
ctggccaaca tggtgaaacc ccgtagctac taaaaataca aaacttagct gggcatggtg   7440
gcaggcgcct gtaatctgag aggagcctgc gatctgagag gagcagcgtt tgaccggaat   7500
atccgactcg tgaccatctg tgtgctctca tccccttgct ttggagtttg ttttccttgc   7560
gttagttggc cttcctgagc catgagctga ggagcaacag aggcacggct gactgtgcag   7620
cacattttag gagcccccg ccccgcccgg ttcccacaca tgctggtgga gtagcctctc   7680
cagctcttca cactccgggg gcccctggga gtcagcagct gcctggggct ggcaatgccc   7740
acccgacggg ttacctctct catctgccct tgcacagggg gcagaactgc ttcgggaccc   7800
gtccctgggg gctcagtttc gggtgcacct ggtgaagatg gtcattctga cagagcctga   7860
ggtaggcatg gagctggaac tcagcacacc atacagagcg ggaagcccaa gtcatcgcat   7920
ctccatcctc tttaacctct tgtcccggat gccccaagca gcatggatca cagaatgcat   7980
```

-continued

| | |
|---|---|
| tcagccagac agaccagctg ccctcccagc tctacccagc actcagcaca ggctgcctga | 8040 |
| ctacttctct gagcctcagt tgtctcatcc ctaacacggg ctagtcatag ggttgttagg | 8100 |
| aggactaact gggaaacaaa ccgaccgcag tcagcaccgt gcctggttgg ggtgtcctaa | 8160 |
| atgcaggctt tgctgtgggt ccgcaggtg ccccaaatat cacagccaac ctcacctcgt | 8220 |
| ccctgctgag cgtctgtggg tggagccaga ccatcaaccc tgaggacgac acggatcctg | 8280 |
| gccatgctga cctggtcctc tatatcacta ggtagccgag ctttctgatg ggtgctggcc | 8340 |
| agccagcctg ggaaggctgc tccctcagcc tcctgccctc tgcaaaggtg accccagggc | 8400 |
| aggcacgtgc cttggcacca cccaagtgac tgttttctct caccgaggtt tgacctggag | 8460 |
| ttgcctgatg gtaaccggca ggtgcggggc gtcacccagc tgggcggtgc ctgctcccca | 8520 |
| acctggagct gcctcattac cgaggacact ggcttcgacc tgggagtcac cattgcccat | 8580 |
| gagattgggc acaggtatgt agccccacca gctgtcccca ggatctggca aggagctgac | 8640 |
| ctgggtaccc agggtggagg tggtcttagc aagcagtggg tccttgtaga gtttctccag | 8700 |
| aggagcctgt accctcacc ccgacagact caggtgtgag gacaggggaa cctgatactg | 8760 |
| tttgattaaa agaactttt ttccaaaaga cgagcaagac acctttagca ggtagaaaat | 8820 |
| aacttctgta gaaaattcag gtaaagaaag agcaggctgt aaaaattatc tcaaatccca | 8880 |
| ccatttagag ataatgtctc ttcacatttt gtatttaatt tcagtctttt ctttacatac | 8940 |
| acacacatat ttcttatttg caaaattggg atttagtttg gatccctgaa aaaaggaaa | 9000 |
| attgtgatta tgctgtgcat tgctttgtta cctgctattt ctttttcttt tcttttcttt | 9060 |
| tttttttttg agatgaagtt tcgctcttgt tgcccaggct ggagggcaat gacgtgatct | 9120 |
| cagctcattg caacctccac ctcctgggtg caagtgattc tcccacctca gcctcccaag | 9180 |
| tagctgggat tacaggcatg tgccaccacg cccagctaat tttgtatttt tagtagagac | 9240 |
| agggtttctc catgttggtc aggctggtct cgaactccca acctcaggtg atccacctgc | 9300 |
| ctcggtctcc cacagtgctg ggattacagg cgtgagccac tgcatccagc cttcttttt | 9360 |
| tcttcctagg gtaagtgcag gatttacctg ttctttatgt aataatatat cccaaacatt | 9420 |
| atcccaggta tcttagaggt gtgcaccgta atttatttaa tcagtcccct cttcttggat | 9480 |
| gtctaggttg tctgaacacg tcttcctgtt gtgaatgtta tgcattcttg tgggcaaacc | 9540 |
| ttcactctta cctataacca tttacctaga gtgatgggtt tcttttcatt tctttagttt | 9600 |
| tttaagtatg aaaataatac ccaattgttg taaaaattca aacagtgcag agatttctaa | 9660 |
| agtaaaaagt gaatttccac attccttgcc caccaacccc cacccgaccc ctttcaaccc | 9720 |
| ctctgagcct gggagggttg aggcagggtt cctgggtgtg ggacaaggca gggctccttc | 9780 |
| tccctcagag ggagcatagt tcccttctgc tcctgtgatg cagaagacgt gagccccaa | 9840 |
| actgggcctt agcctgggag ggttcttggc ttcaccgagg aaagaattca agagggagca | 9900 |
| ggtggtgtta gacagcaact ttgattgatg tggcagtggg cagagtgtac agccctgtga | 9960 |
| ctgtatacag cacagcatag cccctttga agccaggcta ccccatagac actgtgccca | 10020 |
| aaagagcagc tcaaaggcag ggctgcagtc ctagttaata cccacttcta attatatgca | 10080 |
| aattaagggg ccagattatg cagaaatttc tagaaaaagg gcagtaactt ctaggtttc | 10140 |
| gtcatggaaa agggcagta acttctgggt tttgccatgg caatggcaaa ctggtatggc | 10200 |
| acactggtgg gcgtgtctta tggaaagggg cttcccaccc ctccctgttt tagctagtcc | 10260 |
| tctggtccag tgtccaagcg gggcctccag agtggagtcc acctcctacc tcaccggtgc | 10320 |
| ctggcctctc ccaccccatt aggagtcctc catcagttcc gctttgggta aagcaagctc | 10380 |

```
tgttgtgaca gtttggaaac ggttcacctt cctggcctag gaatgcaaac aatggccaag    10440
ggcaagcacg ttttaactga actttaaaat cgtgctttcc tcacagtagg tgaatttcac    10500
gctcaacaca tccatgtaaa cagtccccag agcagccctt caaggccccg gccagtcccc    10560
acctccccac agactcctaa caccatgatt taatgtggct tgcacatttt taaaggcttt    10620
tgatatttat tagcaaaaga tgcgagagcc accctgctgg gctagcgctc ccttctgggg    10680
gaaactgagg cagggcgcac gcgaccctct ccactgcgcc cagttagcag atggcggcgt    10740
caggggtcga cccgggtcgg aaaactcgct ggcgctgcgg cactagggcg ccgggccgct    10800
gactcgccga cccccgtccc gcccccaccc ccgcccccgc ccctgccggc cgccttagcg    10860
caactccccg ccccccgacc agcttcggcc tggagcacga cggcgcgccc ggcagcggct    10920
gcggccccag cggacacgtg atggcttcgg acggcgccgc gccccgcgcc ggcctcgcct    10980
ggtcccctg cagccgccgg cagctgctga gcctgtcag gtagcggccg ccccgtggga    11040
ggggcgcgcg agcctccagc cagcccgctg ggccgccagc gccacctctc tctacgtccg    11100
tccccactcc gcattcagcc ctccttcctg tcccaccct ccgtccaacc cacccctccg    11160
tccaaccccg cgcccaccgc tccgtccgtg gaggggcggg cgcgcgagcc tccagccagc    11220
ccgctgggcc gccgcgcca cccctcccta cgtccgtccc cacctctccc tacgtccgtc    11280
cccactccgc attcagccct ccttcctgtc ctacctctcc atcctgaccc actcctccgt    11340
ccaaccccgc gcccacagct ccgtcccatc ccgctgcgcc cactcctgcg cccacccctc    11400
cgtcccaacc cctgcaccca ccccccgtc ccacccacct gccccacccc ctgcacctcc    11460
ccccgtgctg tcccactctg cggccaccct tctgtccaac ccctgcgccc accgctccgt    11520
tccacccct cctgcgccc accctgcgt cctccctcgc cccttgcgc ccacactttc    11580
gttccagcca atctgggcac gcacccctcc gtccatcccc atcccgcccc ttgactccac    11640
atacactccc tggttctctc ccacttgcct acacccaccc ctgcatccta ccctcctcca    11700
tccacccctc catctcagcc ccctgcaccc accccgttcc tgggcccacc ctgttcctgc    11760
acccaccccc tcacttcacc cccttaccct tcgtctgcct ccaccgccc ctaccctcc    11820
gtccactctc cacgctccat cagtcccaca cccctatctc ccccacccgc gtacatgtat    11880
ccctgcgtcc ccttcccgcc gaccgcaccg ctcccgggcc taacctgcat ctgctccatc    11940
ccactcagac ccgtccctcc gtcgccgctc cctctgctgg ccacccacct ctgcgccggc    12000
aggagcctta gtcttggtcc cagccaagag ccggctcctg gtgggggcg cgggccgaga    12060
actcctgttc ccactcacaa aaggccacgc ttccaaacgc ttccatcctc gtgcccactc    12120
ctccgtcccg cctcctcccg gtgtacaccc cgggactgag ccgggcctga gccgggcctt    12180
gtcgcagcgc aggacgggcg cgctgcgtgt gggacccgcc gcggcctcaa cccgggtccg    12240
cggggcaccc gccggatgcg cagcctggcc tctactacag cgccaacgag cagtgccgcg    12300
tggccttcgg ccccaaggct gtcgcctgca ccttcgccag ggagcacctg gtgagtctgc    12360
cggcggtggc ctgggattgg ctgtgaggtc cctccgcatc acccagctca cgtcccccaa    12420
aacgtgcatg gtgagaacct gctgggtgcc gtgctaggct gaggtactaa gccagggcgg    12480
cttagtttaa tgctgtctgt gccctctaga aattatttaa aatgtttgaa caaaagctcc    12540
aacatttttg tttgactggg ccccacaaat tatgtagcta gtcctgggag ggcccctgtg    12600
cccaaggact cctggctgag tgaggacacc aatcttaaac agttaccaag gacttcccca    12660
tctattgtgg ctggagtcag actggagggc ttcctggagg aagtggcctc taaactgaac    12720
```

```
ccacagcaga agtggggctg gtaggtggag gggagatgaa ggagagcagg cacccccaaaa    12780 gacagacttc ctcgcaggat tgcataggac attcatgggc tccaggcact tttgccttga    12840
tgggccccct cctccacaaa aaaattgaga attatgtttt aatattctta tacaatgtat    12900
aaagttttat gtgttactat aaatacaagt ctttttttt cctttttttt tttttttttg    12960
agacagagtc tccctctctg ctcactgcag gctccgcctg ccagattcac accattctcc    13020
tgcctcagcc tcccgagtag ctgggactac aggcgcccgc caccacgcct ggctaatttt    13080 ttgtatttt agtagagacg gggtttcact gtgttagcca ggatggtctc gatctcctga    13140
cctcgtgatc cgcccgccct ggcctcacaa agtgctggga ttacaggcat gagccacagc    13200
gccccgccaa gtcttttttt ttaaattatt ttgagacagg gcctcgttct gttgcccagg    13260
gtggagtgca gtagcacaat catagctcac tgttgcctca acttcttggg cacaaacgat    13320
cctcccacct cggccttgga gtagctggga ctacaggcac atgccacaat gcccagctaa    13380
tttttaaatt ttttgtagag atggggtctc cctttgttac ccaggcttgt ctaggactcc    13440
tggcttcaag ccatcctccc acctcggcgt cccaaagcac tgggattaca gacatgagcc    13500
accacccacg cctgatcagc aaatctatta atattatata ttacaacatt aattttgacc    13560
tggaagttca ttttttcatt tttttttttt ttttgagaca gagtctcact ctgtcaccca    13620
ggctggagtg cagtggcaca gtcttggctt actgcaacct ccgcctccca ggttcaagtg    13680
attcccgggc ctacgcctcc cgagtagctg ggactacagg catgtgccac catgcccagc    13740
taagttttgt atttttagt agagacaggg tttcatcatg ttggccgggc tggtctcgaa    13800
ttctgacctc aggtgatccg cccgccttgg cctcccaaag tgctgggatt acaggataag    13860
ccaccacacc cagcctagtt catttttttc ttctgatttt attttattta tttatttatt    13920
ttgagacgga gtctcgctct gtcacccagg ctggaatgca gtggctcaat cttggctcac    13980
tgcaagctct gccttcaggg ttcaagccat tctcctgcat cagcctcccg aatagctggg    14040
actacaggtg cctgccacca cacccggcta attttttgta ttttttagtag atgggggtt    14100 tcactgtgtt agccaggatg gtctcgctct cctgacctca tgatttgccc gcctcggcct    14160
tccaaattgc tgggattaca ggcgtgagcc acagtgcccg gccttttttcc ttctgatttt    14220 aaaagaaatt aggccaggtg tggctgcacg cctgtaatcc cagcactttg ggaagccaag    14280
gcaggcggat cacctgaggt cgggagtttg agaccagcct gaccaacatg gagaaatgcc    14340
atctgtgcta aaaatacaaa aaattagccg ggcgtggtgg cgcatgcctg taatcccagc    14400
tactcggaag gctgaggtag gagaattgct tgaacccagg aggcagaggt tgaggtgagc    14460
caagatcgcg ccattgccct ccagcctggg caacaagagc gaaactgtct caaaaaaaa    14520 caagaaagaa aaagaaatta aaacatttgc ctcttgagct tcaagtcagt gacaagttaa    14580
gaaggaaaaa aagaaaaaag acacaaaaaa cacatttcca tgggccccca aaagtgtgac    14640
aggacctggt catggtcccg gttccccatc gatgggtcag tcatgccttg tcctctgagg    14700
gcaccagtgc ccacggtgca gagtgttggc tgtgtcagtg tgtcctgcag tctgggaggg    14760
acagttaagg ttggacactg gcctggaagg ccctggtggc ccctgagctc gccacccacc    14820
tgtccaccct cctaggatat gtgccaggcc ctctcctgcc acacagaccc gctggaccaa    14880
agcagctgca gccgcctcct cgttcctctc ctggatggga cagaatgtgg cgtggagaag    14940
gtcagagcca agagtgaatg agtgggctcc tgtgagcacg tgcacgtggg tgcctccagc    15000
caggccgccc tattcctagg tcaggaggca ggaccagtat ggggcagaga gtcttggagt    15060
tggccttggg gactgtcctt tgggttggtg gtctgacctc tttccttag catttgctcc    15120
```

```
catgcagaat gggaatgtgg gctgcctgtt gtatgggggg tgcccatggg tgtggggttc   15180
ctttgggtgg ggtccctgtg tgaaggtcct tgtggatatg gggtgtctcg ggggatccc    15240 tgtgtaaggg gtccctgtga gtgtagagtc cctgtgggtg gggtccttat gtgtgtgttg   15300
gaggatccct gtgtgttgag gggtccctgg ggggttctgt gtgtatgttg gggggtctct   15360
gggtgttgga ggatccctgt gggtctgggg gatccatgtg gctggggtac ctgtgtgttg   15420
gggggtctct gtgtgtgttg gagatccctg tgtgttgggg gatccctatg ggtgagttcc   15480
ttgtgtgtgt ttgggggtcg ctgtgggtgg ggtccctgtg tgtgttgggg atccctgagg   15540
atgttggggg actctctgtg tgtgttggga gtcctgtggt ggggtcactg tgggatggga   15600
gatgaagcca tccttgcctt gcagtggtgc tccaagggtc gctgccgctc cctggtggag   15660
ctgaccccca tagcagcagt gcatgggcgc tggtctagct ggggtccccg aagtccttgc   15720
tcccgctcct gcggaggagg tgtggtcacc aggaggcggc agtgcaacaa ccccaggtac   15780
cgcagggagg gtgcttttct gtcagggagt gtggccatac catagtccct agttgaaggc   15840
agtggtcacc ctgctgtctc accctcctgt ctgctgggca ttttcagacc tgcctttggg   15900
gggcgtgcat gtgttggtgc tgacctccag gccgagatgt gcaacactca ggtaggcctg   15960
cttcctgggg taggaggggg cagctggtgg caccgggccc tgggggagcc aaagtgacca   16020
tctgtggttc acaccaggac acatttgaga aggacattgg ggccaggtga ggtggcttat   16080
gcctgtaatc ccagcacttt gggaggccaa ggcaggtgga tcacctgagg tcaggggttc   16140
aagaccagcc tggccaacat ggtgaaatct cgtctctaca aaaatacaa aaattagccg   16200 ggcgtggtgg tgggcgcctg tagtcccagc tactcgggaa gctgaggcag gagaatcact   16260
tgaacccagg aggtagagct tgcagtgagc cgagattggg ccattgcact ccagcctggg   16320
cgacagagtg agactctgtc tcaaaaaaaa aataaaaatt aaaaagaga gagaaggaca   16380 ttgggacccc agttcataaa ccaggccagt cctgctgatg cccacagagc ccctgaagcg   16440
tcccgcctcc ctccctgagt gccactttgc cctccagagc gcatctctgc agggagaacc   16500
tccccactag gaatacagtg ygctgctgca tgcctgcaaa ggaattttt aaatattatt    16560 tttatttttt tagacagagt ctctccctgt cacccagact ggagtgcagt ggtgctatct   16620
cagctcactg caacctctgc ctcccaggtt caagcgattc tcctgcctca gtctcctgag   16680
taggctggga ctacaggtgc ccgccaccac gcccggctaa ttttttgtat ttttagtaga   16740
ggagggtttt gcaccgtgtt agccaggatg gccttgatct cctgacctcg tgatccgcct   16800
gcctcggcct cccaaagtgc tgggattaca ggtgtcactg cgcctggccg aaggagtctt   16860
ttatttataa attgaggtga cattcatgta gcatgaaatc aagcatttta aagtggcaac   16920
tcagtggcct ttagtacact cacaaggttg ggcaagtact gcctctgtct agtttcagaa   16980
cgtttccagt actctggagt actctggagt gaaccccata tggtaggctg tcactcccca   17040
tttctcctcc gccactcagc ggccattggt ttcccttctg tctctgtgga ttgacctgtt   17100
ctagacatgc cacgtacctg aggccagaca acaggtgtgc ttcctgcctg ccttcctccc   17160
ccagcggcac gtccccaagg ctcacctgtg ttgtagcctg tgtcagcgcc tcattcctct   17220
ttctggctga atcatattcc actgcaggga tagaccacat tttcatccag tcgtctgctg   17280
atggacatct gaggtgtttt caccttttgg ctcctgtgaa cagagccgct gccaatgtgc   17340
ttgtacatgt ttgaatccct gttttcaatt cttttggcag tatgctgaag agcggagtta   17400
ctggatcgta tgggaattgt atgtttgact tttttttttc ttttttttt ttttgagaca   17460
```

```
gagtcttgct ctgtcgccag gctggagtgc agtggtgcaa tctcagctcc ctgcaacctt   17520
cgcctcctgg gttcaagcga ttcccctgcc tcaccttccg gagtagctgg gattacaggc   17580
acgcgccacc atgcctggct aattttttgt attttagta gagatggagt ttcaccacg    17640
tcagccagga tggtctggat ctcctgacct caggtgatct gcccgccttg gcctcccaaa   17700
ctgttgggat tacaggcatg agccaccgct cccggcctat gtttgacttt tttttttct    17760
tatttttttc tttctttctt tattttttt tttttagaga tggagtctcg ctctgtcgcc    17820
caagctggag tgcggtggcg cgatctcggc tcactctaag ctccgcctcc caggttcacc   17880
ccattctcct gcctcagctt cccgaatagc tgggactaca gacgcccgcc accacgcccg   17940
gctaattttt ttttgtattt ttagtagagg cggggtttca ccatgttagc cgggatggtc   18000
ttgatctcct gacctcgtga tctgcctgcc tcggcctccc aaagggctga gatcacaggc   18060
gtgagccacc gcgcccagca tgtttggctt taaagaaac tgccaaaccg ttttccacag    18120
tgcctgaact gtttcacatt cccaccagca ttgcgccagg gttccagttt ccccacatcc   18180
gctgcagcac ttgctgtttt ctgttgttgt tttttctttt ctcttctttt tttttttttt   18240
tttttaata gagatggggt tttgtcatgt tggccaggct ggtcttgaac tccgaccca    18300
ggtgatccgc ccaccttagc ctcccaaagt gctgggatta cacgygtgag ccatggcgcc   18360
cggcctgttt tctgtttttt gattttggcc atctcgtgg tatgaaatgg tagaaagatt    18420
cttttttacat tgagttaaat tctatctcct gcttcgatgg ccctgggtgt gggtttgtcc   18480
ctggctgtat tacagttctg catgtggtga gaccctccct ttcctccttc tccaaatgga   18540
ccaccaagac ctcccagac cgtgagggga gggtctttgg ctggagcaca gggtggtggg   18600
atttcgtgga ggcagtgtgg tcagtgtggc tgtccaggga gtcaactccg gttatcttct   18660
gtcagcccat aaaagtccaa gacgcctgcc tgagtgcaga ggcttcggtg gtgaggtctt    18720
tgctccatgc tttggttacc tgcctctagg tgcactacct aaagaataca catccccgtc    18780
cctgttttat tgagttcagg ccttggaagc agaggctctg agcgtaatgc tctttcctgg    18840
cttttcttctt cgttgctgcc ctgtgttctt tacggattcc ccgggttttt ccatcaata    18900
gagagaggca ggcacttttg tcaccccagt ttacagagca gggaaccgag gcacggcctg    18960
gagctgaggc cacacccaca tcttgatcct gtactgtagg gtgccatgta gtctcccagt    19020
gacaacaccc gcccccgcc ccaccgccat ccccctcctc tgcctcctcc tggccaggcc   19080
tgcgagaaga cccagctgga gttcatgtcg caacagtgcg ccaggaccga cggccagccg   19140
ctgcgctcct cccctggcgg cgcctccttc taccactggg gtgctgctgt accacacagc   19200
caaggtgggg cctgcggagt gtggggttgg gggaggagcc agccctggag accctcggac   19260
agggcagagt cataggggg ttggcctact atccctccag cactgggcaa agtggttcag     19320
gctctggcat cccacagacc atggatgaca tagtggccag gcctcgctgg tagatcaggc   19380
actgacatcc catctctgag tctcaatttc ccatctgtga atggagata atagcagtag    19440
gtccctccct gggcgctaca aggattcagg gagataatcg gaaaatgcca agtgtgttcc    19500
ttggttcatg atacttttt tgtgagacag agtcttgctc tgtcgccag gctggagtgc      19560
agggcgtaa tctcagctya ctgtaacctc cgcctctggg attcaaggga ttcttgcccc    19620
tcagcctctc gaatagctgg gactacaggc ttgcactacc atgccggcta attttttgt    19680
attttagta gagatggggt ttcgccatgt tggctaggct ggtttcaaac tcctgacgtc   19740
aggtgatccg cctgcctcgg cttcccaaag ttctgggatt acaggcatga accattgcgc   19800
ccagccttgg ttcctaattc aataccatta attattagat tagattagga tcgtgattag   19860
```

```
gattattgcc ttaggaggtg ggatgtgggg aagatagaaa cccttgcccc agatgcaaag    19920
gatgaagctg ggtgggggct gggggacttg cccctcctgc tcggttcagg acacccttt     19980 tcactctgcc ctcccagggg atgctctgtg cagacacatg tgccgggcca ttggcgagag    20040
cttcatcatg aagcgtggag acagcttcct cgatgggacc cggtgtatgc caagtggccc    20100
ccgggaggac gggaccctga gcctgtgtgt gtcgggcagc tgcagggtag gcgtgtgtgg    20160
acattggcga tggccctggg gcctacctgt cctatcggaa ggctcctggg ggcaggttgg    20220
tgggtgctgg ccctgatgga gctgcagtgc cctctgcagg ggagtggtgc tggggaaaag    20280
gatctggact tggagtcagc ctgggttaag ggctgcagtg tgaccttggg caagtcactg    20340
agccctctaa gcttgcttcc tgtgtagatg gtggggtgct atagaagtgt tgctggtttt    20400
gtggatccca gaatctcaga gctggcaggg ctgcagagtc attgaggcca gcaccctcca    20460
gtgacacggg ccctctgtcc ttcccttttgc atagacattt ggctgtgatg gtaggatgga    20520
ctcccagcag gtatgggaca ggtgccaggt gtgtggtggg gacaacagca cgtgcagccc    20580
acggaagggc tctttcacag ctggcagagc gagaggtagg cggcctccct cggggcagag    20640
gctgggcttc ccccagcctc caagatggcc acagcccaga gcgttggtgc agggggctgct   20700 caggtcacag ggcctgcaca ctcactcagc cctggatgcc tcctgtggtg tcagcgtctc    20760
cctcttccac ttcgccaccc ttctgtggca ggctcaggtt ttggccttga tgctgctggg    20820
actgtggtgc ctcagtaatg gtcactcact gtagccgtgc tgcaaaaaaa acacagacat    20880
tggccgggcg ctgtgctcac gcctgtactc ccrgcacttt gggaggctga ggcgggtgga    20940
tcacctgtag tcgggagatc acctacagcc tggccagtat ggtgaaaccc catctctact    21000
aaaaatacaa aaattagctg ggcatgatgg cgggcgcctg tagtcctagc tactcaggag    21060
gctgaggcag gagaattgct tgaacccagg aggcagaggt tgcagtgagc cgagatccct    21120
ctgcactcca gcccgggcaa cagagtgaga cactgtctca aaaaaaaaaa aaaaaaaagt    21180
atggacgttg tgcattctgt ggcagctacc ctcttctctc ctgctcaaga aatcccactg    21240
agagggacac aagtgaatga gagggatggt agttacattt ggaaaatctt tgactttggt    21300
gtatatatga ggtcaaaaac catttgcaaa tgccagtgct tctatggaga gcagagactt    21360
sagccctgcc tccctctggc ttgccccact gtgctggaga accttggacc cggtcccttc    21420
tcccagccag ggcagagcct tggcaggtgg tcctccagcc tgcttttaat tgcccccatg    21480 acagggact cactgctgct ggagccagcc ccatggcatt gttcaatttt tcccgaccag    21540
ctaagatcag ctccctttgt ctgtggtgtg gtggctgtga ggtccacgca tctctccttc    21600 tttcttctt tctagaatat gtcacatttc tgacagttac ccccaacctg accagtgtct    21660
acattgccaa ccacaggcct ctcttcacac acttgggtga gttgactgga ggactcccac    21720
ccagttagct agactgcaaa ggtgcagagc actgttgcca agatgccctc acttctgaca    21780 tcaccccgcaa gttcaggggg ttccccaaac caccctcagg cttgatagtt gactaggaag    21840
actcccagag ctcactgaga gctgtggcac atggctgcgg ctccttccag aagaacacag    21900
gttagaattg tccaagggaa gagatgtagg cagagtctgg gagggtccaa ccaggaggcc    21960
tgatgtctca gggatgtgac acccttctag cattggagcg tggccatacg catgagtat     22020 tgcccacaca gaaagcccac tgagtgggag ttgagagttt ttcctggggt ttgagtgcaa    22080
agacatgatt gactaattgg ccaggtggat actctcagtc tcttggtgac ccagccccta    22140
ycctaaatca catagttggt ctttctggta cagccagccc ctgccctaaa ggaggacact    22200
```

```
tctgcctggt gtgacccgtg tttcctcttg gaagccaaca gcaaaagctg gacttctctt    22260
tgggcaaggc ccgcttcttt gctattgagg gccacagtgg gtctttctgg agtgtgtctg    22320
cacctaacct ttgaagcctt ggttgccggc acttgccatg gggtccctga gccctgagcc    22380
tgttgagttc tgtgcgtgag tgcacttggt catagcactc accaggttgt ggaaagaggc    22440
ctagagcctc cgctgtgggg aagcctctag ctcagatgcc tgtggctcct tagaggaggg    22500
ctggggaccc cggaaggag agtcactgac atgtgcctgt gaggaggatg ggtgctcagc    22560
tccacacggc taacagggct ggttccccga cagcggtgag gatcggaggg cgctatgtcg    22620
tggctgggaa gatgagcatc tcccctaaca ccacctaccc ctccctcctg gaggatggtc    22680
gtgtcgagta cagagtggcc ctcaccgagg accggctgcc ccgcctggag gagatccgca    22740
tctggggacc cctccaggaa gatgctgaca tccaggtcag caggagagcc tgggggaggc    22800
cagtgggggc ttcttcttgg gggctatggc tgcttgctcg tttgtctatc catccattcc    22860
ctgattcgtt catttattca ttcagcggtc acttacaggg gacccactat gtgttgggcc    22920
ctgtgctagg caaaatgtag ctagctcctc caggggctta gggtcccaca aatatccaaa    22980
tgtgyctgtg cccagagccc gtgggagaag gccctgcagt tctgggatca ggtaaggttg    23040
gagggcccaa tgcaggggtc cagggctccc tgggaaagag tgatggagct gaggtgtcag    23100
atgagcagat gttgctgggc caagcaggga aggaagcgta tggctgaggg aacagtgtca    23160
gtgtgggagg gatgaaggaa ggtcctactg tgtgggtttg tggggagatg aaggcatgga    23220
cgcaggtgca gtggcatctg gggagtaggc cttggtgctg aggaagctga aacagatgc    23280 tggctctcac tgcttctttg gtgcagtgtg tgtgggaacc ggaaggcctt gttcaggcgt    23340
gtcctcagtg acgtgtgctc gcccatgtat gtccccattg gtgcttcgct gaggaaggca    23400
cgtggagggt ggagagacat aagcgcaggc tgaaacagac ctgagaacct tgggagaggg    23460
gcccagtctc agcggccgga gcagcgtcct ctgcccctac agcagccaga gacaggaggg    23520
cctcccacag atcaggccag gccgggccaa agcaagcccc tgtgagcggc ttatcccttc    23580
tcttcccctg atatggttcc cttcctcccc tccccttgcc tgggacattg tatccagatg    23640
ctagctgccg agtggctctc ccatcatcct ctgcagtgtg taaaaagca gattcccggg    23700 tcctctgcat attccctgaa tcaggacttc cctgtgttgg gcctgagaaa ccgcaccgta    23760
accaacacag gcttgcggca ctggccagat gtgggcatcg agggggcagg tgcggaatgt    23820
cacctcgccc tgggctctgg cctycaggct ggcctctttc ttgggctggt cttgggcaca    23880
ggacccagtt accctcctga agagccttag gcccaggaac ctgctgaagt tcttcctagt    23940
gctctccggg ccagtcccaa gccagtagct ggccacaggt ccccagggat ccagtttctt    24000
cctgccgacc ctaccacagg tccccaggga tccagtttct tcctgccgac ctacgggcc    24060 tcagctctgg ctccagaagc actttctgtg ctggccctgc cctagcccct cttgggctcc    24120
ttagcccagc ctaaggtggg cctgcctcct ccactgcact ttatcctcta cccagccagc    24180
ttagggaacc ttctctgtgc tgcccaaata ccctatcrtg taacccacca atgacttggt    24240
aattacctcc ccgagccctc tatcccaacc cactgagagc tccttgcagc tcagccagtg    24300
tcctgtgcac tgtgctatcc ccagagcctg gtacaggtca gtgttggtga ttgcttcccg    24360 ttattttgt ctttgttgtt tttttagaga gggtctcact gttggccagg ctggagtgct    24420
atgttgccca ggctgctctg aaactcctgg gctcaagtga tctgcctgcc tcaggctccc    24480
aaagttttgg gttacaggc atgagctacc gtgcctggcc agtgattgct tgctgarcga    24540
aagattatag ggatgcaaga agaagttgga aggcttccca ggggaggtgg ccatgacagt    24600
```

```
gaccctcagg gaacccactg gacaaggcct gaagctcttt gtctgcaggt ttacaggcgg    24660
tatggcgagg agtatggcaa cctcacccgc ccagacatca ccttcaccta cttccagcct    24720
aagccacggc aggcctgggt gtgggccgct gtgcgtgggc cctgctcggt gagctgtggg    24780
gcaggtgaga cctggggaag gctcatccac agcacggctt gccctgcag ggaggcggcc    24840 tagccctccc tcttccctcc cagggctgcg ctgggtaaac tacagctgcc tggaccaggc    24900
caggaaggag ttggtggaga ctgtccagtg ccaagggagc cagcagccac cagcgtggcc    24960
agaggcctgc gtgctcgaac cctgccctcc ctagtgagtg tggtgctgtc tgcgcagctc    25020
caagggggag agagggttcc gctggggctg ctgggctctg tccctggcct atggggccca    25080
tgtggcaggg ccgggctgag ctgctcctgt gcaggctctc attaccctg cccacagccc    25140 tgcaagggg gctctgtgag tgcccccatt ctgcaggtga ggacactgag gcttggggca    25200
gacatggtga caatgtcagc ccagtgggac ccacacctgc tgccaccttg tctgggccac    25260
cgaggcctct cttgagctca ggtactcatg gtgagatgga ggtgattgcc tacctggagg    25320
gttgtaggga gacttgcgga gctcctggtg caaagcccct ggctgtcacc acacctgacg    25380
gggcacactg ttagggacga ggccattcct gctgggtgca ggacagggca gctgctcacc    25440
agcctgtgat tcggttgtcc tcaggctcag ccgtctggca gcctgggaac acctggagag    25500
gctaggctgg ccgtagtgcc cattgcttgt cccagaccgg gggagtacat cagcacctgc    25560
caccccatca ccccaggcca gcctgggacc tggccaggt cccgacgctc tgtctccttc    25620
ctcagctggg cggtgggaga cttcggccca tgcagcgcct cctgtggggg cggcctgcgg    25680
gagcggccag tgcgctgcgt ggaggcccag ggcagcctcc tgaagacatt gcccccagcc    25740
cggtgcagag caggggccca gcagccagct gtggcgctgg aaacctgcaa ccccccagccc   25800 tgccctgcca ggtgagccca gggctaggtg gggctgggag agggccttcc tggcagagct    25860
cgtccctgcg ctgagccccc atccttctga gaatcccctc ctcctgaggc ctccggcggg    25920
gcctcaccat ccagggtgat gggcagtgtc acctggcggt tgtaagtgct gctgtcagag    25980
ttccttacta cccaggagag cctgggccca ttgtttccct ctctgagctt ccgagccct    26040 gctctgaaat ggggatgccg acctgcctgg ggaggggggg cttcgaggat gaggtcaaac    26100
tgaacggagt gggagatgtc actttctcat caccaccatc tccccgtgc ccacgtggct    26160 gcatctcatc ccctcagtgt ccaagttgac agtggcttat catcctgccc tgccactaac    26220
gagctgagtg acagggcaag tcccctcctc tgtgggcttc agttttgcga cctgtccggt    26280 gggagggat tggtctggat tgttggtggc ccactcatag ctctggactc cttcccgc     26340 ctcgtcatcc gtggcagaca aaacagtcac cactcttccc cgctgaggcc agataggcc    26400 tcagaatcct tctcacacag ctctccaggc agccactta gcgcagggct gactcacagc    26460
tgaaacccat tggccaccct tgaacctggt gatccaattc catgtggcac ctgtttctct    26520
gcacctgcta tggtgcatgg agtcagtgat tacctggctg gaggtcggcc tctgcctctg    26580
gagagtagga gggatgggtt ctcttttttt tttttattaa aagacagagt cttgttctct    26640
cacccaggct ggtatgcagt ggcatgatct tggctcactg caacctcctg cctcagcaag    26700
tgtgcgccac caagcccaac taattttgt attttttgta gaaacagggt ttgccatgt    26760 tgcccaggct ggtctccaac tcccgggctc aagcagtctg ctcacctcag cctcctaaag    26820
tgctgagcta ccgtgcctgg ccagggatag gttctgtctc tgcaccctgg gtgcaggtgg    26880
ggtgcctgac tgttgagcag cgagtgcttg ttgaatggga acctgctggc tgatgaatgg    26940
```

```
ggaacccggt gcttcaggga gagaccctgw gcttcacttc tctgtggggc tcctctttgg    27000
gctcctggat gttggggagc aggtcccctt cctccctgcc cctagcagct gggctatacc    27060 ttccctggg tggcagaggc agggcctgat gactgtctca tgccatcctc aggtgggagg    27120
tgtcagagcc cagctcatgc acatcagctg gtggagcagg cctggccttg gagaacgaga    27180
cctgtgtgcc aggggcagat ggcctggagg ctccagtgac tgaggggcct ggctccgtag    27240
atgagaagct gcctgcccct gagccctgtg tcgggatgtc atgtcctcca ggctggggcc    27300
atgtgagtgc cctgggcatg agggtggctg gggctgttga gtcctttacc tggctgggag    27360
aacgaggagc acccattgcc accgtcctcc aggccagagc aagaacacca tccttctgtg    27420
ggaatgctgt ctgagggcca cccctgctca gaaagaagc ttagaaagag gctcagggc    27480 ccctgggaag gctcccattc cccttgcaag ccgggctgag ggaagcatct gaggagagtg    27540
taatgcagct gctgtgcaga gaaatgctgc caggctcccg cctggcgtcc aggggctgga    27600
ggctgactgg ccttgctctc tggcctgggt gctggcaacc ctcgcccctc atggctgggg    27660
ggattgcagg gccaggcatg ctcccatgtc ccactcttgg tccccagctc tcggccaggc    27720
ccacagtgag cactcatgct gctgaggagc ctgcaaaggt ggggtgtgca gcaaggatac    27780
ccgctgcgag accggggagc cgatctcgcc aagggaggag gggagggagc ccctggtgca    27840
cacacgccac ttcctggtct ctctgctgct gcctgagaag atcgacacgg ggatcgctgg    27900
gtcctcagag gaggcccaga cccaccagct tgttgctatt ccccacagct ggatgccacc    27960
tctgcagggg agaaggctcc ctccccatgg ggcagcatca ggacggggc tcaagctgca    28020 cacgtgtgga cccctgyggc agggtcgtgc tccgtctcct gcgggcgagg tgagggcccc    28080
cgggatgctc ctggggacca gcactcatgg taactctcct gtccacttgc atcttgcctc    28140
gttctraaaa gcatttgagg tggattgcag aaaatccaga ctatatggga acacgtggta    28200
atacacaagg agactaagca tagtagctga cagccacttc aaatgtgggt gttgattggc    28260
tgaaaggtag gaaaagacaa taacgcccgg cagtgtggca cgagagccat tccttatggt    28320
cctagcagag cggccggggg gtccccaatt gatgacccga gcagagaaac cttagcttta    28380
agatacacag cgttcttcta ttttcccaat cttgttttat tgcagtataa cacagatatt    28440
ataaaattta ccatccaaac tgtttctccc tgtgcaggtc agtggcataa aagcacagtc    28500
acattgttgt gcggccatca ccaccaacct ctccagaact tttccagttt cgcaaactgg    28560
agctctgtcc ctgtgaaaca cgaactccca tttccccctc cgcagcccct ggcaacctcc    28620
attctccttt ctgtctccag attccacaat tctagggacc ttgtagaagt ggaatcatat    28680
agcatttgcc ttttgttac tagttttcac tcagcatgat gtcctcacag ttcatccatg    28740
ttgtagcatg tgtgagtgtt tccttcttaa ggctgaaaaa gattccattg tgagtgtatc    28800
ctttacakgt ttatccattt attcatcagt ggacacttgg cttccttcca cactttggct    28860
attgtgaata atgcttctgt gaacatgggt gtgcaaatat ctgtttgagt tcctgctttc    28920 agttctttg ggtgtatatc tagaagtgtg gtagctgggt aagatgagaa ttctatgttt    28980 aattttgtg gaactgctgg actgttttcc ccagtggctg caccattta catttccact    29040 aatggtgcat aagagttcca atgtcctccc atccttgcca acactttta tttctatggt    29100 ttttttgtt tttgttttg ttttgagac agagtctcat tctgttgccg aggctggagt    29160
gcagtggcat gatcttggct cattgtaacc ttcgcctccg gggctcaagt gattctcgtg    29220
cttcagcctc ccgagtagct aggactacag gcgtctgcca ccatgcctgg ctaattttt    29280 gtttagtaga gatgggggttt caccatgttg gccaggctgg tcccaaactc ttgacctcag    29340
```

```
gtgatctgcc tgccttggcc tcccaacgtg ctgggattac aggcgtgagc ccccacacct   29400
ggcctatttc tgtgttttt ttataatggc catcctaatg ggcttgagaa gacacaccat    29460
gttcttaaac gaaaaccctg accacttgct cagtaaaatg tcagcctgtt taaaaccgag   29520
accaaaaaga gatttctttt tctctctttt cttttctttt ttgagacaaa aagaaaacc    29580 tctgtcacca ggttggagtg tagtggcaca atcttagctc actacaacct ccaccacctg   29640
ggctgaagcc atcctccccc ctcagcctcc tgaatagcta ctatacccctg ctaattttg   29700 tagttttggc agagatggga tctccctatg ttgcccagcc tgatctcctg agctcaagcg   29760
atccttctgc ctcggcctct caaagtgctg ggattatagg catgagccac tgtgcccaac   29820
caagagattt ttttctttt tctttttttt ctttttttg agactaagag ttttcctctg     29880
tcgcccaggc tgaagtgcag tggtgtgatc ttggctcact gcaacctccg cctcccatgt   29940
tcaaacgatt ctcatgcctc agcctcctga gcagctggga ctccagctat gtgccaccac   30000
acctggctaa ttttttgtat tttattttat yagagagggg gtttcgccat gatggccacg   30060
ctggtctcaa actcctgacc tcaggtgatc cacccgcctt ggcctcccaa agtgctggga   30120
ttacaggcat gagccactga gcctatttct tttgaggata ttcctaaaag agagacttga   30180
gaaaactggc cctaataaca tctttatgat agacacaatc agagattttc atattgtgat   30240 tttttttct tttttyttt tttgagatgg agtctcgctc tgtcacccag gctggagtcc     30300
agtggcgcag tcttggctca ctgcaacctc tgcctcctgg gttcaagtga ttctccgtct   30360
cagcctcctg agtagctggg attacaggtg cgcaccacca cgctcagcta attttgtat   30420 ttttagtaga cacggggttt caccatgttg gtcaggctcg tctcgaactc ctgaccttgt   30480
gatccgccgc ccaaagtgct gtgattacag gcgtgagcca ctgtgcctgg cccatattgc   30540
aattcttata tgcctctcg gtcaacaata acagctacca tttgtcaagt gtctactgtg    30600
tgccaggcac ttgttatctt ccctttaaa aatctttata aatgattctg caaggtagat    30660
gccattatct tttttctaa atctaagatt cagagggtta agtcagttgt ctgaggtcac    30720
acagctggta agtggcagag ccgggattga acccatgcg ggccttatgt gctagaggtg    30780
tccagtgagc ctgggctgca gtccttgctg agcctgtccc ttgggctct gggtctctgc    30840 tttgtccacg caggtctgat ggagctgcgt ttcctgtgca tggactctgc cctcaggtg    30900 cctgtccagg aagagctgtg tggcctggca agcaagcctg ggagccggcg ggaggtctgc   30960
caggctgtcc cgtgccctgc tcggtgagtg aggggagcaa gactgtgtgc tggccttctc   31020
cctgtaagtg ggagaccyga gccttggctc catgcccggt gacctgcgga ggggggcagg   31080
tgctgctggc tgtgcactgt gtgaggctgg accatggccg ccccatcccc ctgcctcact   31140
ccaagtgcag gccagagccc cggcccagcc cctttgagga ctgcaaccca gagccctgcc   31200
ctgccaggtg ggccccttcc caaggagaca ggggtgcta ggtctgcatc ctggctcttt    31260
cctcacctcc aagccagacc ttttgaccct cagtgtcctc accagtggga gcaggtcatt   31320
ttgtgccccc agaagactgg gggagtttaa tgaaaggatt agatgcatgt aaagtacatg   31380
ctaaatgcaa tgagtgtaaa atgcatgctc gatgcaacgc gtgtaaagta cattgcacag   31440
gatctgggat gctgtgggtg cacatggttg ctggtgcgtt tcttcatcgc ctgctctttta  31500 tggagcacct aggccccggg gccgtcctgg agctagggga cacagcagag aacaaggcag   31560
acaaatgtcc ctgacctcct ggagcaaatg caggggaaa gggggacaga taataatagg    31620
acaggygggg aatgcagttt gatggatggt gttcagtgcg atgcagccaa acacagcggg   31680
```

```
aggggaggag gggagggctg gcggggtggg ctccagggcg gtggtgctgg gatcactgtt    31740
gaagacagac atgcagggcc cttgggtgcc cggacccctg cccccactgt ctctgggata    31800
cgacatctgt cgtttgccct cacctttctc ttctgtaaaa tgggtttgtc caaatgttct    31860
gtccactctg ccaagcctct tggtgaggac acaagggggc ctccagaaag agaacctctc    31920
cgggcccttc ccagcttcct gtctcttcct agtctgggga aatgaagggg agacctggct    31980
cccctgggtt cccaggccct ggggctgttt ggggtccctg actccagttt gctccaggtg    32040
gcagtacaag ctggcggcct gcagcgtgag ctgtgggaga gggtcgtgc ggaggatcct     32100
gtattgtgcc cgggcccatg gggaggacga tggtgaggga tcctgttgg acacccagtg     32160
ccagggggctg cctcgcccgg aaccccagga ggcctgcagc ctggagccct gcccacctag   32220
gtgagtcagc cggtgatggg aggggcagct cctggtgtgt gcagatgcca ggccaggcgc    32280
tgtggtgtgt gcctgtaatc gcagctactt ggaaagctga atcaggagaa ccacttgagt    32340
ccaggagtgc aagtccaacc tgggcaacac agtgagacct catctctaaa aaaaaaacaa    32400
gacggggcca ggtgtggtgg ctcacgcctg taatcccagc gctatggaag ctgaagcgg     32460
gtggattacc tgaggtcagg agcttgagac cagcctggcc aacatggtga accccatct    32520
ttactaaaaa tacaacaatt aggctgggcg cggtggctca ctcctgtaat cccagcactt    32580
tgggaggctg aggcgggcag atcacctgag gttgggagtt cgagaccagc ctgtccaaca    32640
tacagaaacc ctgtctctac taaaaataca aaattagccg ggtgtggtgg tacatgcctg    32700
taatcccagt tacttgggag gctgaggcag aatcgcttga accggggagg ccaaggttgt    32760
ggtgagccaa gattacgcca ctggactcca gcctggctaa cagcagcaaa actccatctc    32820
aaaaaaaaa aaaaaaaag aaacccaca aaaattagcc tggcgtggtg gtgtgcacct     32880
gtcatcccag ctacttcaga ggcggaggca ggagaatcgc ttgaacccgg gaggcggagg   32940
ttgcagtgag ccgagatggc gccgctggca ctccagcctg gctacagag cgagactccg    33000
tctcaaaaac aaaacaacaa aacaaaacaa gacggggtgg ggggctcagt ggcccaagag   33060
ccagtctgta aggaatagg ctacctggca ggctgtgcta gttgtgggag gtgaagttta    33120
agcaccatgc aggcagggtg cagtgtgggg aggcctgggg gacagaggag gcagcatttg    33180
agcagaacct aaagctgtga gcaccagcat tctgatgtgg aagacgggag ggatggaggt   33240
ctccacaggg acacacacag ccacactagg acacgggaca gaatcatgtt caagtccgtg    33300
gggtccggag cccagtggta aagggcgaac atttgcctac ctcatttaca attctttaat   33360
ggtttctttt tgtaggtttg cattttttagt aaagaaatac ttttctatat catacagaaa   33420
cgtccagaaa agaatgtaac agacatgtat gttccagcac tccagtttaa tagatagcat    33480
cctactgcca tgtttccttc ctgtccactt acttttattt atttaattta tttattttga    33540
gacggagtct cgctttgttg cccaggcagt gatgcaatct tggctcactg caacctccgc   33600
ctcccgggtt caagccattc tcctgtctca gcctcccaag tagctgggaa tacaggcacc    33660
cacaaccaca cccagctaac ttttgtattt ttagtagaga cagggtttca ccatattggt    33720
caggccgatc ttgaactcct gacctcagga gatctgccta cctcagcatt ccaaagtgct    33780
gggattacag atgtgagcca tcacacctgg ccagcctcct tagtttttaaa taaatccagt   33840
tacagataag atttcactta aatttaggct ggtcatggct cacgcctgta atctcagcac    33900
ttcaggaggc tgagatgggt ggatcatttg agcccaggag tttgagacca gcctggacaa    33960
catgccaaaa ccttgtctct actataaata caaaaattag ccgggcatgg tggtgcatgc    34020
cagtatcccc agctactcgg gaggctgagg caggagaatc acctgaacct tgggaggtca    34080
```

```
aggctgcagt gagcagagat camaccacca ctgcatgcca gcctgggcaa cagcatgaga   34140
ccctgtctca aaaaaaaaaa aaaaaaaaaa aaagattta cttaaattta aaccctgtac    34200
taatctgtga tttatttgga gtatgttgca aagtagggac caaaggattt tttttttttt   34260
ctaaattgtt aactagcatc tgttggacaa gccctgatgc ctccaggtgg ctccttggtg   34320
gtattggtgt gtgttagaat ctatgtctgg gctttctact gggttttttt cttctccttt   34380
ttttttttg agacagtttt tctctgtcac ccagggtggg gtgcagtggc gcgatctcag    34440
ctcactgcaa cctccgcctc cygggttcaa gtgattttca tgcctcagct tcccgagtag   34500
ctgggattac aggtgcccgc caccacccc aactgatttt gtgttttaa tagagacagg     34560
gtttcactat gttggccagg ctggtcttga actcctgacc tcaagtgatc tgccaggttc   34620
tgtttttgt gcttttttt tctagctatt ctcttgccca tacaaaattg ttttaaatgt     34680
tgtagcttta taaccattta acatctgtgt cactagtgtg tcctgatttc tttgcctatg   34740
ctaaagtccc ttggctgtgt gtcccattta tttttccaca tcacatttag agatgatctg   34800
ggatttatg ggaattgcag ggttttcac actgcacgct gcctgcatgg tgcttaaact     34860
tcacctccca cacctagcac agcctaccag gtagccctgt tctctacaga ccacctcttg   34920
ggccactgag cctcccctca cttttttta gagatgggt ctcactatgt tgcccagtct     34980
ggacttgaat tcctgggctc aagtgatcct cctgcttcag cctcccgagt agctgggatg   35040
caggcacaca ctacatgagc tctgccatc cctctgacgt tgctgtagcc acgctggcct    35100
cattgtcctg gaacattcca gggatactcc cctgacttag ggcttctgtg ctagctctcg   35160
ctgcctgatg tcttctgtgg atatcctcga ggccctggat atccctcccc caggctcggc   35220
tcagacacca caactccaaa gtgggcccagt gccctccctg agcgtcggtc cagaacggca   35280
ctctcgtccc tcctgtgacg ctctgcttgg cactttggga ggctgaggcg ggaggattgc   35340
ttgagcccag gagttctaga ccagcctggg caacatagtg agaccccgtc tctacaaaaa   35400
atacaaaaat tggctgtgcg cggtggctta tgcctgtaat cccagcactt tgggaggcga   35460
aggcaggcag atcacgaggt caggagatcg agaccatcct ggctaacacg gtgaaaccct   35520
gtctctacta aaaatacaaa aaattagctg ggtgtagtgg tgggtgcctg tagtcccagc   35580
tacttgggag gctgaggcag gagaatgacg tgaacccagg aggcggagct tgcagtgagc   35640
tgagattgtg ctactgcact ccagcctggg tggttgcagt gagctgagat tgtgccactg   35700
cactccagcc tgggcgatga gtgagactcc atctcaaaaa caaaacaaa caaacaaaaa   35760
ttacaaaaat tagccaggca tgatggcaca tgcctgtagt ctcagctact tgggaggctg   35820
aggtgagagg atggcttgaa ccctggaggt tgaggctgca gtgagccgtg atcacaccac   35880
tgccctccag cctgggtgac agggcgagac cgtgtctcaa agaaaaccat taaataaaa    35940
taaaaaataa aatttctgcg atgcacacga cagcctccac agcaaatcag catccagttg   36000
ctcatgccag tgatgcccca atggagaaca atccacgctc tgagaggagg tggggtctgg   36060
tttggttcac tgccacctcc cagtgtcatg tagaacagtg ccaagccgcg gaaggcacgg   36120
gtccaagagg cagcgctgca gggtcatggg ggagcacagt attgcgatga agatcccagc   36180
tcccttgcag gctgcctggg ttcgtgtctg ggctctgaag aatgcgggcc ataattagtt   36240
attgattgat tacagatcaa catgggcagc cttcccttgc ccaaggaaag ggaactcggc   36300
cttcccttgc agaacgtggg gtgttgagat ctgtctcctg ttacccaggg gctcgcttcc   36360
tgttgctgtt acttgggtcc ataggcaacc cctgggtgc tgacaggtgt tctgtgataa    36420
```

```
aggcgactag aggggggatgt gcaattaggg aaacagggggc ctcttccccc tagggccttt    36480
tggtagctct cctgtggccg tgagccctgg ccccagacag gagggggctca gtggctgcac    36540
tttccatctt gcctggccac ggaagctgtc taggcaactg tccgagtaca cgtgggtgga    36600
gaggggcctg cgtgggggcag tactgtctct ggggagacct agcctctctc tggggtcttc    36660
tcttcctgca ggtggaaagt catgtcccctt ggcccatgtt cggccagctg tggccttggc    36720
actgctagac gctcggtggc ctgtgtgcag ctcgaccaag gccaggacgt ggaggtggac    36780
gaggcggcct gtgcggcgct ggtgcggccc gaggccagtg tcccctgtct cattgccgac    36840
tgcacctacc gctggcatgt tggcacctgg atggaggtga gcacagcggg cactcggaat    36900
ccctatgggg ctgggggtggg catcagctgt ggctcctcat gtgtgaggga gtctaggagg    36960
cattggctca tcgtgtcccc tgaaaggaag gagagagctg cgcccgttgg tgaggggggca    37020
cctagaggca gagagacaga gggcctagag acctgcgggc agctaggact taagaggccc    37080
ttaggtttgg ggacgctgga agatgaatgg caggccactc agctctacac agatgaggga    37140
atgccagctg tgccacgcac ctggcaaggc aggacagaca agggtaaatg gggttcaggc    37200
tgcccccctgg aggggctcgc tcatggtgtg gaggggggcat agggggcacag cagacagaga    37260
tgagccgcag ccccgcagac ctgcttgctc taaggcttgg agggacagag aggccgtgag    37320
ggtgacaggg acccagactt gaattatggc tcctcccacc tatatgaccc atgcaaggtg    37380
ccctctctga gcctcagttt tctcatctgt ggaatggaga cacttaactg cctcccagct    37440
tgtacaagga ttatattgga tcactcctgg cctgtggtta ccactgtcct tgtcaccttc    37500
tggcagggtc agctgtgact cctcctcccc tctcttggca gtgctctgtt tcctgtgggg    37560
atggcatcca gcgccggcgt gacacctgcc tcggaccccca ggcccaggcg cctgtgccag    37620
ctgatttctg ccagcacttg cccaagccgg tgactgtgcg tggctgctgg gctgggccct    37680
gtgtgggaca gggtacgccc agcctggtgc cccacgaaga agccgctgct ccaggacgga    37740
ccacagccac ccctgctggt gcctccctgg agtggtccca ggcccggggc ctgctcttct    37800
ccccggctcc ccagcctcgg cggctcctgc ccgggcccca ggaaaactca gtgcagtcca    37860
gttatgtcct gtcctccttc ctgtcaggca gctgctgcag gagggggtggg caaaggcatc    37920
ttcctctggg aaggactggc acaagcactt ggtccctggg ttgtgtgcct gggaggccgg    37980
gatcagggct ggccctcttt ctccctggca aagcaaaacc tcccttttac tactatcaag    38040
gggaagtaac ttgaaggtag gaacccagct tgtgagcccc ctagcctctg ggctgctctg    38100
catgtgccccc ctcttgctgg atcatctggt agcagccctg tgcctgagg gtgatgctct    38160
gacctatgca gccccccctcc ctgtcctgag aaggcttcca gctgggcctt ggaggacagg    38220
gtccacccct acctcctggt ctccttcctc agcttggaag ccccggagcc tgccctgctg    38280
ggaatcgggg aagcactgct tacctgtctc ctgctcccctt ttcaggtgcc tgtggcaggc    38340
agcaccttga gccaacagga accattgaca tgcgaggccc agggcaggca gactgtgcag    38400
tggccattgg gcggcccctc ggggaggtgg tgaccctccg cgtccttgag agttctctca    38460
actgcagtgc gggtatgtct agggccatgc aagcgatgct gccagttatg ggccctgcca    38520
ggagccagca cgacgctgca tgccccattc ctggcaggag cccatgtgca ttcccacctg    38580
tagtttgcat cccatctcat gactggggag tgatgatctg catttttacag atgaggaaac    38640
tgaggctagg agagattaag tgatgtgccc agttacttag agtcacatag ccagcagtgg    38700
gagaggtggg acttgaactc ggctcagtct accctggagc cactcctctg ctgaccaggc    38760
gtgggagtgc tggaccctca ctgccctgcc gcttcctagg ggacatgttg ctgctttggg    38820
```

```
gccggctcac ctggaggaag atgtgcagga agctgttgga catgactttc agctccaaga    38880
ccaacacgct ggtggtgagg cagcgctgcg ggcggccagg aggtggggtg ctgctgcggt    38940
atgggagcca gcttgctcct gaaaccttct acagaggtat ggccaggcct tctccacctc    39000
ccttgggtgc tccagtcctg gcagggaggc tgggtgggtg ctgctgggga tggggccagt    39060
cccagtgggg cagtgggaag atacggaggg aactgactga gatggaagga actgggggttg   39120 gccagtgtca gtctgcacgt gccagggagg ggtcacagga tgaatgctat atccctcctt    39180
tttgggaccg tgcagcaaga tggacggatg tgggacatgg tccacatcct cagtcagtcc    39240
ctcaggcctc tgccccacac ccacctgccc cgcccccacc cctccagcct ttcaagggct    39300 tttaggggttt tgtggaagcc actgtccctc agccctgttt cagtgcactg gtgtaagcag   39360
acatgcttgt acatgcatgt gcacccacaa gcacacctca ggcagaggat gccacctcag    39420
ggactccagc cttgcccgtg gcccctcga tatcctctga tagccctctc ggttgtcctg     39480
gggggcttgc cctctcccaa cagcccgagc tggccgaagt tggcttccct agctggttcc    39540
agaggttcct cggctccccc aggtgtctgg ggcttagtgg caacagggggc ttagcctctg   39600 cagagaccta gtgcgccgcc tccttgcccc agacctgccc gggcagagag ccgtgtatgt    39660
gtctcagtgc acaggcgctg ctgggccctg ccaaaaggcc acaagcccac tgtcaccgtt    39720
cacattgctt ctcgcttccc ggcccagccc cgcccacaca ggcatctgcc ttgaaagagg    39780
tgcaggaggt acaggcaggt gggggctcca gtgagctctg aggaacagca gtggccgcca    39840
tgggtggagc ctatctttgt tgccagtttc agtgttaaac actcttgcac gtgtgacatc    39900
attgagtcct aaagaccact ctgctcagtg catgccattg tttccttcag ttacagagga    39960
gggaaccaga gcccagaaca tttagccttt gcctaaagtc actgggccag gaagtggtag   40020 aggtgggggtt cagcaggatt tgcctgggaa ccccaatatt gaccacagtg ccatgctgcc    40080
ctgcacggct ccctggctgt gagttgtcct ggcctctggc accaccggtc tgtctgggtt    40140
cctatgtccc tatgtcccac ctgcagaatg tgacatgcag ctctttgggc cctggggtga    40200
aatcgtgagc ccctcgctga gtccagccac gagtaatgca gggggctgcc ggctcttcat    40260
taatgtggct ccgcacgcac ggattgccat ccatgccctg ccaccaaca tgggcgctgg     40320 gaccgaggga gccaatgcca gctacatctt ggtgaggccc agcatgggga cttgtgctgt    40380
gactctggac agctttccct agggcgtgca gggctagggg acccccttca gtttatttca    40440
gactaaaacc ctcaaaatca ttagtgaaag aatgggagaa gatagcttcc tccacatatt    40500
caccaagaaa tgttttttga gctacctaca agagtgaaat agtggctcac aactgtaatc    40560
ccagcacttt gggaggccca ggagggcaga tcactcaagg tcaggagttc gagaccagcc    40620
tggccaacat gatgaaacct tgtctctact aaaaatagaa aaagtagcca ggcatggtgg    40680
cgtgtgcctg taatcccagc tacttgggag gctgaggcac aagaatcact tgaacccggg    40740
aggtggaggt tgcactaagc ccagatcgca ccactgcact ccagcctggg caacagagtg    40800
agactctgtc tcaaaaaaaa aaaaaaaaa aagcgaaatg gtaaagaatg gtaaagacct     40860
ttctgatgta gactgacagc taacccagga ctgaagcata attttacagt ctgatataac    40920
ttggacagaa tagcaccctg caccctcccc gaggtttcat gtgtcctggg agaactgtgt    40980
tctgcagggt atcagcttcc ccagaggagg cagcctgggc ccgctctggc accctgactg    41040
tgtgtccttg gggaagtgat gtaacgtccc tggacctcgg ttttctgggt agagtaatgg    41100
cgtattccta gtagggcttt gtaagcatta aatgtgatcc ggaatctgtg agcccttgca    41160
```

```
cacgaaggct tccgtgagtg ctaattatta cttgtggccg gtccttctgg gctgcccctt   41220
ttctctcaga tccgggacac ccacagcttg aggaccacag cgttccatgg gcagcaggtg   41280
ctctactggg agtcagagag cagccaggct gagatggagt tcagcgaggg cttcctgaag   41340
gctcaggcca gcctgcgggg ccagtactgg accctccaat catgggtacc ggagatgcag   41400
gaccctcagt cctggaaggg aaaggaagga acctgagggt cattgaacat tgttccgtg    41460 tctggccagc cctggagggt tgaccctggg tctcagtgct ttccaattcg aacttttcc   41520 aatcttaggt atctacttta gagtcttctc caatgtccaa aaggctaggg ggttggaggt   41580
ggggactctg gaaaagcagc ccccatttcc tcgggtacca ataaataaaa catgcaggct   41640
gaccggcgtt tttttcttat aagctgtcca gacctggctt gaaaacccat cccatggcaa   41700
ggcagggatt cgctggccgc ggttggctct atcttgatct gagcaagccg ctggacgtcc   41760
ctagttatct tcttcctatc caggaagaaa atccaatcag gattccactc cgaggatggc   41820
gcattagcca gctccctgcg aagccccacc cgtgtgtcct ggtgtgaggc tctgaccgct   41880
aaggtgtctg cgcgcctcca ggccccgccc cctatgctaa taagcgcccg cctcctttgg   41940
gagcaagtcg ccgcaaactg cgagccccg  ccccctacgc taatgacgcc cgccccctc    42000 gggcacacct ctccgatgcc tgcgagcccc gccccgtatg ctaacgagct ccccacccc   42060 agctcctcgc cgcagcctgc gggtcccgcc cctacaata atgagcacct acctcccctc   42120
aaacgcccct agtcgcggca tgagggtccc gctcactatg ttaatgagca cccgcctccc   42180
ttcgggcgcg cctcgccgca gcctgaaagc cccgcccct atgctaatat gctccctctc   42240
ccacaaggca gcgcgccggc tcggacgcgg ccggctaccg agccctttgt gagggctgtg   42300
agctgcgcct gacggtggca ccatgagcag ctcaggtggg gcgcccgggg cgtccgccag   42360
ctctgcgccg cccgcgcagg aagagggcat gacgtggtgg taccgctggc tgtgtcgcct   42420
gtctggggtg ctgggggcag tctgtgagta tccagtcggg gagaggggcc ggccccgccg   42480
cgcatgcgct cctcgccctg ccctgccccg ccccgccccg gcggcccag  gggaaaggac   42540 ccgctggggg tcgggggtct gccgggcgcc tcccggggcg gaggaatggc gggggccgccg   42600 ggagccggcg tcctggggtt gccatggtta cccgctcggg cctgggcgcc ttggtacccc   42660
gggctgggct gggctggcgc ttctgggaac attcccggag ggaccagaaa ccccagggcg   42720 gggggggcggc ggggggcgggg gggcggcggg ggcgggggggg cggcggggc ggggggcgggg  42780 gtggggcacc ggcctgggc acgtgactga gccctccccc cgctccccag ggcttttgt    42840 gagactttct cggtgatgct cacggggcgc atgcccacct ggcccgtact aaagcgtcaa   42900
ctgttgactt gggcgtaggt gacggcagcc acattgctaa cctttgggca aggattgttt   42960
gtaagggagg cgggtgcacg gctggctaga tttctggcag gaagccactg gcggaagtt    43020 tgctgagggt caggtggtgt cagggcacag gtggcccctg gggccgcggg gcagtgagct   43080
gagggcccgg cctctcctg  gtcctctgt ccgctctcat atctccccg  ttgctgctgc    43140 cttagccgcc tgtcaccggc cttcctcccc ttctccgcac gcatcccagt cacagaccct   43200
gaccttaggc tgccagggaa gctaggctct taagcacagc cagaaaagga caaagaggga   43260
ggcaggtcag ctccaggagt gaatggaagc cgtacagctg gccttccagg gaaagacaag   43320
tctgtctgag tgatacccct tccttttcctg tctgccctca atcttgtgga ttactggagt   43380
gggcaaggtc ttagagaatg tctgtcgagg atgtctgcag ggtttaaaca gtgcctgcct   43440
ggcagagagg gctagctctg ggcctgggca gggcaggccc catcagcaat cctgccagaa   43500
ggaccacctt ttcagggtca ccttgggttc cacagccttt ccaggtgggt agagggtgga   43560
```

-continued

```
gggaggttga ggcaggaggg tgctgggcta ggagtgtgct gccctcgcta ggcatgccct   43620
tatccagagg caacggatac ggtagggcag gccctacccc caaatcacaa aaaggccccg   43680
agtttgtgtc actgctcttc agggcaagta cgcttttgac tttgtagtag agactggtgg   43740
gtttgaagtt aggcattgga tccagtcctg tcatgtctgg ttagctgttt tccctgcaga   43800
ttagggtggg cagtgcagtg gggtgacatg gtcagtggtg agaaaggaaa ggtcctgact   43860
atggcctgta ggccacacct ccttccttct tggtcagtgg ccctgccgac tcccagattt   43920
gctgtggagt cttactcagt tctgtgcctc tcaaagtgag gtacctctgc ctttcctggg   43980
agttcctggg gctctgttgg gtctacagat gaagcttcag gagaaacttg cggcattgcc   44040
ctgagttgtc agttgcatct gcagattttt gggggcatgg ttatgtgaac atcaaaatgc   44100
tgtattacag ggtagaatgc aaaaatgcag ggtgttttag agatgcggca ggagttcaga   44160
caagggttgt gtgccgggct ggtccttggg taaggttttc ctcctccagg gtgagggggat  44220
cagagagagt acctggagag ggtctaccct gggtcctaag agcatctgga ggtgatacct   44280
tgggagggga caggattgca tggtgacagc cccctcacgt ggaagatatc agcattgagg   44340
cccccaagtg gacatcctcc agccctttat tgctaaagga ttcctggctg gagcctgctg   44400
gtctggcttg acacctggtc ctcccccaag gctggctgtg ggttggacag ctggggtagg   44460
gttggagctg gaggccaaat gctgactgca gcaggaagca cagccgagct gtcaggtgag   44520
gccaggcaca gcagagaggc agggagccgt gtcacccttt gggcactctg ctaggacagg   44580
caggcccctg tgtacctgtg gttctggaac accttgctgt ctgaaggcag atgtctaagg   44640
ctgtgctgag gagcagtgca acgcttgagt ccttttgtttt agaaggagac cctgggggcc   44700
catgaagcag tcccattgca gttcggctca ctttatctgg cttctttgcc tgctgtctgc   44760
ataaggttac ctgggaaaat ggaaaacagc agaattccag acccaggtgg agggatcagg   44820
tgcagaggag ctgctgcaag tttaatgagc tgggtgctaa ttgctgcctc caaggccccc   44880
ctcagtgatg gcctgggctt gctccctgcc cagcagccac ctccttggac ctgccttgaa   44940
ggctcctgga gttcctggtg aagccaggct gcaggctgtg ggtggaggag ggagttgggt   45000
gcaagagacc ctgctggtga ggtgcagctg ggaggcgggg cgtcaaggct gcacatctga   45060
gcatcagaga agccacgttc tggggtggaa acgatgcccc ctcccttc ctggccttat    45120
ggcatttcag cggtgggtgg ctgggctgtg ggacttgctc atgtgcaaga ggagaaacgg   45180
gtctaggaag atgaagatag cgtgccagtg gcacagggct ggtgaggaag ttagagctgg   45240
aactgctgct cagtcttacc tggttcccat ctctgttctg agagaggcac cccttgtccc   45300
aaccaaaatc caagccacat tttctgagtc agaggacttc ttgtgtggcc ggccctgtga   45360
atggtggcaa gtgacccta ccgaaggctg agtcttgggg gagcactggc ctgaatcctt   45420
gagggacatt cactctttaa tccttcttta atcctaacct cccttgagg tggatattga    45480
tgtagctggg gtcagagggc cagctcctct gagccctgaa acggggagag gatgctgtga   45540
gatccacctg ccaccttgct gccaccttgc tgtgggggcct ggggcaagca aggcactgca   45600
cctctctgcg tctcctcacc tgtctcagac gatagagggc aggcttctgg gtgctgtgag   45660
aactgtgtgc tgagcatccg cagagactct cgtcctttcc agtcatctcc caaggccgcc   45720
ttcccagcgg gctccgcctg cctccctgct gactcctgcc cgtgtctctt gtttcaagct   45780
tgcgcgatct ctggcctctt caactgcatc accatccacc ctctgaacat cgcggccggc   45840
gtgtggatga tgtgagtaat gcatggccgt cccaccccgg gggtcttgct ggtcgggaat   45900
```

```
ctgctgggca cctcccggga cagaggagtg gcaggggccg tgggagtggg catccttgtg   45960
gttgccatgg ctactggctc cagcctgggt gcctcggcac tgtgagtttc tggccacagc   46020
atgcggcttc ttccccttca tacccccacc atgtttagtt tcctaatgag aggtcaaggc   46080
ccagggaatg cccaccccgg ccttcatccg gtgcaggggc aaggccatca gtgctccaga   46140
catttctgga gcatccactg agactgcaga tgccaagtcc actatactgg ggccctcgcc   46200
ctctgggagc tcccaggact ggggtgggga aggctgttca ttggggctgg ctgaggactg   46260
ggttgaatgg tctgctggga gagggcactc gagctcggag ctgtgccaaa gatagatggg   46320
agaggcgggt cggagttgtc acgggaaccc gtggtcagaa caccctcatg tgcgttccat   46380
gcccacctcc tgccagggtt tcgccatccc atcggaaggg aaggcggggt gagggcaggc   46440
ccgtgtggct tggggcacgt gagaagtggc ggtgcaccag gaattgatga gtgtcctcat   46500
ggggcttggt gccttgaggg gtacagagct agacgagatt caggtcccgt ccccagtgac   46560
ctatggccag tggagagcct cggggggcct ctgtggtggg gtcctcagtg cttgtgctgg   46620
ccagtggtgg atagggaagg gggatggaca gagaggcgcc cagcccagct tcaggggtg   46680 gagtcggagc ctggccgagt ttgaagtgga agggctggcc cagcacagag tgagcccgtg   46740
cttggaggcc tggtgtgtgg gaggctcggg gcgggtgcag tggttaagag ttgtgaagag   46800
agtgcctgcc ccgggcttgg ggtggctctt aggtgtcctg agcctgcatt tctgttacac   46860
aggcataatg atggcacttt tctcccaggc ctggggacag aagggcctgg ctcagtgtct   46920
gctaactgat tgttatccat gcatagagaa taccaagacc acagcagaca ccttccgtca   46980
ccagtggctt agctgttccc accccaaaca tagggctgga tgcaaggact tgctaaagtt   47040
cttcctcccc agcgtgggct tccctgggt gtccccgggc ctggggccgg tgcatcagg   47100 tgtgtgggca gctctccgtg actgtttcgg gactgcgtgg ctccagctct ctgcctccct   47160
ggtggggcag ccttcctggt gctggtgcca ctgacggctt ttggtggcca tggcgataat   47220
actaacagca gacagaggac acagctgcca gtgctccatc tgtggatgaa cctgccgcag   47280
cgttgtagca gtgccatgat gtggggtccc ctttcctcca tgtcacacag gaggaggata   47340
aagggaagca gaagcccagg ggcttccctc taggagtgtt cagttcagct ggggagatgg   47400
gtgtgcagga gcagctgggg agtgctggag tcttcagcag aggctctccg aggggtacga   47460
gcaggtgccc tggagcagcc gggcggcttc ccagaggagg agggatgagg gcaggagggt   47520
gagggaggtg gcattcctta tggcactggc actgggggcc gccctcatcc tcctgggatt   47580
gtcagtcgct gctcttctcc tgccctggtc cctgcagcat gaatgccttc atcttgttgc   47640
tgtgtgaggc gcccttctgc tgccagttca tcgagtttgc aaacacagtg gcggagaagg   47700
tggaccggct gcgctcctgg cagaaggctg tcttctactg cgggtgaggg gttgctgggc   47760
agggtcccgt gacacagttc cccaaaaccc cactgacaaa ataggaccca aaagtcaggt   47820
gagggtgggc agtgtattca gttcctctct gtggaagtgt aaactgggat tgcctttgtg   47880
cacagtgatt tgctcatagc tgccaaaacg tgcccagtg gttctgcgcc caggaactca   47940
gctgtcgctg tgccgtagtc actggaaggt tcagaggtat atgagcatgt gtggcagcat   48000
ccgtgcagtg gagagaaagt gggaagcgtc tggaattttg gtccgtccac tgggagttgt   48060
taaccagatg atagtaggtc tgtaggacat gtttctctgc agcctttccg aagagtgggt   48120
tcatctagat gtcctgacgt gaaggggag aagcaggttg cagagcagaa aatgtggttg   48180
ccctctaaat acacttgtta aaatttttcc catttctaac aatgaaatca atatgtaata   48240
cttctcctct cagtcataag aaggaactaa tttcaggata agcttaatac acggaaactc   48300
```

```
ctagaataat gcctctagtg cataggaggc tggtggcagc tgtattcatt attgtctagg    48360
ttatctttag aaagaagtct agatgcaagc ttgcttcccc ttcagagagg cccggtagtt    48420
ttgatggtaa gagcacaagc cacatgctta gttctggagc catcttgtgc catatctaaa    48480
tcacgaagaa cacaggatca caaagctctt atctacacgc agtgtcatgt ccttaggggt    48540
tcaaaaaact gtattttaaa aatgctagac atcatagaaa ttcattcaca ataatttgga    48600
atatagaaca atgttactcg aagcccgctg cctgctaatc ttctgatgtg tgtgcttcct    48660
gtctgcaggc atttttaaa agcctgcttt taacacagtt ataaccatta tgaataagtt     48720
tgtatcctgc ctttttcac ttagagtaat gatataagca tttgaacatc accacagact     48780
ttataacatt ctttcaatac aggaatattc attcagctgg atgtatcatg ctgttcttaa    48840
tttcttaact ggtgtaaatc gaggtgtgat aaacatgtgt ctgctaaaac tttttctgtg    48900
tttatgatga tttccttaat atctattttc aggtgtggaa ttactgggtc aaagattctg    48960
atcattaaaa atattttaag atgcgtggct acgttgcttt ccaaagaggt cccttgagtc    49020 tctccccgc ccccacccca gcccagggct gcacaccact tcacattcgc atttatctat     49080
ttgttatcta agagggaaaa atattttccc acgtgtttcc attgcatttt ctgatatgaa    49140
aattttcgag tttactttt aacctgtggg aacctcagtg ttctgcttag caagttcagt     49200
gtgttttctg tattaaagat ttcatgatcc ttggttgtat ttcctgcaac tatttttcca    49260
ggctcttgtt tgccttaat tttgttttg tcagaaggtt ccccgccgtg gtcttttct      49320 ttgtaatttc tattattatt ttatcatttt gaaattttt aacgacagaa aaatctcaca    49380
accacatgtc tacaagaatg gaaactgagg tagaatgcaa ttggccacga gtcttgtcct    49440
cctgcacagg cagcctcctc tagggaggcg acaggacaga gcgctggcct ccaggctgca    49500
ggtatcctcc tggcccagtt agcccaggaa ttgctgctgg cctggaaatt ccagccagga    49560
tggagaatca gccccgggga cgcttaagcc ccagtggacc ctgccaccag gtgacgccaa    49620
actgcagcaa ggtctgggcc gaccccgcag acccgcagc ctgcagccct cccatgatga     49680
gaccctgtgt tccatgtggt tgaattccag ggaccttact tgtggcgatg tggctggtgt    49740
tactctataa ctcagagcat ttatttagtg cctgtggtgg tcagcattgt gtaggtaaca    49800
tgactgacct cggacaagct tgatcccct ctccgcggtg gagattccga gtaacttgcc     49860
cgcgaagcta gtaggtcctg gatgggaagc cagattctct gtcacaggca ctttctggcc    49920 agttttctc acagtgaggg cactggacca tctcgttact gtttagctct tttgggatc     49980 acagacccct tcaaaaatct gatgaaagct ttggatccta ttcccagaat ggaacagttt    50040
tacagacaag ttcagggctg atgaaggact ttctgaagct gtgtctcagt tgattttgg    50100 ggatccttcc tgtgccctgg gtgtctagga aggatgctgg gccgagtctg ggaagcgggg    50160
aaggatgtgg tggctgtggg gccggagtgc cccttgacc tctgctttcc ccccaggatg     50220
gcggtcgttc ccatcgtcat cagcctgacc ctgaccacgc tgctgggcaa cgccatcgcc    50280
tttgctacgg gggtgctgta cggactctct gctctgggca aaaagtgcgt ctgccaggcc    50340
cagcccctgg gcagggcctt cctccctccg ccccccgaag tccttcagtg aggaggatct    50400
gagagtggcc cctttagct agtggagacc gaggcagagg tcccagtaac tcattggtgc    50460
ctccagggct cagctcgagt gggtgaagac agaggactta caacacttct gcgtggccca    50520
gtcttgcccc gtcacggcct gcagcaagga tagcaaaaac atggctggtg ggagccccctt   50580 cccctcccag gtctgcaccg ggcattgtac tcagttgcca ccctctctcc tgcagagccc    50640
```

-continued

```
agactgaggc tggttccttc acagcccagc atcccaggga gcctgggcca ttctcagagg   50700
ggacaagaca ggcctttgcc accccagcag ttgtctctgg ggaaatcaga atgcctgcag   50760
gtcacacctg ggtcacaggg caggaaccgg gcagtggtca ggagggctgt gggcatgggg   50820
ctggtgctcc acgtgacgct gcctctctct ctccccaggg gcgatgcgat ctcctatgcc   50880
aggatccagc agcagaggca gcaggcggat gaggagaagc tcgcggagac cctggagggg   50940
gagctgtgaa gggctgggcg cccctccctc cctgtcccct cttctggctc tgtgtgggtc   51000
caagtgaggc ctggactgtc cacgctgagg cacagcctgg agagggcct ttgcacgtgt   51060
ccctacacct ggagtcctct gctcctttct ccagactggc ttaagccagg agccactggc   51120
tgctggtgtg agggtctggg ctgctggact tgaggcagag cctgcagcag ctgtgtggac   51180
actacccagc cctactcctc tgctgggtgg gtctgcagat ctcacaccac agacagggct   51240
gcctgtgacc tgctgtgacc tgggagcagc ttcccctgga gatgctggtc ctggcttgag   51300
gggaggggca agtgggaccc tgccacctgg gcactgagca gagggacctc ccccagctct   51360
cttagcaggt ggagccccag ggcctgggac agcctgccgc tgccagcaac ctcccactgc   51420
tgcctagggt gcagcgccca ctgtcaccct gccttctgaa gaagcccaca gggctcctaa   51480
ggtgcacccc ggtacctgga actgcagcct tggcagtgac tggacagctg ggtgggggat   51540
gctccctgct ggccctggga accttggaca ggccacctca aggcccctcg gctgcccctc   51600
ctccctgggc ctgctggggc cctaggttc tgcccatcac ccccgcccc tgctggcctt   51660
ggtgctaagg aagtggggag agcaggctct ccctggcacc gagggtgccc accctctccc   51720
tggtgtggcc ccgtcaacat cagccacagc ccagccccat tagtgggtta gcgggtctga   51780
cctcagcccc actcaggtgc tcctgctggc ctgcccaagc cctgccctca gggagcttct   51840
gccttttaag aactgggcag aggccacagt cacctcccca cacagagctg tccccactgc   51900
cctgggtgcc aggctgtccg gagccaggcc tacccaggga ggatgcagag agctggtgcc   51960
caggatgtgc accccatat tccctctgcc ctgtggcctc agcccgctgg cctctctgac   52020
cgtgaggctg gctctcagcc atcgggcagg tgcctggtcg ggcctggctt agcccaggtg   52080
gggcttggca gaagcgggcg ggtgtggaag atattccatc tggggccaac cccaggctgg   52140
gcctgcgctg agcttctgga gcgcaggtac tgggtcttgc taagtgaact gtttcccagg   52200
aacacctctc gggcccatct gcgtctgagg ctggagtgg catctgaggc cgggagtggc   52260
atctgaggcc aggagtggca ggctggtggg ctgggcgtgg ggttttctgg gccctgccca   52320
gtactgccct ggggacttgg tgggctcctg ggtcagcagc atcccacccc tgggagtctg   52380
gccagctgag cccagggtg gcaggggcat tatagcctgg tggacatgtg ccttcagggt   52440
tcctccgggg ccaccttcct caggccagtg ctgggttcaa agggctgtgt gtgtgtgtgt   52500
gtgtgtgtgt gtatgtatat gtgtgtgggt gcacacatct gtcccatgta tgcagtgaga   52560
cctgtctacc tcccacaagg agcaagggct ctgcccgccc tctgctcatt cctacccagg   52620
tagtgggacc ccgggccccc ttctgcctgg cttgcctgct tctgcccttt ccagagggt   52680
ctcactgaca gccagagaca gcaggagaag ggttggctgt ggatcaagga aggctgcccc   52740
tgtaccctgt ggggaaatgg tgggtgcatg gctggatgca gaggtggaag gccctgggcc   52800
acaggcgaga gtgggcgtgt cacctgtccc aggttcccag caagtctgca gctgtgcagt   52860
cctgggtcc ctgaccctgt cgcccagggg gcgtgctgtc cagcagggc cctgccttgc   52920
aaggaacgtc tcttccggcg gctgggccgc tcctgcctgg tctgggctgt gtgtggcgcc   52980
cttccttct tgtttgttcc tctgtgttct gtgtgcgtct taagcaataa agcgtggccg   53040
```

-continued

```
tggctcgcgt gcctgccctc tgctcccttc tgccttggtg cctgtgtgtg agtgtggaag    53100
ccaggcagga gccgctggcc caggaaataa ctacaggtcc tgtcccgagg ctgccccag     53160 catcccagac aaggaaagtg acctgcccaa ggtcacacag ctagaaagag cctgttaagg    53220
gtgggcctcg cagtgggctt cccctcactg cagccttttc cctgccctgc ttttgctatg    53280
gatcagcagt cagtggccct ggcaaccttg gctggttcgg gtctagcctg gctgctgtgg    53340
gggctcctgg agtagacccc actctttttcc tcgctaggac tacgggtcca gttcctttat   53400
ttttacaaaa gggtgaacac agtttgcaga taggagctgc ctgttcccag aggttgggct    53460
ggggcaggag gaagtggcca cgccaggtcc tttgccctgg cttttttttt ttttttttg     53520 gcaggggtg gggacggagt ttcactctcg ttgcccaggc tggagtgcaa tggcatgatc     53580
tcagctcatt gcagcctcca cctcccgggt tcaagcaatg ctgcctcagc ctcccaagta    53640
gctggaacta cgggtgtgtg ccaccacacc cagcttttttt gtattttta gtagagacgg    53700 ggtttcacca tgttggccag gctggtcttg aactcctggc cttgggtaat ccacctgctt    53760
tggcctccca aagtgctggg attacaggcg tgagccactg tgcccggcct gcctggctt    53820 tttaagtcca ggatgttccc tgtggtgccc ataagacttg tgagggcaaa gccgggtctt    53880
ccttgcacag ccagatgcca ccagatcaga gcgcgatgat atgactacgt tacttggctg    53940
cctccagccc tgtcctctca gtcctccccg tagccttctg tggggcgtgt ccttcacgca    54000
agggaaaggg actaggcctg aggtcaccca gcagggccgt gtccctggat gcagggttgt    54060
atgcactcct gcggcccatg gctacgtgca gcactgtggg ctgcctgggc tggggctgtg    54120
gctggacagc agtgctacct gtcccgagcc aggggcaccc gctgctgagg ccccatcaca    54180
ctgctcttcc tgtgctctgg ctggtggcag ggatgactgc tgcctcttgg tcccagggtg    54240
caggtttgta gccaacacag aggcccagcc actgggggtt tggcccccte caggcgggga    54300 ccttgaccta gcgcaagaag gaccttctcc ccatgcggaa gaaggactcg atctgctcca    54360
gggaccgtcc cttggtctcg ggcacacagc agcctgtgaa caccaggctc accaagcaga    54420
tggccgcgaa gaagaagaaa ggcacctgga ggccgaaggt gctctgcggg tgaagagcgg    54480
ggccgggtca cagggagaag ctccagggtc ctcctgcccc agaggagctc gtgggcgctg    54540
ctggtagtga ccagccctgt ggggccttca tctggtcctt cctgtgttca gagaccgccc    54600
ccccacacca gggctccccc actgtcccca ggacaaatcc gaagtagccc ttgaagtctg    54660
catcccgtct gcccctcggc cttcctcagg ggctgggccc tctggcgtca gctcaggtac    54720
cccctccaca cccctaccc agcgctggca tcccagctgt tccatgccgc ggcctgcagg    54780
aggcccgccc tgcagcctgg tgggcacgca ggttcttctt ggaccctcta ggctgatgga    54840
ctcactctgg gttgcctgcc ctcccccaac cccctgccc tgaccactgc agggacagct     54900
taggcgctgg cctaggctgc cctagccagc ttctccctca tgggaactta ctctgggcct    54960
cacagattct ggctggtcac agggcccgta gtttgaacc aggaggcagg gggagtgggt     55020 gggggttgagg ggggagtgtg gctgctgctg agacccagcg cccaggagga cgggagatga    55080
ggcacggtgg ggaggtggct tccggggccc ctggcagggt cctgggccat gtcctgccct    55140
ggcccaggag gtaacctgac ttcccagaac agttgcctac gcccgttcct gttcttata    55200 atgaagagcg tttgctaggc tatcacgtga ccactctggg gtctctgagt tcaggggtg     55260 tgtgctcatc tcctagggtc actgagagtt agggtcctga cagcaggcct tggcacagcc    55320
cctggcactg agaagggtcc tggccagtca gcgagggcct agggcctgg ggcctggggc     55380
```

-continued

```
tgaacactca ccaccactgg caggaaggac ttggtgagga cgaaggcggt gagccagctg    55440
gccagcacgc agagccctga ggccacgcca cgggcacgca ggggcaggac ctcagacatg    55500
agcagccagg tgatgggacc ccagcccacg gcgtagcctg ctcggaggag gaggcaggtt    55560
caggccctgt ggggtgactg gaggcggctg tgtctgtctc cgctgagctg ctggagaccc    55620
ccctctccag ccaccccaga cacatcaccc atcccttaac acccaagaca gcctgcccct    55680
ctgagccacc accacaccta cccatgatga agagcatggt ggccagcagg ggcaccaggg    55740
tgaggtagcc agcgggtgct gccagggggct gcgccaagtc cccccaggac tcgctttcca    55800
ggcccgcagt gctgttgggg ctcagaggcc tggggccaaa gtggatgtac agccccagag    55860
tcaggttggc agcaaacatg atggccgctg tggacagaca ggtggcctcg tggggccagg    55920
accctctgag ccagctgttt ctctcagagc tccttctgca gagccccttg atacttgcgt    55980
ggtccagctc gtgtctggga ctagagaccc ccagcagggc agcaagctct gtctccagcc    56040
gcgtgttagg ctcccaccgt ggagtgtcac agccagtgtg tccactcgga gccccagcgg    56100
accttctgg accactggcc tgggccaggg ccctgccgat gctagggagg caggtgctct    56160
gcagttccca gccacacagc cccaccccga ggcaggcctg cacacccagc ccagccctga    56220
cccatgcgga ggagtggggc aggagggctg cctgcagggt gcttacctga gacgaagagc    56280
agcaccttgc ggcctgcgag gtccatggtg agggcggcga tcagcacgga caggagccgc    56340
acggccccaa cgatggctgc gtcgtccttg gggggctatc gggggagac caccagggct    56400
gagggacctg cctgctgttc ccatcccct ccaggaccca gcttgtcccg gcaggcattg    56460
cagggctca ggccagcagc tcagtgcagt actgagtggc ctggcacctg cagcgtgctg    56520
ggcatctata ctgtccgagc ctatggggct cctgggcagg acacatctg ctctgcccac    56580
cactatgccc agctggcaca gaatccaggc gtgatgatga cttgctgaac cgtgctgtta    56640
ctaatcttca aatctcatct cactttgagc cttggggcag gctgatggag atgtgctgct    56700
atcttcatct tgcagaggag gaagttgagg ttcagagggg aaagtgactt ccctcattaa    56760
gtggcagatg ccacagggct ctgaacctgg ggtctgtggc ctcaagggggt ccacgtttct    56820
ataaagctgg tttcctttgt aatcccatgt atttttattta attttttaaaa tttctatatg    56880
tttttagaga cagggtcctg ctctgtcacc aggatggagc gcagtggtga gatcgtggcc    56940
actgcagtct cacactcctg ggcttaagtg atcctcccgc cttggcctcg tgttgggatt    57000
ttgccagtat tttatttttaa aacacttaag cttatcttaa aaacattctg agaacaggtg    57060
aaggcactgg aactgtctcc acaaggccca gatctcagat cttgctgtgg catccctgac    57120
acccggcaca gagcaggtgt gggtaagacc aggggttggg taagtgcagg agcaggccct    57180
gcctcccctg ccctgccagc ctccagggga ccccgtgggt gggcgccggc cggggctggg    57240
ctctcaccag caggacagcg gtgctgtcga agatggactg caggtagacc aggatgggcg    57300
tgatgcccgt cagctgctgc aggaggcgca tcagcaaggc cacggtgatg ggccggcaca    57360
cgtgtggggc ccgtgcctca gcccacgata ctcggctgct ctgaaacaca aggccgccgc    57420
tgagggcgtt gggccagcct ctccagcagg cgccatcctg ccctggaccg ccaggggttg    57480
tgtgggagac ctccttttttc cctcctccag gaaagaacca gcttaccagg ccacccaggc    57540
tctgggaaca gccccccacc ccaacccagg cacttggatt agtgggaact actgtggtcc    57600
tgtcttccag gaaaagcctc cacggccaca cacagctgaa gtgctggagg tgggcctgcc    57660
cggttcgggc gcacccctc ctgcacctgt tccggacgt tgtcctggat ctgctcgaac    57720
tcccagtgga catcgacgtc cgtcccacgc agccaggcca gcgcccgcag ggcctcttcg    57780
```

```
tccctgcccc gagagagcag gaagcgcggc gagttgggca tgaagctgag cagcaggatc    57840
atgatgagca caggcgcctc cccggccaca gccagccagc gccacggcag caggaggcct    57900
gggggcgagg ggtgggtgag gggccaggtc caggcctggt acagccoctt ccctctggag    57960
cctctgaata acctcatctg cccttcaagg tctagtccaa gggccatctc ctacaggaag    58020
cctaccctga ttgccccagg cagggtgggg ctgcagggat tgctcagccc ctggcacata    58080
gtgggaagtc cttggaaagt cttagggcca gggcaggatg aggaaggggt aggttgggca    58140
ggcaaggccc taggcctcca cccaagacct ccacgccccc tcaactgagc agctgcacgc    58200
actgtgattt cttttctatc tggacttccc atctgagatg gcatttgatg gaagctttct    58260
gccgttaaaa gatagtctgg cgactgtggg tccaggagaa gccctggctg ccccagctag    58320
agactgggcc tgtggctaga ggggcaggcc ctgcctggag gtgcccagca aggtgctgac    58380
tgagtggggc cgggatgcca gatctcttgc ctctcagccc aggatctgtt ctgggacaaa    58440
tcattcccct tccacccacg tctaccttgg cggcacccac ccctcccacc agcctgcaca    58500
caggagtgcg gggccatact tgccaagggc gtagagggac agggatccga acactgccat    58560
gagctggggt gtggccccca gagccccacg aacgcctggg ggagcaatct cagacacgta    58620
cacctgcaag acacagccgc cgcaccaggt tttgctgaaa atactggttc ctaggcccgg    58680
ccgagatggg agagtcagcc cctgtgaacc ccggaaagtg ggaagtggag gctttctggt    58740
ggggctgagt cctggtcatg actcactgca agaccttggg cggcctgcct gatctctctc    58800
tgtcctcagt ttccctaact gtgacgtggg tggaagtacg cagctcggaa atgggcagca    58860
tgacgctggg aaggaggccc gagggctccc aggcttcagg gctgagcagg tgagtccatg    58920
cctcccagtg agttttgtct cctctgctgg gctcaccacc aggccccgtg tggagtacca    58980
cataagataa gaaggtcccg gggagggtgt agggcaggga cttccctctc ctacccattg    59040
ctcaatgcgg attttctcca attgagtaat acatctgacc ggtcaagaaa cggggtagaa    59100
ggcttggaaa gtccagagtg ggggcagctg gggacctgga gacaatttcc cccaaattag    59160
ctgccctgct gggggtgagc tgaggcgccc tgggcatccg cagggaaggc aaacaattct    59220
cattgcccag aaggcatgga ggctgggagg ccttagtcag atggaggctc agcaccaata    59280
cagaggcatt gggcgcctg ggtgggaagg cctggcctta ccgggatgca ggcagctgtg    59340
agccccccgg cgaagcccgt cagcgtcctt ccgagcagca gcatccagag gccgtgcgca    59400
cccgccatga gcgcatagcc ggccgccgac ggcacagctg agaacatgat gctcagcttc    59460
cggcccagga ggtcgttgag gatcatggca ctcaggcctc cggccgctgc tcccagggtg    59520
aacacggact gcaggggaag ggggtgcagg gcagatatgt ctgggcactt ggcacccag    59580
tctcatcaga gtccagggac agcttcttcc ctaggccgac cccaggagct ggtcaagcac    59640
ttggccaagt caagcacttg aaacagggag cctcctgtct tcaaggaaca gccatttgtt    59700
agggatgccc aaacggggaa ttctgctcta aggaagaggt gctgcgccac atatccacag    59760
tggttctgtc cagcctgatg tttaaatgtc taatatttta atacaggaga attctgtgac    59820
ttgaaggtac tgggctttaa gatttggagg ttcttaagtt ccctgtacag cagcaactgg    59880
gacccctct ggactctgct aactggtagt gggacctggg cacattgccc agcctgtctg    59940
cacctcagtt tcttcagctg tcttatgggg agagcgcaag ttctacctcg tggcgttggc    60000
cctgagaatc aatgaacgtt cagtgcccaa cacatgcctg gcacatagga agtgctcagt    60060
aaaccttggg aattttttatc ttaactacta tgttaacaac tctacatatg aggctattaa    60120
```

| | |
|---|---|
| gattataatt ttagactctg ggactctggg atc | 60153 |

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8

| | |
|---|---|
| gctttgctct cctgagcttc | 20 |

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9

| | |
|---|---|
| gtggtgcagt tcactgtcgt | 20 |

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10

| | |
|---|---|
| gttgcagtga gctgagatcg | 20 |

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11

| | |
|---|---|
| tgcaggggtt ttatctccta | 20 |

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12

| | |
|---|---|
| tgggtgacag agcaagactg | 20 |

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13

| | |
|---|---|
| cttgtatcca cgcacagagg | 20 |

<210> SEQ ID NO 14
<211> LENGTH: 20
<212> TYPE: DNA
<213> ORGANISM: Artificial Sequence

```
<220> FEATURE:
<223> OTHER INFORMATION: Synthetic

<400> SEQUENCE: 14
agcctgggtg acagagtgag                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tacaccaatt ccccaggtgt                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ccctgaactg caaccatctt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
caaaccccaa agctgatgta                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tcggtctccc caagtgttag                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
aacagggttg acagcagctt                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tctagaacca tcgccctctg                                               20
```

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ccgagccatt ctacctgagt                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gcctctccag ctcttcacac                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gcattctgtg atccatgctg                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
acgggctagt catagggttg                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
tacaaggacc cactgcttgc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
cttccaaacg cttccatcct                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ccctcccagg actagctaca                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tctgggaggg acagttaagg                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
tactggtcct gcctcctgac                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
gggatcccta tgggtgagtt                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
cctggtgtga accacagatg                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
gcacttttgt caccccagtt                                                20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ccagagcctg aaccactttg                                                20

<210> SEQ ID NO 34

```
<211> LENGTH: 20
<212> TYPE: DNA
<213> ORGANISM: Artificial Sequence
<220> FEATURE:
<223> OTHER INFORMATION: Synthetic

<400> SEQUENCE: 34
cccagatgca aaggatgaag                                                     20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
atccagggct gagtgagtgt                                                     20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
tttttcccga ccagctaaga                                                     20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
tcagaagtga gggcatcttg                                                     20

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
ccgggaagga gagtcactg                                                      19

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
ccctgtaagt gaccgctga                                                      19

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
```
gtgattgctt gctgaacgaa                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cagtgtcctc acctgcagaa                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
gaacacctgg agaggctagg                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
acttacaacc gccaggtgac                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
gaacctgctg gctgatgaat                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
ggatggtgtt cttgctctgg                                               20

<210> SEQ ID NO 46
<211> LENGTH: 18
<212> TYPE: DNA
<213> ORGANISM: Artificial Sequence
<220> FEATURE:
<223> OTHER INFORMATION: Synthetic

<400> SEQUENCE: 46
cacacacgcc acttcctg                                                 18

<210> SEQ ID NO 47
<211> LENGTH: 22
<212> TYPE: DNA

```
<213> ORGANISM: Artificial Sequence
<220> FEATURE:
<223> OTHER INFORMATION: Synthetic

<400> SEQUENCE: 47
ccacgtgttc ccatatagtc tg                                              22

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
cacagctggt aagtggcaga                                                 20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
cacagctggt aagtggcaga                                                 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tcccagcttc ctgtctcttc                                                 20

<210> SEQ ID NO 51
<211> LENGTH: 21
<212> TYPE: DNA
<213> ORGANISM: Artificial Sequence
<220> FEATURE:
<223> OTHER INFORMATION: Synthetic

<400> SEQUENCE: 51
tctcctgatt cagctttcca a                                               21

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
agtacacgtg ggtggagagg                                                 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ctttcagggg acacgatgag                                                 20
```

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ttaactgcct cccagcttgt                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
ctttgccagg gagaaagagg                                              20

<210> SEQ ID NO 56
<211> LENGTH: 19
<212> TYPE: DNA
<213> ORGANISM: Artificial Sequence
<220> FEATURE:
<223> OTHER INFORMATION: Synthetic

<400> SEQUENCE: 56
acagggtcca cccctacct                                               19

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
cccagttcct tccatctcag                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
tattgaccac agtgccatgc                                              20

<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59
tggtgaatat gtggaggaag g                                            21

<210> SEQ ID NO 60
<211> LENGTH: 20
<212> TYPE: DNA
<213> ORGANISM: Artificial Sequence
<220> FEATURE:

<223> OTHER INFORMATION: Synthetic

<400> SEQUENCE: 60
cctcggtttt ctgggtagag                                                     20

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
ccatcctcgg agtggaatc                                                      19

<210> SEQ ID NO 62
<211> LENGTH: 19
<212> TYPE: DNA
<213> ORGANISM: Artificial Sequence
<220> FEATURE:
<223> OTHER INFORMATION: Synthetic

<400> SEQUENCE: 62
cagtgcaaca accccagac                                                      19

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
ggcacctgtc ccatacctg                                                      19

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
gtgtcgtcct cagggttgat                                                     20

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
ggctctgtca gaatgaccat c                                                   21

<210> SEQ ID NO 66
<211> LENGTH: 22
<212> TYPE: DNA
<213> ORGANISM: Artificial Sequence
<220> FEATURE:
<223> OTHER INFORMATION: Synthetic

<400> SEQUENCE: 66
tgccaggtgg gaggtgtcag ag                                                  22

```
<210> SEQ ID NO 67
<211> LENGTH: 22
<212> TYPE: DNA
<213> ORGANISM: Artificial Sequence
<220> FEATURE:
<223> OTHER INFORMATION: Synthetic

<400> SEQUENCE: 67
gcctggcctt tgagaacgag ac                                             22

<210> SEQ ID NO 68
<211> LENGTH: 19
<212> TYPE: DNA
<213> ORGANISM: Artificial Sequence
<220> FEATURE:
<223> OTHER INFORMATION: Synthetic

<400> SEQUENCE: 68
cattggcgag agcttcatc                                                 19

<210> SEQ ID NO 69
<211> LENGTH: 18
<212> TYPE: DNA
<213> ORGANISM: Artificial Sequence
<220> FEATURE:
<223> OTHER INFORMATION: Synthetic

<400> SEQUENCE: 69
atggggaggg agccttct                                                  18

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
accctgagcc tgtgtgtgtc                                                20

<210> SEQ ID NO 71
<211> LENGTH: 18
<212> TYPE: DNA
<213> ORGANISM: Artificial Sequence
<220> FEATURE:
<223> OTHER INFORMATION: Synthetic

<400> SEQUENCE: 71
gcagaggtgg catccaga                                                  18

<210> SEQ ID NO 72
<211> LENGTH: 30
<212> TYPE: DNA
<213> ORGANISM: Artificial Sequence
<220> FEATURE:
<223> OTHER INFORMATION: Synthetic

<400> SEQUENCE: 72
tcgatcctcg agtctagagc cgccaccatg                                     30

<210> SEQ ID NO 73
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 73

Asp Tyr Lys Asp Asp Asp Lys
1               5

<210> SEQ ID NO 74
<211> LENGTH: 35
<212> TYPE: DNA
<213> ORGANISM: Artificial Sequence
<220> FEATURE:
<223> OTHER INFORMATION: Synthetic

<400> SEQUENCE: 74
gactacaagg acgacgacga caagtaggcg gccgc                          35

<210> SEQ ID NO 75
<211> LENGTH: 16
<212> TYPE: PRT
<213> ORGANISM: Artificial Sequence
<220> FEATURE:
<223> OTHER INFORMATION: Synthetic

<400> SEQUENCE: 75

Ser Gln Thr Ile Asn Pro Glu Asp Asp Thr Asp Pro Gly His Ala Asp
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic

<400> SEQUENCE: 76

Glu Ser Phe Ile Met Lys Arg Gly Asp Ser Phe Leu Asp Gly Thr Arg
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: Synthetic

<400> SEQUENCE: 77

Gly Arg Leu Thr Trp Arg Lys Met Cys Arg Lys Leu Leu Asp
1               5                   10

<210> SEQ ID NO 78
<211> LENGTH: 16
<212> TYPE: PRT
<213> ORGANISM: Artificial Sequence
<220> FEATURE:
<223> OTHER INFORMATION: Synthetic

<400> SEQUENCE: 78

Cys Pro Glu Met Gln Asp Pro Gln Ser Trp Lys Gly Lys Glu Gly Thr
1               5                   10                  15
```